US012773546B2

(12) United States Patent
Georges et al.

(10) Patent No.: US 12,773,546 B2
(45) **Date of Patent: *Oct. 27, 2026**

(54) MODULAR MAMMALIAN BODY IMPLANTABLE FLUID FLOW INFLUENCING DEVICE AND RELATED METHODS

(71) Applicant: Puzzle Medical Devices Inc., Montreal (CA)

(72) Inventors: Gabriel Georges, Sherbrooke (CA); François Trudeau, Quebec (CA); Jade Doucet-Martineau, Pierrefonds (CA)

(73) Assignee: Puzzle Medical Devices Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 19/257,103

(22) Filed: Jul. 1, 2025

(65) Prior Publication Data

US 2026/0069850 A1 Mar. 12, 2026

Related U.S. Application Data

(63) Continuation of application No. 18/755,246, filed on Jun. 26, 2024, which is a continuation of application
(Continued)

(30) Foreign Application Priority Data

Apr. 5, 2019 (WO) ................ PCT/CA2019/050421

(51) Int. Cl.
*A61M 60/139* (2021.01)
*A61M 60/13* (2021.01)
(Continued)

(52) U.S. Cl.
CPC .......... *A61M 60/139* (2021.01); *A61M 60/13* (2021.01); *A61M 60/17* (2021.01);
(Continued)

(58) Field of Classification Search
CPC .... A61M 60/139; A61M 60/13; A61M 60/17; A61M 60/178; A61M 60/237;
(Continued)

(56) References Cited

U.S. PATENT DOCUMENTS 4,625,712 A 12/1986 Wampler
4,646,719 A 3/1987 Neuman et al.
(Continued)

FOREIGN PATENT DOCUMENTS

AU 2012256089 B2 * 8/2016 .......... A61M 60/232
CA 2701810 A1 4/2009
(Continued)

OTHER PUBLICATIONS

Extended European Search Report for European Application No. EP21736214.4 dated Jan. 3, 2024, 9 pages.
(Continued)

*Primary Examiner* — Michael J Lau
(74) *Attorney, Agent, or Firm* — Borden Ladner Gervais LLP; Geoffrey Dekleine

(57) ABSTRACT

A docking unit for use in a modular mammalian body implantable device. The docketing unit comprising an elongated body. The body has: a longitudinal axis, at least one receiving surface extending parallel to the longitudinal axis, a distal end and a proximal end, and at least one proximal guide hole. Each receiving surface has at least one proximal guide hole associated therewith. The docking unit is dimensioned and shaped to be deliverable to an implantation site within a conduit of a conduit system of the mammalian body via a catheter.

25 Claims, 51 Drawing Sheets

Related U.S. Application Data

No. 17/316,090, filed on May 10, 2021, now Pat. No. 12,053,623, which is a continuation of application No. 17/047,598, filed as application No. PCT/ZA2020/050022 on May 4, 2020, now Pat. No. 11,179,557, and a continuation-in-part of application No. PCT/CA2019/050421, filed on Apr. 5, 2019, said application No. 17/316,090 is a continuation of application No. PCT/ZA2020/050022, filed on May 4, 2020.

(60) Provisional application No. 63/007,899, filed on Apr. 9, 2020, provisional application No. 63/000,439, filed on Mar. 26, 2020.

(51) Int. Cl.

| | |
|---|---|
| ***A61M 60/17*** | (2021.01) |
| ***A61M 60/178*** | (2021.01) |
| ***A61M 60/237*** | (2021.01) |
| ***A61M 60/416*** | (2021.01) |
| ***A61M 60/804*** | (2021.01) |
| ***A61M 60/861*** | (2021.01) |
| ***A61M 60/865*** | (2021.01) |

(52) U.S. Cl.
CPC ........ *A61M 60/178* (2021.01); *A61M 60/237* (2021.01); *A61M 60/416* (2021.01); *A61M 60/804* (2021.01); *A61M 60/861* (2021.01); *A61M 60/865* (2021.01)

(58) Field of Classification Search
CPC .............. A61M 60/416; A61M 60/804; A61M 60/861; A61M 60/865; A61M 60/857; A61M 60/859; A61M 60/873
See application file for complete search history.

(56) References Cited

U.S. PATENT DOCUMENTS 4,753,221 A 6/1988 Kensey et al.
4,957,504 A 9/1990 Chardack
4,964,864 A 10/1990 Summers et al.
5,092,879 A * 3/1992 Jarvik ................ A61M 60/577 600/16
5,112,349 A 5/1992 Summers et al.
5,368,438 A 11/1994 Raible
5,749,855 A 5/1998 Reitan
5,888,241 A 3/1999 Jarvik
5,957,672 A 9/1999 Aber
6,015,272 A 1/2000 Antaki et al.
6,050,987 A 4/2000 Rosenbaum
6,176,848 B1 1/2001 Rau et al.
6,210,318 B1 4/2001 Lederman
6,245,007 B1 6/2001 Bedingham et al.
6,527,800 B1 3/2003 McGuckin, Jr. et al.
6,669,624 B2 12/2003 Frazier
6,827,733 B2 12/2004 Boneau
6,942,611 B2 9/2005 Siess
6,981,942 B2 1/2006 Khaw et al.
7,022,100 B1 4/2006 Aboul-Hosn et al.
7,027,875 B2 4/2006 Siess et al.
7,070,555 B2 7/2006 Siess
7,144,364 B2 12/2006 Barbut et al.
7,393,181 B2 7/2008 McBride et al.
7,479,102 B2 * 1/2009 Jarvik ................ A61M 60/139 600/16
7,762,977 B2 7/2010 Porter et al.
7,841,976 B2 11/2010 McBride et al.
7,909,862 B2 3/2011 Garrison et al.
7,914,436 B1 3/2011 Kung
7,918,880 B2 4/2011 Austin
7,942,851 B2 * 5/2011 Faries, Jr. ............ A61M 5/148 604/114
7,993,259 B2 8/2011 Kang et al.
7,998,190 B2 8/2011 Gharib et al.
7,998,954 B2 8/2011 Otsubo et al.
8,012,079 B2 9/2011 Delgado, III
8,070,800 B2 * 12/2011 Lock .................... A61F 2/2412 623/2.14
8,075,472 B2 12/2011 Zilbershlag et al.
8,157,758 B2 4/2012 Pecor et al.
8,308,798 B2 11/2012 Pintor et al.
8,333,687 B2 12/2012 Farnan et al.
8,343,029 B2 1/2013 Farnan et al.
8,394,010 B2 3/2013 Farnan
8,439,859 B2 5/2013 Pfeffer et al.
8,449,443 B2 5/2013 Rodefeld et al.
8,489,190 B2 7/2013 Pfeffer et al.
8,579,858 B2 11/2013 Reitan et al.
8,585,572 B2 11/2013 Mehmanesh
8,617,239 B2 12/2013 Reitan
8,690,749 B1 4/2014 Nunez
8,727,959 B2 5/2014 Reitan et al.
8,734,331 B2 5/2014 Evans et al.
8,777,832 B1 7/2014 Wang et al.
8,784,291 B2 7/2014 Farnan et al.
8,814,933 B2 8/2014 Siess
8,821,366 B2 9/2014 Farnan et al.
8,944,748 B2 2/2015 Liebing
8,974,374 B2 * 3/2015 Schostek ............... A61B 34/30 600/118
9,022,916 B2 5/2015 Farnan et al.
9,211,367 B2 12/2015 Farnan et al.
9,216,298 B2 12/2015 Jacobson
9,217,442 B2 12/2015 Wiessler et al.
9,314,559 B2 4/2016 Smith et al.
9,328,741 B2 5/2016 Liebing
9,339,597 B2 5/2016 Khanal et al.
9,358,330 B2 6/2016 Schumacher
9,375,580 B2 6/2016 Bonner et al.
9,416,791 B2 8/2016 Toellner
9,421,311 B2 * 8/2016 Tanner ................ A61M 60/829
9,446,179 B2 9/2016 Keenan et al.
9,492,600 B2 * 11/2016 Strueber ............... A61M 60/17
9,572,915 B2 2/2017 Heuring et al.
9,616,159 B2 4/2017 Anderson et al.
9,744,281 B2 8/2017 Siegenthaler
9,750,860 B2 9/2017 Schumacher
9,808,633 B2 11/2017 Bonner et al.
9,861,729 B2 1/2018 Morello et al.
9,872,947 B2 1/2018 Keenan et al.
9,878,079 B2 1/2018 Pfeffer et al.
D811,588 S 2/2018 Kaiser et al.
9,889,242 B2 2/2018 Pfeffer et al.
D826,401 S 8/2018 Epple
10,039,873 B2 8/2018 Siegenthaler
10,119,550 B2 11/2018 Bredenbreuker et al.
10,137,232 B2 11/2018 Yomtov et al.
10,143,788 B2 12/2018 Rudser et al.
10,179,197 B2 1/2019 Kaiser et al.
10,183,104 B2 1/2019 Anderson et al.
10,279,094 B2 5/2019 Williams et al.
10,293,090 B2 5/2019 Bonde et al.
D855,175 S 7/2019 Epple
10,363,349 B2 7/2019 Muller et al.
10,413,648 B2 9/2019 Delgado, III
10,426,880 B2 10/2019 Kushwaha et al.
10,443,738 B2 10/2019 Durst et al.
10,449,276 B2 10/2019 Pfeffer et al.
10,478,538 B2 11/2019 Scheckel et al.
10,478,539 B2 11/2019 Pfeffer et al.
10,478,540 B2 11/2019 Scheckel et al.
10,500,323 B2 12/2019 Heuring et al.
10,596,019 B2 3/2020 Melsheimer et al.
10,722,631 B2 7/2020 Salahieh et al.
10,799,624 B2 10/2020 Pfeffer et al.
10,898,626 B2 1/2021 Siegenthaler
10,926,013 B2 2/2021 Schumacher et al.
10,980,927 B2 4/2021 Pfeffer et al.
11,103,690 B2 8/2021 Epple
11,123,539 B2 9/2021 Pfeffer et al.
11,129,978 B2 9/2021 Pfeffer et al.

(56) References Cited

U.S. PATENT DOCUMENTS 11,154,704 B2 10/2021 Farnan et al.
11,167,124 B2 11/2021 Pfeffer et al.
11,179,557 B2 * 11/2021 Georges ................ A61M 60/13
11,202,902 B2 12/2021 Najar
11,235,137 B2 2/2022 Salys
11,235,138 B2 2/2022 Groß-Hardt et al.
11,241,569 B2 2/2022 Delgado, III
11,318,017 B2 5/2022 Besselink
11,324,940 B2 5/2022 Earles et al.
11,331,465 B2 5/2022 Epple
11,351,359 B2 6/2022 Clifton et al.
11,452,859 B2 9/2022 Earles et al.
11,471,665 B2 10/2022 Clifton et al.
11,534,593 B2 12/2022 Franano et al.
11,690,997 B2 7/2023 Georges et al.
11,697,016 B2 7/2023 Epple
12,053,623 B2 8/2024 Georges et al.
12,161,853 B2 12/2024 Crête et al.
2001/0044624 A1 11/2001 Seraj et al.
2005/0220636 A1 10/2005 Henein et al.
2006/0036127 A1 2/2006 Delgado
2006/0036157 A1 2/2006 Tumer
2007/0156006 A1 * 7/2007 Smith ................ A61M 60/216
600/16
2007/0213690 A1 9/2007 Phillips et al.
2007/0250120 A1 10/2007 Flach et al.
2008/0004652 A1 1/2008 Abboud et al.
2008/0132748 A1 6/2008 Shifflette
2008/0154328 A1 6/2008 Thompson et al.
2009/0112050 A1 4/2009 Farnan et al.
2009/0112312 A1 4/2009 LaRose et al.
2009/0149950 A1 6/2009 Wampler
2009/0247945 A1 10/2009 Levit et al.
2010/0249489 A1 9/2010 Jarvik
2010/0249491 A1 9/2010 Farnan et al.
2010/0268017 A1 10/2010 Siess
2011/0004046 A1 1/2011 Campbell et al.
2011/0106120 A1 5/2011 Haselby et al.
2012/0028490 A1 2/2012 Litzler et al.
2012/0041255 A1 2/2012 Delgado, III
2012/0046515 A1 2/2012 Woo et al.
2012/0053670 A1 3/2012 Purdy
2012/0101455 A1 4/2012 Liebing
2012/0149229 A1 6/2012 Kearsley et al.
2012/0172654 A1 7/2012 Bates
2012/0172655 A1 7/2012 Campbell et al.
2012/0178985 A1 7/2012 Walters et al.
2012/0178986 A1 7/2012 Campbell et al.
2012/0203328 A1 8/2012 Yribarren
2012/0226309 A1 9/2012 Jönsson
2012/0253387 A1 10/2012 Teichman et al.
2012/0310036 A1 12/2012 Peters et al.
2013/0138205 A1 5/2013 Kushwaha et al.
2013/0172661 A1 * 7/2013 Farnan ................ A61M 60/508
600/16
2013/0204362 A1 8/2013 Toellner et al.
2013/0253344 A1 9/2013 Griswold et al.
2013/0253347 A1 9/2013 Griswold et al.
2014/0012065 A1 1/2014 Fitzgerald et al.
2014/0031607 A1 1/2014 Zilbershlag et al.
2014/0066979 A1 3/2014 Jönsson
2014/0128659 A1 5/2014 Heuring et al.
2014/0275726 A1 9/2014 Zeng
2014/0278232 A1 * 9/2014 Miller .................... G16H 50/50
702/168
2014/0324165 A1 * 10/2014 Burke ................ A61M 60/237
623/3.27
2015/0250935 A1 9/2015 Anderson et al.
2015/0290372 A1 10/2015 Muller et al.
2015/0306291 A1 10/2015 Bonde et al.
2015/0320991 A1 11/2015 Sabin et al.
2016/0022890 A1 1/2016 Schwammenthal et al.
2016/0030652 A1 2/2016 Arndt et al.
2016/0089482 A1 3/2016 Siegenthaler
2016/0183824 A1 * 6/2016 Severino ................ A61B 5/287
600/523
2016/0206798 A1 7/2016 Williams et al.
2016/0256620 A1 9/2016 Scheckel et al.
2016/0279310 A1 9/2016 Scheckel et al.
2017/0035954 A1 2/2017 Muller et al.
2017/0087288 A1 3/2017 Groß-Hardt et al.
2017/0119945 A1 5/2017 Neumann
2017/0173242 A1 6/2017 Anderson et al.
2017/0274128 A1 9/2017 Tamburino et al.
2017/0340789 A1 11/2017 Bonde et al.
2017/0340877 A1 11/2017 Ollivier
2018/0099078 A1 * 4/2018 Tuseth ................ A61M 60/216
2018/0110909 A1 * 4/2018 LaRose et al. ..... A61M 60/419
2018/0126130 A1 5/2018 Nitzan et al.
2018/0193543 A1 7/2018 Sun
2018/0214141 A1 8/2018 Mendez
2018/0243551 A1 8/2018 Nagaoka et al.
2018/0250457 A1 9/2018 Morello et al.
2018/0311421 A1 * 11/2018 Tuseth .................. A61M 60/17
2018/0311425 A1 * 11/2018 Tuseth ................ A61M 60/818
2019/0046703 A1 2/2019 Shambaugh et al.
2019/0105437 A1 4/2019 Siess et al.
2019/0126014 A1 5/2019 Kapur et al.
2019/0183367 A1 * 6/2019 Turgeman .......... A61B 18/1492
2019/0358382 A1 11/2019 Delgado, III
2020/0023109 A1 1/2020 Epple
2020/0023158 A1 1/2020 Epple
2020/0054806 A1 2/2020 Sun
2020/0261633 A1 8/2020 Spanier et al.
2020/0306432 A1 10/2020 Pekkan
2020/0316277 A1 10/2020 Delgado, III
2020/0330665 A1 10/2020 Josephy et al.
2020/0405926 A1 12/2020 Alexander et al.
2021/0008261 A1 1/2021 Calomeni et al.
2021/0008263 A1 1/2021 Leonhardt
2021/0077687 A1 3/2021 Leonhardt
2021/0106808 A1 4/2021 Siegenthaler
2021/0170081 A1 6/2021 Kanz
2021/0170083 A1 6/2021 Seifert et al.
2021/0177425 A1 6/2021 Kapur et al.
2021/0260360 A1 8/2021 Georges et al.
2022/0080183 A1 3/2022 Earles et al.
2022/0080184 A1 3/2022 Clifton et al.
2022/0134082 A1 5/2022 Pfeffer et al.
2022/0226634 A1 7/2022 Groß-Hardt et al.
2022/0249830 A1 8/2022 Kanz
2022/0257920 A1 8/2022 Earles et al.
2022/0296852 A1 9/2022 Georges
2022/0296880 A1 9/2022 Clifton et al.
2022/0323744 A1 10/2022 Georges et al.
2022/0331576 A1 10/2022 Leonhardt
2023/0056440 A1 2/2023 Georges et al.
2023/0068315 A1 * 3/2023 Safran ..................... G06T 17/00
2023/0137466 A1 5/2023 Georges et al.
2023/0157569 A1 * 5/2023 Govari .................. G16H 20/40
600/374
2023/0210437 A1 * 7/2023 Beeckler ................ A61B 5/367
600/523
2023/0253726 A1 8/2023 Imfeld et al.
2023/0293880 A1 9/2023 Georges et al.
2024/0090882 A1 3/2024 Georges et al.
2024/0198078 A1 6/2024 Crête et al.
2024/0342460 A1 10/2024 Georges et al.
2025/0082923 A1 * 3/2025 Georges ................ A61M 60/81

FOREIGN PATENT DOCUMENTS

CA 3014105 A1 8/2017
CA 3054771 A1 9/2018
CN 104225696 A * 12/2014 .......... A61M 60/135
CN 106456857 B 11/2018
CN 109069716 A 12/2018
CN 112870547 A 6/2021
CN 110049792 B 1/2022
DE 19613565 C1 7/1997
DE 102004054714 A1 5/2006
DE 202009018416 U1 8/2011
EP 1912174 A2 * 4/2008 ............ A61B 5/103

(56) References Cited

FOREIGN PATENT DOCUMENTS

| | | | |
|---|---|---|---|
| EP | 2860849 | A1 | 4/2015 |
| EP | 3456367 | A1 | 3/2019 |
| EP | 3539584 | A1 | 9/2019 |
| EP | 2745805 | B2 | 5/2022 |
| WO | WO-0227225 | A1 | 4/2002 |
| WO | WO-03103745 | A2 | 12/2003 |
| WO | WO-2008017289 | A2 | 2/2008 |
| WO | WO-2008027366 | A2 | 3/2008 |
| WO | WO-2010133567 | A1 | 11/2010 |
| WO | WO-2012094641 | A2 | 7/2012 |
| WO | WO-2013062859 | A1 | 5/2013 |
| WO | WO-2013093058 | A1 | 6/2013 |
| WO | WO-2014070472 | A1 | 5/2014 |
| WO | WO-2015109028 | A1 | 7/2015 |
| WO | WO-2015148821 | A1 | 10/2015 |
| WO | WO-2015177793 | A2 | 11/2015 |
| WO | WO-2016185473 | A1 | 11/2016 |
| WO | WO-2017185082 | A1 | 10/2017 |
| WO | WO-2017217946 | A1 | 12/2017 |
| WO | WO-2018096531 | A1 | 5/2018 |
| WO | WO-2018129177 | A1 | 7/2018 |
| WO | WO-2018158635 | A1 | 9/2018 |
| WO | WO-2018226991 | A1 | 12/2018 |
| WO | WO-2019057636 | A1 | 3/2019 |
| WO | WO-2019083989 | A1 | 5/2019 |
| WO | WO-2019094963 | A1 | 5/2019 |
| WO | WO-2019152875 | A1 | 8/2019 |
| WO | WO-2019183247 | A1 | 9/2019 |
| WO | WO-2019191851 | A1 | 10/2019 |
| WO | WO-2020036886 | A1 | 2/2020 |
| WO | WO-2020198765 | A2 | 10/2020 |
| WO | WO-2021062565 | A2 | 4/2021 |
| WO | WO-2021062566 | A1 | 4/2021 |
| WO | WO-2021117021 | A1 | 6/2021 |
| WO | WO-2021138673 | A1 | 7/2021 |
| WO | WO-2021234638 | A1 | 11/2021 |
| WO | WO-2022094690 | A1 | 5/2022 |
| WO | WO-2022096941 | A1 | 5/2022 |
| WO | WO-2023178431 | A1 | 9/2023 |
| WO | WO-2024092349 | A1 | 5/2024 |
| WO | WO-2024229567 | A1 | 11/2024 |
| WO | WO-2025019957 | A1 | 1/2025 |

OTHER PUBLICATIONS

Extended European Search Report for European Application No. EP23166411.1 dated Oct. 6, 2023, 10 pages.

International Preliminary Report on Patentability for PCT Application No. PCT/CA2023/051450 mailed May 15, 2025, 7 pages.

International Preliminary Report on Patentability issued in PCT/CA2019/050421, dated Oct. 6, 2020, 9 pages.

International Preliminary Report on Patentability issued in PCT/CA2020/051673, dated Apr. 5, 2022, 7 pages.

International Preliminary Report on Patentability issued in PCT/CA2020/051677, dated Apr. 5, 2022, 7 pages.

International Preliminary Report on Patentability issued in PCT/CA2023/050378, dated Sep. 24, 2024, 5 pages.

International Preliminary Report on Patentability issued in PCT/US2021/012083, dated Jul. 14, 2022, 7 pages.

International Preliminary Report on Patentability issued in PCT/ZA2020/050022, dated Sep. 28, 2021, 5 pages.

International Search Report and Written Opinion for International Application No. PCT/CA2023/050378 dated Jun. 9, 2023, 8 pages.

International Search Report and Written Opinion for International Application No. PCT/CA2023/051450 dated Jan. 16, 2024, 9 pages.

International Search Report and Written Opinion for PCT Application No. PCT/CA2024/050620 mailed Jul. 24, 2024, 8 pages.

International Search Report and Written Opinion for PCT Application No. PCT/CA2024/051004 mailed Oct. 21, 2024, 12 pages.

International Search Report and Written Opinion for PCT Application No. PCT/CA2025/050038 mailed May 2, 2025, 15 pages.

International Search Report and Written Opinion for PCT/ZA2020/050022, dated Sep. 24, 2020, 6 pages.

International Search Report and Written Opinion issued in PCT/CA2019/050421 dated Jul. 8, 2019, 12 pages.

International Search Report and Written Opinion issued in PCT/CA2020/051673 dated Mar. 26, 2021, 12 pages.

International Search Report and Written Opinion issued in PCT/CA2020/051677, dated Mar. 15, 2021, 11 pages.

International Search Report and Written Opinion issued in PCT/CA2021/050469 dated Jul. 28, 2021, 10 pages.

International Search Report and Written Opinion issued in PCT/IB2020/061913 dated Mar. 19, 2021, 11 pages.

International Search Report and Written Opinion issued in PCT/IB2021/052925 dated Jul. 28, 2021, 1-14.

International Search Report and Written Opinion issued in PCT/IB2021/054395 dated Aug. 12, 2021, 9 pages.

International Search Report and Written Opinion issued in PCT/US2021/012083 dated Mar. 31, 2021, 7 pages.

Lo Coco, V. et al. "Right ventricular failure after left ventricular assistance device implantation: a review of the literature," J. Thorac. Dis., Feb. 2021, 13(2):1256-1269.

Non-Final Office Action for U.S. Appl. No. 17/316,090 dated Jan. 31, 2024, 15 pages.

Notice of Allowance for U.S. Appl. No. 17/316,090 dated Mar. 25, 2024, 9 pages.

Notice of Allowance issued in U.S. Appl. No. 17/047,598 dated May 3, 2021, 7 pages.

Notice of Reasons for Refusal for Japanese Application No. 2021-560164 mailed Apr. 11, 2025, with English Translation, 4 pages.

Office Action for Australian Patent Application No. 2020248173, dated Apr. 14, 2025, 4 pages.

Office Action for Canadian Patent Application No. CA3135041 dated Mar. 8, 2024, 8 pages.

Office Action for Japanese Application No. 2021-560164 mailed Sep. 17, 2024, 6 pages.

Office Action for Japanese Application No. JP20210560164 mailed Feb. 27, 2024, 9 pages.

Rhee and Blackshear, "Left Ventricular Assist Using a Jet Pump," ASAIO Trans., Jul.-Sep. 1990, 36(3):M515-M518.

Rogers, T. et al. NIH, National Heart, Lung, and Blood Institute "First in Man Testing of a Dedicated Closure Device for Transcaval Access for Transcatheter Aortic Valve Replacement," NCT03432494, Publication Date Unknown, 16 pages.

Search Report for Japanese Application No. JP2021-560164 dated Feb. 21, 2024, 40 pages with English Translation.

Supplemental International Search Report issued in PCT/ZA2020/050022, dated Jul. 13, 2021, 8 pages.

* cited by examiner

MODULAR MAMMALIAN BODY IMPLANTABLE FLUID FLOW INFLUENCING DEVICE AND RELATED METHODS

CROSS-REFERENCE

The present application is a continuation of U.S. patent application Ser. No. 18/755,246, filed Jun. 26, 2024, entitled "Modular Mammalian Body Implantable Fluid Flow Influencing Device and Related Methods", which is a continuation of U.S. patent application Ser. No. 17/316,090, filed May 10, 2021, entitled "Modular Mammalian Body Implantable Fluid Flow Influencing Device and Related Methods", now U.S. Pat. No. 12,053,623, which is a continuation of International Patent Application No. PCT/ZA2020/050022, filed May 4, 2020, entitled "Modular Mammalian Body Implantable Fluid Flow Influencing Device and Related Methods". U.S. patent application Ser. No. 17/316,090 is also a continuation of U.S. patent application Ser. No. 17/047,598, 371(c) date Oct. 14, 2020, entitled "Modular Mammalian Body Implantable Fluid Flow Influencing Device and Related Methods", now U.S. Pat. No. 11,179,557. The aforementioned '598 U.S. Application is the United States National Stage (371(c)) of International Patent Application Serial No. PCT/ZA2020/050022, filed May 4, 2020, entitled "Modular Mammalian Body Implantable Fluid Flow Influencing Device and Related Methods". The aforementioned '598 U.S. Application (through the aforementioned '022 International Patent Application) is a continuation-in-part of International Patent Application Serial No. PCT/CA2019/050421, filed Apr. 5, 2019, entitled "Fluid Circulation Support System and Method". The present application (through the aforementioned '598 U.S. Application and the aforementioned '022 International Patent Application) claims priority to (1) U.S. Provisional Patent Application Ser. No. 62/824,101, filed Mar. 26, 2019, entitled "Fluid Circulation Support System and Method"; (2) the aforementioned '421 International Patent Application; (3) U.S. Provisional Patent Application Ser. No. 63/000,439, filed Mar. 26, 2020, entitled "Modular Mammalian Body Implantable Fluid Flow Influencing Device and Related Methods"; and (4) U.S. Provisional Patent Application Ser. No. 63/007,899, filed April 2020, entitled "Modular Mammalian Body Implantable Fluid Flow Influencing Device and Related Methods". The entirety of each of the aforementioned applications is incorporated herein by reference.

FIELD

The present technology relates to modular mammalian body implantable fluid flow influencing devices and related methods.

BACKGROUND

Fluid carrying conduits in patients, such as blood vessels or other conduits near the heart, liver or kidneys carrying fluids other than blood (e.g., urine, lymph, etc.), may require fluid flow influencing (e.g. an increase in fluid flow rate, a decrease in fluid flow rate, a stoppage of fluid flow, etc.) in various medical situations.

Heart failure is an example of a common such situation. In patients with heart failure, their heart becomes unable to pump enough blood to meet their body's needs for blood and oxygen.

Heart failure is a disease affecting upwards of 6 million Americans and 26 million people worldwide at any given time. There is no cure. For those suffering from heart failure, their ability to function in everyday life and their overall quality of life steadily and unavoidably declines. There may be times of rapid deterioration. Even with the best of medical care, heart failure sufferers' symptoms will slowly, inevitably progress. They will rapidly become limited in their activities. At some point in time, they will experience increasing symptoms of the disease even at rest and under optimal medical therapy. People with end-stage heart failure disease currently have a 2-year estimated chance of survival of only 20%.

To try to improve this somber forecast of the probable course and outcome of the disease, multiple strategies for caring for people having heart disease have been developed. Such strategies include both short-term mechanical patient support options, as well as longer-term patient support options. Unfortunately, none of the options currently available are optimal.

Prior to review of the current conventional treatment possibilities, it should be noted that all such treatments are surgical in nature. They may be carried out on a patient suffering from the disease either via "open surgery" (i.e., the traditional surgical method of the cutting of skin and tissues so that the surgeon has a full view of the structures or organs involved) or via "minimally invasive surgery" (i.e., newer surgical techniques that do not require large incisions). Examples of minimally invasive surgical techniques are transcatheter techniques, in which a catheter (e.g., a relatively long flexible tube) is inserted into the patient's body and the intervention is performed through the lumen (i.e., the hollow cavity) of the catheter at a site distal to (e.g., away from) the catheter insertion site. As compared with open surgical techniques, transcatheter techniques generally are lower risk to the patient, shorter in time for the surgeon to perform, and have shorter patient recuperation times. They are usually preferred by patients.

One current treatment possibility for heart disease is a heart transplant. Heart transplantation involves the removal of a patient's diseased heart and its replacement with a healthier heart from a heart donor. There are, however, an extremely limited number of donor hearts available. In North America for example, only about 3,000 donor hearts are available each year. So, heart transplantation is not an option which is generally available to patients as the number of donor hearts is far less than the number of sufferers of the disease. Further, heart transplantation obviously requires very invasive open surgery. It carries additional significant risks, including (but in no way limited to) transplant coronary artery disease and life-long suppression of the recipient's immune system. For all of these reasons, heart transplantation is in most cases limited to younger patients, and therefore younger patients are prioritized on heart transplant lists.

Another current treatment possibility for heart disease is through the removal of a patient's diseased heart and its replacement with an artificial heart device (typically known as a "total artificial heart"). While the number of total artificial hearts is not limited (as is the case with donor human hearts) as they are manufactured devices, at the moment their use is limited to being only temporary. No total artificial heart is available for permanent implantation. Thus, total artificial hearts are used in patients who are in the end-stages of heart disease, but for whom no donor heart is yet available. Their use is quite limited, as the number of donor hearts is limited. In addition, implantation of a total artificial heart still requires very invasive open surgery, and carries risks as noted above. There are very few total artificial heart products currently available for use in patients. One product is the SynCardia™ Temporary Artificial Heart. Another potential product, which is still in development, is the Carmat™ artificial heart.

A third current treatment possibility for heart disease, and the most common, is through the implantation and use of what is known as a "Ventricular Assist Device" (commonly abbreviated to and referred to as a 'VAD'). A VAD is a mechanical pump that is surgically implanted within a patient to help a weakened heart pump blood. Unlike a total artificial heart, a VAD does not replace a patient's own heart, instead it helps the patient's native heart pump blood. VADs may be used to help the left side of a patient's heart, in which case they are known as LVADs. Or, they may be used to help the right side of a patient's heart, in which case they are known as RVADs. LVADs are far more commonly used. Currently, VADs may either be used as a bridge until a heart transplant can be performed (as is the case with total artificial hearts) or they may be used long term in patients whose condition makes it impossible to get heart transplant or who require immediate long-term support. There are different types and configurations of VADs, some of which will be discussed below.

Common to almost all currently available VADs is that their implantation requires open surgery, and carries the downsides and risks thereof noted above, and others. The complication rate and the mortality rate associated with the use of VADs are both significant. For example, patients are at risk of embolic stroke (e.g., a stroke caused by the blockage of a blood vessel due to a blood clot having formed), for amongst other reasons, the positioning of a VAD at the apex of the heart. Patents are also at risk of a cerebral (i.e. brain) or gastro-intestinal hemorrhage as most VADs pump blood continuously (as opposed to a normal heart, which pumps blood in pulses). This continuous pumping of blood causes the patient's blood vessels to become more fragile (and thus prone to hemorrhaging) and also causes a decrease in the patent's von Willebrand factor (which is a molecule in human blood that is part of the process to prevent and stop bleeding). Further, owing to the complexity of the VAD implantation surgery, VADs are only implanted in specialized centers. Indeed, the number one reason for patients refusing to undergo VAD implantation is the patient's fear of such invasive implantation surgery and the complications arising therefrom. For all of these reasons, although more than 250,000 heart disease suffers in North America alone could benefit from VAD implantation, there are less than 4,000 yearly VAD implants in the United States.

In terms of types and configurations of VADs, multiple generations of VADs were developed over the past few decades. The following discussion of such generations is not intended to be exhaustive but merely exemplary.

The first-generation of VADs were membrane-based and provided pulsatile flow (e.g., Thoratec™ PVAD, IVAD, Heartmate™ XVE, Heartmate™ IP1000 and VE, World-Heart™ Novacor™ and Arrow International LionHeart™ LVD2000). Some of the major disadvantages of first-generation VAD's were their high energy requirements, their large size (which complicated surgical implantation), and their limited durability.

Second-generation VADs featured continuous axial flow pumps. These devices were smaller and featured fewer moving parts, which resulted in an overall better design than their first-generation predecessors. The internal rotor of the second-generation VADs were suspended on contact bearings which created high shear stress zones at risk of thrombus formation and hemolysis. The Thoratec™ Heartmate™ II was the most widely used VAD in its class. Other examples of second-generation VADs include the Jarvik Heart Jarvik™ 2000 and the MicroMed™ Heart Assist 5.

Third-generation VADs have all of the advantages of the second-generation VADs (over the first-generation ones). And, they featured non-contact magnetic levitation of the centrifugal rotor, which reduces overall shear stress generated by the pump. They are thus less prone to thrombus formation and hemolysis compared to second-generation devices. Currently available third-generation VADs include the Terumo™ DuraHeart™, the Medtronic™ Heartware™ HVAD and the Abbott™ Heartmate™ III.

All of these generations of VADs described above that are currently in use (or previously had been used) require (or required) invasive classic open surgery (e.g., a median sternotomy or a less invasive mini-thoracotomy). During the implantation procedure, a VAD is surgically attached (e.g., sutured) to the heart while the main VAD body remains external to the patient's vasculature (e.g., heart and blood vessels). The pump inlet of the VAD is sutured to the left or right ventricle of the heart (depending on whether the VAD is an LVAD or an RVAD) and the outflow tubing from the VAD is sutured to the aorta (in the case of an LVAD) or the pulmonary artery (in the case of an RVAD).

As was described above, however, patients prefer minimally invasive transcatheter interventions to open surgery. And thus, the most recent efforts in the development of mechanical support strategies for people with heart disease have been made towards the development of pumps that do not require open surgery, but rather could be implantable transcatheter.

Currently, the only commercial product that can be implanted transcatheter is the Impella™ family of micropump devices from Abiomed™. An Impella™ device has a single micro axial pump (e.g., having an impeller) with a canula (e.g., a small tube-like structure). The device is implanted within the left ventricle (in the case of an LVAD) or right ventricle (in the case of an RVAD) of the heart so as to cross the aortic valve (in the case of an LVAD) or tricuspid and pulmonary valve (in the case of an RVAD). The inlet of the pump is within the ventricle or within the vessels that discharge fluid into the ventricle and the outlet of the pump is outside of the heart, in the aorta (in the case of an LVAD) and in the pulmonary artery (in the case of an RVAD). As the pump impeller turns, blood is drawn into the device through the pump inlet. The blood then travels under pressure having been imparted by the pump through the canula and exits the device through the pump outlet in the aorta or pulmonary artery (as the case may be). In this manner, the VAD provides pumping assistance to the ventricle of the heart.

An Impella™ device is implanted via a percutaneous procedure. In a percutaneous procedure access to the patient's internal organs is made via needle-puncture of the skin (e.g., via the well-known conventional Seldinger technique). Typically, in such procedures, the needle-puncture site is relatively remote from the actual internal organs that the surgeon will be operating on. For example, although it is the heart that a surgeon will be operating on, the initial needle puncture of the skin takes places in the patent's groin area so that the surgeon can access the patient's vasculature through the femoral vessels. Once access is obtained, the surgeon can advance the necessary tools to conduct the surgical procedure through the patient's vasculature to their heart. The surgeon then conducts the procedure on the heart, usually via wires extending from the tools, travelling through the patient's vasculature and outside of the patient's body via the access opening that the surgeon had previously made. Once the procedure has been completed, the surgeon removes the tools from the patient's vasculature in the same manner. In such procedures, access via the femoral artery (in the patient's groin area) or the axillary artery (about the patient's clavicle) are more common.

One difficulty that arises with respect to such percutaneous procedures and devices such an Impella™ device, is that the size of the device is significantly limited because of the remote peripheral insertion location of the device (through femoral or axillary artery, as the case may be). I.e., the size of the structures that will travel through the patient's blood vessels is limited to being only slightly larger than those vessels themselves, as those vessels can only stretch a limited amount before they will become damaged. In the context of an Impella™ device, what this means is that the actual physical size of the pump (including the motor) is limited since the pump must travel through the patient's blood vessels to the patient's heart. This, in turn, limits the actual physical size of the canula of the pump through which the pumped blood will flow. Thus, in order for the Impella™ device pump to provide a sufficient volume of blood flow through the canula to adequately assist the patient's heart, the impeller of the pump will have to rotate at a very high speed. (Generally, the higher the rotation speed of the impeller, the more blood the pump will pump.) This high impeller rotation speed can be problematic, however. High impeller rotation speed generates substantial shear stress forces on the blood elements being pumped, leading to known detrimental phenomena such as platelet activation, von Willebrand factor multimer destruction, destruction of red blood cells and thrombus formation. All of which can lead to embolic strokes or pump thrombosis, as described above.

Other drawbacks of an Impella™ type device leading to potential harm are damage to the aortic valve (as the pump body crosses the aortic valve from the left ventricle to the aorta in the case of an LVAD), and in-use device movement (as the device is unanchored when in use). These drawbacks prevent an Impella™ type device from being used as an outpatient solution. Such devices must be used in a clinical setting. Thus, the Abiomed™ Impella™ pump device is approved for short term support in cardiogenic shock or high-risk percutaneous coronary interventions.

In view of this, improved transcatheterly-implantable VAD solutions are currently in development. Such devices include devices developed by Magenta Medical™ or Second Heart Assist™ and the recently approved Heartmate™ PHP by Abbott™. These devices all have a common goal of overcoming the limitations of the Impella™ devices by using impellers that have the capability of being expanded in vivo. In this manner, the device can be implanted transcatheter with the pump impeller being in a small configuration (sufficient to be able to travel through the patient's blood vessels without causing damage). At the implantation site, the impeller then can be expanded to be of a larger size. In this manner, the impeller can be operated at relatively lower speeds (as compared one of an Impella™ device), as the expandable impeller, in its operating configuration is relatively larger than the Impella™ device impeller. In this manner, these devices attempt to reduce the risks present in devices with high-speed impellers.

Expandable propellers, however, all have a common projected pitfall, durability. And this will be the case whether elastic materials (Magenta Medical™, Heartmate™ PHP) or mechanical joints (Second Heart Assist™) are employed. (All currently approved non-expandable device impellers are manufactured from durable materials, such as titanium, and thus do not suffer from durability issues).

Another aspect of the design of devices employing expandable propellers is that although the impeller can be made expandable, the motor turning the impeller cannot. No such expandable motor exists. This is a significant limitation of such devices, as the power needed by the motor to rotate such an impeller, once expanded, is significantly higher than that required to rotate the smaller impellers found in the Impella™ devices, for example. To resolve this problem, all the transcatheterly-implantable pumps employing expandable impellers do not have a motor that is in the implanted device body. Rather they use a flexible driveshaft interconnecting the expanded impeller to a motor outside of the patient's vasculature. This leads to serious concerns of durability, heat generation and reliability for long-term use of these pumps. Although they are still in development, it is very probable that these mechanical limitations will preclude the long-term use of such transcatheterly-implantable expandable-impeller based designs.

A very recently theoretical alternative to the use of expandable impellers as a solution to overcoming the high sheer stress rate caused by impellers rotating at high speeds, are modular pump assemblies. Modular pump assemblies are devices that can employ multiple pumping units (or modules) that are deliverable to the implantation site separately but that can be combined together inside the patient's vasculature, at the implantation site, to form a single pumping device. This single pumping device, with multiple pumping units working in parallel, is able to provide the required blood flow rate while producing far less shear stress and preserving reliability and durability. Two such modular pump assembly devices have been described in the patent literature to date, Anderson et al. and Bonde et al.

The first description occurs in U.S. Patent Application Publication No. 2015/0250935 A1 (Anderson et al.), published Sep. 10, 2015, entitled "Modular Implantable Ventricular Assist Device", assigned to Medtronic Vascular Galaway (now U.S. Pat. No. 9,616,159 B2). Anderson et al. discloses " . . . modular implantable ventricular assist devices configured to be, at least in part, assembled within a patient. The devices generally include a pump assembly and an expandable frame. The frame is configured to engage tissue of a patient when implanted. The pump assembly is configured to be operably coupled to the frame when the frame is implanted and in the expanded configuration" (Abstract.)

In this patent publication, it is taught that an expandable frame be anchored to a vessel wall, followed by attachment of a scaffold to the frame. Or alternatively, in other embodiments, the expandable frame and scaffold are single structure, which is expandable. In either case, the scaffold has multiple openings therein that are meant to receive and retain individual pumping units (modules). The patent teaches such individual pumping units are then advanced through the patient's vasculature by the surgeon and then pushed into the scaffold openings. One serious concern with this design is exactly how the surgeon will be able to guide the individual pumping units into the exact precise position that will be required to insert them into the scaffold openings. This is essentially a task (that will need to be repeated multiple times) which will require the surgeon to manipulate a guide wire or an individual pumping unit to reach the correct positioning and orientation in three dimensions, while being guided only via standard conventional twodimensional fluoroscopy. Assuming this is even possible, the amount of time required for the intervention will be prohibitive.

Additionally, in such a device, having a scaffold transversely obstructing the vessel lumen may lead to thrombosis of the scaffold (and thus embolic strokes) and even complete lumen obstruction (if thrombi extend to the inlet or outlet of the pumping units) leading to the death of the patient.

Also, there is no mention as to how the wires (cables) of the individual pumping units are to be dealt with. This is of serious concern as each pumping unit will have at least one wire (and likely more than one). Given that there are multiple pumping units, their wires may become entangled, leading both to difficulties in removing the individual units (and the device). And, entangled wires can serve as a scaffold for thrombus formation (again leading a risk of embolic stroke).

Further, there is no teaching in Anderson et al. as to how such a device may be removed from a patient's vasculature in the context of a pumping unit failure (be it mechanical, thrombus-related, otherwise) or should the patient recuperate and need to be weaned-off the device. While one can imagine that the individual pumping units may be pulled out of the scaffold, the frame and scaffold themselves appear to be non-retrievable by transcatheter techniques and would thus require open surgical intervention to be removed. Failure to remove the frame and scaffold, depending on their implantation site, could lead to lumen obstruction (if implanted in a vessel) or valve insufficiency (if implanted inside a valve), which are both highly detrimental to a patient.

The second description of a modular pump assembly device occurs in U.S. Patent Application Publication No. 2015/0250935 A1 (Bonde et al.), published Oct. 29, 2015, entitled "Percutaneous Device and Method for Promoting Movement of a Bodily Fluid", assigned to Yale University (now U.S. Pat. No. 10,293,090 B2). Bonde et al. discloses: " . . . a minimally-invasive percutaneous device that can be positioned within the body of a subject to aid in the movement or pumping of a bodily fluid. In one embodiment, the device comprises a plurality of pump units configured to transform from a first compressed configuration where the pump units are organized in a serial arrangement into a second expanded configuration where the pump units are reorganized into a parallel arrangement." (Abstract.)

This publication depicts a modular pump assembly where the micro-axial pumping units are all interconnected to one another by a flexible frame. When the assembly is in a compressed configuration for transcatheter delivery to the implantation site, the pumping units are positioned in series. At the implantation site, once delivered, the frame expands in such a way that the pumping units physically spatially change configuration to convert from being in series to being in parallel. This structure may avoid at least some of the feasibility pitfalls of the structure described in the Anderson et al. publication in terms of difficulty of in vivo assembly of the device modules by the surgeon, since the device converts on its own from one configuration to the other. However, unlike the structure described in Anderson et al., the structure described in Bonde et al. provides little to no control to the surgeon over the in vivo assembly of the pump assembly, as it solely relies on conformational changes of pre-shaped materials and does not allow for the control by the surgeon. Thus, in order provide a structure which is easily assembled, the Bonde et al. structure gives up control over such assembly. This situation may lead to vessel wall damage if the movement of the pumping units cannot be controlled in some way. Such vessel damage may lead to serious conditions (e.g., vessel wall dissection, vessel wall rupture, etc.) requiring immediate open surgical intervention to save the patient.

In addition, as was the case as in Anderson et al., there is no mention in Bonde et al. of the individual pumping unit wires and their management either. The drawbacks described above in relation to this aspect of Anderson et al. apply to Bonde et al. as well.

Furthermore, an unfilled gap may remain between the assembled cylindrical pumping units of the Bonde et al. device. This may lead to thrombus formation between the pumping units, with risks of embolization as described above.

Finally, in certain embodiments depicted in the figures Bonde et al., a conformational change of the frame interconnecting the pumping units requires the pumping unit orientation to change (distal end «-» proximal end). This conformational change would need to occur inside of patient's blood vessel at the implantation site. Sufficient space would need to be present at that site to allow for this conformational change, and the device of Bonde et al. would need to be limited in size to effect such conformational changes within that space. This would almost certainly limit the length of the pumping unit to less than the cross-sectional diameter of the vessel at the implantation site where the conformational change of the pumping units during device assembly occurs. Limiting the pumping unit length may limit the size of the motor, which may impact the performance of the pumping unit. Further, there absolutely no description of how the wires extending from an individual pumping unit will be managed before, during, or after such a conformational change within a patient's blood vessel at the implantation site.

It is believed drawbacks of the modular pump assemblies described in Anderson et al. and Bonde et al., both those described herein and others, limit their utility and adoption. No product is currently available that embodies the technology described in those patents, which means that no product employing any type of modular technology is currently available for use at all.

Notwithstanding the fact that the designs for VADs using a modular pump assembly structure in Anderson et al. and Bonde et al. have not reached a stage of development where they are appropriate for use in patients, given their potential in overcoming some of the drawbacks of other types of VADs, VADs employing modular pump assemblies structures are believed to be an area in which further development is desirable. However, neither the structure described in Anderson et al. nor the one described in Bonde et al. is believed to be an appropriate starting point from which to continue such development. A new modular pump assembly design "starting from scratch" is believed to be required.

SUMMARY

Objects

It is an object of the present technology to improve upon prior technology in this area by providing a modular pump assembly that is implantable within a human body and that has a design that differs from those described herein above.

It is an object of the present technology that the novel modular pump assembly design described herein, may, depending on the particular physical embodiment of the technology being utilized and the particular circumstance in which that embodiment is being used, have at least one (and may have more) reduced risks and/or drawbacks as compared with at least some of the prior art when used in the same circumstance. Such risks and drawbacks may include (but are not limited to): risk of hemolysis occurring; risk of thrombosis occurring; risk of platelet activation occurring; risk of destruction of blood clotting factor(s) and/or of proteins involved in primary hemostasis occurring; risk of vessel wall damage occurring; undesirable heat generation; undesirable power requirements; undesirable physical size requirements; reliability issues; durability issues; wire/cable management issues; implantation issues (e.g., difficulty, complexity, controllability, assemblability, timing-consuming, etc.); explantation issues (e.g. possibility, difficulty, complexity, controllability, disassemblability, timing-consuming, etc.); operational issues; etc. This list is not intended to be exhaustive.

It should be understood, however, that living beings are incredibly complex organisms and do not present predictable situations or circumstances. Thus, although the present technology attempts to achieve the objectives noted above, there is no guarantee (and thus no promise is made) that in any particular circumstance and/or with any particular embodiment of the present technology such objects will, in fact, be attained.

General

As was discussed above, there are no modular pump assemblies currently in use, or even in development as far as the developers of the present technology are aware. Nonetheless, it is believed that such assemblies (in some forms, at least) will provide benefits over the VADs that are currently (or have been previously) in use. In particular, modular pump assemblies can be designed to be implantable transcatheter, operable and explantable, and thus have the attendant benefits of minimally invasive interventions as was described above.

A transcatheterly-implantable modular pump assembly can (once assembled in vivo) employ multiple pumping units in parallel as opposed to the transcatheterly-implantable pumps that have actually been used in humans to date, which have a single pumping unit. Using multiple pumping units in parallel potentially allows the total amount of work that needs to be done by the VAD to be divided (whether evenly or not) between the multiple pumping units (depending on the design and operation of the device). (In the context of the present technology, multiple units are in parallel when no inlet of any pumping unit is downstream of any of the outlets of any of the other pumping units, downstream referring to the direction of the flow from inlet towards outlet). This may lead to several benefits as compared with different types of prior art VADs. For example, when compared with an Impella™ type device, the impellers of the individual pump units can be of the same size, but can rotate at a slower speed (again depending on the design and operation of the device); but as there are multiple pumping units, the same amount of fluid could be pumped. In certain circumstances having the impellers rotate at lower speeds will yield a lower sheer stress rate, thus potentially reducing the risk of hemolysis, thrombosis, platelet activation and/or destruction of blood clotting factor(s) occurring. In another example, when compared with a pumping device employing a expandable impeller, the impellers of the individual pump units of a modular pump assembly, can be of a smaller size (and non-expandable if so designed) and thus require less power to be rotated (depending on the design and operation of the device). As a result, a motor may be able to be housed inside the pumping unit body, and thus be implanted inside the body of the patient. Such a configuration would not require a flexible driveshaft to extend through the vasculature of the patient to be driven by a motor outside of the patient's vasculature, alleviating the drawbacks of such a construction (e.g., risk of heat generation, complexity, durability and/or reliability.)

The present technology, although originally conceived of and developed for use in a vascular assist device (VAD), is not so limited. Devices employing the present technology can be used for other purposes and/or in other locations of the body, if so designed. As a non-limiting example, it is foreseen that a device employing the present technology can be designed to be transcatheterly-implantable in a renal pelvis to influence the flow of urine (e.g., by providing a urine pump as opposed to a blood pump).

Similarly, the present technology, although originally conceived of and developed for use to increase the flow rate of a fluid in the conduit into which the device is implanted, could be used to otherwise influence the flow of a fluid. For example, the device could be designed and/or operated to decrease the flow rate of the fluid and/or to block fluid flow completely, depending on the circumstance.

Finally, the present technology, although originally conceived and developed for use in human beings, can be employed in devices destined to be used in mammals other than human being, if a device employing the present technology is appropriately so designed (e.g. sized, dimensioned, and/or shaped).

For all of these reasons, the discussion of the present technology below is initially phrased in much more broad and general terms (than simply a VAD).

Device

In order to overcome (or at least ameliorate) at least one (and preferably more) of the drawbacks associated with devices described in the Anderson et al. and/or Bonde et al. references referred to above, embodiments of the present technology provide a modular mammalian body implantable fluid flow influencing device, comprising: (1) A docking unit. The docking unit has an elongated body having a longitudinal axis, at least one receiving surface extending parallel to the longitudinal axis, a distal end and a proximal end, and at least one proximal guide hole. Each receiving surface has at least one proximal guide hole associated therewith. The docking unit is dimensioned and shaped to be deliverable to an implantation site within a conduit of a conduit system of the mammalian body via a catheter. (For the purposes of the present disclosure, cavities and chambers in generally hollow organs should be understood to be conduits in a conduit system with which those cavities or chambers are in fluid communication. Thus, for example, the chambers of the heart should be considered to be part of the vasculature of the body, for present purposes.) (2) A first functional unit. The first functional unit has an elongated body having a longitudinal axis, a docking surface extending parallel to the longitudinal axis, a distal end and a proximal end. The docking surface is shaped to mate with a first one of the at least one receiving surface of the docking unit. The elongated body is at least one of sized, shaped, and structured to be unable to pass through a one of the at least one proximal guide hole of the docking unit associated with the first one of the at least one receiving surface of the docking unit. A control wire extends proximally from the proximal end of the elongate body, goes through the one of the at least one proximal guide hole of the docking unit associated with the first one of the at least one receiving surface of the docking unit, and then extends proximally away from the docking unit. The first functional unit is dimensioned and shaped to be deliverable to the implantation site via the catheter. The first functional unit has a docked configuration in which the docking surface of the first functional unit mates with the first one of the at least one receiving surface of the docking unit. The first functional unit also has an undocked configuration in which the docking surface of the first functional unit is unmated with and spaced apart from the first one of the at least one receiving surface of the docking unit. The first functional unit is moveable at the implantation site between the undocked configuration and the docked configuration via movement of the control wire of the first functional unit. The first functional unit is moveable into the docked configuration from the undocked configuration by pulling the control wire of the first functional unit. The first functional unit is moveable from the docked configuration into the undocked configuration by pushing the control wire of the first functional unit.

As was noted above, a device employing the present technology has at least a docking unit and a functional unit. The primary function of the docking unit is to provide a structure onto which the functional units of the device may be docked. Although not required, docking units of the present technology may have additional functions as well, such as for example, anchoring the device in place via an anchor (as will be described in further detail below).

The distal end and proximal end of the elongate body of the docking unit are defined from the point of view of the surgeon implanting the device. Thus, the distal end of the elongate body of the docking unit will be at a greater distance (i.e. further or more remote) from the surgeon than the proximal end of the docking unit during the intervention. The distal end and the proximal end of the elongate body of the functional unit(s) and other structures are similarly so defined.

In the context of the present technology, a guide hole is any structure that retains a control wire and through which a retained control wire (of the functional unit, for example) may move without becoming dislodged. It is thus not necessary that guide hole be completely surrounded by material in order to carry out its functions. For example, an appropriately structured hook, from which the control wire cannot become dislodged, can serve to provide a guide hole in some embodiments.

In use, on a very simplistic level (but as is described in greater detail hereinbelow), the functional unit and the docking unit are in a delivery sheath (or some other type of catheter), with the functional unit being in its undocked configuration and distal to the docking unit. The device is thus unassembled and in what may be termed a delivery configuration. When the device is in the delivery configuration the longitudinal axes of the elongate bodies of the units are generally colinear within one another. Thus, when the device is in the delivery configuration it presents a smaller cross-sectional profile (as compared with an assembled device), and the device may therefore be delivered through conduits having a smaller lumen cross-sectional area than were the device to be in an assembled configuration The device is an assembled configuration when the functional unit is in its docked configuration. In the assembled configuration, the longitudinal axes of the elongate bodies of the units are no longer generally colinear with one another. Instead the longitudinal axis of the elongate body of the functional unit is radially outward from the longitudinal axis of the elongate body of the docking unit, with the two being generally coplanar.

As the functional unit is distal to the docking unit within the delivery sheath in the delivery configuration, the functional unit is delivered to the implantation site first (i.e., prior to the docking unit), with its control wire extending from its elongate body, through a guide hole of the docking unit, then through the patient's conduit system (e.g., vasculature) and then out of the patient's body through the surgeon's access point. The docking unit is then delivered to the implantation site. The guide hole and the receiving surface of the docking unit are positioned, one with respect to the each, such that the surgeon can pull the control wire of the functional unit to bring the functional unit into its docked configuration. (Prior to this action, the surgeon may have anchored the docking unit place (as is described below). Alternatively, during this action, the surgeon may hold the docking unit in place via its control cable (as is described below) or some other means.). As the elongate body of the functional unit is unable to pass through the guide hole, the functional unit cannot "overshoot" the docked configuration, for example, when its control wire is being pulled by the surgeon.

The guide hole is a "proximal" guide hold in that it is disposed closer to the proximal end than the distal end of the elongate body of the docking unit. Although this may not be the case in all embodiments, the guide hole being proximal will mean that force exerted on the structure of the docking unit defining the guide hold when the control wire of a functional unit is being pulled to bring the functional unit into docked configuration will not tend to try to "flip" the docking unit (i.e. reverse its distal and proximal ends) within the conduit at the implantation site.

In some embodiments, the elongated body of the docking unit is non-expandable. As was discussed hereinabove, expandability of mechanical structures may (depending on the embodiment and the circumstances of its use) reduce the durability and/or reliability of the structure.

In some embodiments, a diameter of a minimum bounding right circular cylinder of the docking unit is not greater than a diameter of a minimum bounding right circular cylinder of the functional unit. In the present context, a minimum bounding right circular cylinder is the smallest right circular cylinder having an axis generally parallel to the axis to the longitudinal axis of the elongate body of the unit in question into which the entirety of that unit (with the exception of any control wires/cables extending therefrom) will fit. In such embodiments, the greatest cross-section area of the docking unit transverse to the longitudinal axis of its elongate body will generally be smaller than the greatest cross-sectional area of the functional unit transverse to the longitudinal axis of its elongate body. In this manner, it will the size of the functional unit that will be limiting with respect to the implantation of the device (and not the size of the docking unit), in that it will be the maximum cross-sectional area of the functional unit(s) that will determine through which conduits in the conduit system (if any) the device may be percutaneously implanted transcatheter.

In some embodiments, the docking unit is a central docking unit. In the present context, a docking unit is "central" when each of the functional unit(s) forming part of the device, are positioned at the periphery of the docking unit when in their docked configuration.

While at its basic level, the present technology can be implemented with a device having a single functional unit, it is foreseen that most embodiments will have multiple functional units. In this respect, there is no absolute theoretical number maximum number of functional units that a device employing the present technology can have. As long as device is capable of implantation and operation having the number of functional units that it has (under the given circumstances of its implantation and operation) then that number of functional units is within the scope of the present technology. Embodiments have been envisaged having a number of functional units between 2 and 10. In various embodiments having multiple functional units the function and characteristics (e.g. size, shape, dimensions, materials of construction, etc.) of each of the functional units with respect to the others are the same. In other embodiments, they are different.

Thus, in some embodiments, the device further comprises a second functional unit. The second functional unit has an elongated body having a longitudinal axis, a docking surface extending parallel to the longitudinal axis, a distal end and a proximal end. The docking surface is shaped to mate with a second one of the at least one receiving surface of the docking unit. The elongated body is at least one of sized, shaped, and structured to be unable to pass through a one of the at least one proximal guide hole of the docking unit associated with the second one of the at least one receiving surface of the docking unit. A control wire extends proximally from the proximal end of the elongate body, goes through the one of the at least one of the proximal guide hole of the docking unit associated with the second one of the at least one receiving surface of the docking unit, and then extends proximally away from the docking unit. The second functional unit is dimensioned and shaped to be deliverable to the implantation site via the catheter. The second functional unit has a docked configuration in which the docking surface of the second functional unit mates with the second one of the at least one receiving surface of the docking unit. The second functional unit also has an undocked configuration in which the docking surface of the second functional unit is unmated with and spaced apart from the second one of the at least one receiving surface of the docking unit. The second functional unit is moveable between the undocked configuration and the docked configuration via movement of the control wire of the second functional unit. The second functional unit is moveable into the docked configuration from the undocked configuration by pulling the control wire of the second functional unit. The second functional unit is moveable from the docked configuration into the undocked configuration by pushing the control wire of the second functional unit. (The control wire of the second functional unit also extends through the patient's conduit system (e.g., vasculature) and then out of the patient's body through the surgeon's access point.)

Further, in some embodiments, the device further comprises a third functional unit. The third functional unit has an elongated body having a longitudinal axis, a docking surface extending parallel to the longitudinal axis, a distal end and a proximal end. The docking surface is shaped to mate with a third one of the at least one receiving surface of the docking unit. The elongated body is at least one of sized, shaped, and structured to be unable to pass through a one of the at least one proximal guide hole of the docking unit associated with the third one of the at least one receiving surface of the docking unit. A control wire extends proximally from the proximal end of the elongate body, goes through the one of the at least one proximal guide hole of the docking unit associated with the third one of the at least one receiving surface of the docking unit, and then extends proximally away from the docking unit. The third functional is being dimensioned and shaped to be deliverable to the implantation site via the catheter. The third functional unit has a docked configuration in which the docking surface of the third functional unit mates with the third one of the at least one receiving surface of the docking unit. The third functional unit also has an undocked configuration in which the docking surface of the third functional unit is unmated with and spaced apart from with the third one of the at least one receiving surface of the docking unit. The third functional unit is moveable between the undocked configuration and the docked configuration via movement of the control wire of the third functional unit. The third functional unit is moveable into the docked configuration from the undocked configuration by pulling the control wire of the third functional unit. The third functional unit is moveable from the docked configuration into the undocked configuration by pushing the control wire of the third functional unit. (The control wire of the third functional unit also extends through the patient's conduit system (e.g., vasculature) and then out of the patient's body through the surgeon's access point.)

Devices having further numbers of functional units are not described further herein for the sake of brevity. The above descriptions of the second and third functional units would applicable to such fourth, fifth, sixth, etc. functional units, mutatis mutandis.

In embodiments where there is more than one functional unit, the device will be in its delivery configuration when each of the functional units is in its undocked configuration with the longitudinal axes of each of the elongate bodies of the units all being generally colinear. In the delivery sheath, all of the functional units of the device will be distal to the docking unit (i.e., the docking unit will be proximal to all of the functional units). During delivery of the device to the implantation side, the functional units will all be delivered prior to delivery of the docking unit. The surgeon will then bring each of the functional units into its docked configuration, thus bringing the device into its assembled configuration. Depending on the design of the device, and the size of the lumen of the conduit at the implantation site, in some embodiments/implementations, it may or may not be necessary for the surgeon to bring the functional units into their docked configurations in a particular order. For example, if the size of the lumen of the conduit at the implantation site is relatively large (such that there is no interference between functional units and their control wires once the functional units have exited the delivery sheath), the surgeon may be able to bring the functional units into their docked configuration in any order that he or she so chooses, irrespective of the order in which the functional units were disposed when they were within the delivery sheath (and thus exited the delivery sheath). In another illustrative example, if the size of the lumen of the conduit at the implantation site is relatively small, then the surgeon may have to bring the functional units into their docked configuration in a particular order; for example, in the reverse order from which they exited the delivery sheath (i.e. the last functional unit to exit the delivery sheath with be the first functional unit that the surgeon must bring into its docked configuration).

In some embodiments, the docking unit and the functional units are sized and shaped such that when the device is in its assembled configuration, the device does not completely obstruct the lumen of the conduit at the implantation site. In this manner, fluid can flow around the device. In various embodiments, depending on the function of the device and its location of implantation, fluid flow around the device may be important. For example, if the device is a VAD, having fluid be able to flow around the device may be an important design characteristic as in a situation in which all of the pumping units of the device were to fail (e.g., a power failure without battery backup) blood would still be able to flow within the patient's vasculature by virtue of it being able to flow around the device.

By contrast, in other embodiments, the device is designed so that it will completely obstruct the lumen of the conduit at the implantation site, such that fluid cannot flow around the pump. This would be the case, for example, were the entire purpose of the device to be prevent fluid flow past the point of device implantation.

In some embodiments, each of the receiving surfaces of the docking unit are positioned equidistantly radially along an exterior surface of the elongate body of the docking unit. One way to determine whether the receiving surfaces of the docking unit are positioned equidistantly radially is to, in plane perpendicular to the longitudinal axis of the elongate body passing through the receiving surfaces, determine the angles formed by the lines connecting the midpoints of adjacent receiving surfaces with the longitudinal axis. If all of the angles formed are generally the same, then the receiving surfaces are positioned equidistantly radially. In some embodiments, where there are three receiving surfaces, the cross-sectional shape of the docking unit resembles a 'Y'. In some embodiments, particularly those where the functional units are all identical, having the receiving surfaces (and thus the functional units in their docked configuration) positioned equidistantly radially may help with the mass balancing of the assembled device. It may also help with fluid flow around the device, depending on the circumstances.

In other embodiments, by contrast, the receiving surfaces are not so equidistantly radially positioned along an exterior surface of the elongate body of the docking unit. This may help with the mass balancing as well, for example, in embodiments where the functional units are not identical. It may also help with flow fluid around the device, depending on the circumstances (e.g., size and/or shape of the functional units).

In some embodiments, each of the receiving surfaces are positioned equally longitudinally along an exterior surface the elongate body of the docking unit. Again, in some embodiments, particularly those where the functional units are all identical, having the receiving surfaces (and thus the functional units in their docked configuration) positioned equally longitudinally may help with the mass balancing of the assembled device. It may also help with flow fluid around the device, depending on the circumstances.

In other embodiments, by contrast, the receiving surfaces are unequally longitudinally positioned (e.g. they may be staggered longitudinally or otherwise at different distances from the proximal end, the distal end, or both) such the functional units, in their docked configuration will be unequally longitudinally positioned as well. This may help with the mass balancing as well, for example, in embodiments where the functional units are not identical. It may also help with flow fluid around the device, depending on the circumstances.

In some embodiments, each of the at least one receiving surface of the docking unit is concave. In some embodiments, the docking surface of each functional unit extends along a curved convex exterior side wall of the elongate body of that functional unit. In some such embodiments, the curvature of the docking surface matches precisely the curvature of the corresponding receiving surface.

In some embodiments, the docking surface of each functional unit fluid non-ingressivenessly registers with the receiving surface of the docking unit with which that docking surface of that functional unit mates when that functional unit is in the docked configuration. In the context of the present technology, "fluid non-ingressivenessly registers" should be understood to mean that when the two surfaces are mated, they perfectly mate with one another (i.e. register with one another) and in such a manner that fluid surrounding the device in vivo cannot enter (ingress) in between the surfaces. Such a design may be beneficial, for example, in the case where the fluid is blood, as no thrombus-forming gap will be present between the surfaces when they fluid non-ingressivenessly register with each other. (Thrombus formation being generally something to be avoided.)

In some embodiments, the control wire of each functional unit extends from an apex of the proximal end of the elongate body of that functional unit. In some embodiments, having the control wire of a functional unit extend from the apex in this manner will facilitate moving the functional unit into its docked configuration in vivo, as the unit will not tend to "flip" or "turn" (with respect to its longitudinal axis-attempting to reverse its distal and proximal ends) in the conduit, but rather will move "straight forward" when its control wire is pulled.

In some embodiments, the control wire of each functional unit extends from the proximal end of the elongate body of that functional unit at a position offset from the longitudinal axis of the elongate body of that functional unit. In some embodiments, having the control wire of a functional unit extend offset in this manner will facilitate moving the functional unit into its docked configuration in vivo, as the unit will tend to rotate (radially) within the conduit into a position in which its docking surface is aligned with the appropriate receiving surface of the docking unit in order to properly mate therewith. Further, in some embodiments, having the control wires of the functional units offset in this manner will yield a more compact design of the docking unit. As the control wires of each functional unit each go through a guide hole of the docking unit, having the control wires offset in this manner, may allow the guide holes to be radially closer to the longitudinal axis of the elongate body of the docking unit (than if the control wires had extended from a position on the longitudinal axis of the elongate body of their respective functional units, for example). Thus, the diameter of elongate body of the docking unit can be reduced in the former circumstance as compared with the latter one. (And, as was discussed above, in some embodiments, it may be desirable to have the docking unit have a small diameter so that its diameter is smaller than the diameter of the functional unit having the largest diameter.)

In some embodiments, each of the at least one receiving surface of the docking unit has an associated proximal end abutment (e.g. a stop) in which the proximal guide hole associated with that docking surface is disposed. Further, in some embodiments, the proximal end of the elongate body of each functional unit has an abutment contacting surface. In some embodiments, when each functional unit is in its docked configuration, the abutment contacting surface of the proximal end of the elongate body of that functional unit mates with the proximal end abutment associated with the at least one receiving surface of the docking unit with which the docking surface of the elongate body of that functional unit mates. In some embodiments, these cooperating structures may assist the surgeon in bringing that functional unit into its docked configuration; e.g. via feeling or visualization.

In some embodiments, when each functional unit is in its docked configuration, the abutment contacting surface of the proximal end of the elongate body of that functional unit fluid non-ingressivenessly registers with the proximal end abutment associated with the at least one receiving surface of the docking unit with which the docking surface of the elongate body of that functional unit mates. Again, the purpose of such registration, at least in some embodiments, is to avoid having a potentially thrombus-forming gap formed in between the structures.

In some embodiments, when each functional unit is in its docked configuration, the abutment contacting surface of the proximal end of the elongate body of that functional unit and the proximal end abutment associated with the at least one receiving surface of the docking unit with which the docking surface of the elongate body of that functional unit mates, are shaped, one with respect to the other, such that when the control wire of that functional unit is tensioned (which will generally be the case once the device is assembled in vivo and is in operation), the docking surface of the elongate body of that functional unit is biased towards the at least one receiving surface of the docking unit with which the docking surface of the elongate body of that functional unit mates. This bias will tend to maintain that functional unit in its docked configuration. Indeed, in some embodiments, the functional unit is maintained in its docked configuration solely in this manner, and no physical structure is required to maintain the functional unit in this configuration.

In some embodiments, when each functional unit is in its docked configuration, a position from which the control wire of each functional unit extends from the proximal end of the elongate body of that functional unit and a position of the proximal guide hole in the proximal end abutment associated with the at least one receiving surface of the docking unit with which the docking surface of the elongate body of that functional unit mates, are located, one with respect to the other, such that when the control wire of that functional unit is tensioned (which will generally be the case once the device is assembled in vivo and is in operation), the docking surface of the elongate body of that functional unit is biased towards the at least one receiving surface of the docking unit with which the docking surface of the elongate body of that functional unit mates. This bias will tend to maintain that functional unit in its docked configuration. Indeed, in some embodiments, the functional unit is maintained in its docked configuration solely in this manner, and no physical structure is required to maintain the functional unit in this configuration. In other embodiments, the functional unit is maintained in its docked configuration in this manner in combination with the manner described in the previous paragraph, and again, no physical structure is required to maintain the functional in this configuration.

In some embodiments, the device may also have one or more retaining elements for retaining the functional units in their docked configuration (and the device in its assembled configuration). In some embodiments, the retaining element is or includes a retaining ring extending around the docking unit. The retaining ring may have a proximal end connected to the elongate body of the docking unit and a distal end extending outwardly therefrom. The retaining ring may be resiliently biased towards a receiving surface(s) of the docking unit. Alternatively, the retaining ring may be made of a shape memory alloy arranged to take up an expanded configuration when delivered in vivo to secure the functional units and the docking unit together at the implantation site. The retaining element may include other types of arrangements or structures that can retain the device in its assembled configuration at the implantation site.

In some embodiments when each of the functional units is in its docked configuration, the abutment contacting surface of the proximal end of the elongate body of each functional unit mates with one of the proximal end abutments of the docking unit, and unmated exterior-facing portions of the proximal end of the elongated body of each of the functional units are each sloped towards the apex of the proximal end. In some embodiments, the shaping of the unmated exterior-facing portions of the proximal end of the elongated body of each of the functional units in this manner provides a structure that, when the fluid is blood, reduces the risk of thrombus formation since it helps the blood to smoothly flow around the device as opposed to stagnating or being obstructed in any area.

In some embodiments, when each of the functional units is its docked configuration fluid flow channels are located intermediate any two adjacent functional units. Again, when the fluid is blood, these structures reduce the risk of thrombus formation since they help the blood to smoothly flow around the device as opposed to stagnating or being obstructed in any area.

In some embodiments, the docking unit is sized, shaped and/or structured, to ensure that there is no gap in between any two adjacent functional units. Again, when the fluid is blood, these structures reduce the risk of thrombus formation since they help the blood to smoothly flow around the device as opposed to stagnating or being obstructed in any area.

In some embodiments, the control wire of each functional unit is a control wire assembly. The control wire assembly has at least an electrical component for delivering electrical power to that functional unit via the control wire assembly and a mechanical component for structurally reinforcing the control wire assembly of that functional unit. Electrical power may be required by the functional unit for a variety of reasons, including, but not limited to, powering a motor and/or a sensor of the functional unit.

In some embodiments: The electrical component of the control wire assembly of each functional unit is a plurality of electrical wires. The mechanical component of the control wire assembly of each functional unit is a structural wire. The control wire assembly of each functional unit further has an outer sheath bundling together and surrounding the plurality of electrical wires of and the structural wire of that functional unit. In some such embodiments, wherein the plurality of electrical wires of each functional unit is three electrical wires, and each of the electrical wires of and the structural wire of that functional unit have about the same diameter; e.g. for efficient mechanical packaging purposes within the outer sheath.

In some embodiments: The electrical component of the control wire assembly of each functional unit is a plurality of electrical wires. The mechanical component of the control wire assembly of each functional unit is an outer sheath bundling together and surrounding the plurality of electrical wires of that functional unit.

In some embodiments, the elongated body of the docking unit has a longitudinally extending central cavity. Such a central cavity may be used for a variety of purposes, including, but not limited providing a passage for control wires, tubes, etc. In some such embodiments, the longitudinally extending central cavity is aligned with the longitudinal axis of the elongated body of the docking unit. In some embodiments, this location of the longitudinally extending cavity may be optimal for one or more reasons, e.g., mass balancing, mechanical packaging, optimization of the functionality of the elements passing through the cavity, etc.

In some embodiments the device is anchorable at the implantation site, thereby releasably maintaining the device at the implantation site.

In some embodiments, anchoring occurs as the device is sized and shaped such that, when the device is in its assembled configuration at least parts of the device will be larger than the lumen of the conduit at the implantation site, and thus the device will be "wedged into position" and held there by mechanical forces. For example, the normal human thoracic aorta is less that 6 cm in diameter, so the device, in its assembled configuration, could have portions larger than that to "wedge" it in place. Although generally, you do not want to stretch the aorta more than about 15% of its natural diameter (to avoid damage to the aorta.)

In other embodiments, the device further comprises an anchor assembly connected to the docking unit, with the anchor assembly having an anchored configuration and an unanchored configuration. In some embodiments, the anchor assembly is actuatable at the implantation site to convert between its unanchored configuration and its anchored configuration to anchor (and to unanchor) the docking unit at the implantation site.

In some embodiments, the device further comprises an anchor assembly actuation wire disposed within the central cavity of the elongated body of the docking unit. The anchor assembly actuation wire is operatively connected to the anchor assembly to actuate conversion of the anchor assembly between the anchored configuration and the unanchored configuration. (The anchor assembly actuation wire, where present, extends through the patient's conduit system (e.g., vasculature) and then out of the patient's body through the surgeon's access point.)

In other embodiments, where present, the anchor assembly is biased towards the anchored configuration. Insertion of the anchor assembly into the catheter (e.g., delivery sheath) causes the anchor assembly to convert to its unanchored configuration. Removal of the anchor assembly from the catheter causes the anchor assembly to convert to its anchored configuration. In some such embodiments, the anchor assembly includes an anchor member which is resiliently biased away from the elongate body of the docking unit. In some such embodiments, such an anchor member has a ring connected to the docking unit and an arm portion extending outwardly away from the docking unit. In other such embodiments, such anchor assembly includes an expandable element. The expandable element may be configured to expand when implanted, or when deployed through other means. In still other such embodiments, the anchor member has a stent-like structure or an expandable scaffold.

In some embodiments, the device further comprises an expandable barrier assembly connected to the docking unit. The barrier assembly has an expanded configuration and a collapsed configuration.

In some embodiments, the barrier assembly is actuatable at the implantation site to convert between its collapsed configuration and its expanded configuration to prevent fluid from flowing around the device by blocking space around the device at the implantation site. For example, in some embodiments when the device is a VAD, and at the implantation site there is space around the device between the device and the conduit (when the device is in its assembled configuration), recirculation of pumped blood may occur. Specifically, during diastole there will be no native flow of blood through the conduit into which the device has been implanted, yet the pump may still be pumping. This creates a negative pressure at the pump inlet, drawing in blood located around the device. As the blood at that time is not natively moving, some of the blood drawn into the inlet may blood that has already exited the outlet of a pump but is drawn back alongside of the device (in a direction opposite the direction of the native blood flow) up to and into the inlet (because of this negative pressure). Such recirculation of blood is generally not desirable, as (1) it reduces the efficiency of the pump in terms of its volumetric flow rate (as the blood being recirculated takes the place of non-recirculated blood that could have otherwise been pumped), and (2) recirculated blood is again subject to the shear stress induced by the pump each time it is recirculated (thus increasing the chance of negative effects caused by such shear stress detailed hereinabove of occurring). Thus, in some embodiments, the barrier assembly is designed so that when it is in its expanded configuration it is structured and positioned to at least partially, if not completely, block the path of pumped fluid recirculating from around the device (from a pump outlet to a pump inlet). (As a non-limiting example, a VAD pump with a speed of 18,000 RPM will see increase in its throughput from 3 L/min to 5 L/min when such recirculation is prevented.)

In some embodiments, the device further comprises a barrier assembly actuation wire disposed within the central cavity of the elongated body of the docking unit. The barrier assembly actuation wire is operatively connected to the barrier assembly to actuate conversion of the barrier assembly between the expanded configuration and the collapsed configuration. (The barrier assembly actuation wire, where present, extends through the patient's conduit system (e.g., vasculature) and then out of the patient's body through the surgeon's access point.)

In some embodiments, where present, the barrier assembly is biased towards the expanded configuration. Insertion of the barrier assembly into the catheter (e.g., delivery sheath) causes the barrier assembly to convert to its collapsed configuration. Removal of the barrier assembly from the catheter causes the barrier assembly to convert to its expanded configuration.

In some embodiments, the barrier assembly, when in the expanded configuration, also anchors the docking unit at the implantation site.

In some embodiments, the device further comprises a control cable attached to the docking unit. An outer diameter of the control cable is sized to be able to pass through the conduit system of the mammalian body to the implantation site. (In the present disclosure, no particular difference is intended by use of the words "wire" and "cable", the distinction has been made merely to improve clarity and avoid confusion on the part of the reader.)

In some embodiments, the control cable is hollow with a cavity formed therein.

In some embodiments, the control wire of each functional unit (including some embodiments where the control wire is a control wire assembly), after exiting the proximal guide hole associated with the at least one receiving surface of the docking unit with which the docking surface of the elongate body of that functional unit mates, enters and passes through the cavity within the control cable. In this manner, when the device is in the assembled configuration, the control wires, being within the cavity of the control cable, are not exposed generally exposed to the conduit system of the body. When the conduit system is the vasculature of the body, this reduces the risk of thrombosis formation as the blood will not be exposed to the individual control wires (whether or not those wires might be entangled with one another). In such embodiments, once the control cable has exited the body of the patient, the control wires exit the control cable cavity such that each of the control wires and the control cable itself are individually actionable by the surgeon (without actioning the others).

In some embodiments, the device further comprises a seal positioned at least in one of the docking unit and the cavity of the control cable. The seal prevents fluid from entering the cavity of the control cable while allowing movement of the control wire of each functional assembly through the seal.

When the fluid is blood, seal will prevent the patient from losing blood flowing through the cavity of the control cable and exiting the patient's body.

In some embodiments, the anchor assembly actuation wire (where present) moveably passes through the seal and enters the cavity within the control cable. In some such embodiments, once the control cable has exited the body of the patient, the anchor assembly actuation wire also exits the control cable cavity such that the anchor assembly actuation wire, each of the control wires and the control cable are individually actionable by the surgeon (without actioning the others).

In some embodiments, the barrier assembly actuation wire (where present) moveably passes through the seal and enters the cavity within the control cable. In some such embodiments, once the control cable has exited the body of the patient, the barrier assembly actuation wire also exits the control cable cavity such that the barrier assembly actuation wire, each of the control wires and the control cable are individually actionable by the surgeon (without actioning the others).

In some embodiments, the cavity of the control cable is divided into a plurality of distinct isolated chambers. In some such embodiments, the control wire of each functional unit, after exiting the proximal guide hole in the proximal end abutment associated with the at least one receiving surface of the docking unit with which the docking surface of the elongate body of that functional unit mates, enters a one of the plurality of isolated chambers of the cavity within the control cable apart from the control wire of all other functional units. In this manner, interference and entanglement of the control wires with one another can be prevented. In such embodiments, once the control cable has exited the body of the patient, the control wires exit their chambers of the control cable cavity such that each of the control wires and the control cable are individually actionable by the surgeon (without actioning the others).

In some embodiments, the device further comprises at least one seal positioned at least in one of the docking unit, the cavity of the control cable, and a chamber of the cavity of the control cable. The seal prevents fluid from entering the chambers of the cavity of the control cable assembly while allowing movement of the control wire of each functional assembly through the at least one seal.

In some embodiments, the assembly actuation wire (where present), after exiting the central cavity of the elongated body of the docking unit, enters a one of the plurality of isolated chambers of the cavity apart from others of the plurality of isolated chambers in which the control wires of the functional units enter. In some such embodiments, once the control cable has exited the body of the patient, the anchor assembly actuation wire also exits its chamber of the control cable cavity such that the anchor assembly actuation wire, each of the control wires and the control cable are individually actionable by the surgeon (without actioning the others).

In some embodiments, the barrier assembly actuation wire (where present), after exiting the central cavity of the elongated body of the docking unit, enters a one of the plurality of isolated chambers apart from others of the plurality of isolated chambers in which the control wires of the functional units enter. In some such embodiments, once the control cable has exited the body of the patient, the barrier assembly actuation wire also exits its chamber of the control cable cavity such that the barrier assembly actuation wire, each of the control wires and the control cable are individually actionable by the surgeon (without actioning the others).

In some embodiments, an inner diameter of each isolated chamber within the cavity of the control cable and an outer diameter of the control wire (or actuation wire, as the case may be) entering that isolated chamber, are sized, one with respect to the other, to prevent fluid from flowing around the control wire in that isolated chamber while still allowing movement of the control wire in that isolated chamber. In this manner, when the fluid is blood for example, the patient is prevented from losing blood by blood being able to flow through the chambers in the cavity of the control cable and exit the patient's body. Such a design can also be present in embodiments where a seal is a present, to serve as backup blood "leakage" prevention should the seal fail.

In some embodiments, the first functional unit is a first pumping unit. In some embodiments, the second functional unit is a second pumping unit. In some embodiments, the third functional unit is a third pumping unit. (It is not required that all functional units of the device have the same function, although they may. Different embodiments of the present technology will differ in this respect).

In some embodiments, each pumping unit has a fluid flow cavity therein. The fluid flow cavity extends between a first opening in the elongate body (e.g., in the side, at the end, etc.) of that pumping unit and a second opening in the elongate body (e.g., in the side, at the end, etc.) of that pumping unit.

In some embodiments, the first opening of each pumping unit is positioned on a side of the elongate body of that pumping unit such that the first opening is unobstructed when that pumping unit is in the docked configuration. Further, in some embodiments, the second opening of each pumping unit is positioned at the distal end of the elongate body of that pumping unit.

In some embodiments, the docking surface of each pumping unit is devoid of openings therein. Depending on the design of the docking unit and the pumping unit, having the docking surface devoid of openings may prevent thrombus formation in between the receiving surface of the docking unit and the docking surface of the pumping unit.

In some embodiments, one of the first opening and the second opening of each pumping unit is a fluid inlet and the other of the first opening and the second opening of each pumping unit is a fluid outlet. In some embodiments, the pumping unit is structured such that fluid can only flow in one direction through the fluid flow cavity when the pumping unit is in operation. In such cases, the fluid inlet and fluid outlet are not reversable (one with respect to the other). Thus, the same one of the first opening and the second opening is always the fluid inlet or the fluid outlet (as the case may be) when the device is in operation. In other such embodiments, the pumping unit is structured such that fluid can flow in either direction through the fluid flow cavity (depending on how the pumping unit is being operated). In such cases, the fluid inlet and the fluid outlet may be either of the first opening and the second opening depending on the operating conditions or parameters of the pumping unit.

In some embodiments, the fluid inlet of each pumping unit has a flow straightener associated therewith.

In some embodiments, an impeller is rotatably disposed within the fluid flow cavity of each pumping unit. Rotation of the impeller causes fluid to be drawn into the fluid flow cavity of that pumping unit via the fluid inlet of that pumping unit and fluid to be expelled from the fluid flow cavity of that pumping unit via the fluid outlet of that pumping unit. As a non-limiting example, in embodiments where the fluid can flow in either direction through the fluid flow cavity, the impeller may be capable of rotation in both directions, and it is the direction of rotation of the impeller that will determine direction of fluid flow through the cavity (and thus, which of the openings is the fluid inlet and which is the fluid outlet).

In some embodiments: A motor is housed within the elongate body of each pumping unit. An impeller shaft is housed within the elongate body of each pumping unit and is rotatably drivable by the motor of that pumping unit. The impeller of that pumping unit is rotatably drivable by the impeller shaft of that pumping unit. (Embodiments where there is no motor housed within the elongate body of a pumping unit are also within the scope of the present technology. In such cases, the impeller may be driven by a flexible driveshaft as described hereinabove.)

In some embodiments, the impeller of each pumping unit is non-expandable. As was discussed hereinabove, in many situations, expandable impeller pumps have undesirable drawbacks.

In some embodiments, fluid expelled from the fluid outlet of each pumping unit promotes entrainment flow of fluid flowing around the device. In some embodiments, where the device is a VAD for example, having such entrainment flow preserves pulsatility of the blood flow and/or promotes or augments native blood flow. (In should be understand that in various embodiments a device of the present technology can be designed to operate in solely pulsatile flow, solely in continuous flow, or selectively in either.)

In some embodiments, the conduit system of the body is the vasculature and heart chambers of the body, and the fluid is blood.

In some embodiments, the device is a ventricular assist device (VAD) and the implantation site is one selected from a group consisting of an aorta, a left ventricle, a vena cava, a pulmonary artery, and a right ventricle. And, the fluid is blood.

In some embodiments, the implantation site is a thoracic duct of the lymphatic system.

In some embodiments, each of the functional units is a flow fluid blocking unit such that when all of the functional units are in their docked configuration fluid flow through and around the device is blocked. Such interruption of flow might be required, for example, in order to close fistulas or arterial branches when implanting covered stents to avoid endoleaks In some embodiments, at least one of the functional units is a substance delivery unit structured and arranged to deliver a substance at the implantation site. The substance delivered may be a medicament, or another fluid (e.g., blood, blood plasma, saline, glucose solution, etc.)

In some such embodiments, the control wire of each substance delivery unit is a control wire assembly. The control wire assembly has at least a tube for conveying the substance to the substance delivery unit.

In some embodiments, at least one of the functional units is a fluid extraction unit structured and arranged to allow fluid to be extracted from the implantation site. (For example, blood may be withdrawn from the body via the fluid extraction unit.)

In some such embodiments, the control wire of each fluid extraction unit is a control wire assembly. The control wire assembly has at least a tube for conveying the fluid from the implantation site.

In some embodiments, at least one of the functional units is a sensor unit configured to sense one or more physical conditions (e.g., temperature, pH, fluid flow rate, etc.)

In the context of the present technology, a functional unit is not limited to have a single function, it may, but not need not, have multiple functions. As non-limiting example, in some embodiments, a functional unit is a pumping unit and a sensor unit. In other embodiments a functional unit is a substance delivery unit and a fluid extraction unit. Any number and type of non-incompatible functions may be combined in a functional unit of the present technology.

In some embodiments, the catheter is a delivery sheath.

Device in Sheath

As was briefly referred to above, in some embodiments, in a delivery configuration the device is unassembled and has a sheath surrounding the docking unit and all of the functional units, with each of the functional units being in the undocked configuration. The sheath has a proximal end and a distal end. In the sheath, the units are aligned end-to-end with the proximal end of the docking unit being closest to the proximal end of the sheath and the proximal end of the first functional unit facing the distal end of the docking unit. The control wire of the first functional unit: (i) Extends proximally from the proximal end of the elongate body of the first functional unit within the sheath towards the proximal end of the sheath. (ii) Passes within the sheath alongside the elongate body of the docking unit. (iii) Passes through the proximal guide hole of the docking unit associated with the first one of the at least one receiving surface of the docking unit. (iv) And then, extends proximally away from the docking unit within the sheath towards the proximal end of the sheath.

In some embodiments, the control wire of the first functional unit extends outside of the proximal end of the sheath.

In some embodiments, the control wire of the first functional unit extends proximally away from the docking unit within the cavity of a control cable (as was described above) towards the proximal end of the sheath.

In some embodiments, the control cable extends outside of the proximal end of the sheath.

In some embodiments, the longitudinal axis of the elongate body of the docking unit and the longitudinal axis of the elongate body of the first functional unit are generally colinear. Depending on the design of the device, the longitudinal axes may not be exactly colinear due to the presence of other elements in the sheath.

In some embodiments, the proximal end of the second functional unit (where present) faces the distal end of the first functional unit. The control wire of the second functional unit: (i) Extends proximally from the proximal end of the elongate body of the second functional unit within the sheath towards the proximal end of the sheath. (ii) Passes within the sheath alongside the elongate body of the first functional unit. (iii) Passes within the sheath alongside the elongate body of the docking unit. (iv) Goes through the proximal guide hole of the docking unit associated with the second one of the at least one receiving surface of the docking unit. (v) And then, extends proximally away from the docking unit within the sheath towards the proximal end of the sheath.

In some embodiments, the control wire of the first functional unit and the control wire of the second functional unit each extend outside of the proximal end of the sheath.

In some embodiments, the control wire of the first functional unit and the control wire of the second functional unit each extend proximally away from the docking unit within the cavity of the control cable towards the proximal end of the sheath.

In some embodiments, the control cable extends outside of the proximal end of the sheath.

In some embodiments, the longitudinal axis of the elongate body of the docking unit, the longitudinal axis of the elongate body of the first functional unit, and the longitudinal axis of the elongate body of the second functional unit are all generally colinear. Depending on the design of the device, the longitudinal axes may not be exactly colinear due to the presence of other elements in the sheath (e.g., a control wire of one pumping unit passing alongside the body of another control unit).

In some embodiments, the proximal end of the third functional unit (where present) faces the distal end of the second functional unit. The control wire of the third functional unit: (i) Extends proximally from the proximal end of the elongate body of the third functional unit within the sheath towards the proximal end of the sheath. (ii) Passes within the sheath alongside the elongate body of the second functional unit. (iii) Passes within the sheath alongside the elongate body of the first functional unit. (iv) Passes within the sheath alongside the elongate body of the docking unit. (v) Goes through the proximal guide hole of the docking unit associated with the third one of the at least one receiving surface of the docking unit. (vi) And then, extends proximally away from the docking unit within the sheath towards the proximal end of the sheath.

In some embodiments, the control wire of the first functional unit, the control wire of the second functional unit and the control wire of the third functional unit each extend outside of the proximal end of the sheath.

In some embodiments, the control wire of the first functional unit, the control wire of the second functional unit and the control wire of the third functional unit each extend proximally away from the docking unit within the cavity of the control cable towards the proximal end of the sheath.

In some embodiments, the control cable extends outside of the proximal end of the sheath.

In some embodiments, the longitudinal axis of the elongate body of the docking unit, the longitudinal axis of the elongate body of the first functional unit, the longitudinal axis of the elongate body of the second functional unit and the longitudinal axis of the third functional unit are all generally colinear. Depending on the design of the device, the longitudinal axes may not be exactly colinear due to the presence of other elements in the sheath (e.g., a control wire(s) of one (or more) pumping unit passing alongside the body of another control unit).

In some embodiments, the sheath is a loader, or other rigid tube-like structure.

In some embodiments, the sheath is a delivery sheath, or other flexible tube-like structure.

Docking Unit

In another aspect, embodiments of the present technology provide a docking unit for use in a modular mammalian body implantable device, comprising an elongated body. The elongated body has: (i) A longitudinal axis. (ii) At least one receiving surface extending parallel to the longitudinal axis. (iii) A distal end and a proximal end. (iv) At least one proximal guide hole. Each receiving surface has at least one proximal guide hole associated therewith. The docking unit is dimensioned and shaped to be deliverable to an implantation site within a conduit of a conduit system of the mammalian body via a catheter.

The descriptions with respect to docking units of the various embodiments set forth hereinabove apply as well to this aspect of the present technology, mutatis mutandis. They are not repeated here for the purposes of brevity.

Functional Unit

In another aspect, embodiments of the present technology provide a functional unit for use in a modular mammalian body implantable device, comprising: (1) An elongated body having a longitudinal axis, a docking surface extending parallel to the longitudinal axis, a distal end and a proximal end. (2) A control wire extends proximally from the proximal end of the elongate body. The functional unit is dimensioned and shaped to be deliverable to an implantation site within a conduit of a conduit system of the mammalian body via a catheter.

The descriptions with respect to functional units of the various embodiments set forth hereinabove apply as well to this aspect of the present technology, mutatis mutandis. They are not repeated here for the purposes of brevity.

Control Cable Assembly

In another aspect, embodiments of the present technology provide a control cable assembly for use in a modular mammalian body intra-luminal device implantable transcatheter, comprising: a hollow control cable having a cavity therein, the control cable having an outer diameter being sized to be able to pass through a conduit system of a mammalian body.

The descriptions with respect to control cable assemblies (including the various structures such as control wires, etc. therein) of the various embodiments set forth hereinabove apply as well to this aspect of the present technology, mutatis mutandis. They are not repeated here for the purposes of brevity.

Methods of Device Assembly (Ex Vivo)

In another aspect, implementations of the present technology provide a method of assembling (to be in its delivery configuration) ex vivo of a modular mammalian body implantable fluid flow influencing device (to configure the device to be appropriate for implantation). The device has: a docking unit and a first functional unit. The docking unit has an elongated body having: a longitudinal axis, at least one receiving surface extending parallel to the longitudinal axis, a distal end and a proximal end, and at least one proximal guide hole. Each receiving surface has at least one proximal guide hole associated therewith. The docking unit is dimensioned and shaped to be deliverable to an implantation site within a conduit of a conduit system of the mammalian body via a catheter. The first functional unit has an elongated body and a control wire. The elongated body has a longitudinal axis, a docking surface extending parallel to the longitudinal axis, a distal end and a proximal end. The docking surface is shaped to mate with a first one of the at least one receiving surface of the docking unit. The elongated body is at least one of sized, shaped, and structured to be unable to pass through a one of the at least one proximal guide hole of the docking unit associated with the first one of the at least one receiving surface of the docking unit. The control wire extends proximally from the proximal end of the elongate body. The first functional unit is dimensioned and shaped to be deliverable to the implantation site via the catheter.

The method comprises: a) Causing the control wire of the first functional unit to pass from a distal side of the one of the at least one guide hole associated with the first one of the at least one receiving surface of the docking unit through to the proximal side of that guide hole. b) Placing the docking unit and the first functional unit within a sheath (I) such that the docking unit and the first functional unit are aligned end-to-end with the proximal end of the first functional unit facing the distal end of the docking unit. (II) And, such that the control wire of the first functional unit extends proximally from the proximal end of the elongate body of the first functional unit within the sheath towards an end of the sheath, passes within the sheath alongside the elongate body of the docking unit, passes through the one of the at least one proximal guide hole of the docking unit associated with the first one of the at least one receiving surface of the docking unit, and then extends proximally away from the docking unit within the sheath towards the end of the sheath.

In some implementations, the device further has a second functional unit. The second functional unit has an elongated body and a control wire. The elongated body has a longitudinal axis, a docking surface extending parallel to the longitudinal axis, a distal end and a proximal end. The docking surface is shaped to mate with a second one of the at least one receiving surface of the docking unit. The elongated body is at least one of sized, shaped, and structured to be unable to pass through a one of the at least one proximal guide hole of the docking unit associated with the second one of the at least one receiving surface of the docking unit. The control wire extends proximally from the proximal end of the elongate body. The second functional unit is dimensioned and shaped to be deliverable to the implantation site via the catheter. In such implementations, the method comprises: a) Causing the control wire of the first functional unit to pass from a distal side of the one of the at least one guide hole associated with the first one of the at least one receiving surface of the docking unit through to the proximal side of that guide hole. b) Causing the control wire of the second functional unit to pass from a distal side of the one of the at least one guide hole associated with the second one of the at least one receiving surface of the docking unit through to the proximal side of that guide hole. c) Placing the docking unit, the first functional unit and the second functional unit within a sheath (I) such that the docking unit and the first functional unit are aligned end-to-end with the proximal end of the first functional unit facing the distal end of the docking unit, the first functional unit and the second functional unit are aligned end-to-end with the proximal end of the second functional unit facing the distal end of the first functional unit. (II) And, such that the control wire of the first functional unit extends proximally from the proximal end of the elongate body of the first functional unit within the sheath towards an end of the sheath, passes within the sheath alongside the elongate body of the docking unit, passes through the one of the at least one proximal guide hole of the docking unit associated with the first one of the at least one receiving surface of the docking unit, and then extends proximally away from the docking unit within the sheath towards the end of the sheath. (III) And, such that the control wire of the second functional unit extends proximally from the proximal end of the elongate body of the second functional unit within the sheath towards the end of the sheath, passes within the sheath alongside the elongate body of the first functional unit, passes within the sheath alongside the elongate body of the docking unit, passes through the one of the at least one proximal guide hole of the docking unit associated with the second one of the at least one receiving surface of the docking unit, and then extends proximally away from the docking unit within the sheath towards the end of the sheath.

In some implementations, the device further has a third functional unit. The third functional unit has an elongated body and a control wire. The elongated body has a longitudinal axis, a docking surface extending parallel to the longitudinal axis, a distal end and a proximal end. The docking surface is shaped to mate with a third one of the at least one receiving surface of the docking unit. The elongated body is at least one of sized, shaped, and structured to be unable to pass through a one of the at least one proximal guide hole of the docking unit associated with the third one of the at least one receiving surface of the docking unit. The control wire extends proximally from the proximal end of the elongate body. The third functional unit is dimensioned and shaped to be deliverable to the implantation site via the catheter. In such implementations, the method comprises: a) Causing the control wire of the first functional unit to pass from a distal side of the one of the at least one guide hole associated with the first one of the at least one receiving surface of the docking unit through to the proximal side of that guide hole. b) Causing the control wire of the second functional unit to pass from a distal side of the one of the at least one guide hole associated with the second one of the at least one receiving surface of the docking unit through to the proximal side of that guide hole. c) Causing the control wire of the third functional unit to pass from a distal side of the one of the at least one guide hole associated with the third one of the at least one receiving surface of the docking unit through to the proximal side of that guide hole. d) Placing the docking unit, the first functional unit, the second functional unit and the third functional unit within a sheath (I) such that the docking unit and the first functional unit are aligned end-to-end with the proximal end of the first functional unit facing the distal end of the docking unit, the first functional unit and the second functional unit are aligned end-to-end with the proximal end of the second functional unit facing the distal end of the first functional unit, the second functional unit and the third functional unit are aligned end-to-end with the proximal end of the third functional unit facing the distal end of the second functional unit. (II) And such that the control wire of the first functional unit extends proximally from the proximal end of the elongate body of the first functional unit within the sheath towards an end of the sheath, passes within the sheath alongside the elongate body of the docking unit, passes through the one of the at least one proximal guide hole of the docking unit associated with the first one of the at least one receiving surface of the docking unit, and then extends proximally away from the docking unit within the sheath towards an end of the sheath. (III) And, such that the control wire of the second functional unit extends proximally from the proximal end of the elongate body of the second functional unit within the sheath towards the end of the sheath, passes within the sheath alongside the elongate body of the first functional unit, passes within the sheath alongside the elongate body of the docking unit, passes through the one of the at least one proximal guide hole of the docking unit associated with the second one of the at least one receiving surface of the docking unit, and then extends proximally away from the docking unit within the sheath towards the end of the sheath. (IV) And, such that the control wire of the third functional unit extends proximally from the proximal end of the elongate body of the third functional unit within the sheath towards the end of the sheath, passes within the sheath alongside the elongate body of the second functional unit, passes within the sheath alongside the elongate body of the first functional unit, passes within the sheath alongside the elongate body of the docking unit, passes through the one of the at least one proximal guide hole of the docking unit associated with the third one of the at least one receiving surface of the docking unit, and then extends proximally away from the docking unit within the sheath towards the end of the sheath.

In some of the aforementioned implementations, the control wire of the first functional unit, the control wire of the second functional unit (where present) and the control wire of the third functional unit (where present) each extends outside of the end of the sheath.

In some of the aforementioned implementations, the device further has a control cable attached to the docking unit. An outer diameter of the control cable being sized to be able to pass through the conduit system to the implantation site. Placing the docking unit, the first functional unit, the second functional unit (where present) and the third functional unit (where present) within the sheath is further placing the docking unit, the first functional unit, the second functional unit (where present), and the third functional unit (where present) within the sheath such that the control cable of the docking unit extends proximally away from the docking unit within the sheath towards the end of the sheath.

In some implementations, the device further has a control cable attached to the docking unit. An outer diameter of the control cable is sized to be able to pass through the conduit system to the implantation site. The control cable is hollow with a cavity formed therein. In such implementations, the method comprises: a) Causing the control wire of the first functional unit to pass from a distal side of the one of the at least one guide hole associated with the first one of the at least one receiving surface of the docking unit through to the proximal side of that guide hole. b) Causing the control wire of the first functional unit to enter and pass through the cavity within the control cable. c) Placing the docking unit and the first functional unit within a sheath (I) such that the docking unit and the first functional unit are aligned end-to-end with the proximal end of the first functional unit facing the distal end of the docking unit. (II) And, such that the control wire of the first functional unit extends proximally from the proximal end of the elongate body of the first functional unit within the sheath towards an end of the sheath, passes within the sheath alongside the elongate body of the docking unit, passes through the one of the at least one proximal guide hole of the docking unit associated with the first one of the at least one receiving surface of the docking unit, and then passes into the cavity of the control cable. (III) And, such that the control cable extends proximally away from the docking unit within the sheath toward the end of the sheath.

In other such implementations, the method comprises: a) Causing the control wire of the first functional unit to pass from a distal side of the one of the least one guide hole associated with the first one of the at least one receiving surface of the docking unit through to the proximal side of that guide hole. b) Causing the control wire of the first functional unit to enter and pass through the cavity within the control cable. c) Causing the control wire of the second functional unit to pass from a distal side of the one of the at least one guide hole associated with the second one of the at least one receiving surface of the docking unit through to the proximal side of that guide hole. d) Causing the control wire of the second functional unit to enter and pass through the cavity within the control cable; e) Placing the docking unit, the first functional unit and the second functional unit within a sheath (I) such that the docking unit and the first functional unit are aligned end-to-end with the proximal end of the first functional unit facing the distal end of the docking unit, and the first functional unit and the second functional unit are aligned end-to-end with the proximal end of the second functional unit facing the distal end of the first functional unit. (II) And, such that the control wire of the first functional unit extends proximally from the proximal end of the elongate body of the first functional unit within the sheath towards an end of the sheath, passes within the sheath alongside the elongate body of the docking unit, and then passes through the one of the at least one proximal guide hole of the docking unit associated with the first one of the at least one receiving surface of the docking unit, and then passes into the cavity of the control cable. (III) And, such that the control wire of the second functional unit extends proximally from the proximal end of the elongate body of the second functional unit within the sheath towards the end of the sheath, passes within the sheath alongside the elongate body of the first functional unit, passes within the sheath alongside the elongate body of the docking unit, and then passes through the one of the at least one proximal guide hole of the docking unit associated with the second one of the at least one receiving surface of the docking unit, and then passes into the cavity of the control cable. (IV) And, such that the control cable extends proximally away from the docking unit within the sheath towards the end of the sheath.

In still other such implementations, the method comprises: a) Causing the control wire of the first functional unit to pass from a distal side of the one of the at least one guide hole associated with the first one of the at least one receiving surface of the docking unit through to the proximal side of that guide hole. b) Causing the control wire of the first functional unit to enter and pass through the cavity within the control cable. c) Causing the control wire of the second functional unit to pass from a distal side of the one of the at least one guide hole associated with the second one of the at least one receiving surface of the docking unit through to the proximal side of that guide hole. e) Causing the control wire of the second functional unit to enter and pass through the cavity within the control cable. f) Causing the control wire of the third functional unit to pass from a distal side of the one of the at least one guide hole associated with the third one of the at least one receiving surface of the docking unit through to the proximal side of that guide hole. g) Causing the control wire of the third functional unit to enter and pass through the cavity within the control cable. h) Placing the docking unit, the first functional unit, the second functional unit and the third functional unit within a sheath (I) such that the docking unit and the first functional unit are aligned end-to-end with the proximal end of the first functional unit facing the distal end of the docking unit, the first functional unit and the second functional unit are aligned end-to-end with the proximal end of the second functional unit facing the distal end of the first functional unit, the second functional unit and the third functional unit are aligned end-to-end with the proximal end of the third functional unit facing the distal end of the second functional unit. (II) And, such that the control wire of the first functional unit extends proximally from the proximal end of the elongate body of the first functional unit within the sheath towards an end of the sheath, passes within the sheath alongside the elongate body of the docking unit, and then passes through the one of the at least one proximal guide hole of the docking unit associated with the first one of the at least one receiving surface of the docking unit, and then passes into the cavity of the control cable. (III) And, such that the control wire of the second functional unit extends proximally from the proximal end of the elongate body of the second functional unit within the sheath towards the end of the sheath, passes within the sheath alongside the elongate body of the first functional unit, passes within the sheath alongside the elongate body of the docking unit, and then passes through the one of the at least one proximal guide hole of the docking unit associated with the second one of the at least one receiving surface of the docking unit, and then passes into the cavity of the control cable. (IV) And, such that the control wire of the third functional unit extends proximally from the proximal end of the elongate body of the third functional unit within the sheath towards the end of the sheath, passes within the sheath alongside the elongate body of the second functional unit, passes within the sheath alongside the elongate body of the first functional unit, passes within the sheath alongside the elongate body of the docking unit, and then passes through the one of the at least one proximal guide hole of the docking unit associated with the third one of the at least one receiving surface of the docking unit, and then passes into the cavity of the control cable. (V) And, such that the control cable extends proximally away from the docking unit within the sheath towards the end of the sheath.

In some of the aforementioned implementations, the control cable extends outside of the end of the sheath.

In some of the aforementioned implementations, placing the docking unit, the first functional unit, the second functional unit (where present) and the third functional unit (where present) within the sheath is further placing the docking unit, the first functional unit, the second functional unit (where present) and the third functional unit (where present) within the sheath such that the longitudinal axis of the elongate body of the docking unit, the longitudinal axis of the elongate body of the first functional unit, the longitudinal axis of the elongate body of the second functional unit (where present) and the longitudinal axis of the elongate body of the third functional unit (where present) are all generally colinear.

In some of the aforementioned implementations, the sheath is a loader, or other rigid tube-like structure.

In some of the aforementioned implementations, the sheath is a delivery sheath, or other flexible tube-like structure.

In some of the aforementioned implementations, the first functional unit, the second functional unit (where present) and the third functional unit (where present) are each a pumping unit.

In some of the aforementioned implementations, the conduit system of the body is the vasculature and heart chambers of the body of the body and the fluid is blood.

In some of the aforementioned implementations, the modular implantable device is a ventricular assist device and the implantation site is one selected from a group consisting of an aorta, a left ventricle, a vena cava, a pulmonary artery, and a right ventricle.

The descriptions with respect the various embodiments set forth hereinabove apply as well to this aspect of the present technology, mutatis mutandis. They are not repeated here for the purposes of brevity.

Method of Device Implantation

In another aspect, implementations of the present technology provide a method of implanting a modular fluid flow influencing device into a mammalian body, the device having: a docking unit and a first functional unit. The docking unit has an elongated body having a longitudinal axis, at least one receiving surface extending parallel to the longitudinal axis, a distal end and a proximal end, and at least one proximal guide hole. Each receiving surface has at least one proximal guide hole associated therewith. The docking unit is dimensioned and shaped to be deliverable to an implantation site within a conduit of a conduit system of the mammalian body via a catheter. The first functional unit has an elongated body and a control wire. The elongated body has a longitudinal axis, a docking surface extending parallel to the longitudinal axis, a distal end and a proximal end. The docking surface is shaped to mate with a first one of the at least one receiving surface of the docking unit. The elongated body is at least one of sized, shaped, and structured to be unable to pass through a one of the at least one proximal guide hole of the docking unit associated with the first one of the at least one receiving surface of the docking unit. The control wire extends proximally from the proximal end of the elongate body, goes through the one of the at least one proximal guide hole of the docking unit associated with the first one of the at least one receiving surface of the docking unit, and then extends proximally away from the docking unit. The first functional unit is dimensioned and shaped to be deliverable to the implantation site via the catheter. The first functional unit has a docked configuration in which the docking surface of the first functional unit mates with the first one of the at least one receiving surface of the docking unit, and an undocked configuration in which the docking surface of the first functional unit is unmated with and spaced apart from the first one of the at least one receiving surface of the docking unit.

The method comprises:

a) Obtaining access to the conduit system of the mammalian body. As would be understood by skilled addressee, obtaining access to the conduit system may or may not involve a surgical procedure, depending on the circumstances. For example, obtaining access to a patients' vasculature would typically require surgical intervention (e.g., via a Seldinger technique). Whereas, obtaining access to a patient's urinary tract might not (if access could be had via the patient's urethra, for example.)
b) Guiding a delivery sheath to the implantation site. As would be understood by a skilled addressee, guiding a delivery sheath may or may not involve the use of a guidewire and railing the delivery sheath along the guidewire, depending on the circumstances. (In the context of the present technology, a delivery sheath is a type of catheter. The method may also be carried out with any other suitable type of catheter.)
c) Inserting the first functional unit in the undocked configuration distal end first into the delivery sheath. As would be understood by a skilled addressee, this may or may not involve the use of a loader, depending on the circumstances.
d) Inserting the docking unit distal end first into the delivery sheath. As would be understood by a skilled addressee, this also may or may not involve the use of a loader, depending on the circumstances.
e) Guiding the first functional unit and the docking unit within the delivery sheath to the implantation site. As would be understood by a skilled addressee, this may or may not involve the use of a loader or a push rod or may involve manipulation of the control wire or a control cable of the docking unit (where present), depending on the design of the device and the circumstances.
f) Promoting exit of the first functional unit from the delivery sheath at the implantation site. As would be understood by a skilled addressee, this may be accomplished by the surgeon manipulating one or more of the delivery sheath, the control wire of the first functional unit, a control cable of the docking unit (where present), or a push rod, depending on the design of the device and the circumstances.

g) Promoting exit of the docking unit from the delivery sheath at the implantation site. As would be understood by a skilled addressee, this may be accomplished by the surgeon manipulating one or more of the delivery sheath, the control wire of the functional unit, a control cable of the docking unit (where present), or a push rod, depending on the design of the device and the circumstances.

h) Withdrawing the delivery sheath from the body leaving an internal segment of the control wire of the first functional unit within the conduit system of the body and an external segment of the control wire of the first functional unit outside the conduit system of the body. As would be understood by a skilled addressee, this may be accomplished by the surgeon manipulating one or more of the delivery sheath, the control wire of the first functional unit, and the control cable of the docking unit (where present).

i) Pulling the external segment of the control wire of the first functional unit to guide the first functional unit into the docked configuration. As would be understood by a skilled addressee, this may also be accompanied by the surgeon manipulating the control cable of the docking unit (where present).

As a skilled addressee would understand, the actions set forth above do need to be carried out exactly in the order that they have been set forth above. Solely for the purposes of brevity, all of the different permutations of those actions have not been set forth herein. But they are all intended to be within the scope of the present technology. As an example, as a skilled addressee would understand, the actions involving pulling the control cables and assembling the device must be carried out after peripheral access has been achieved and the fluid flow influencing device components have been delivered close to the implantation site In some such implementations, the device further has an anchor assembly connected to the docking unit, and the method further comprises, after g) and prior to i), anchoring the anchor assembly at the implantation site.

In some implementations, the device further has a second functional unit. The second functional unit has an elongated body and a control wire. The elongated body has a longitudinal axis, a docking surface extending parallel to the longitudinal axis, a distal end and a proximal end. The docking surface is shaped to mate with a second one of the at least one receiving surface of the docking unit. The elongated body is at least one of sized, shaped, and structured to be unable to pass through a one of the at least one proximal guide hole of the docking unit associated with the second one of the at least one receiving surface of the docking unit. The control wire extends proximally from the proximal end of the elongate body, goes through the one of the at least one proximal guide hole of the docking unit associated with the second one of the at least one receiving surface of the docking unit, and then extends proximally away from the docking unit. The second functional unit is dimensioned and shaped to be deliverable to the implantation site via the catheter. The second functional unit has a docked configuration in which the docking surface of the second functional unit mates with the second one of the at least one receiving surface of the docking unit, and an undocked configuration in which the docking surface of the second functional unit is unmated with and spaced apart from the second one of the at least one receiving surface of the docking unit.

And, in such implementations, the method comprises: a) Obtaining access to the conduit system of the mammalian body. b) Guiding a delivery sheath to the implantation site. c) Inserting the second functional unit in the undocked configuration distal end first into the delivery sheath. d) Inserting the first functional unit in the undocked configuration distal end first into the delivery sheath. e) Inserting the docking unit distal end first into the delivery sheath. f) Guiding the second functional unit, the first functional unit and the docking unit within the delivery sheath to the implantation site. g) Promoting exit of the second functional unit from the delivery sheath at the implantation site. h) Promoting exit of the first functional unit from the delivery sheath at the implantation site. i) Promoting exit of the docking unit from the delivery sheath at the implantation site. j) Withdrawing the delivery sheath from the body, leaving an internal segment of the control wire of the second functional unit within the conduit system of the body and an external segment of the control wire of the second functional unit outside the conduit system of the body, and leaving an internal segment of the control wire of the first functional unit within the conduit system of the body and an external segment of the control wire of the first functional unit outside the conduit system of the body. k) Pulling the external segment of the control wire of the second functional unit to guide the second functional unit into the docked position. l) Pulling the external segment of the control wire of the first functional unit to guide the first functional unit into the docked position. (The descriptions related to the steps of the previous implementation (method) with a single first functional unit, are applicable to the present implementation, mutatis mutandis. They have been omitted here solely for brevity. Further, as was also noted above in respect of the previous implementation, as a skilled addressee would understand, the actions set forth above do need to be carried out exactly in the order that they have been set forth above. Solely for the purposes of brevity, all of the different permutations of those actions have not been set forth herein. But they are all intended to be within the scope of the present technology. As an example, as a skilled addressee would understand, action j) could done before actions k) & l) if the control cables were long enough.)

In some such implementations, the device further has an anchor assembly connected to the docking unit, and the method further comprises, after i) and prior to k), anchoring the device at the implantation site.

In some implementations, the device further has a third functional unit. The third functional unit has an elongated body and a control wire. The elongated body has a longitudinal axis, a docking surface extending parallel to the longitudinal axis, a distal end and a proximal end. The docking surface is shaped to mate with a third one of the at least one receiving surface of the docking unit. The elongated body is at least one of sized, shaped, and structured to be unable to pass through a one of the at least one proximal guide hole of the docking unit associated with the third one of the at least one receiving surface of the docking unit. The control wire extends proximally from the proximal end of the elongate body, goes through the one of the at least one proximal guide hole of the docking unit associated with the third one of the at least one receiving surface of the docking unit, and then extends proximally away from the docking unit. The third functional unit is dimensioned and shaped to be deliverable to the implantation site via the catheter. The third functional unit has a docked configuration in which the docking surface of the third functional unit mates with the third one of the at least one receiving surface of the docking unit, and an undocked configuration in which the docking surface of the third functional unit is unmated with and spaced apart from the third one of the at least one receiving surface of the docking unit.

And, in such implementations, the method comprises: a) Obtaining access to a conduit system of the mammalian body. b) Guiding a delivery sheath to the implantation site. c) Inserting the third functional unit in the undocked configuration distal end first into the delivery sheath. d) Inserting the second functional unit in the undocked configuration distal end first into the delivery sheath. e) Inserting the first functional unit in the undocked configuration distal end first into the delivery sheath. f) Inserting the docking unit distal end first into the delivery sheath. g) Guiding the third functional unit, the second functional unit, the first functional unit and the docking unit within the delivery sheath to the implantation site. h) Promoting exit of the third functional unit from the delivery sheath at the implantation site. i) Promoting exit of the second functional unit from the delivery sheath at the implantation site. j) Promoting exit of the first functional unit from the delivery sheath at the implantation site. k) Promoting exit of the docking unit from the delivery sheath at the implantation site. l) Withdrawing the delivery sheath from the body, leaving an internal segment of the control wire of the third functional unit within the conduit system of the body and an external segment of the control wire of the third functional unit outside of the body, leaving an internal segment of the control wire of the second functional unit within the conduit system of the body and an external segment of the control wire of the second functional unit outside the conduit system of the body, and leaving an internal segment of the control wire of the first functional unit within the conduit system of the body and an external segment of the control wire of the first functional unit outside the conduit system of the body. m) Pulling the external segment of the control wire of the third functional unit to guide the third functional unit into the docked position. n) pulling the external segment of the control wire of the second functional unit to guide the second functional unit into the docked position; o) pulling the external segment of the control wire of the first functional unit to guide the first functional unit into the docked position. (The descriptions related to the steps of the previous implementation (method) with a single first functional unit, are applicable to the present implementation, mutatis mutandis. They have been omitted here solely for brevity. Further, as was also noted above in respect of the previous implementations, as a skilled addressee would understand, the actions set forth above do need to be carried out exactly in the order that they have been set forth above. Solely for the purposes of brevity, all of the different permutations of those actions have not been set forth herein. But they are all intended to be within the scope of the present technology. As an example, as a skilled addressee would understand, actions m), n), and o) could be carried out simultaneously.)

In some such implementations, the device further has an anchor assembly connected to the docking unit, and the method further comprises, after k) and prior to m), anchoring the device at the implantation site.

In some implementations, the device further has an anchor assembly actuation wire. The anchor assembly actuation wire is operationally connected to the anchor assembly to actuate conversion of the anchor assembly between an anchored configuration and an unanchored configuration. Anchoring the anchor assembly includes the surgeon manipulating an external segment of the anchor assembly actuation wire outside of the conduit system of the body to actuate conversion of the anchor assembly to the anchored configuration from the unanchored configuration. During such manipulation, the surgeon may also manipulate other elements such as the delivery sheath, the control cable of the docking unit (where present), etc.

In some implementations, the anchor assembly is biased towards an anchored configuration. Anchoring the anchor assembly occurs when the anchor assembly exits the delivery sheath.

In some implementations, the device further has a control cable attached to the docking unit. An outer diameter of the control cable is sized to be able to pass through a conduit system of the body to the implantation site. Guiding the third functional unit (where present), the second functional unit (where present), the first functional unit and the docking unit within the delivery sheath to the implantation site includes (the surgeon) pushing the control cable attached to the docking unit.

In some implementations, the control cable is hollow and has a cavity therein. The internal segment of the control wire of the first functional unit, the internal segment of the control wire of the second functional unit (where present) and the internal segment of the control wire of the third functional unit (where present) are each within the cavity of the control cable.

In some implementations, guiding the third functional unit (where present), the second functional unit (where present), the first functional unit and the docking unit within the delivery sheath to the implantation site includes pushing the docking unit.

In some implementations, guiding the third functional unit (where present), the second functional unit (where present), the first functional unit and the docking unit within the delivery sheath to the implantation site includes pushing the docking unit with a push rod.

In some implementations, guiding the third functional unit (where present), the second functional unit (where present), the first functional unit and the docking unit within the delivery sheath to the implantation site includes pushing the control wires(s) of the functional units.

In some of the above implementations, promoting exit of the third functional unit (where present) from the delivery sheath includes pushing the control wire of the third functional unit.

In some of the above implementations, promoting exit of the second functional unit (where present) from the delivery sheath includes pushing the control wire of the second functional unit.

In some of the above implementations, promoting exit of the first functional unit from the delivery sheath includes pushing the control wire of the first functional unit In some of the above implementations, promoting exit of the docking unit from the delivery sheath includes pushing the control cable of the docking unit.

In some of the above implementations, the first functional unit, the second functional unit (where present), and the third functional unit (where present) are each a pumping unit.

In some of the above implementations, the conduit system of the body is the vasculature and heart chambers of the body, and the fluid is blood.

In some of the above implementations, the device is a ventricular assist device and the implantation site is one selected from a group consisting of an aorta, a left ventricle, a vena cava, a pulmonary artery, and a right ventricle.

As a skilled addressee would understand, for specific embodiments of a device of the present technology, depending on the design of the device, and in particular whether the device has no sharp edges, the above method may be carried out without the use of a delivery sheath (or other similar catheter). In such an implementation, direct delivery of the device by railing the components onto a guidewire without a sheath may be a viable alternative.

Method of Device Explantation

In another aspect, implementations of the present technology provide a method of explanting a modular fluid flow influencing device having been implanted into a conduit of a conduit system of a mammalian body. The device has a docking unit and first functional unit. The docking unit has an elongated body having a longitudinal axis, at least one receiving surface extending parallel to the longitudinal axis, a distal end and a proximal end, and at least one proximal guide hole. Each receiving surface has at least one proximal guide hole associated therewith. The docking unit is dimensioned and shaped to be retrievable from the implantation site via a catheter. The first functional unit has an elongated body and a control wire. The elongated body has a longitudinal axis, a docking surface extending parallel to the longitudinal axis, the docking surface shaped to mate with a first one of the at least one receiving surface of the docking unit, a distal end and a proximal end. The elongated body is at least one of sized, shaped, and structured to be unable to pass through a one of the at least one proximal guide hole of the docking unit associated with the first one of the at least one receiving surface of the docking unit. The control wire extending proximally from the proximal end of the elongate body. The first functional unit is dimensioned and shaped to be retrievable from the implantation site via the catheter. The first functional unit has a docked configuration in which the docking surface of the first functional unit mates with the first one of the at least one receiving surface of the docking unit, and an undocked configuration in which the docking surface of the first functional unit is unmated with and spaced apart from the first one of the at least one receiving surface of the docking unit.

In such implementations, with the first functional unit being in the docked configuration at the implantation site and an internal segment of the control wire of the first functional unit being within the conduit system of the body and an external segment of the control wire of the first functional unit being outside the conduit system of the body, the method comprises:

a) Obtaining access to the conduit system of the mammalian body. As would be understood by skilled addressee, obtaining access to the conduit system may or may not involve a surgical procedure, depending on the circumstances.

b) Guiding a retrieval sheath to the implantation site. As would be understood by a skilled addressee, guiding a retrieval sheath may or may not involve the use of a guidewire and/or railing the retrieval sheath along the guidewire and/or the control wires of the functional unit and/or control cable of the docking unit (where present), depending on the design of the device and the circumstances. (In the context of the present technology, a retrieval sheath is a type of catheter. The method may also be carried out with any other suitable type of catheter.)

c) Pushing the external segment of the control wire of the first functional unit to guide the first functional unit into the undocked position. As would be understood by a skilled addressee, this may be accomplished by the surgeon manipulating one or more elements, such as the control wire of the first functional unit and/or the control cable of the docking unit (where present), depending on the design of the device and the circumstances.

d) Promoting entry of the docking unit into the retrieval sheath, proximal end first, at the implantation site. As would be understood by a skilled addressee, this may be accomplished by the surgeon manipulating one or more elements, such as the retrieval sheath, the control cable of the docking unit (where present) and/or a snare, depending on the design of the device and the circumstances.

e) Promoting entry of the first functional unit into the retrieval sheath proximal end first at the implantation site. As would be understood by a skilled addressee, this may be accomplished by the surgeon manipulating one or more elements, such as the retrieval sheath, the control wire of the first functional unit, the control cable of the docking unit (where present) and/or a snare, depending on the design of the device and the circumstances.

f) Withdrawing the retrieval sheath and the device from the body. As would be understood by a skilled addressee, this may be accomplished by the surgeon manipulating one or more elements, such as the retrieval sheath, the control wire of the first functional unit and/or the control cable of the docking unit (where present), depending on the design of the device and the circumstances.

As was also noted above in respect of the previous implementations, as a skilled addressee would understand, the actions set forth above do need to be carried out exactly in the order that they have been set forth above. Solely for the purposes of brevity, all of the different permutations of those actions have not been set forth herein. But they are all intended to be within the scope of the present technology. As an example, as a skilled addressee would understand, action c) could be done before action b).

In some such implementations, the device further has an anchor assembly connected to the docking unit, the anchor assembly anchoring the device at the implantation site, the method further comprising, prior to d), unanchoring the anchor assembly.

In some implementations, the device further has a second functional unit. The second functional unit has an elongated body and a control wire. The elongated body has a longitudinal axis, a docking surface extending parallel to the longitudinal axis, the docking surface shaped to mate with a second one of the at least one receiving surface of the docking unit, a distal end and a proximal end. The elongated body is at least one of sized, shaped, and structured to be unable to pass through a one of the at least one proximal guide hole of the docking unit associated with the second one of the at least one receiving surface of the docking unit. The control wire extends proximally from the proximal end of the elongate body. The second functional unit is dimensioned and shaped to be retrievable from the implantation site via the catheter. The second functional unit has a docked configuration in which the docking surface of the second functional unit mates with the second one of the at least one receiving surface of the docking unit, and an undocked configuration in which the docking surface of the second functional unit is unmated with and spaced apart from the second one of the at least one receiving surface of the docking unit.

In such implementations, with (i) the first functional unit being in the docked configuration at the implantation site, (ii) the second functional unit being in the docked configuration at the implantation site, (iii) an internal segment of the control wire of the first functional unit being within the conduit system of the body and an external segment of the control wire of the first functional unit being outside the conduit system of the body, and (iv) an internal segment of the control wire of the second functional unit being within the conduit system of the body and an external segment of the control wire of the second functional unit being outside the conduit system of the body, the method comprises: a) Obtaining access to the conduit system of the mammalian body. b) Guiding a retrieval sheath to the implantation site. c) Pushing the external segment of the control wire of the second functional unit to guide the second functional unit into the undocked position. d) Pushing the external segment of the control wire of the first functional unit to guide the first functional unit into the undocked position. e) Promoting entry of the docking unit into the retrieval sheath proximal end first at the implantation site. f) Promoting entry of the first functional unit into the retrieval sheath proximal end first at the implantation site. g) Promoting entry of the second functional unit into the retrieval sheath proximal end first at the implantation site. h) Withdrawing the retrieval sheath and the device from the body. (The descriptions related to the steps of the previous implementation (method) with a single first functional unit, are applicable to the present implementation, mutatis mutandis. They have been omitted here solely for brevity. Further, as was also noted above in respect of the previous implementations, as a skilled addressee would understand, the actions set forth above do need to be carried out exactly in the order that they have been set forth above. Solely for the purposes of brevity, all of the different permutations of those actions have not been set forth herein. But they are all intended to be within the scope of the present technology.)

In some such implementations, the device further has an anchor assembly connected to the docking unit, the anchor assembly anchoring the device at the implantation site, the method further comprising, prior to e), unanchoring the anchor assembly.

In some implementations, the device further has a third functional unit. The third functional unit has an elongated body and a control wire. The elongated body has a longitudinal axis, a docking surface extending parallel to the longitudinal axis, the docking surface shaped to mate with a third one of the at least one receiving surface of the docking unit, a distal end and a proximal end. The elongated body is at least one of sized, shaped, and structured to be unable to pass through a one of the at least one proximal guide hole of the docking unit associated with the third one of the at least one receiving surface of the docking unit. The control wire extends proximally from the proximal end of the elongate body. The third functional unit is dimensioned and shaped to be retrievable from the implantation site via the catheter. The third functional unit has a docked configuration in which the docking surface of the third functional unit mates with the third one of the at least one receiving surface of the docking unit, and an undocked configuration in which the docking surface of the third functional unit is unmated with and spaced apart from the third one of the at least one receiving surface of the docking unit.

In such implementations, with (i) the first functional unit being in the docked configuration at the implantation site, (ii) the second functional unit being in the docked configuration at the implantation site, (iii) the third functional unit being in the docked configuration at the implantation site, (iv) an internal segment of the control wire of the first functional unit being within the conduit system of the body and an external segment of the control wire of the first functional unit being outside the conduit system of the body, (v) an internal segment of the control wire of the second functional unit being within the conduit system of the body and an external segment of the control wire of the second functional unit being outside the conduit system of the body and (vi) an internal segment of the control wire of the third functional unit being within the conduit system of the body and an external segment of the control wire of the third functional unit being outside the conduit system of the body, the method comprises: a) Obtaining access to the conduit system of the mammalian body. b) Guiding a retrieval sheath to the implantation site. c) Pushing the external segment of the control wire of the third functional unit to guide the third functional unit into the undocked position. d) Pushing the external segment of the control wire of the second functional unit to guide the second functional unit into the undocked position. e) Pushing the external segment of the control wire of the first functional unit to guide the first functional unit into the undocked position. f) Promoting entry of the docking unit into the retrieval sheath proximal end first at the implantation site. g) Promoting entry of the first functional unit into the retrieval sheath proximal end first at the implantation site. h) Promoting entry of the second functional unit into the retrieval sheath proximal end first at the implantation site. i) Promoting entry of the third functional unit into the retrieval sheath proximal end first at the implantation site. j) Withdrawing the retrieval sheath and the device from the body. (The descriptions related to the steps of the previous implementation (method) with a single first functional unit, are applicable to the present implementation, mutatis mutandis. They have been omitted here solely for brevity. As was also noted above in respect of the previous implementations, as a skilled addressee would understand, the actions set forth above do need to be carried out exactly in the order that they have been set forth above. Solely for the purposes of brevity, all of the different permutations of those actions have not been set forth herein. But they are all intended to be within the scope of the present technology.)

In some such implementations, the device further has an anchor assembly connected to the docking unit, the anchor assembly anchoring the device at the implantation site, the method further comprising, prior to f), unanchoring the anchor assembly.

In some of the aforementioned implementations, the device further has an anchor assembly actuation wire. The anchor assembly actuation wire is operationally connected to the anchor assembly to actuate conversion of the anchor assembly between an anchored configuration and an unanchored configuration. Unanchoring the anchor assembly includes the surgeon manipulating an external segment of the anchor assembly actuation wire outside of the conduit system of the body to actuate conversion of the anchor assembly from the anchored configuration to the unanchored configuration.

In some such implementations, the anchor assembly is biased towards an anchored configuration, and unanchoring the anchor assembly occurs when the anchor assembly enters the retrieval sheath.

In some of the aforementioned implementations, the device further has a control cable attached to the docking unit. An outer diameter of the control cable is sized to be able to pass through the conduit system to the implantation site. In some such implementations, guiding the retrieval sheath to the implantation site includes railing the retrieval sheath over the control cable.

In some of the aforementioned implementations, promoting entry of the docking unit into the retrieval sheath includes pulling the control cable attached to the docking unit.

In some of the aforementioned implementations, promoting entry of the first functional unit into the retrieval sheath includes pulling the control wire of the first functional unit.

In some of the aforementioned implementations, promoting entry of the second functional unit (where present) into the retrieval sheath includes pulling the control wire of the second functional unit.

In some of the aforementioned implementations, promoting entry of the third functional unit (where present) into the retrieval sheath includes pulling the control wire of the third functional unit.

In some of the aforementioned implementations, withdrawing the retrieval sheath and the device includes pulling the control wire(s) of the functional unit(s) until the docking unit and functional unit(s) exit at the proximal end of the retrieval sheath outside of the conduit system.

In some of the aforementioned implementations, withdrawing the retrieval sheath and the device includes pulling the control wire(s) of the functional unit(s) and control cable of the docking unit until the docking unit and functional unit(s) exit at the proximal end of the retrieval sheath outside of the conduit system.

In some of the aforementioned implementations, withdrawing the retrieval sheath and the device includes pulling the control wire(s) of the functional unit(s), the control cable of the docking unit and the retrieval sheath until the docking unit, functional unit(s) and retrieval sheath exit the conduit system.

In some of the aforementioned implementations, the first functional unit, the second functional unit (where present) and the third functional unit (where present) are each a pumping unit.

In some of the aforementioned implementations, the conduit system of the body is the vasculature and heart chambers of the body, and the fluid is blood.

In some of the above implementations, the device is a ventricular assist device and the implantation site is one selected from a group consisting of an aorta, a left ventricle, a vena cava, a pulmonary artery, and a right ventricle.

As a skilled addressee would understand, for specific embodiments of a device of the present technology, depending on the design of the device, and in particular whether the device has no sharp edges, the above method may be carried out without the use of a retrieval sheath (or other similar catheter). In such an implementation, direct retrieval of the device by placing the functional units into the undocked configuration and then pulling the components out via their cables or wires (as the case may be) may be able to be accomplished.

Method of Removing In Vivo a Functional Unit from an Implanted Device

In another aspect, implementations of the present technology provide a method of in vivo removal of a functional unit from a modular fluid flow influencing device having been implanted into a conduit of a conduit system of a mammalian body. The device has a docking unit and the first functional unit. The docking unit has an elongated body having a longitudinal axis, at least one receiving surface extending parallel to the longitudinal axis, a distal end and a proximal end, and at least one proximal guide hole. Each receiving surface has at least one proximal guide hole associated therewith. The docking unit is dimensioned and shaped to be retrievable from the implantation site via the conduit system. The functional unit has an elongated body having a longitudinal axis, a docking surface extending parallel to the longitudinal axis, a distal end and a proximal end. The docking surface is shaped to mate with a one of the at least one receiving surface of the docking unit. The elongated body is at least one of sized, shaped, and structured to be unable to pass through a one of the at least one proximal guide hole of the docking unit associated with the one of the at least one receiving surface of the docking unit. A control wire extends proximally from the proximal end of the elongate body. An internal segment of the control wire is within the conduit system of the body and an external segment of the control cable being outside the conduit system of the body via a first access to the conduit system. The functional unit is dimensioned and shaped to be retrievable from the implantation site via the conduit system. The functional unit has a docked configuration in which the docking surface of the functional unit mates with the one of the at least one receiving surface of the docking unit, and an undocked configuration in which the docking surface of the functional unit is unmated with and spaced apart from the one of the at least one receiving surface of the docking unit.

In such implementations, with the functional unit being in the docked configuration at the implantation site, the method comprises:

a) Obtaining a second access to the conduit system of the mammalian body. The second access is different from the first access through which the device was implanted.
b) Guiding a snare via the second access through the conduit system to the implantation site.
c) Pushing the external segment of the control wire of the functional unit to guide the functional unit into the undocked configuration;
d) Ensnaring the first functional unit in the undocked configuration with the snare.
e) Pulling the snare with the ensnared functional unit out of the mammalian body via the second access; and
f) Pulling the control wire of the functional unit out of the mammalian body via the second access.

As was also noted above in respect of the previous implementations, as a skilled addressee would understand, the actions set forth above do need to be carried out exactly in the order that they have been set forth above. Solely for the purposes of brevity, all of the different permutations of those actions have not been set forth herein. But they are all intended to be within the scope of the present technology. As an example, as a skilled addressee would understand, action c) could be carried out before action b).

Method of Adding In Vivo a Functional Unit to an Implanted Device

In another aspect, implementations of the present technology provide a method of in vivo addition of a functional unit to a modular fluid flow influencing device having been implanted into a conduit of a conduit system of a mammalian body. The device has a docking unit and a control cable. The docking unit has an elongated body having a longitudinal axis, at least one receiving surface extending parallel to the longitudinal axis, a distal end and a proximal end, and at least one proximal guide hole. Each receiving surface has at least one proximal guide hole associated therewith. The docking unit is dimensioned and shaped to be deliverable to the implantation site via a catheter. A control cable is attached to the docking unit. An outer diameter of the control cable is sized to be able to pass through the conduit system to the implantation site. The control cable is hollow and has a cavity therein. An internal segment of the control cable is within the conduit system of the body and an external segment of the control cable is outside the conduit system of the body via a first access to the conduit system. The functional unit has an elongated body and a control wire. The elongated body has a longitudinal axis, a docking surface extending parallel to the longitudinal axis, and a distal end and a proximal end. The docking surface is shaped to mate with a one of the at least one receiving surface of the docking unit. The functional unit has a docked configuration in which the docking surface of the functional unit mates with the one of the at least one receiving surface of the docking unit, and an undocked configuration in which the docking surface of the functional unit is unmated with and spaced apart from the one of the at least one receiving surface of the docking unit. The elongated body is at least one of sized, shaped, and structured to be unable to pass through a one of the at least one proximal guide hole of the docking unit associated with the one of the at least one receiving surface of the docking unit. The control wire extends proximally from the proximal end of the elongate body. The functional unit is dimensioned and shaped to be deliverable to the implantation site via the conduit system.

In such implementations, with the docking unit being at the implantation site, the method comprising:

- a) Inserting a guide wire within the cavity of the external segment of the control cable.
- b) Pushing a guide wire
  - i. through the cavity to the one of the at least one proximal guide hole of the docking unit associated with the at least one receiving surface, and
  - ii. through the one of the at least one proximal guide hole of the docking unit associated with the at least one receiving surface until the guide wire exits the one of the at least one proximal guide hole of the docking unit associated with the at least one receiving surface at the implantation site.
- c) Obtaining a second access to the conduit system of the mammalian body.
- d) Guiding a snare via the second access through the conduit system to the implantation site.
- e) Ensnaring the guide wire with the snare.
- f) Pulling the snare with the ensnared guide wire out of the mammalian body via the second access while leaving an external segment of the guide wire exiting the conduit system via the first access.
- g) Releasing the guide wire from ensnarement.
- h) Attaching the control wire of the functional unit to the guide wire.
- i) Pulling the external segment of the guide wire that exits the first access
  - i. causing the control wire of the functional unit to enter the conduit system via the second access,
  - ii. causing the elongated body of the functional unit to enter the conduit system via the second access,
  - iii. causing the elongated body of the functional unit to travel through the conduit system to the implantation site,
  - iv. guiding the functional unit into the docked configuration,
  - v. causing the control wire of the functional unit to exit the mammalian body via the first access.
- j) Detaching the guide wire from the control wire of the functional unit leaving an external segment of the control wire exiting the mammalian body via the first access.

As was also noted above in respect of the previous implementations, as a skilled addressee would understand, the actions set forth above do need to be carried out exactly in the order that they have been set forth above. Solely for the purposes of brevity, all of the different permutations of those actions have not been set forth herein. But they are all intended to be within the scope of the present technology. As an example, as a skilled addressee would understand, actions c) and d) could be carried out before actions a) and b).

Method of Replacing In Vivo a Functional Unit of an Implanted Device

In another aspect, implementations of the present technology a method of in vivo replacement of a first functional unit of a modular fluid flow influencing device having been implanted into a conduit of a conduit system of a mammalian body with a second functional unit. The device has a docking unit and the first functional unit. The docking unit has an elongated body having a longitudinal axis, at least one receiving surface extending parallel to the longitudinal axis, a distal end and a proximal end, and at least one proximal guide hole. Each receiving surface has at least one proximal guide hole associated therewith. The docking unit is dimensioned and shaped to be retrievable from the implantation site via the conduit system. The first functional unit has an elongated body having a longitudinal axis, a docking surface extending parallel to the longitudinal axis, a distal end and a proximal end. The docking surface is shaped to mate with a one of the at least one receiving surface of the docking unit. The elongated body is at least one of sized, shaped, and structured to be unable to pass through a one of the at least one proximal guide hole of the docking unit associated with the one of the at least one receiving surface of the docking unit.

The first functional unit has a control wire extending proximally from the proximal end of the elongate body of the first functional unit. An internal segment of the control wire is within the conduit system of the body and an external segment of the control cable is outside the conduit system of the body via a first access to the conduit system. The first functional unit is dimensioned and shaped to be retrievable from the implantation site via the conduit system. The first functional unit has a docked configuration in which the docking surface of the first functional unit mates with the one of the at least one receiving surface of the docking unit, and an undocked configuration in which the docking surface of the first functional unit is unmated with and spaced apart from the one of the at least one receiving surface of the docking unit.

The second functional unit has an elongated body having a longitudinal axis, a docking surface extending parallel to the longitudinal axis, a distal end and a proximal end. The docking surface is shaped to mate with the one of the at least one receiving surface of the docking unit. The second functional unit has a docked configuration in which the docking surface of the second functional unit mates with the one of the at least one receiving surface of the docking unit, and an undocked configuration in which the docking surface of the second functional unit is unmated with and spaced apart from the one of the at least one receiving surface of the docking unit. The elongated body is at least one of sized, shaped, and structured to be unable to pass through the one of the at least one proximal guide hole of the docking unit associated with the one of the at least one receiving surface of the docking unit. A control wire extends proximally from the proximal end of the elongate body of the second functional unit. The second functional unit is dimensioned and shaped to be deliverable to the implantation site via the conduit system.

The first functional unit is in the docked configuration at the implantation site, the method comprises:

a) Attaching a guide wire to the external segment of the control wire of the first functional unit.

b) Pushing the external segment of the control wire of the first functional unit to guide the first functional unit into the undocked configuration.

c) Obtaining a second access to the conduit system of the mammalian body.

d) Guiding a snare via the second access through the conduit system to the implantation site.

e) Ensnaring the first functional unit in the undocked configuration with the snare.

f) Pulling the snare with the ensnared first functional unit out of the mammalian body via the second access.

g) Pulling the control wire of the first functional unit and a portion of the guide wire out of the mammalian body via the second access while leaving an external segment of the guide wire exiting the conduit system via the first access.

h) Detaching the control wire of the first functional unit from the guide wire.

i) Attaching the control wire of the second functional unit to the guide wire.

j) Pulling the external segment of the guide wire at the first access, i. causing the control wire of the second functional unit to enter the conduit system via the second access, ii. causing the elongated body of the second functional unit to enter the conduit system via the second access, iii. causing the elongated body of the second functional unit to travel through the conduit system to the implantation site, iv. guiding the second functional unit into the docked configuration, v. causing the control wire of the second functional unit to exit the mammalian body via the first access.

k) Detaching the guide wire from the control wire of the second functional unit leaving an external segment of the control wire exiting the mammalian body via the first access.

As was also noted above in respect of the previous implementations, as a skilled addressee would understand, the actions set forth above do need to be carried out exactly in the order that they have been set forth above. Solely for the purposes of brevity, all of the different permutations of those actions have not been set forth herein. But they are all intended to be within the scope of the present technology.

General

In the context of the present specification, the words "first", "second", "third", etc. have been used as adjectives only for the purpose of allowing for distinction between the nouns that they modify from one another, and not for the purpose of describing any particular relationship between those nouns. Thus, for example, it should be understood that, the use of the terms "first unit" and "third unit" is not intended to imply any particular type, hierarchy or ranking (for example) of/between the units.

In the context of the present specification, the word "embodiment(s)" is generally used when referring to physical realizations of the present technology and the word "implementations" is generally used when referring to methods that are encompassed within the present technology (which generally involve also physical realizations of the present technology). The use of these different terms is not intended to be limiting of or definitive of the scope of the present technology. These different terms have simply been used to allow the reader to better situate themselves when reading the present lengthy specification.

Embodiments and implementations of the present technology each have at least one of the above-mentioned objects and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments and/or implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Figure 88:
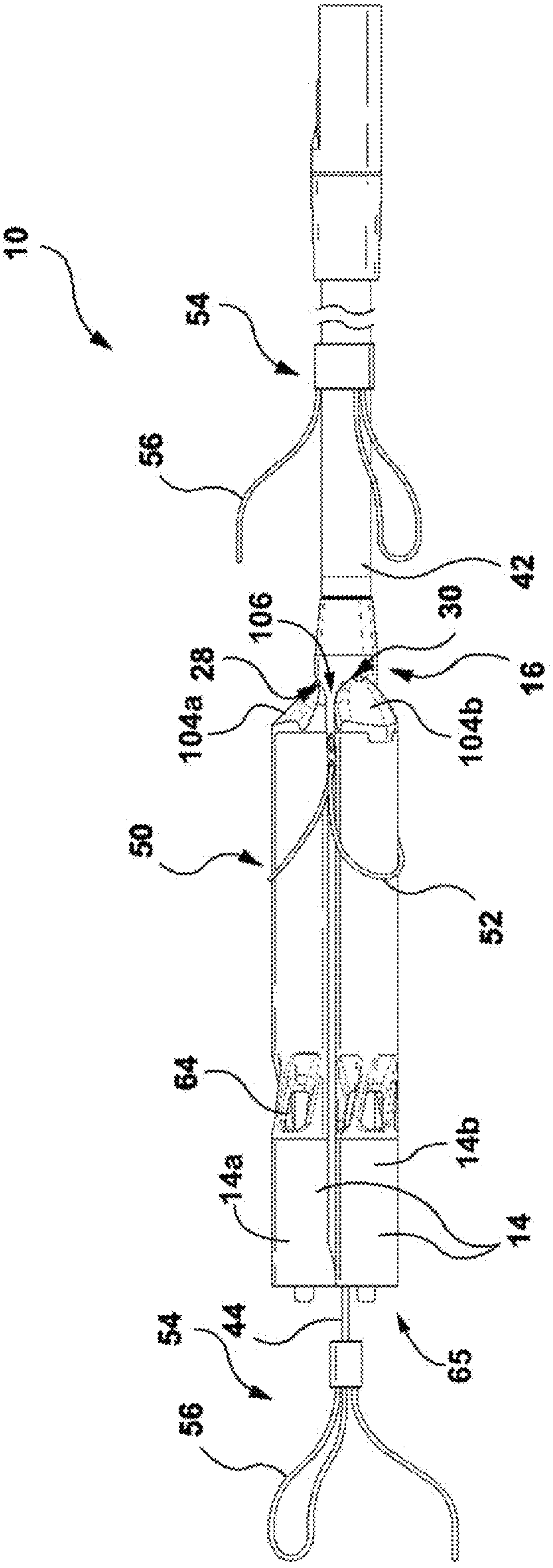
FIG. 88 is a side view of the VAD of FIG. 87, shown in an assembled configuration.

Referring to FIG. 88, there is shown a modular mammalian body implantable fluid flow influencing device being a ventricle assist device (VAD) 10, which is one embodiment of the present technology. It is to be expressly understood that the VAD 10 is merely one embodiment, amongst many, of the present technology. Thus, the description thereof that follows is intended to be only a description of an illustrative example of the present technology. This description is not intended to define the scope or set forth the bounds of the present technology. In some cases, what are believed to be helpful examples of modifications to VAD 10 and/or additional embodiments may also be set forth below. This is done merely as an aid to understanding, and, again, not to define the scope or set forth the bounds of the present technology. These modifications are not an exhaustive list, and, as a skilled addressee would understand, other modifications are likely possible. Further, where this has not been done (i.e., where no examples of modifications have been set forth), it should not be interpreted that no modifications are possible and/or that what is described is the sole manner of implementing that element of the present technology. As a skilled addressee would understand, this is likely not the case. In addition, it is to be understood that the VAD 10 may provide in certain instances a simple embodiment of the present technology, and that where such is the case it has been presented in this manner as an aid to understanding. As a skilled addressee would understand, various embodiments of the present technology will be of a greater complexity.

VAD—General Description

Referring to FIG. 88, VAD 10 is modular and has a docking unit 16 and three pumping units 14. (In this description, the pumping units are collectively referenced as 14. The first pumping unit is individually referenced when necessary as **14*a*. The second pumping unit is individually referenced when necessary as 14*b*. The third pumping unit is individually referenced when necessary as 14*c***.)

Docking Unit

Figure 89:
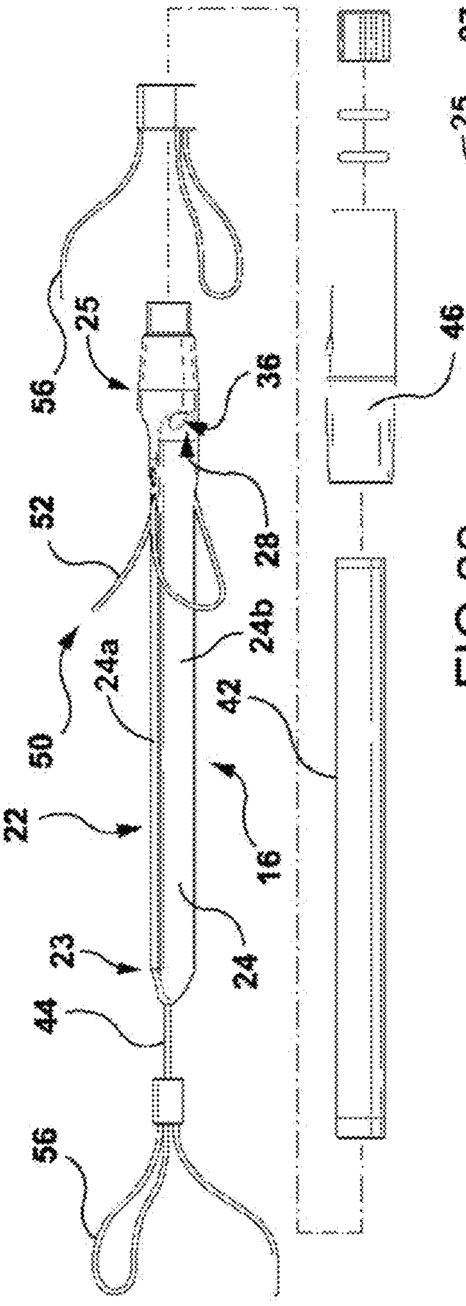
FIG. 89 is an exploded view of the docking unit and control cable of the VAD of FIG. 87.
Figure 90:
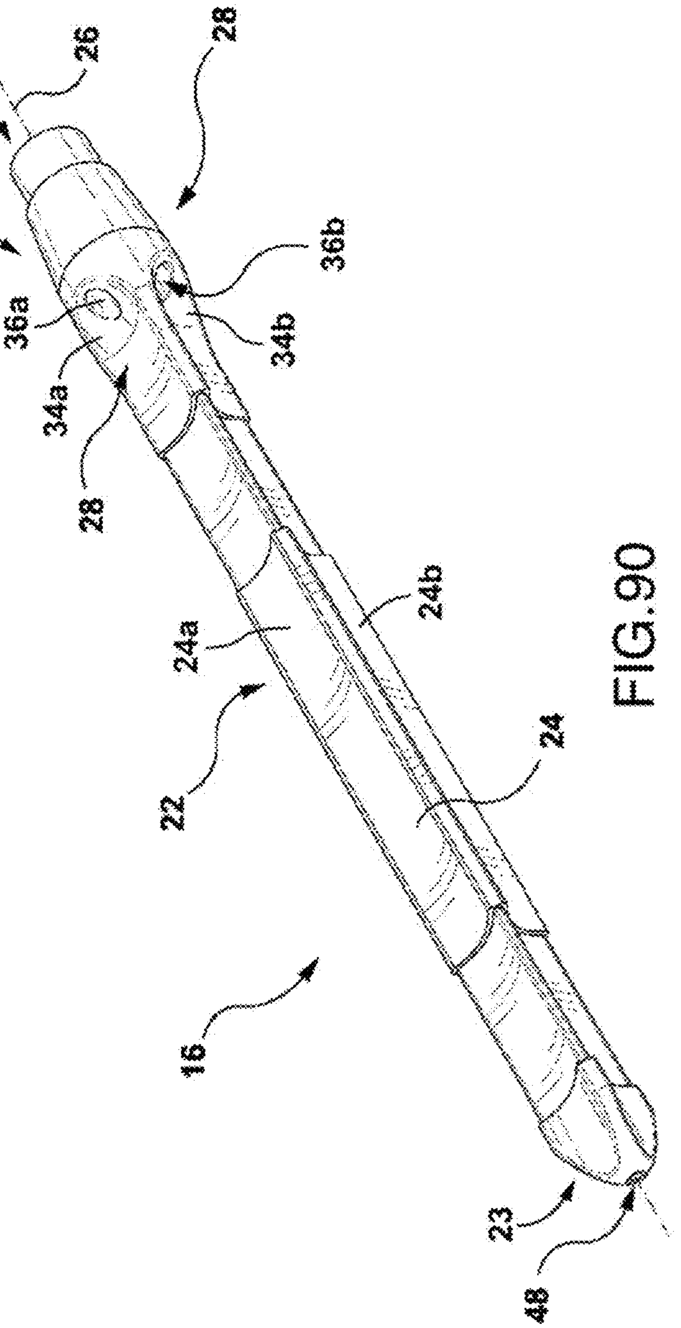
FIG. 90 is a distal end isometric view of the docking unit of the VAD of FIG. 87.
Figure 91:
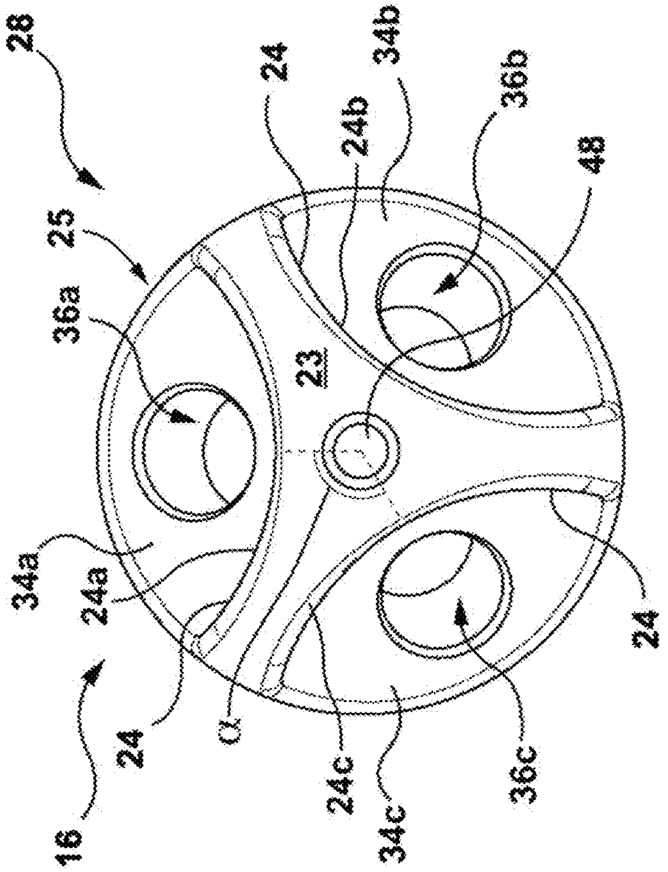
FIG. 91 is a distal end view of the docking unit of the VAD of FIG. 87.

Referring to FIGS. 88-91, the docking unit 16 has an elongated body 22. The elongate body 22 has a longitudinal axis 26, three receiving surfaces 24 extending parallel to the longitudinal axis 26, a distal end 23 and a proximal end 25. (In this description, the receiving surfaces are collectively referenced as 24. The first receiving surface is individually referenced when necessary as **24*a*. The second receiving surface is referenced when necessary as 24*b*. The third receiving surface is referenced when necessary as 24*c*.). The three receiving surfaces 24 are positioned equidistantly radially along an exterior surface of the elongate body 22. The angle formed between (i) a line connecting the midpoint of any one of the receiving surfaces 24 and the longitudinal axis 26 and (ii) a line connecting the midpoint of any adjacent receiving surface 24 to that one receiving surface 24 and the longitudinal axis 26, is 120°. (See, for example, angle alpha in FIG. 91.) Each receiving surface 24 is concave and, as is discussed hereinbelow, is shaped to confirm to and mate with a curved convex exterior side wall 58 of an elongate body 80 of a pumping unit 14. As can be seen in FIG. 91, when looking at the docking unit 16 from its distal end 23, because of the three concave receiving surfaces, the docking unit 16 resembles a "Y". In this embodiment, each receiving surface 24 is identical to the others, and is about 6 cm in length. (In other embodiments, that will not be the case.) In this embodiment, the docking unit 16** is a central docking unit.

The elongated body 22 is made of titanium and is effectively non-expandable, at least between storage, room, and body temperatures). In other embodiments, the body could be made of stainless steel, titanium alloys (e.g., Nitinol) or chromium-cobalt alloy.

The elongate body 22 further has three proximal guide holes 36. (In this description, the proximal guide holes are collectively referenced as 36. The first proximal guide hole is individually referenced when necessary as **36*a*. The second proximal guide hole is individually referenced when necessary as 36*b*. The third proximal guide hole is individually referenced when necessary as 36*c*.) Each receiving surface 24, has one proximal guide hole 36 associated therewith. Thus, the first proximal guide hole 36*a* is associated with the first receiving surface 24*a*. The second proximal guide hold 36*b* is associated with the second receiving surface 24*b*. The third proximal guide hole 36*c* is associated with the third receiving surface 36*c*. In this embodiment, each proximal guide hole 36 is identical to the others. (In other embodiments, that will not be the case.) In this embodiment, the guide holes 36 are in the form a channel through the proximal end 25 of the docking unit 16. One open end of each guide hole 36 is adjacent the receiving surface 24 with which that guide hole 36 is associated. The other end of each guide hole 36 opens within an opening 27 to which the which the control cable 42** is attached. In this embodiment, the diameter of the guide holes is about 1.4 mm and their length is about 1.0 cm.

Further, each receiving surface 24 as a proximal end abutment 34 in which the proximal guide hole 26 associated with that receiving surface 24 is disposed. (In this disclosure, the proximal end abutments are collectively referenced as 34. The first proximal end abutment is individually referenced when necessary as 34*a*. The second proximal end abutment is individually referenced when necessary as 34*b*. The third proximal end abutment is individually referenced when necessary as 34*c*.) Thus, the first proximal guide hole 36*a* is disposed in the first proximal end abutment 34*a*. The second proximal guide hole 36*b* is disposed in the second proximal end abutment 34*b*. The third proximal guide hole 36*c* is disposed in the third proximal end abutment 34*c*. In this embodiment, each proximal end abutment 36 is identical to the others, having a concave shape. (In other embodiments, that will not be the case.)

The elongate body 22 has a longitudinal-extending central cavity 48 disposed along its longitudinal axis 26.

The docking unit 16 is dimensioned and shaped to be percutaneously deliverable transcatheter to an implantation site within the aorta of an adult human body via a delivery sheath through the vasculature of a patient. In this embodiment the length of the docking unit is about 8 cm and its largest diameter is about 5.9 mm. In other embodiments, the length could be between about 1 cm and 20 cm, with a length between about 5 cm to 12 cm being preferred within that range. In other embodiments, the largest diameter is not greater than 10 mm.

Control Cable

A control cable 42 is attached to and seals (so blood cannot enter) the proximal end 25 of the docking unit. The control cable 42 has a cavity therein which communicates with the opening 27 in the proximal end 25. The cavity is dimensioned so that the control wires 38 (see below) of the various pumping units 14 (and any other wire extending from the docking unit 16) can pass through the cavity in the control cable 42. The control cable itself is dimensioned to be able to pass through the vasculature of the patient and to avoid occluding or promoting thrombosis in the smaller vessels through which it travels (e.g., diameters of approximately 1 mm to 6 mm). In this embodiment, the control cable has an external diameter of about 4 mm and is about 50 cm in length. In this embodiment, the control cable is made of thermoplastic polyurethane.

Pumping Units—Structure

Figure 92:
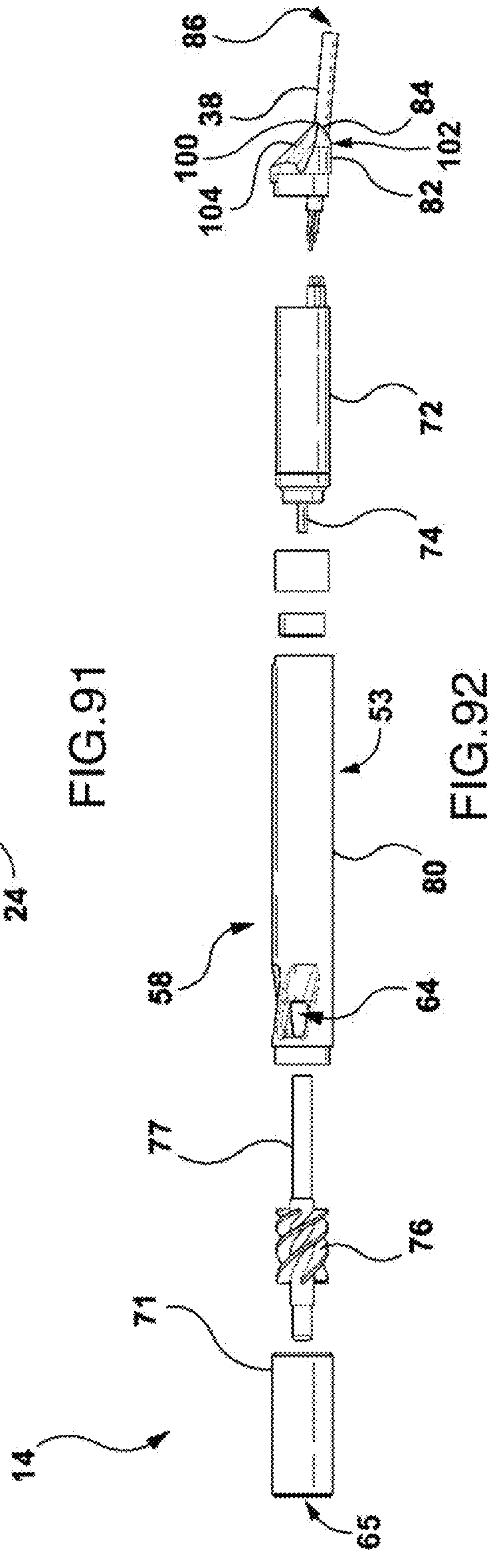
FIG. 92 is an exploded view of a pumping unit of the VAD of FIG. 87.
Figure 93:
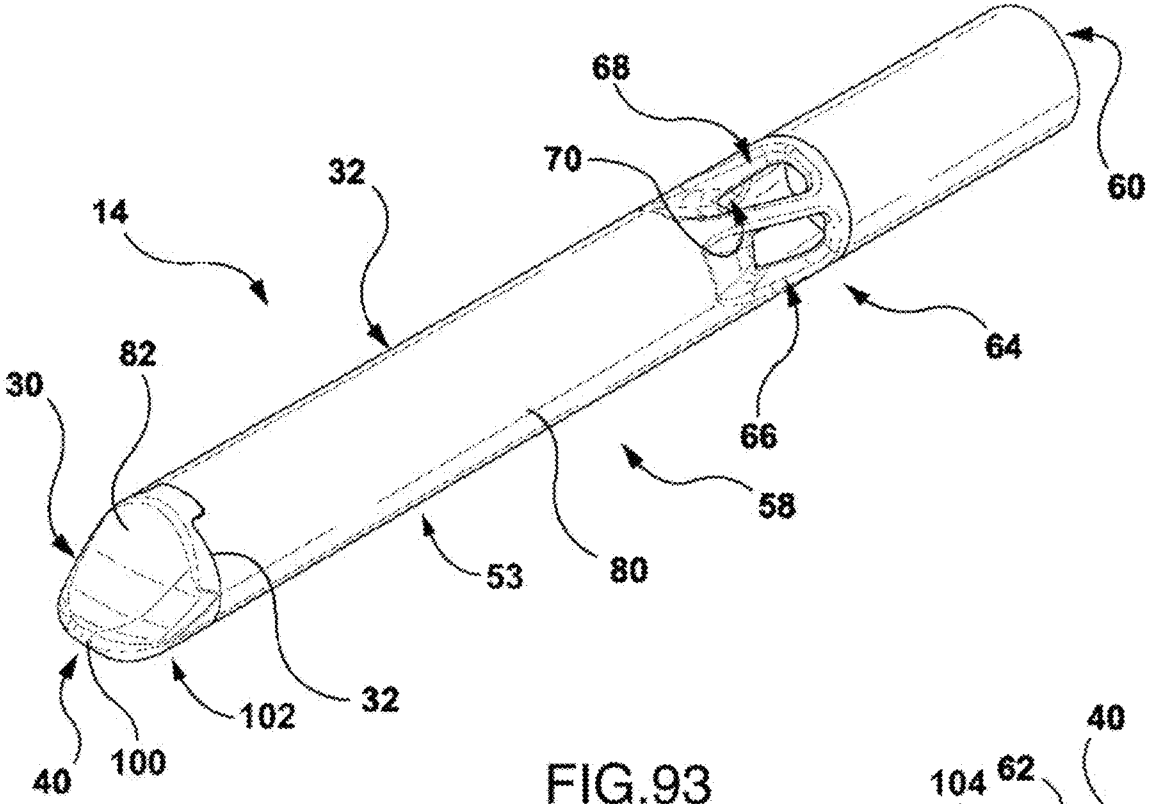
FIG. 93 is a proximal end isometric view of the pumping unit of the VAD of FIG. 87.
Figure 94:
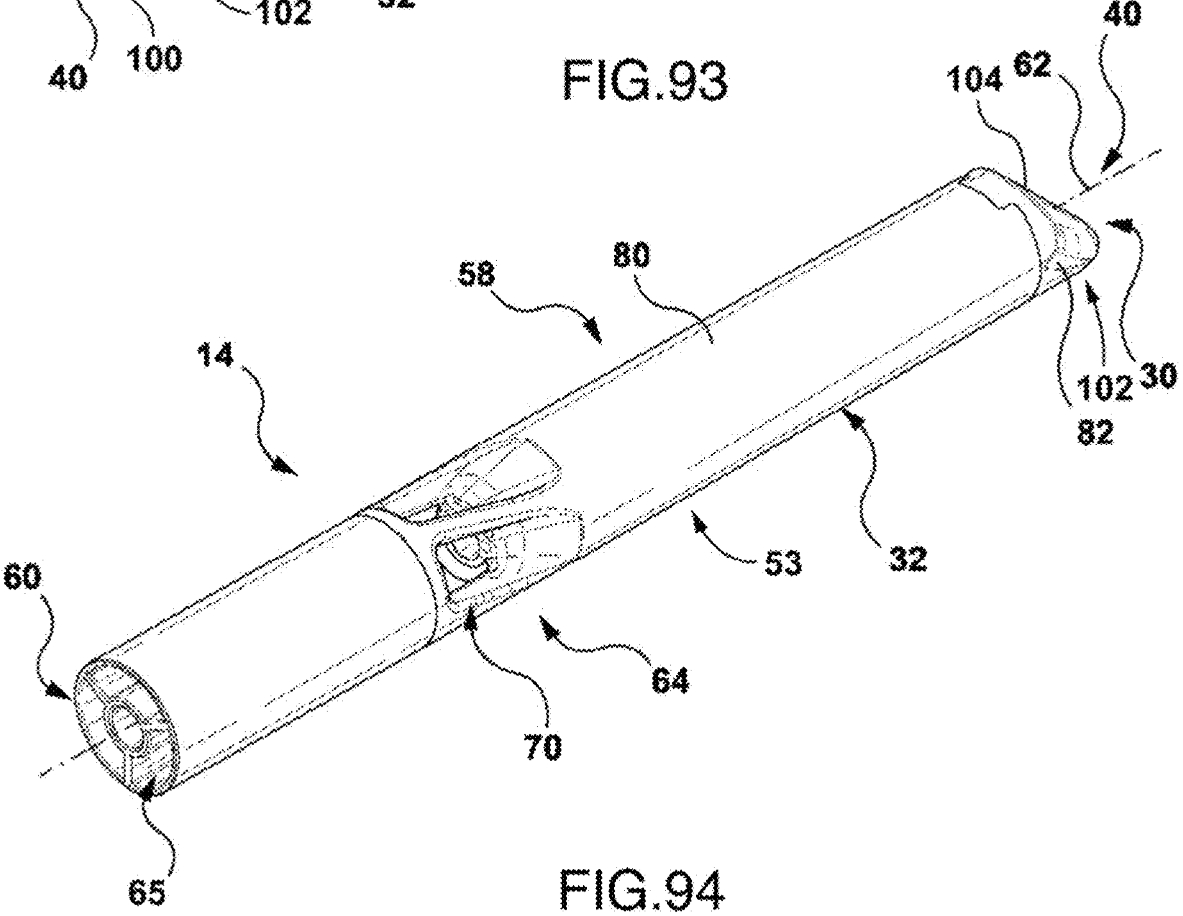
FIG. 94 is a distal end isometric view of the pumping unit of the VAD of FIG. 87.

Referring to FIGS. 92-94, all of the pumping units 14 are identical to each other (in this embodiment, although this will be the case in other embodiments.) Each pumping unit 14 has an elongate body 80 and a control wire 38. The elongate body 80 of each pumping unit 14 is generally cylindrical and has a longitudinal axis 62 and a docking surface 53 extending parallel to its longitudinal axis 62 along the generally cylindrical outer surface 58 of the elongate body 80. The elongate body 80 of each pumping unit 14 also has a distal end 60 and a proximal end 40. The elongate body 80 of each pumping unit is sized, shaped, and structured to be unable to pass through the proximal guide holes 36 of the docking unit 16.

The docking surface 53 of each pumping unit 14 is shaped to mate with one of the receiving surfaces 24 of the docking unit 16. Thus, each docking surface 53 is convex and has the same radius of curvature as the receiving surface 24 of the docking unit 16. Each pumping unit 14 is dimensioned and shaped to be percutaneously deliverable transcatheter to an implantation site within the aorta of an adult human body via a delivery sheath through the vasculature of a patient. In this embodiment the length of the pumping unit is about 6 cm and its largest diameter is about 6 mm.

The elongated body 80 of each pumping unit 14 is made of titanium. In other embodiments, the body could be made of stainless steel, titanium alloys (e.g., Nitinol) or chromium-cobalt alloy. The elongated body 80 of each pumping unit 14 is effectively non-expandable, at least between storage, room, and body temperatures). Other components of the pumping unit are made of polyether ether ketone (PEEK) in this embodiment, although in other embodiments, any otherwise appropriate biocompatible plastic could be used.

Referring to FIGS. 88 and 92-96, each pumping unit 14 has a blood flow cavity 108 therein. The blood flow cavity 108 extends between a first set of openings 64 in the cylindrical outer surface 58 of the elongate cylinder 80 and a second opening 65 at the distal end 60 of the elongate body 80 of the pumping unit 14. The openings (66, 68, 70) of the first set of openings 64 are positioned on the side 58 of the elongate body 60 of the pumping unit 14 such that the first set of openings 64 are all unobstructed when the pumping unit 14 is in its docked configuration. The docking surface 24 of each pumping unit 14 is devoid of openings therein. Depending on the rotation of the impeller 76 (described below) either the first set of openings 64 serve as an inlet to the blood fluid flow cavity 108 and the second opening 65 serves as an outlet from the blood flow cavity, or the second opening 65 serves as inlet to the blood flow cavity 108 and the first set of openings 64 serve as the outlet from the blood flow cavity. (Optionally, one or both of the first set of openings 64 or the second opening 65, can have a flow straightener associated therewith.)

Referring specifically to FIG. 92, an impeller 76 is rotatably disposed within the blood flow cavity 108 of each pumping unit 14. Rotation of the impeller 76 causes blood to be drawn into the blood flow cavity 108 of the pumping unit 14 via the fluid inlet (one of openings 64 or 65) of the pumping unit 14 and blood to be expelled from the blood flow cavity 108 of the pumping unit 14 via the fluid outlet (the other of the openings 64 or 65, as the case may be for the pumping unit 14). A motor 72 is housed within the elongate body 80 of the pumping unit 14. An impeller shaft 77 is housed within the elongate body 80 of the pumping unit 14. The impeller shaft 77 is rotatably drivable by the motor 72 of the pumping unit 14 via the motor's output shaft 74. The impeller shaft 77 rotatably drives the impeller 76 of that pumping unit 14. In this embodiment, a shroud 71 forms part of the elongate body 80, when the pumping unit 14 is assembled. The shroud 71 houses the impeller 76 and forms a part of the blood flow cavity 108. A flow straighter is disposed within the shroud 71. In this embodiment the motor is a 6 mm motor with a maximum RPM of 50,000.

The impeller 76 of each pumping unit 14 is non-expandable. In this embodiment the pumping unit components are also made of titanium and PEEK.

Pumping Unit—Control Wire

The control wire 38 extends proximally from the proximal end 40 of the elongate body 80. In this embodiment, the control wire 38 of each pumping unit 14 extends from an apex 100 of the proximal end 40 of the elongate body 80 of that pumping unit 38. Further, in this embodiment, the control wire 38 of each pumping unit 14 extends from the proximal end 40 of the elongate body 80 of that pumping unit 14 at a position offset from the longitudinal axis 62 of that pumping unit 14.

Figure 97:
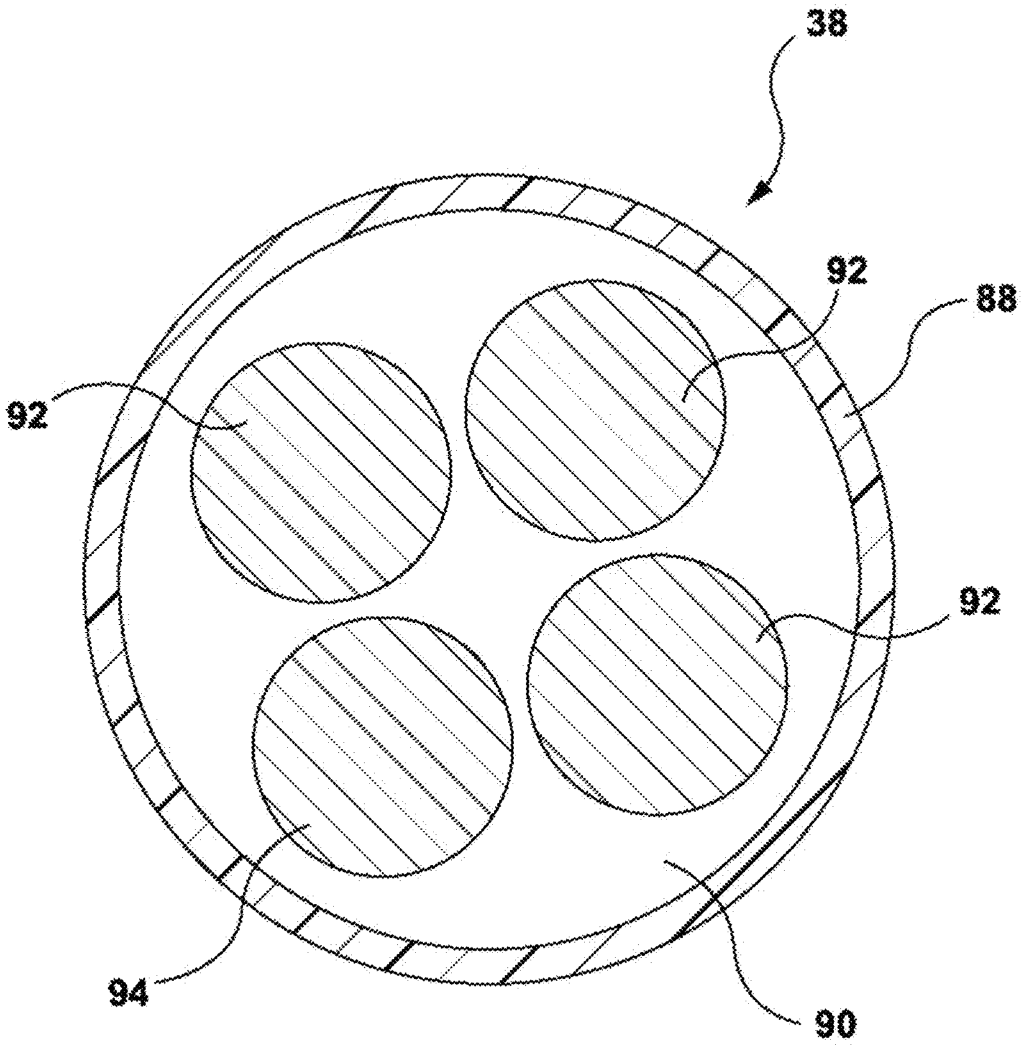
FIG. 97 is a cross-section of a control wire of a pumping unit of the VAD of FIG. 87.

Referring to FIG. 97, the control wire 38 of each pumping unit is a control wire assembly, about 1.3 mm in diameter and about 70 cm in length. The control wire assembly has an electrical component for delivering electrical power to that pumping unit 14 via the control wire assembly and a mechanical competent for structurally reinforcing the control wire assembly of that pumping unit. As an external segment of the control wire 38 of each pumping unit will be manipulated by a surgeon to move the pumping units between their various configurations at the implantation site—as will be explained in further detail below—the control wire needs to be structurally mechanically sufficient for this to occur.

In this embodiment, the electrical component is three electrical wires 92. In other embodiments, the number of electrical wires will differ depending on the electrical requirements of components (e.g. a motor) requiring electrical power. In this embodiment, the mechanical component is a structural wire (which does not serve any electrical purpose—but may in other embodiments). In other embodiments, the mechanical components will differ. In this embodiment, the control wire assembly has an outer sheath bundling 88 together and surrounding the plurality of electrical wires 92 of and the structural wire 94. Reference number 90 in FIG. 97 identifies a cavity within the outer sheath 88 in which the wires 92, 94 are located.

In another embodiment, the electrical component of the control wire assembly of each pumping unit is a number of electrical wires and the mechanical component is an outer sheath bundling together and surrounding the electrical wires. This embodiment is not shown but would look similar to FIG. 97 with mechanical wire 94 being absent.

The control wire 38 extends proximally from the proximal end 40 of the elongate body 80. When the device 10 is assembled for implant, the control wire 38 goes through one proximal guide hole 36 associated with one receiving surface 26 of the docking unit 16, and then extends proximally away from the docking unit 16. Thus, when the device 10 is assembled for implant, the control wire **38*a* of the first pumping unit 14*a*, after extending away from the proximal end 40*a* of the elongate body 80*a* of the first pumping unit 14*a*, goes through the first proximal guide hole 36*a* which is associated with the first receiving surface 24*a* of the docking unit, and then extends proximally away from the docking unit 16 within the cavity of the control cable 42 of the docking unit 16. Similarly, when the device 10 is assembled for implant, the control wire 38*b* of the second pumping unit 14*b*, after extending away from the proximal end 40*b* of the elongate body 80*b* of the second pumping unit 14*b*, goes through the second proximal guide hole 36*b* which is associated with the second receiving surface 24*b* of the docking unit, and then extends proximally away from the docking unit 16 within the cavity of the control cable 42 of the docking unit 16. Finally, when the device 10 is assembled for implant, the control wire 38*c* of the third pumping unit 14*c*, after extending away from the proximal end 40*c* of the elongate body 80*c* of the third pumping unit 14*c*, goes through the third proximal guide hole 36*c* which is associated with the third receiving surface 24*c* of the docking unit, and then extends proximally away from the docking unit 16 within the cavity of the control cable 42 of the docking unit 16**.

In this manner, when the device is implanted in the patient, the control wires 38 can pass through the vasculature of the patient within the control cable 42 and not be exposed to the patient's vasculature itself. The control wires 38 will exit the patient's body within the control cable 42. Once the control cable 42 is outside of the patient's body, the control wires 38 will exit the cavity of the control cable 42 through a seal 46 and will then be individually manipulatable by the surgeon.

Pumping Unit—Configurations

Figure 62:
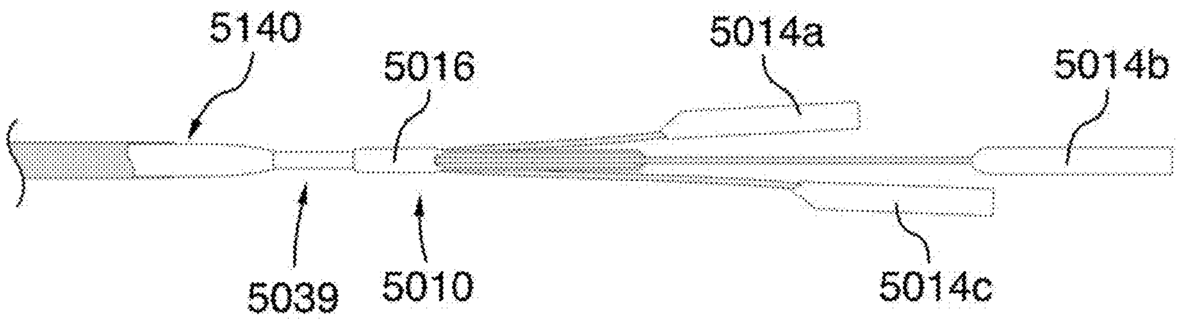
FIG. 62 is another schematic view of the VAD of FIG. 61.

Each pumping unit 14 has a docked configuration in which the docking surface 53 of that pumping unit 14 mates with a receiving surface 24 of the docking unit. Each pumping unit 14 also has an undocked configuration in which the docking surface 53 of that pumping unit 14 is unmated with and spaced apart from that receiving surface 24 of the docking unit 16. Thus, the first pumping unit **14*a* has a docked configuration in which the docking surface 53 of the first pumping unit 14*a* mates with the first receiving surface 24*a* of the docking unit 16. The first pumping unit 14*a* also has an undocked configuration in which the docking surface 53 of the first pumping 14*a* is unmated with and spaced apart from the first receiving surface 24*a* of the docking unit 16. Similarly, the second pumping unit 14*b* has a docked configuration in which the docking surface 53 of the second pumping unit 14*b* mates with the second receiving surface 24*b* of the docking unit 16. The second pumping unit 14*b* also has an undocked configuration in which the docking surface 53 of the second pumping unit 14*b* is unmated with and spaced apart from the second receiving surface 24*b* of the docking unit 16. Finally, the third pumping unit 14*c* has a docked configuration in which the docking surface 53 of the third pumping unit 14*c* mates with the third receiving surface 24*c* of the docking unit 16. The third pumping unit 14*c* also has an undocked configuration in which the docking surface 53 of the third pumping unit 14*c* is unmated with and spaced apart from the third receiving surface 24*c* of the docking unit 16. In FIG. 88, the first pumping unit 14*a*, the second pumping unit 14*b* and the third pumping unit 14*c* are each in their docked configuration. In FIG. 62, the first pumping unit 5014*a* (of VAD 5010), the second pumping unit 5014*b*, and the third pumping unit 5014*c*** are in an undocked configuration.

Each pumping unit 14 is moveable at the implantation site between the undocked configuration and the docked configuration via movement of the control wire 38 of that pumping unit 14. Specifically, each pumping unit 14 is moveable at the implantation site into its docked configuration from its undocked configuration by pulling the control wire 38 of that pumping unit 14. Also, each pumping unit 14 is moveable at the implantation site from the docked configuration into the undocked configuration by pushing the control wire 38 of that pumping unit 14. Thus, the first pumping unit **14*a* is moveable at the implantation site into its docked configuration from its undocked configuration by pulling the control wire 38*a* of the first pumping unit 14*a*. Also, the first pumping unit 14*a* is moveable at the implantation site from the docked configuration into the undocked configuration by pushing the control wire 38*a* of the first pumping unit 14*a*. Similarly, the second pumping unit 14*b* is moveable at the implantation site into its docked configuration from its undocked configuration by pulling the control wire 38***b* of the second pumping unit 14*b*. Also, the second pumping unit 14*b* is moveable at the implantation site from the docked configuration into the undocked configuration by pushing the control wire 38*b* of the second pumping unit 14*b*. Finally, the third pumping unit 14*c* is moveable at the implantation site into its docked configuration from its undocked configuration by pulling the control wire 38*c* of the third pumping unit 14*c*. Also, the third pumping unit 14*c* is moveable at the implantation site from the docked configuration into the undocked configuration by pushing the control wire 38*c* of the third pumping unit 14*c*.

Pumping Units—Additional Details

In this embodiment, the docking surface 53 of each pumping unit 14 fluid non-ingressivenessly registers with the receiving surface 24 of the docking unit 16 with which that the docking surface 53 of that pumping unit 14 mates when that pumping unit 14 is in the docked configuration. Thus, the docking surface 53 of the first pumping unit 14*a* fluid non-ingressivenessly registers with the receiving surface 24*a* of the docking unit 16 when the first pumping unit 14*a* is in its docked configuration. Similarly, the docking surface 53 of the second pumping unit 14*b* fluid non-ingressivenessly registers with the receiving surface 24*b* of the docking unit 16 when the second pumping unit 14*b* is in its docked configuration. Finally, the docking surface 53 of the third pumping unit 14*c* fluid non-ingressivenessly registers with the receiving surface 24*c* of the docking unit 16 when the third pumping unit 14*c* is in its docked configuration.

The proximal end 40 of the elongate body 80 of each pumping unit 14 has an abutment contacting surface 102. As can best be seen in FIG. 95, when each pumping unit 14 is in its docked configuration, the abutment contacting surface 102 of the proximal end 40 of the elongate body 80 of that pumping unit 14 mates with the proximal end abutment 34 associated with the receiving surface 24 of the docking unit 16 with which the docking surface 53 of the elongate body 80 of that pumping unit 14 mates. Thus, when the first pumping unit 14*a* is in its docked configuration, the abutment contacting surface 102*a* of the proximal end 40*a* of the elongate body 80*a* of the first pumping unit 14*a* mates with the proximal end abutment 34*a* of the receiving surface 24*a* of the docking unit 16. Similarly, when the second pumping unit 14*b* is in its docked configuration, the abutment contacting surface 102*b* of the proximal end 40*b* of the elongate body 80*b* of the second pumping unit 14*b* mates with the proximal end abutment 34*b* of the receiving surface 24*b* of the docking unit 16. Finally, when the third pumping unit 14*c* is in its docked configuration, the abutment contacting surface 102*c* of the proximal end 40*c* of the elongate body 80*c* of the third pumping unit 14*c* mates with the proximal end abutment 34*c* of the receiving surface 24*c* of the docking unit 16.

In this embodiment, when each pumping unit 14 is in its docked configuration, the abutment contacting surface 102 of the proximal end 40 of the elongate body 80 of that pumping unit 14 fluid non-ingressivenessly registers with the proximal end abutment 34 associated with the at least one receiving surface 24 of the docking unit 53 with which the docking surface of the elongate body 80 of that pumping unit 14 mates.

In this embodiment, when each pumping unit 14 is in its docked configuration, the abutment contacting surface 102 of the proximal end 40 of the elongate body 80 of that pumping unit 14 and the proximal end abutment 34 associated with the receiving surface 24 of the docking unit 16 with which the docking surface 53 of the elongate body 80 of that pumping unit14 mates, are shaped, one with respect to the other, such that when the control wire 38 of that pumping unit 14 is tensioned, the docking surface 53 of the elongate body 80 of that pumping unit is biased towards the receiving surface 24 of the docking unit 16 with which the docking surface 53 of the elongate body 80 of that pumping unit 14 mates.

In this embodiment, when each pumping unit 14 is in its docked configuration, a position from which the control wire 38 of each pumping unit 14 extends from the proximal end 40 of the elongate body 80 of that pumping unit and a position of the proximal guide hole 36 in the proximal end abutment 34 associated with the receiving surface 24 of the docking unit 16 with which the docking surface 53 of the elongate body 80 of that pumping unit mates are located, one with respect to the other, such that when the control wire 38 of that pumping unit 14 is tensioned, the docking surface 53 of the elongate body 80 of that pumping unit 14 is biased towards the receiving surface 24 of the docking unit 16 with which the docking surface 53 of the elongate body 80 of that pumping unit 14 mates.

Figure 95:
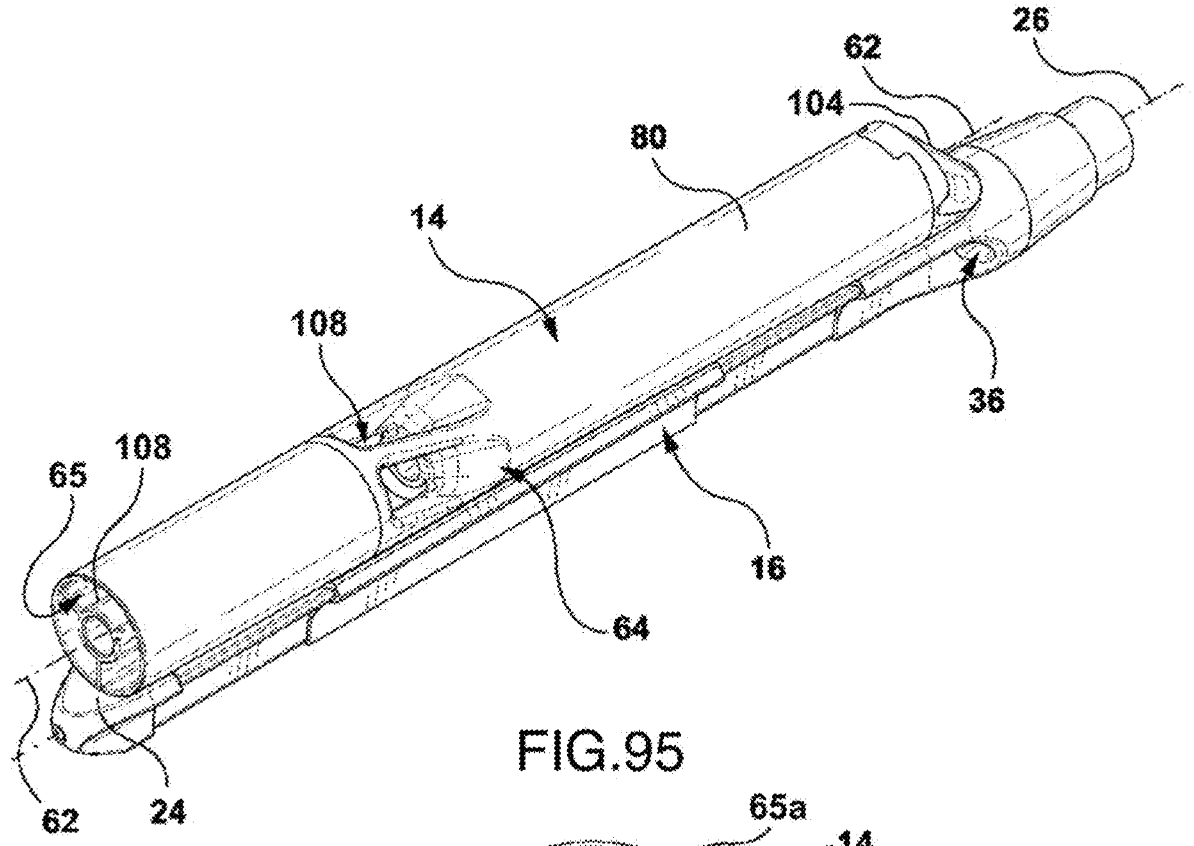
FIG. 95 is a distal end isometric view of the pumping unit of the VAD of FIG. 87 shown in FIG. 94 in its docked configuration with the docking unit of the VAD.
Figure 96:
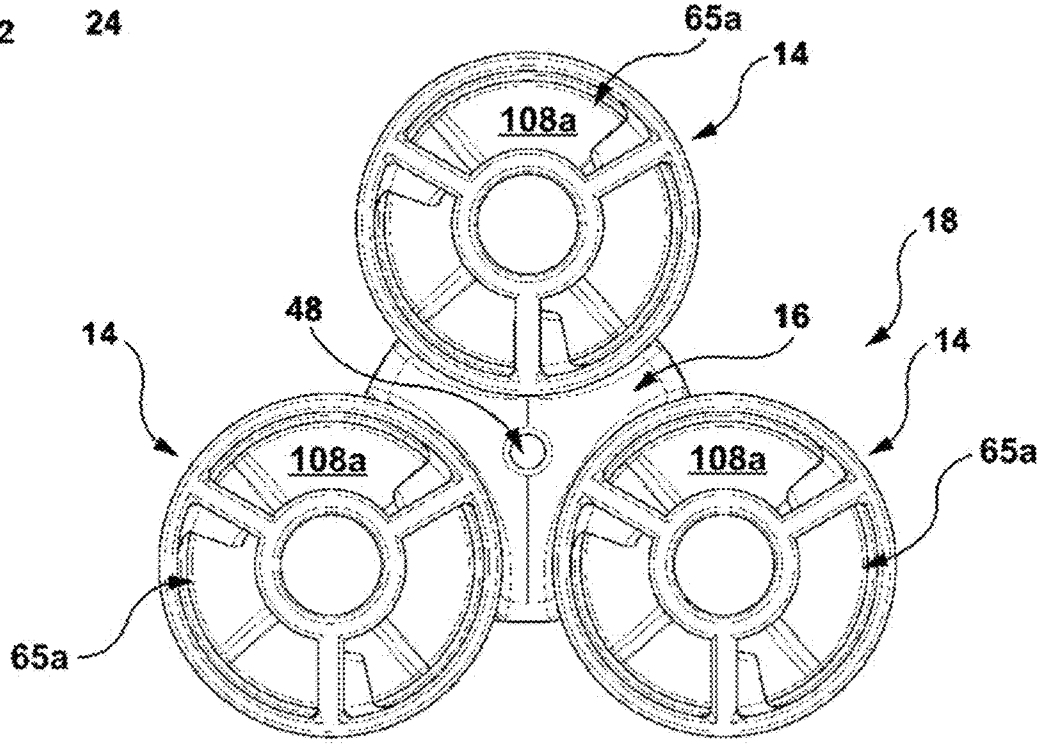
FIG. 96 is a distal end view of the VAD of FIG. 87, as shown in FIG. 88 in an assembled configuration.

Referring to FIGS. 88 and 95, when each of the pumping units 14 is in its docked configuration, the abutment contacting surface 102 of the proximal end 40 of the elongate body 80 of each pumping unit 14 mates with one of the proximal end abutments 34 of the docking unit 16, and unmated exterior-facing portions 104 of the proximal end 40 of the elongated body 80 of each of the pumping units 14 are each sloped towards the apex 100 of the proximal end 40. Further, when each of the pumping units 14 is its docked configuration fluid flow channels 106 (FIG. 88) are located intermediate any two of the pumping units 14.

Device Delivery & Assembled Configuration

Figure 87:
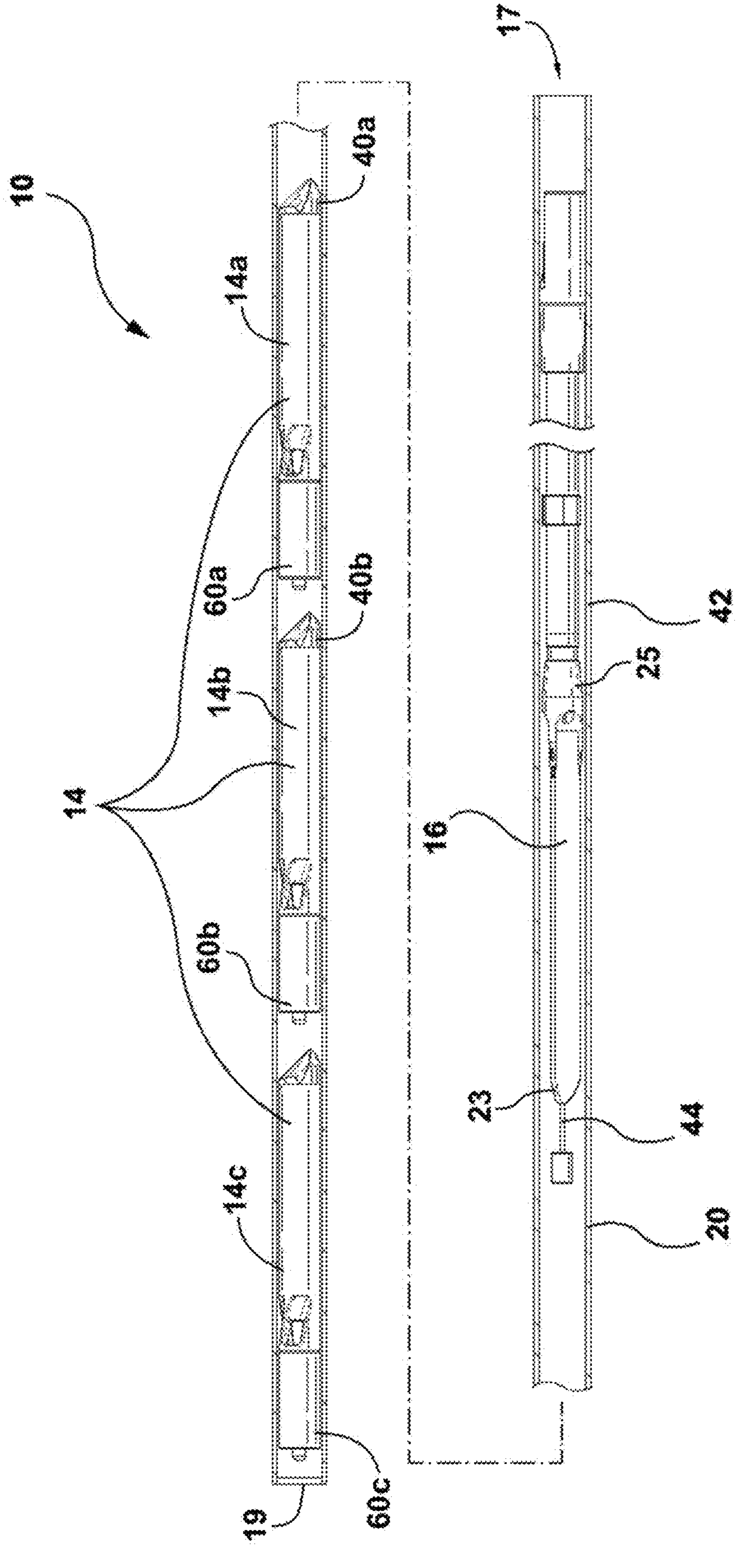
FIG. 87 is a schematic side view of a first embodiment of the present technology, a ventricular assist device (VAD), shown in a delivery configuration in a sheath.

FIG. 87 shows a schematic of the VAD 10 in its delivery configuration within a sheath 20. For ease of understanding certain elements (e.g., the control wires 38 of the various pumping units 14) are not shown in FIG. 87. In the delivery configuration, each of the pumping units 14 is in an undocked configuration with the longitudinal axes of each being generally colinear. The sheath 20 has a proximal end 17 and a distal end 19 (which are defined relative to the orientation of the device during implantation). Nearest to the distal end 19 of the sheath 20 is the third pumping unit 14*c*, orientated with its distal end 60*c* closer to the distal end 19 of the sheath 20 and its proximal end 40*c* closer to the proximal end 17 of the sheath 20. Next to and proximal to the third pumping unit 14*c* is the second pumping unit 14*b*. The second pumping unit 14*b* is oriented with its distal end 60*b* closer to the distal end 19 of the sheath 20 and its proximal end 40*b* closer to the proximal end 17 of the sheath 20. Next to and proximal to the second pumping unit 14*b* is the first pumping unit 14*a*. The first pumping unit 14*a* is oriented with its distal end 60*a* loser to the distal end 19 of the sheath 20 and its proximal end 40*a* closer to the proximal end 17 of the sheath 20. Next to and proximal to the first pumping unit 14*a* is the docking unit 16. The docking unit is oriented with its distal end 23 closer to the distal end 19 of the sheath 20 and its proximal end 25 closer to the proximal end 17 of the sheath 20. (FIGS. 65-67 described below show a similar schematic to that in FIG. 87 but illustrating the control wires 7038 as well.)

FIG. 88 shows the VAD 10 in its assembled configuration. In the assembled configuration, each of the pumping units 14 is in its docked configuration. As has otherwise been described herein, at the implantation site, the surgeon brings the pumping units 14 from the undocked configuration to their docked configuration by pulling their control wires (not shown in FIG. 88). The largest diameter of the device in the assembled configuration is about 16 mm. The flow rate of VAD 10 may vary between 1.0 L/min and 5.0 L/min, with a generally operating flow rate of 2.5 L/min.

Anchor Assembly

Referring to FIGS. 89 and 90, the docking unit 16 has an anchor assembly 56 connected to the elongate body 22. The anchor assembly 56 has an anchored configuration (in which the docking unit 16 is mechanically anchored in place at the implementation site) and an unanchored configuration (in which the docking unit 16 is not anchored in place at the implementation site). The anchor assembly 56 is biased towards the anchored configuration. Insertion of the anchor assembly 56 into the delivery sheath 20 (FIG. 87) causes the anchor assembly 26 to convert to its unanchored configuration. Removal of the anchor assembly 56 from the delivery sheath causes the anchor assembly 56 to convert to its anchored configuration. Distal anchor assembly 56 is connected to the docking unit 16 via wire 44.

In other embodiments, the anchor assembly 56 is actuatable at the implantation site to convert between the unanchored configuration and the anchored configuration to anchor the docking unit 16 at the implantation site. In some such embodiments, there is an anchor assembly actuation wire (not shown) disposed within the central cavity 48 of the elongated body 22. The anchor assembly actuation wire is operatively connected to the anchor assembly 56 to actuate conversion of the anchor assembly 56 between the anchored configuration and the unanchored configuration.

Schematics

Figure 1:
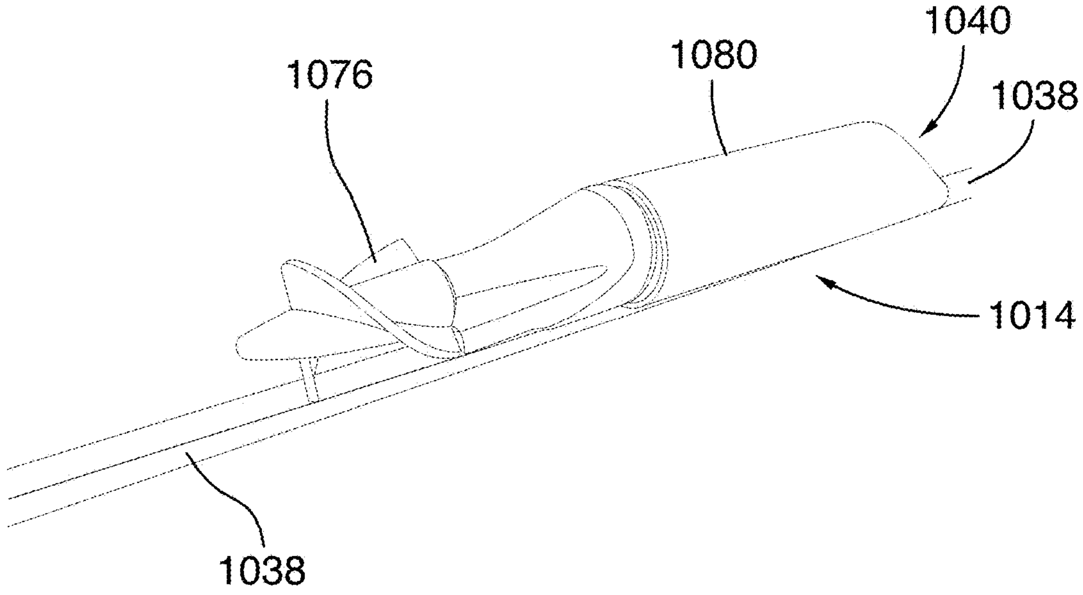
FIGS. 1 to 57 are schematic figures illustrating the configuration, implantation, and use of a second embodiment of the present technology, a ventricular assist device (VAD).
Figure 57:
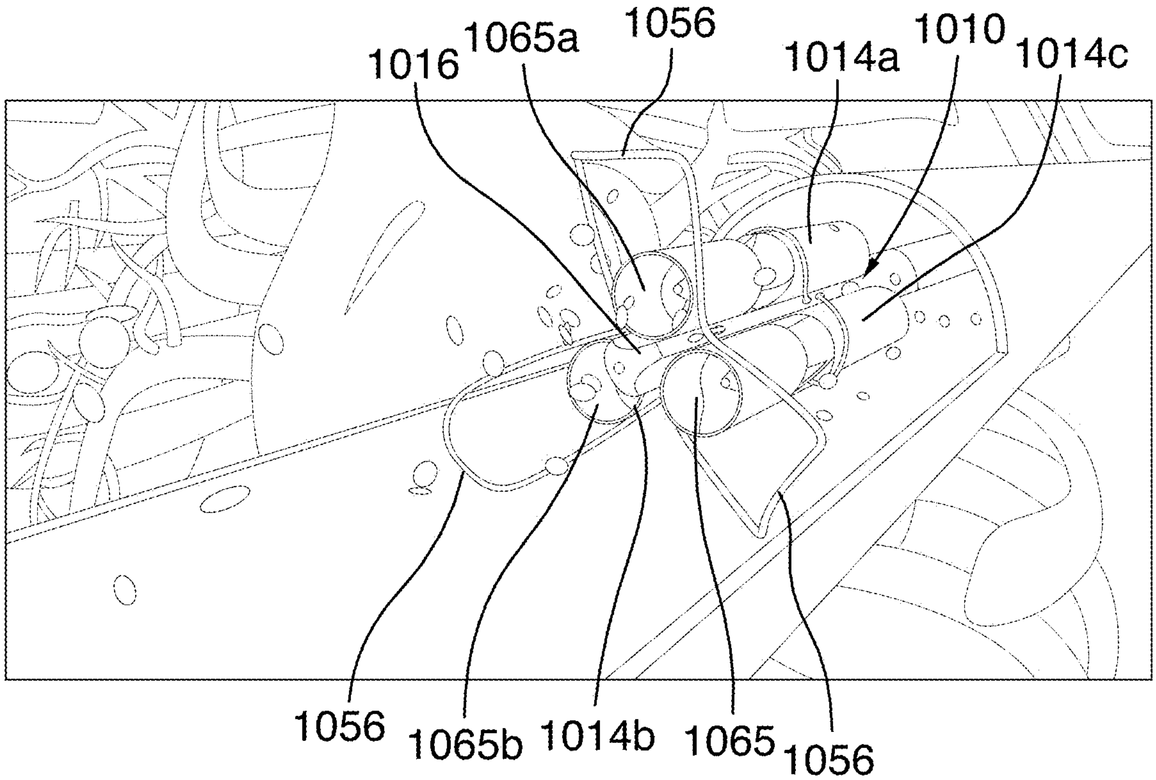

FIGS. 1-57 are schematic figures illustrating the configuration, implantation, and use of an embodiment of the present technology, a ventricular assist device (VAD) 1010, which is very similar to VAD 10. It should be understood that these figures are only meant to be illustrative and instructive to the skilled addressee. The figures are not meant to be engineering drawings. In some cases, elements of the device and/or human anatomy may have been illustrated only in approximation and/or are missing, as true-to-life detail is not believed to be necessary for the understanding of the skilled addressee. In addition, conventional methods and/or steps may not have been shown, as they would be readily understood by the skilled addressee.

FIG. 1 illustrates a pumping unit 1014 of the VAD. The shroud surrounding the impeller 1076 at the distal end of the elongate body 1080 has been removed for illustrative purposes. The control wires 1038 of the pumping unit 1014 and of other pumping units (not shown) can be seen. The proximal end 1040 of the elongate body 1080 is shown. The view in FIG. 1 is taken from the distal end of the unit.

Figure 2:
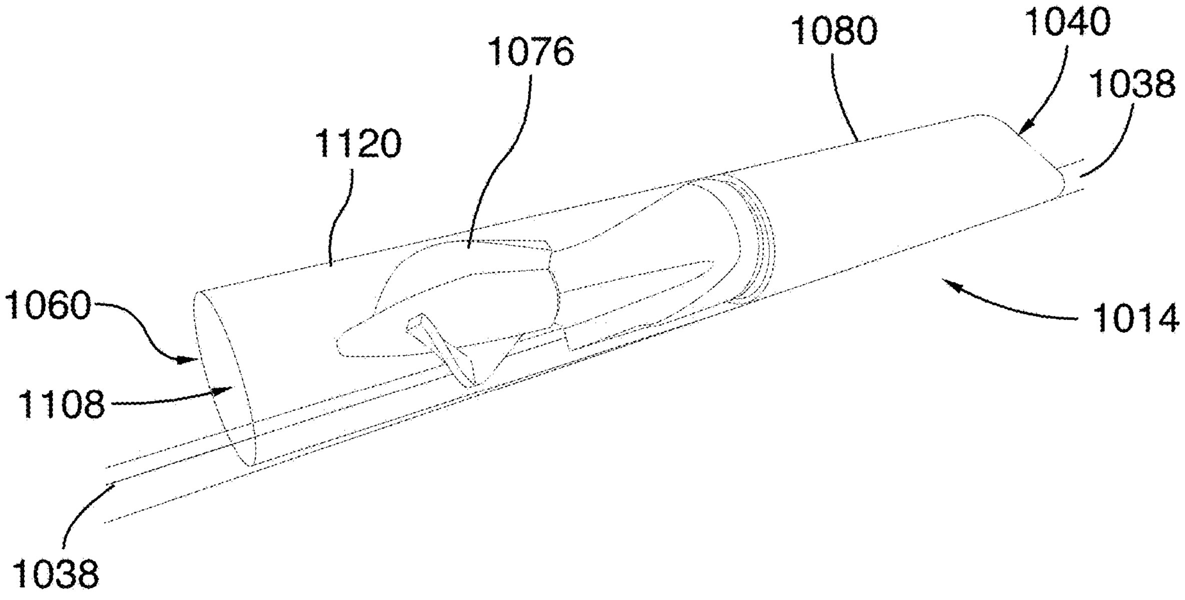

FIG. 2 is similar to FIG. 1 except that the shroud 1120 is now transparently shown, allowing for visualization of the flow cavity 1108 within the pumping unit 1014. The shroud 1120 forms part of the elongate body 1080 of the pumping unit 1014, and the distal end 1060 of the elongate body 1080 is shown.

Figure 3:
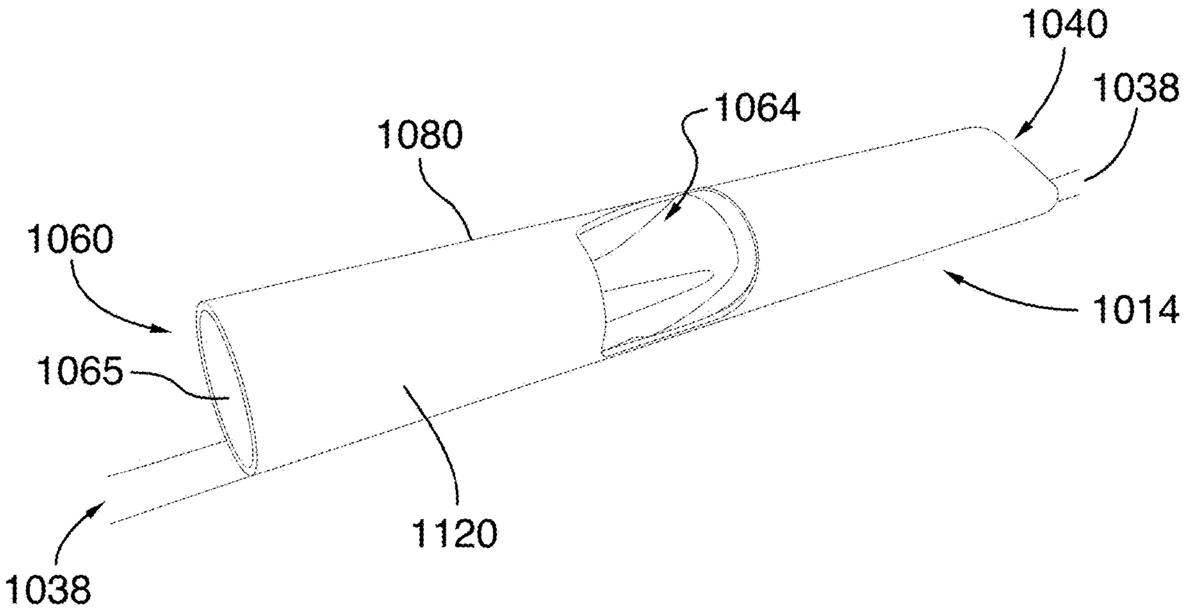

FIG. 3 is similar to FIG. 2 except that the shroud 1120 is now opaquely shown, allowing for visualization of the first set of openings 1064 into the flow cavity in the side of the elongate body 1080 and the second opening 1065 into the flow cavity at the distal end 1060 of the elongate body 1080 to be shown.

Figure 4:
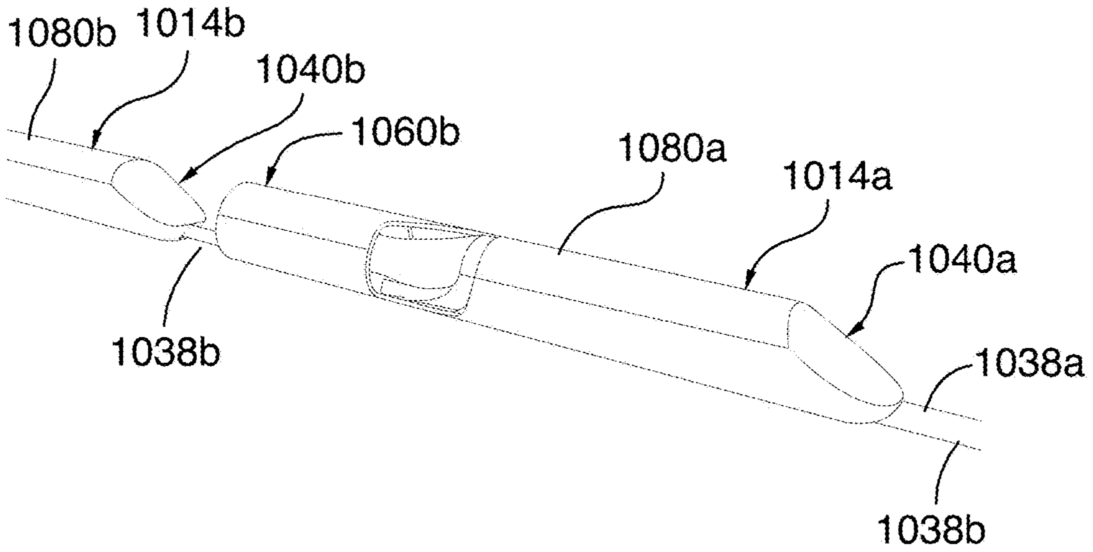

FIG. 4 shows the pumping unit of FIGS. 1-3 being a first pumping unit 1014*a*. A second pumping unit 1014*b*, similar to the first pumping unit 1014*a* is also shown. The proximal end 1040*b* of the second pumping unit 1014*b* faces the distal end 1060*a* of the first pumping unit 1014*a*. The longitudinal axes (not shown) of the elongate bodies 1080*a*, 1080*b* are generally colinear. The control wires 1038*a*, 1038*b* of the first pumping unit 1014*a* and the second pumping unit 1014*b* (respectively) are shown. The view in FIG. 4 is taken from the proximal end of the first pumping unit.

Figure 5:
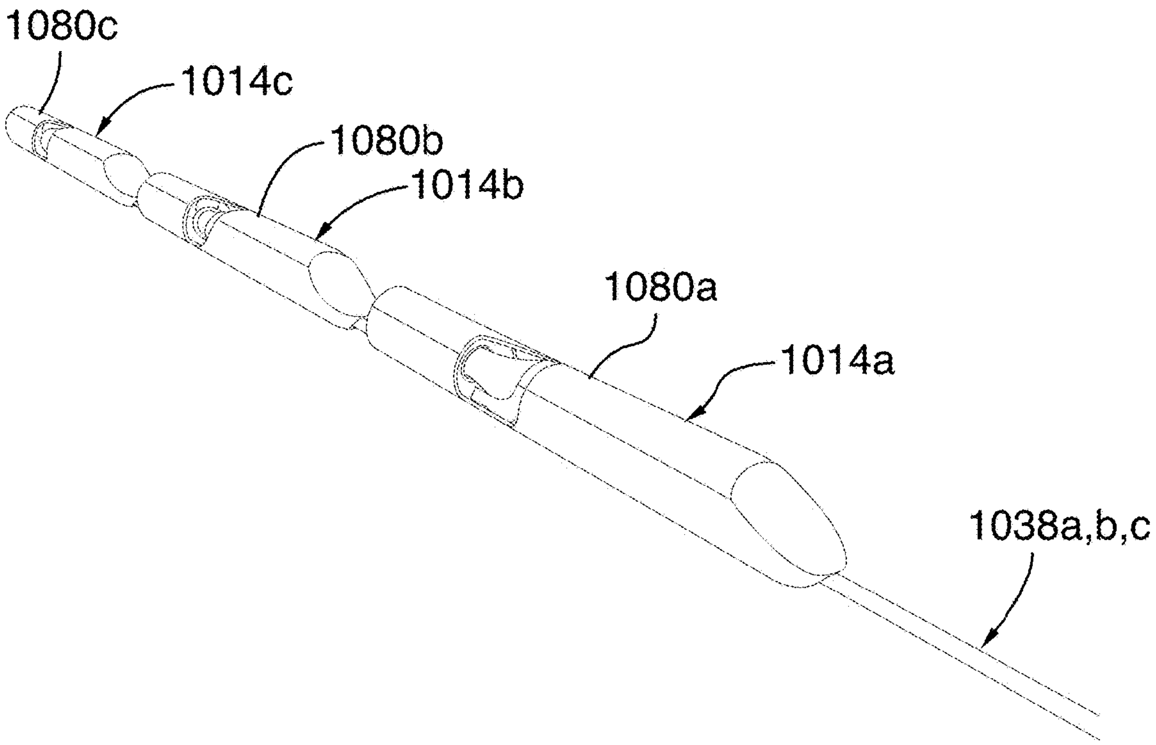

FIG. 5 is similar to FIG. 4 except that three pumping units 1014*a*, 1014*b*, 1014*c* are shown. The longitudinal axes (not shown) of the elongate bodies 1080*a*, 1080*b*, 1080*c* are generally colinear. The control wires 1038*a*, 1038*b*, 1038*c* of each of the pumping units 1014*a*, 1014*b*, 1014*c* (respectively) are also shown. Each of the pumping units 1014*a*, 1014*b*, 1014*c* are in their undocked configuration.

Figure 6:
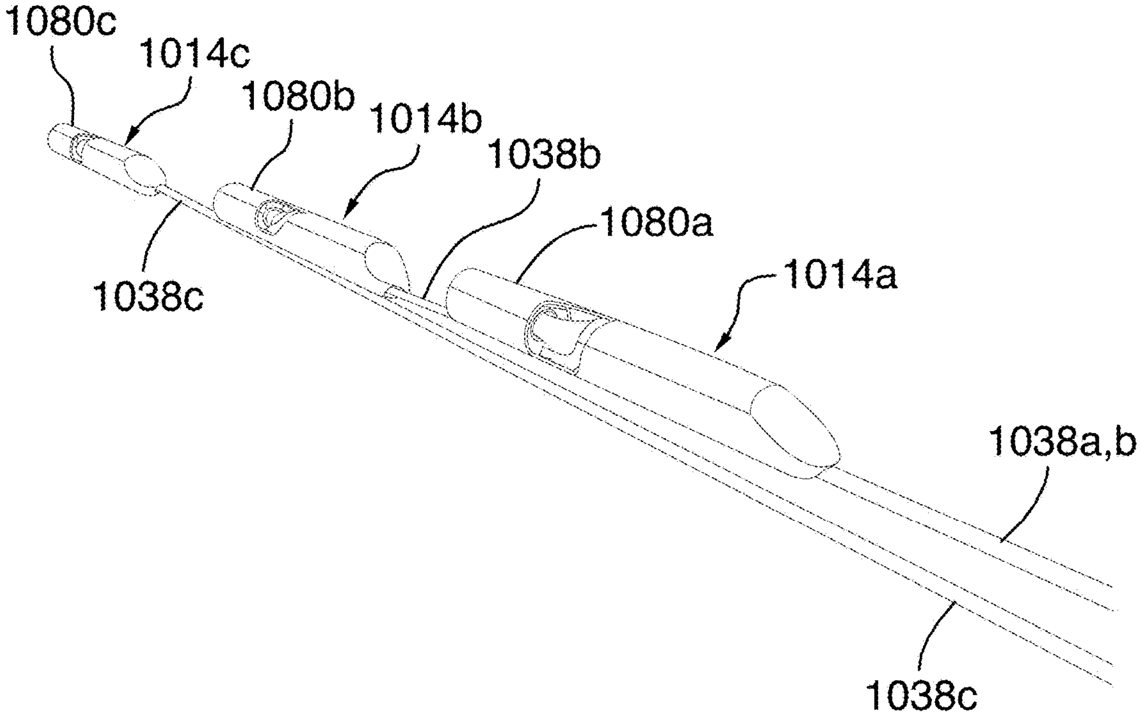

FIG. 6 is similar to FIG. 5 except the three pumping units 1014*a*, 1014*b*, 1014*c* are shown such that the longitudinal axes (not shown) of the elongate bodies 1080*a*, 1080*b*, 1080*c* are no longer generally colinear. The control wires 1038*a*, 1038*b*, 1038*c* of each of the pumping units 1014*a*, 1014*b*, 1014*c* (respectively) are also shown.

Figure 7:
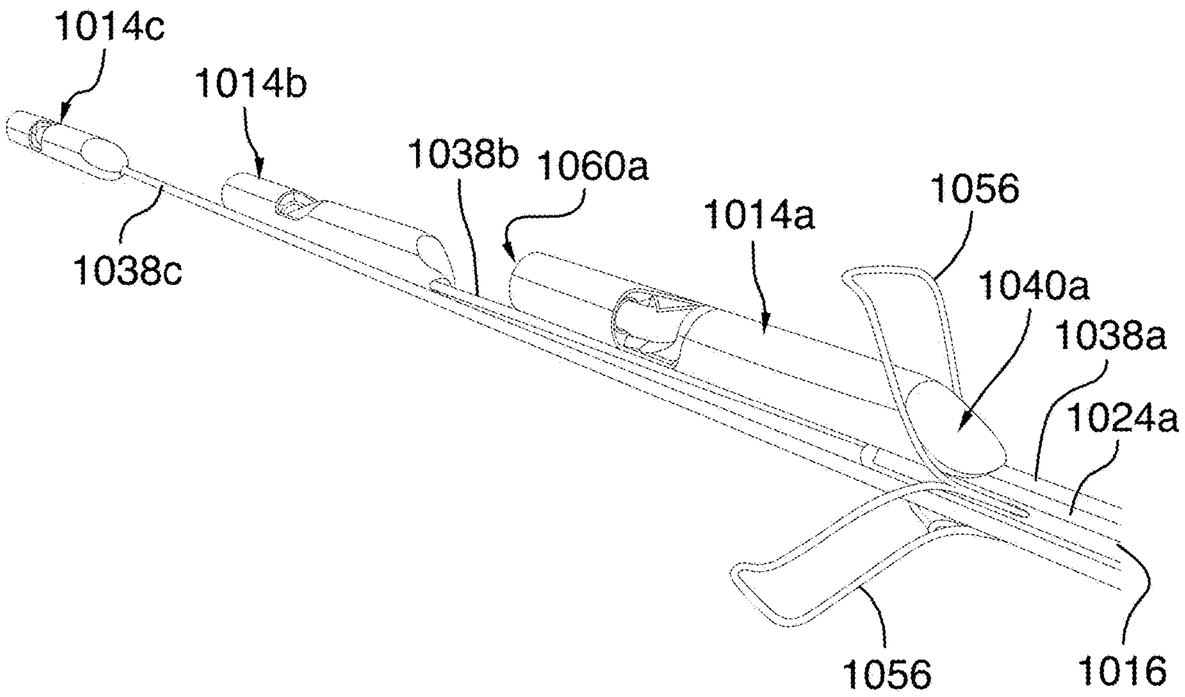

FIG. 7 is similar to FIG. 6, except that docking unit 1016 is shown. The first pumping unit 1014*a* has been pulled forward by its control wire 1038*a* having been pulled so that its docking surface (not shown) will slide along the first receiving surface 1024*a* of the docking unit 1016. In FIG. 7, the proximal end 1040*a* of the first pumping unit 1014*a* is shown between portions of the anchor assembly 1056 of the docking unit 1016.

Figure 8:
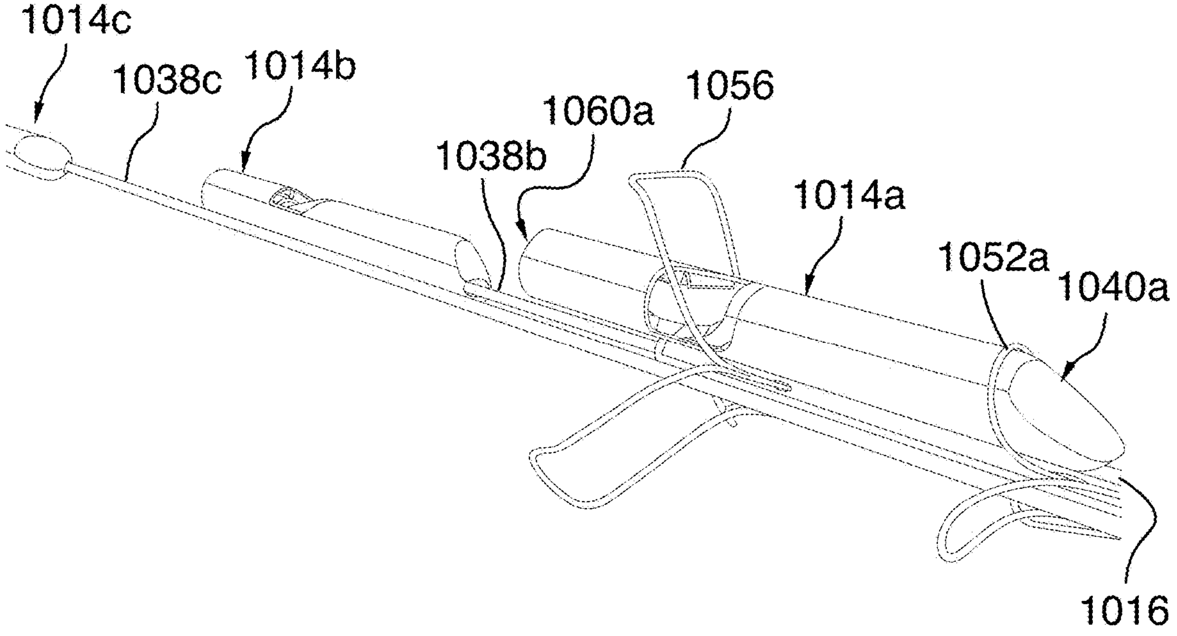

FIG. 8 is similar to FIG. 7, except that the first pumping unit 1014*a* has been pulled even further forward by its control wire 1038*a* having been pulled so its docking surface has slid further along the first receiving surface 1024*a* of the docking unit 1016. In FIG. 8, the proximal end 1040*a* of the first pumping unit 1014*a* is shown entering the first retaining element 1052*a* which will retain the first pumping unit 1014*a* in place when the first pumping unit 1014*a* is in its docked configuration.

Figure 9:
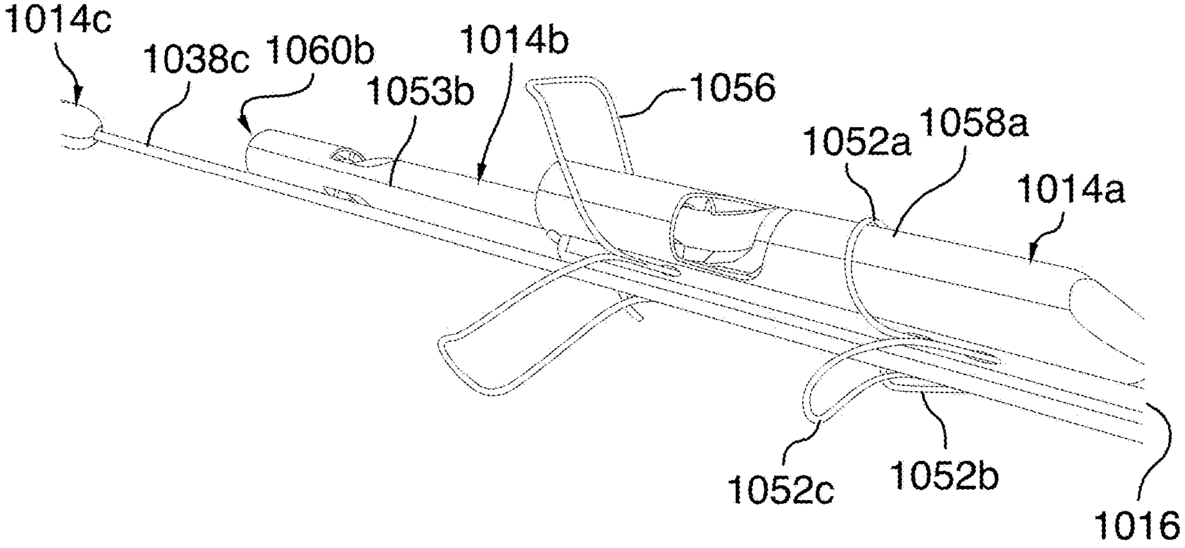

FIG. 9 is similar to FIG. 8, except that the first pumping unit 1014*a* has been pulled even further forward by its control wire 1038*a* having been pulled so that its docking surface has slid further along the first receiving surface 1024*a* of the docking unit 1016 such that that docking surface and the first receiving surface 1024*a* mate with one another. The first pumping unit 1014*a* is thus in its docked configuration. In FIG. 8, the first retaining element 1052*a* is biased against the exterior side wall 1058*a* of the elongate body 1080*a* of the first pumping unit 1014*a*, retaining it in place. The distal end 1060*a* of the first pumping unit 1014*a* is between the portions of the anchor assembly 1056 of the docking unit 1016. The second pumping unit 1014*b* has been pulled forward by its control wire 1038*b* having been pulled such that it is in a position similar to that of the first pumping unit 1014*a* in FIG. 7. The docking surface 1053*b* of the second pumping unit 1014*b* can be seen in FIG. 9.

Figure 10:
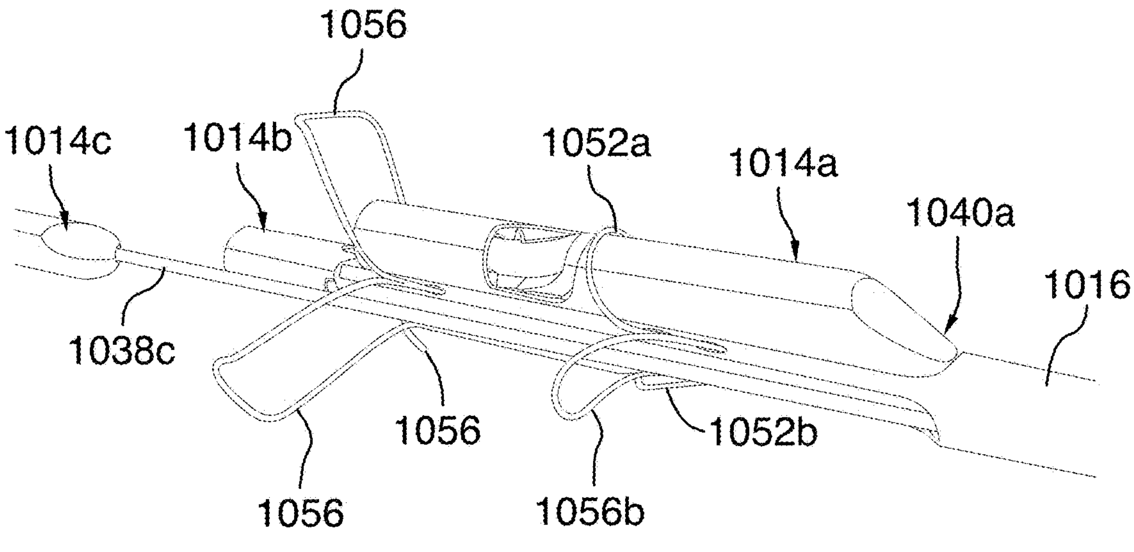

FIG. 10 is similar to FIG. 9, except that the second pumping unit 1014*b* has been pulled even further forward by its control wire 1038*b* having been pulled so that its docking surface 1053 has slid further along the second receiving surface (not shown) of the docking unit 1016. The second pumping unit 1014*b* is in a position similar to that of the first pumping unit 1014*a* in FIG. 8. The third pumping unit 1014*c* has been pulled slightly forward by its control wire 1038*c* having been pulled.

Figure 11:
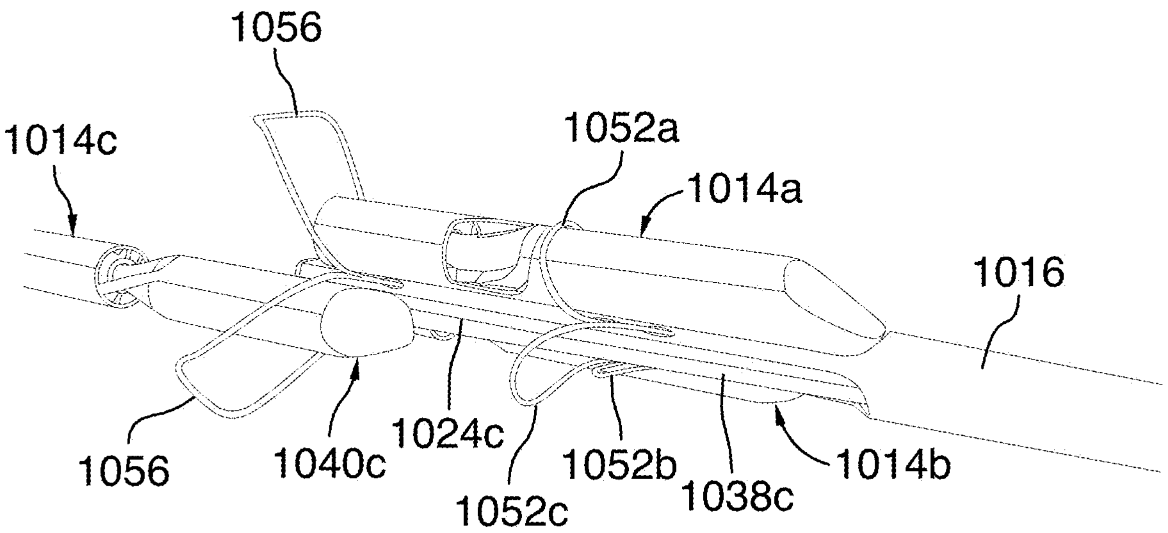

FIG. 11 is similar to FIG. 10, except that the second pumping unit 1014*b* has been pulled even further forward by its control wire 1038*b* having been pulled so that its docking surface 1053*b* has slid further along the second receiving surface of the docking unit 1016 such that the docking surface 1053*b* and the second receiving surface mate with one another. The second pumping unit 1014*b* is thus also in its docked configuration. In FIG. 11, the second retaining element 1052*b* is biased against the exterior side wall of the elongate body of the second pumping unit 1014*b*, retaining it in place. The third pumping unit 1014*c* has been pulled forward by its control wire 1038*c* having been pulled such that it is in a position similar to that of the first pumping unit 1014*b* in FIG. 7.

Figure 12:
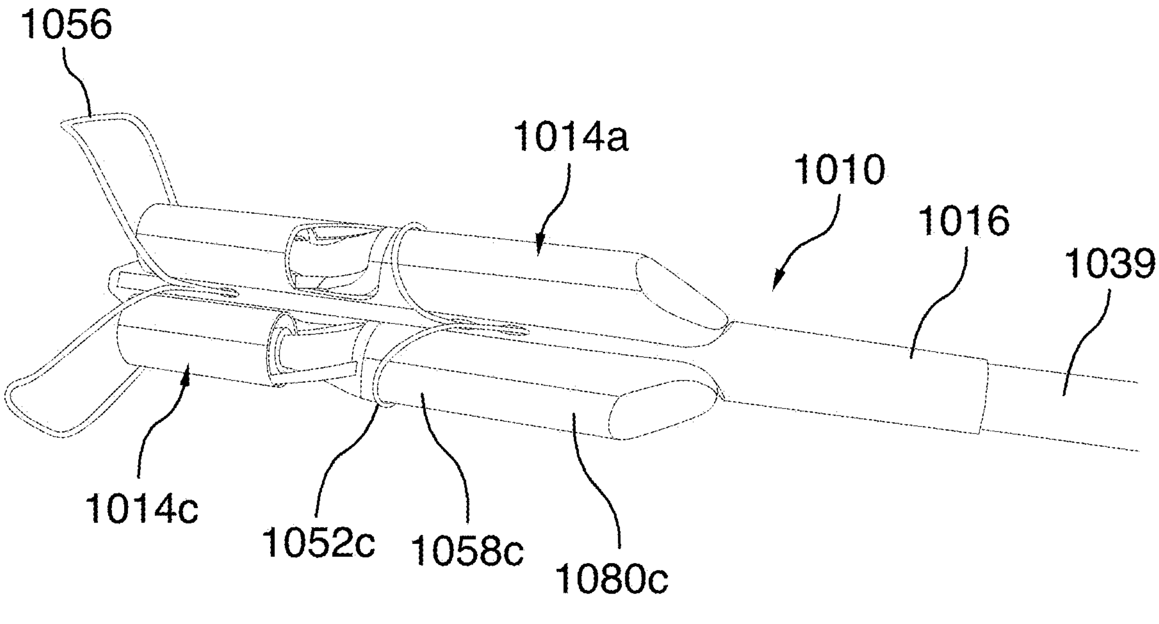

FIG. 12 is similar to FIG. 11, except that the third pumping unit 1014*c* has been pulled even further forward by its control wire 1038*c* having been pulled so that is docking surface (not shown) has slid further along the third receiving surface 1024*c* of the docking unit 1016 such that the docking surface and the third receiving surface 1024*c* mate with one another. The third pumping unit 1014*c* is thus also in its docked configuration. In FIG. 12, the third retaining element 1052*c* is biased against the exterior side wall 1058*c* of the elongate body 1080*c* of the third pumping unit 1014*c*, retaining it in place. In FIG. 12, the VAD 1010 is in its assembled configuration, as each of the pumping units 1014*a*, 1014*b*, 1014*c* are in their docked configuration. Also, as can best be seen by comparing FIGS. 11 and 12, the control wires 1038 of each pumping unit 1014 enter into the docking unit 1016 through guide holes and travel within a cavity (not shown) of the docking unit 1016 control cable 1039. This is why no control wires 1038 are shown in FIG. 12. As has been discussed hereinabove, movement of the control wires 1038 (e.g., pulling, pushing) is not impeded by their being within cavity of the control cable 1039.

Figure 13:
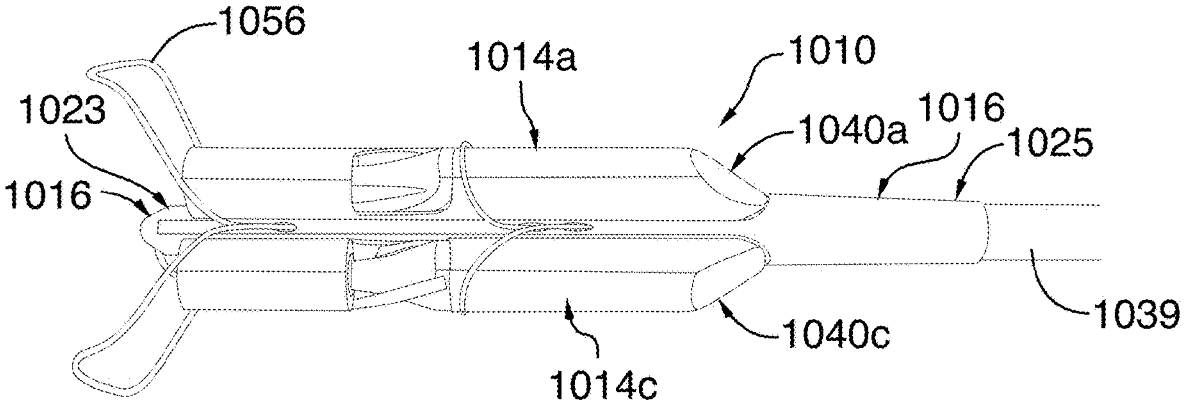

FIG. 13 is similar to FIG. 12 except that it is a view from the side of the device 1010. The device 1010 is still in its assembled configuration. The distal end 1023 of the docking unit 1016 is shown in FIG. 13 (as well as the proximal end 1025).

Figure 14:
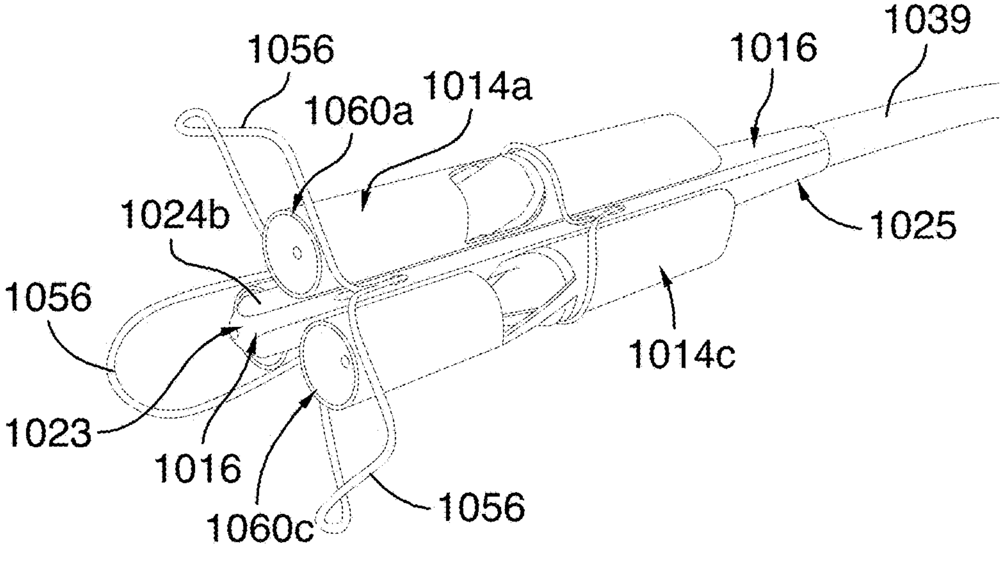

FIG. 14 is similar to FIG. 13 except that it is a view from the distal end of the device 1010. The device 1010 is still in its assembled configuration.

Figure 15:
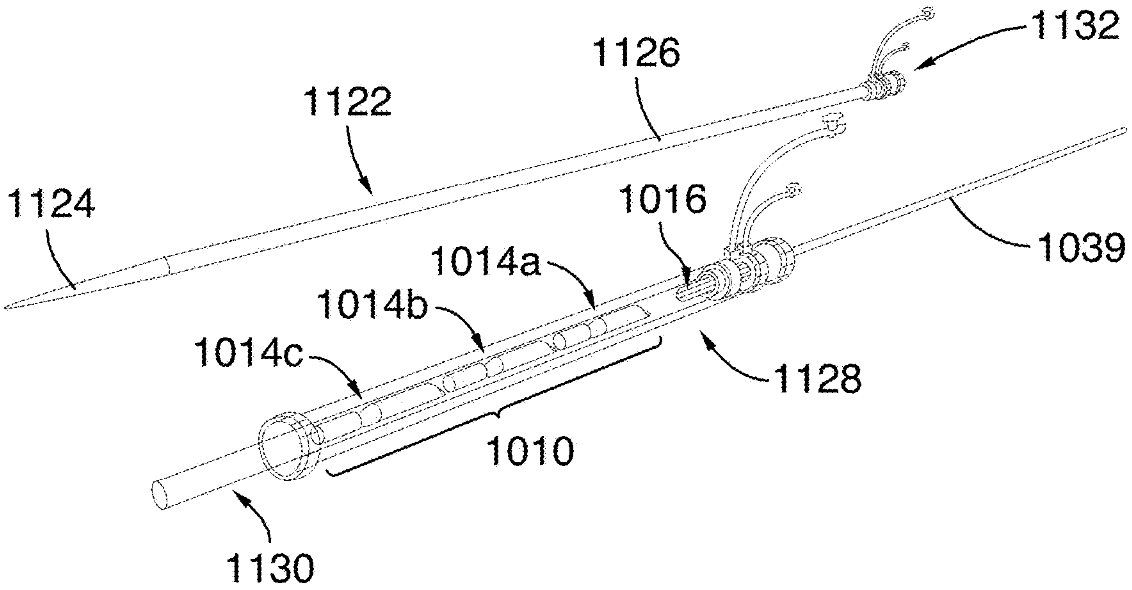

FIG. 15 shows the device 1010 prior to implantation into a human body (via, for example, a conventional Seldinger technique, in part). Specifically, there is shown an introducer 1122, which includes a dilator 1024 and a delivery sheath 1126. There is also shown a loader 1128, into which the device 1010 has been loaded (in its delivery configuration). The loader has a front end (distal) portion 1130 that is sized and shape to mate with a rear end (proximal) portion 1132 of the delivery sheath 1126. The control cable 1039 (with the control wires 1038 contained in the cavity thereof) extends from the rear end portion 1132 of the loader 1128. In FIG. 15 the loader 1128 is shown transparent to allow the device 1010 inside to be seen. The view in FIG. 15 is from the distal ends of the structures.

Figure 16:
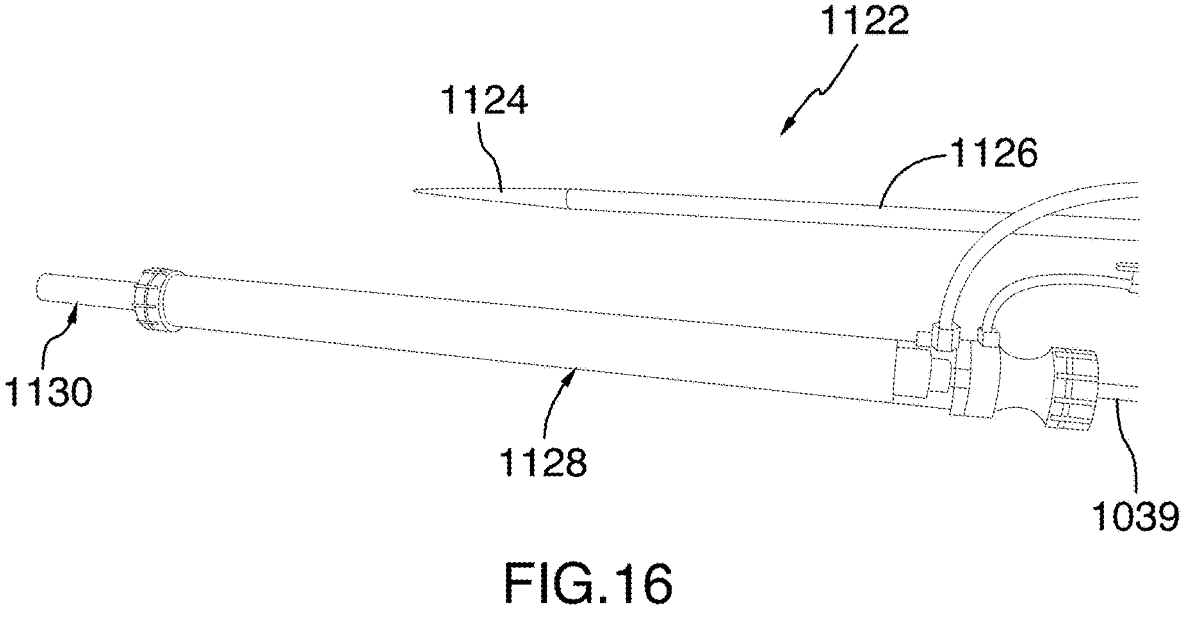

FIG. 16 is similar to FIG. 15 but shows a close-up view of the loader 1128 (shown opaquely).

Figure 17:
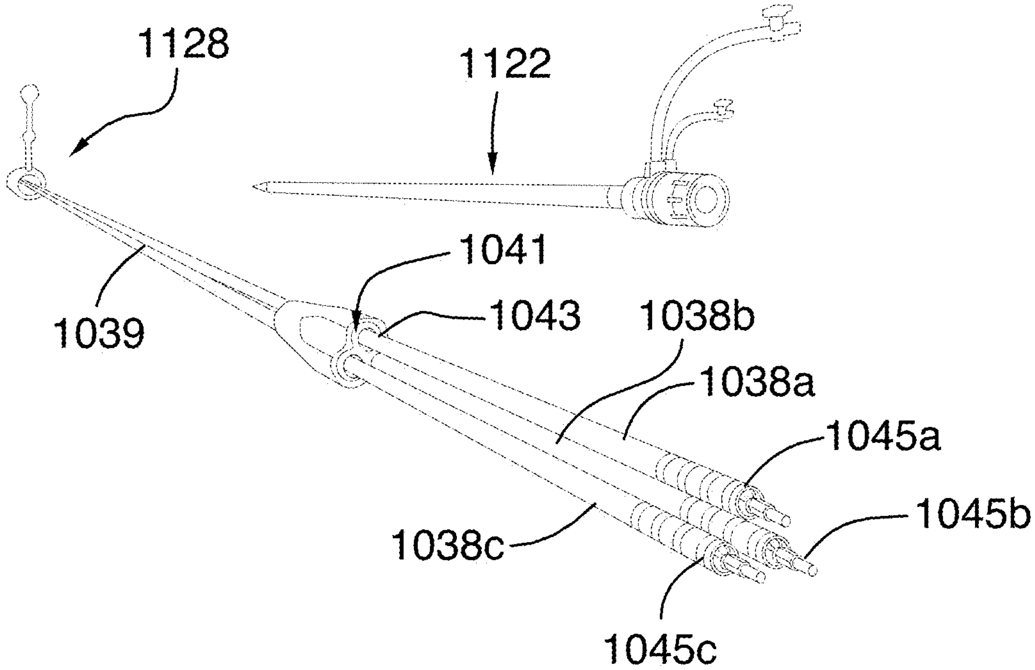

FIG. 17 is similar to FIG. 15, except that the view is form the proximal ends of the structures. The proximal end 1041 of the control cable 1039 of the docking unit 1016 is shown. Emerging from seals 1043 in the proximal end 1041 of the control cable 1039 of the docking unit 1016 are the proximal ends of the control wires 1038*a*, 1038*b*, 1038*c* of the pumping units 1014*a*, 1014*b*, 1014*c* (respectively). There is an electrical connector tip 1045*a*, 1045*b*, 1045*c* on each control wire 1038*a*, 1038*b*, 1038*c* (respectively). The control wires 1038 are both mechanically structural (they can be manually pulled and pushed) and electrical (they can carry electricity and electrical signals).

Figure 18:
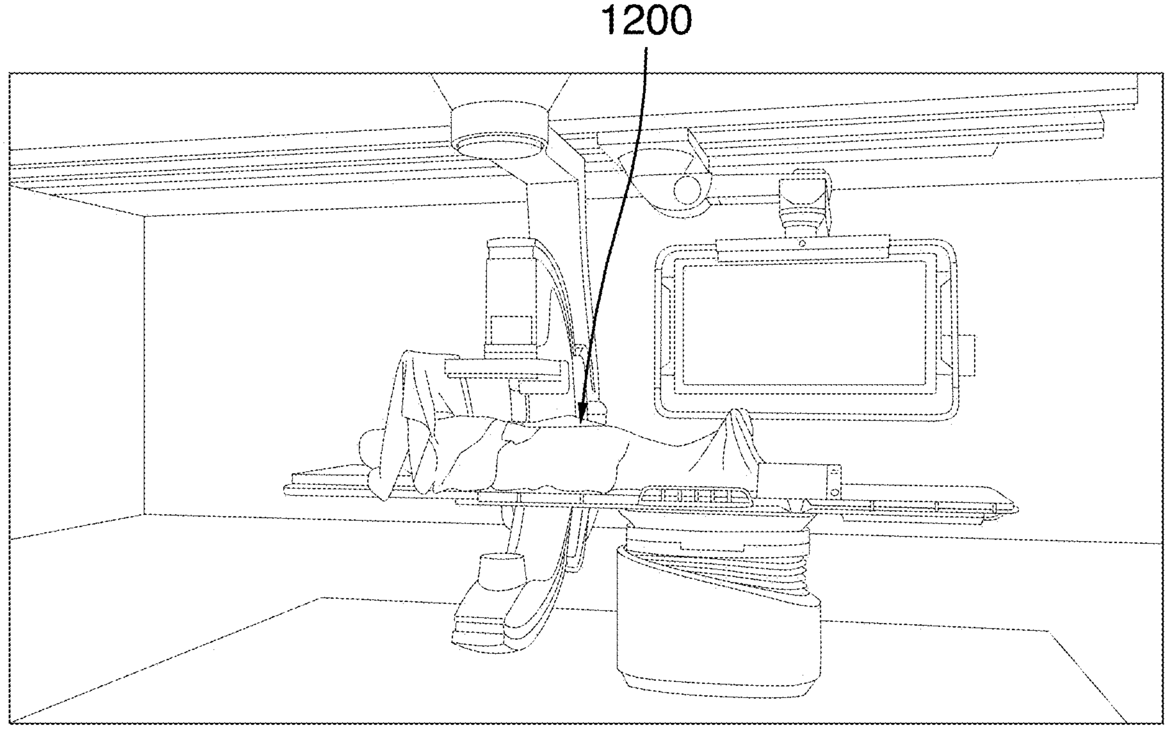

FIG. 18 shows a mock patient 1200 in a catheter lab, prepared for implantation of the device 1010.

Figure 19:
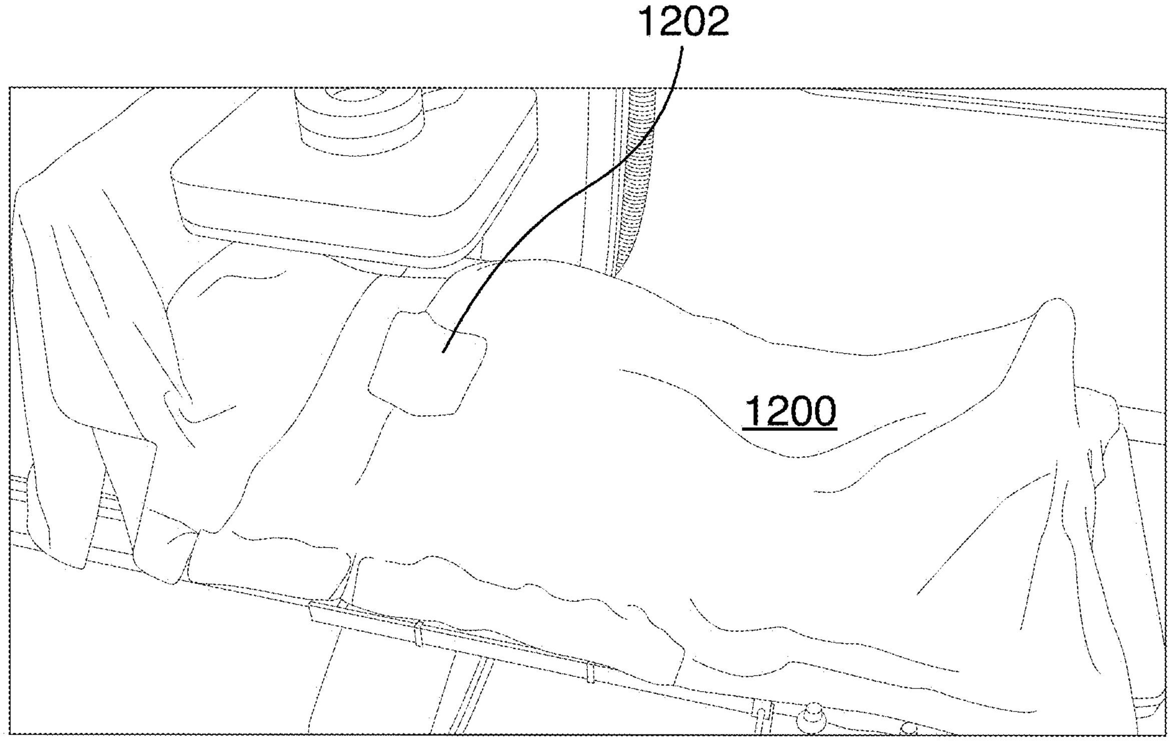

FIG. 19 shows the mock patient 1200 with a right femoral access area 1202 having been prepared (e.g., surgically).

Figure 20:
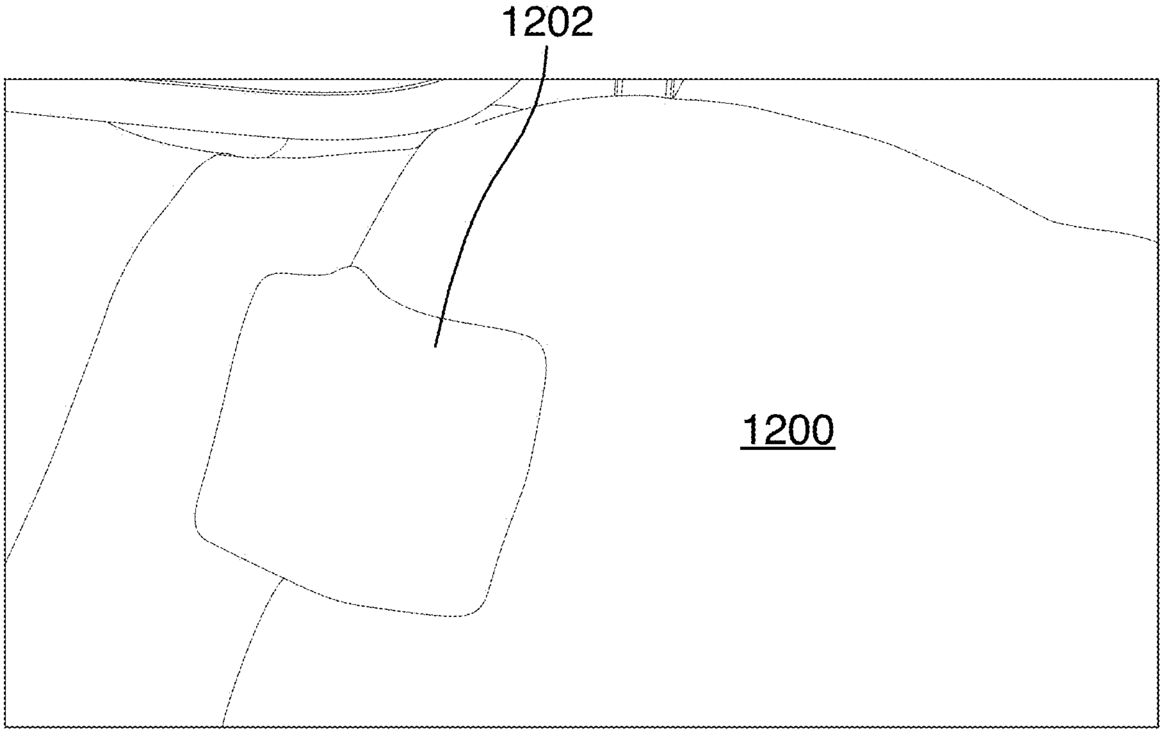

FIG. 20 shows a close-up of the right femoral access area 1202.

Figure 21:
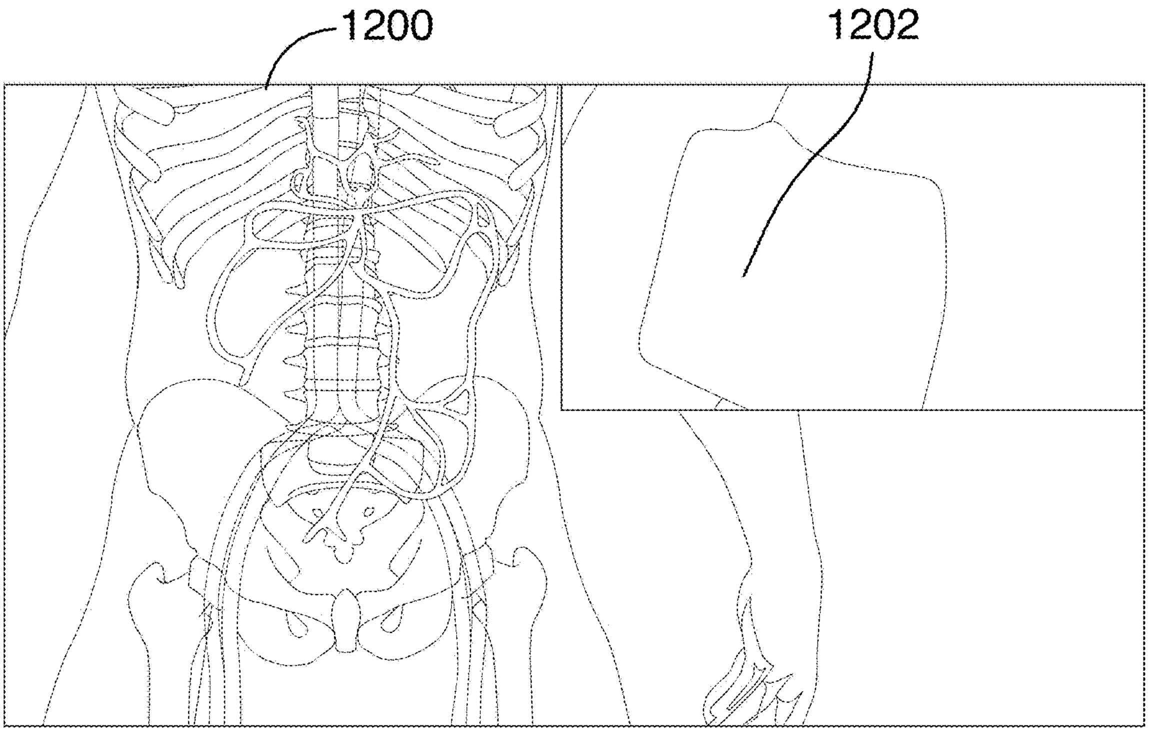

FIG. 21 shows a schematic view of portions of the patient's 1200 skeleton and vasculature. An inset of the right femoral access area 1202 is also shown.

Figure 22:
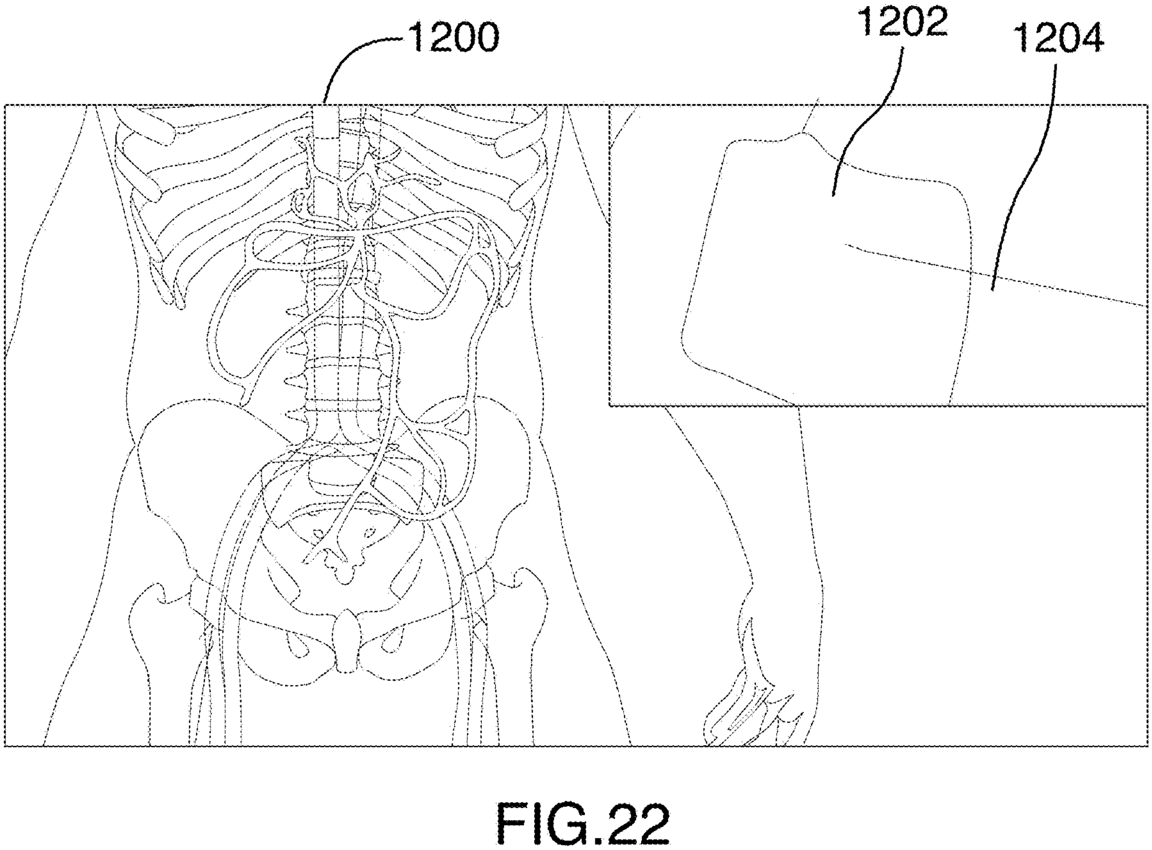

FIG. 22 is similar to FIG. 21, except that a guide wire 1204 (e.g., as part of a conventional minimal surgical intervention) is shown about to be inserted into the patient 1200.

Figure 23:
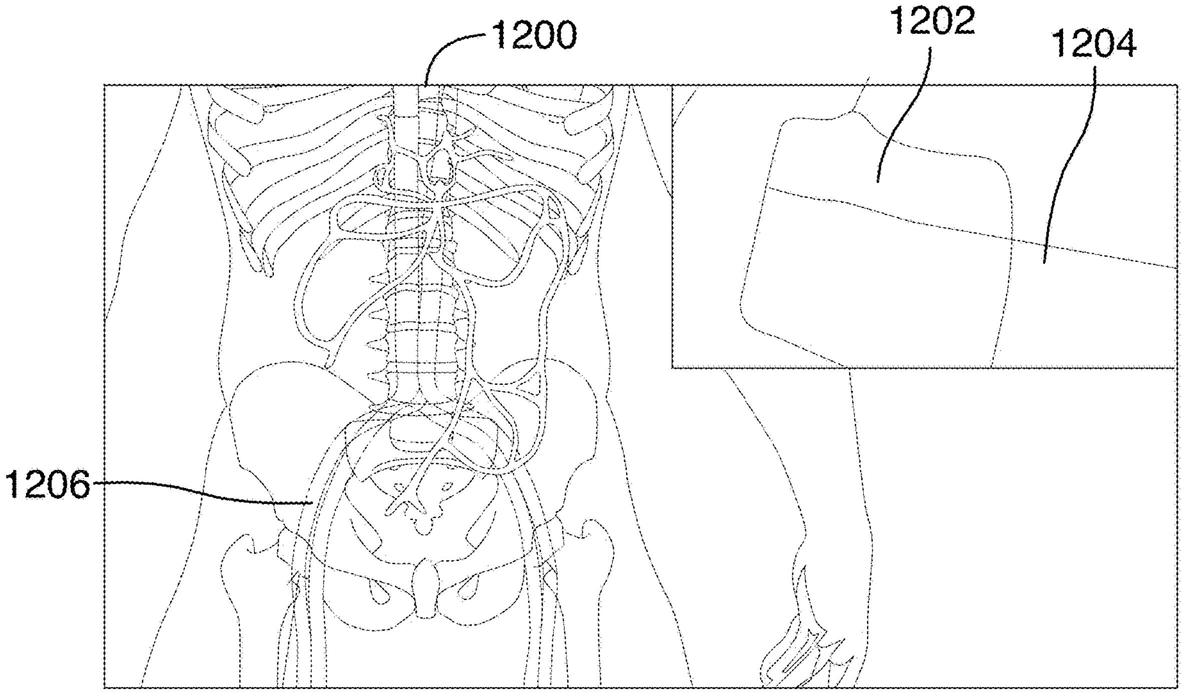

FIG. 23 is similar to FIG. 22, except that the guide wire 1204 has been inserted into the patent's 1200 right femoral artery 1206, which can be seen in the main image (as well as the insert).

Figure 24:
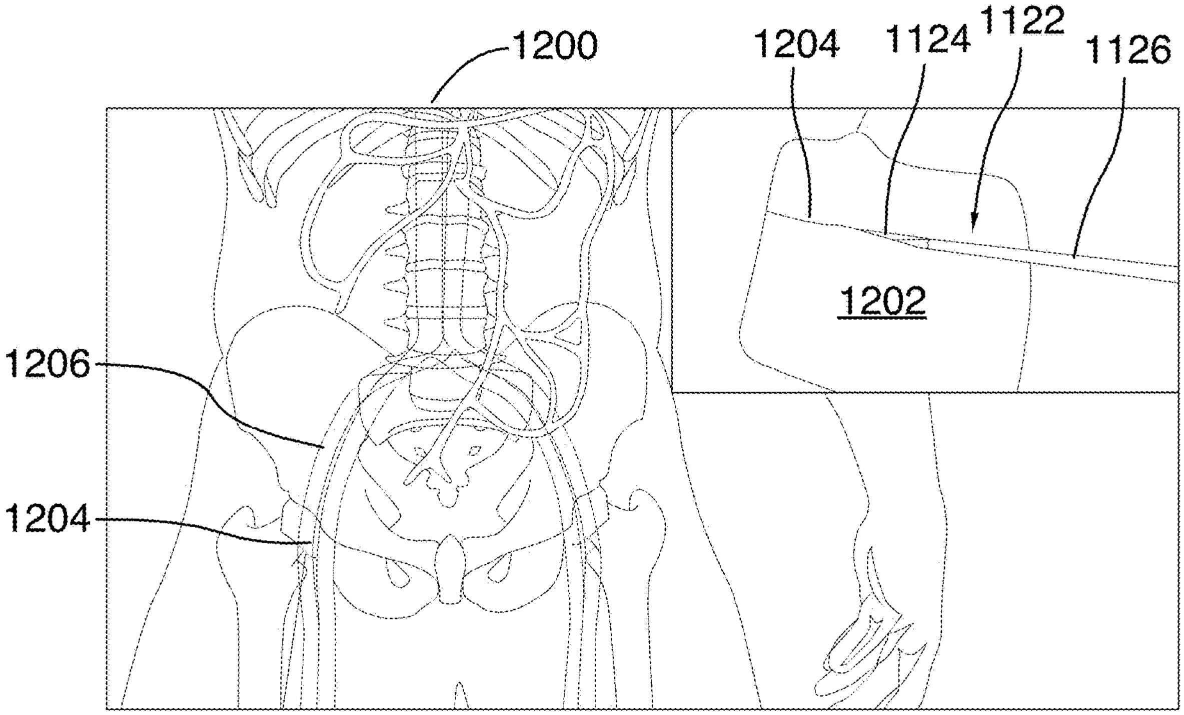

FIG. 24 is similar to FIG. 23, except that the introducer 1122 is shown about to be inserted into the patient 1200. Both the dilator 1124 and the delivery sheath 1126 of the introducer 1122 can be seen in the inset.

Figure 25:
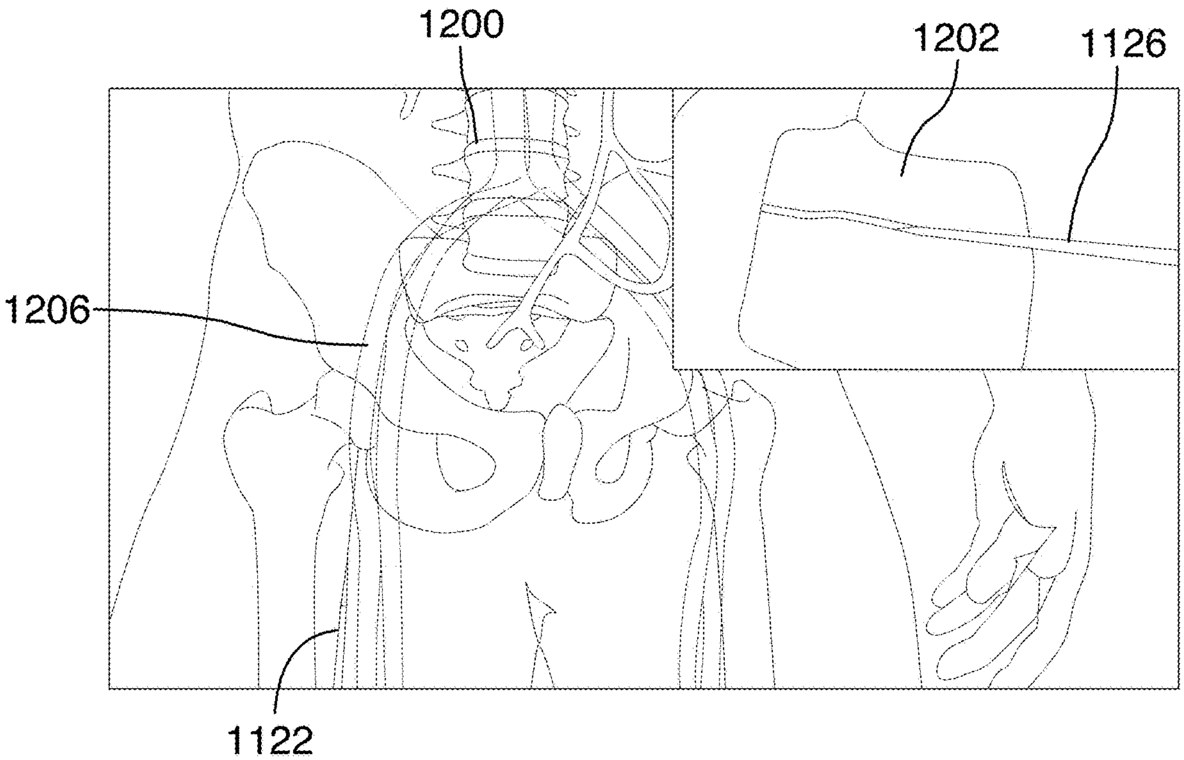

FIG. 25 is similar to FIG. 24, except that the introducer 1122 has been inserted into the patient's femoral artery 1206 (the introducer 1122 is railed along the guide wire 1204 by the surgeon, in a conventional manner).

Figure 26:
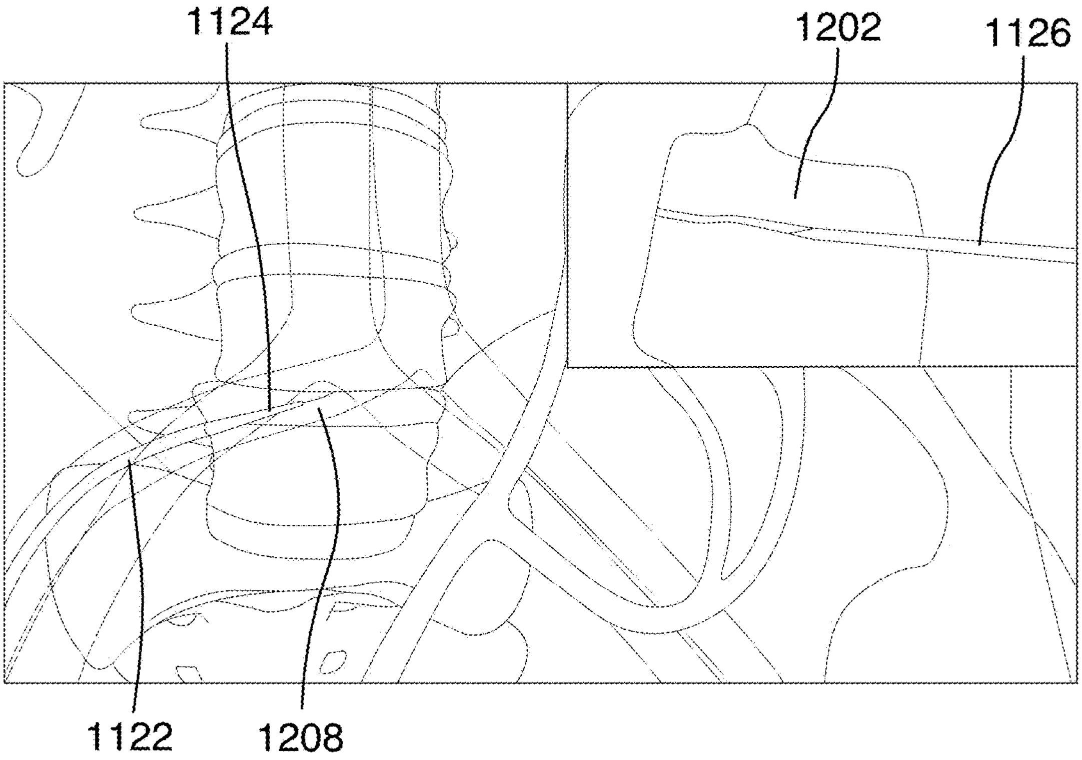

FIG. 26 is similar to FIG. 25, except that the introducer 1122 is now further into the patient's 1200 vasculature, at the patient's right common iliac artery 1208.

Figure 27:
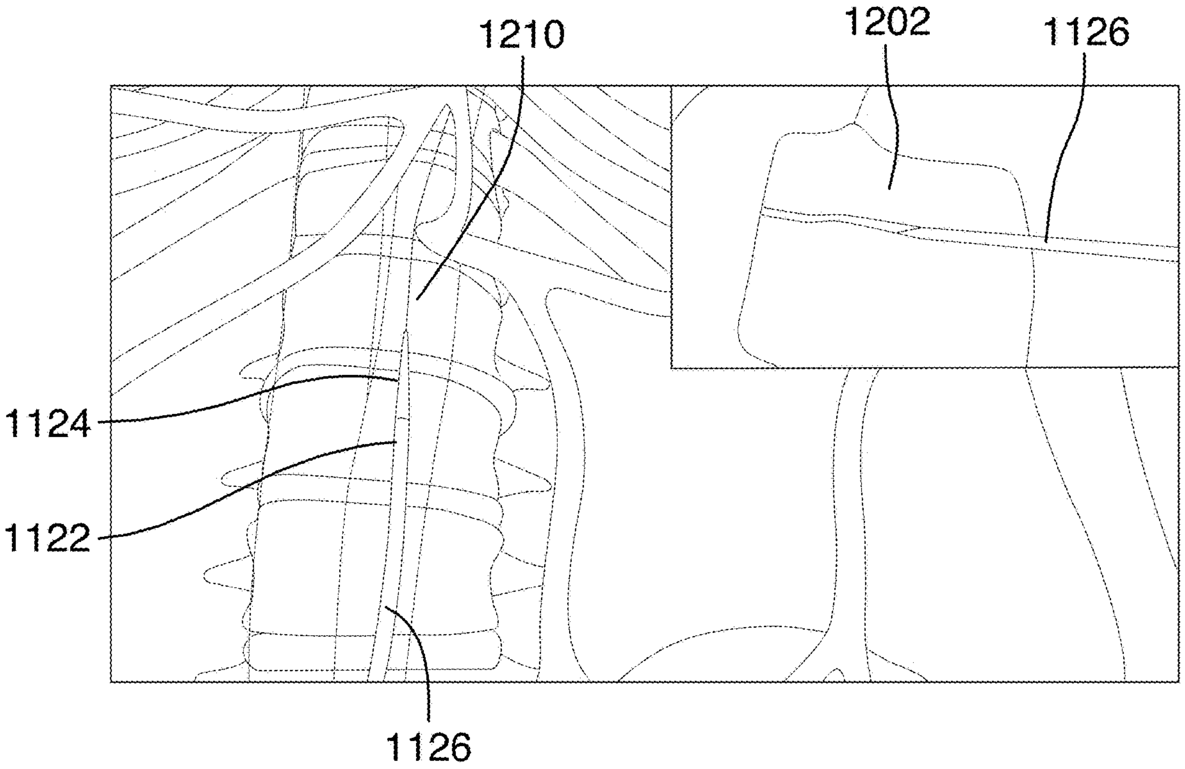

FIG. 27 is similar to FIG. 26, except that the introducer 1122 is now even further into the patient's 1200 vasculature, at the patient's descending abdominal aorta 1210.

Figure 28:
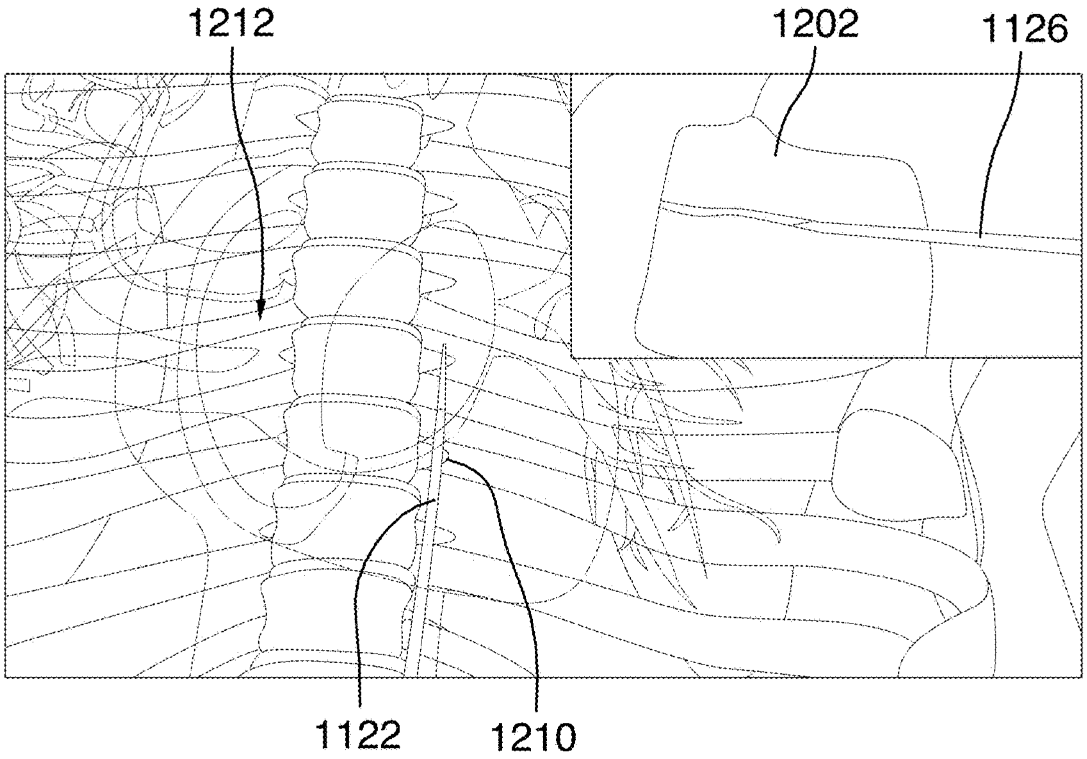

FIG. 28 is similar to FIG. 27, except that the introducer 1122 is now still further into the patient's 1200 vasculature, at the patient's descending thoracic aorta 1212, behind the patient's heart 1214 (in this view).

Figure 29:
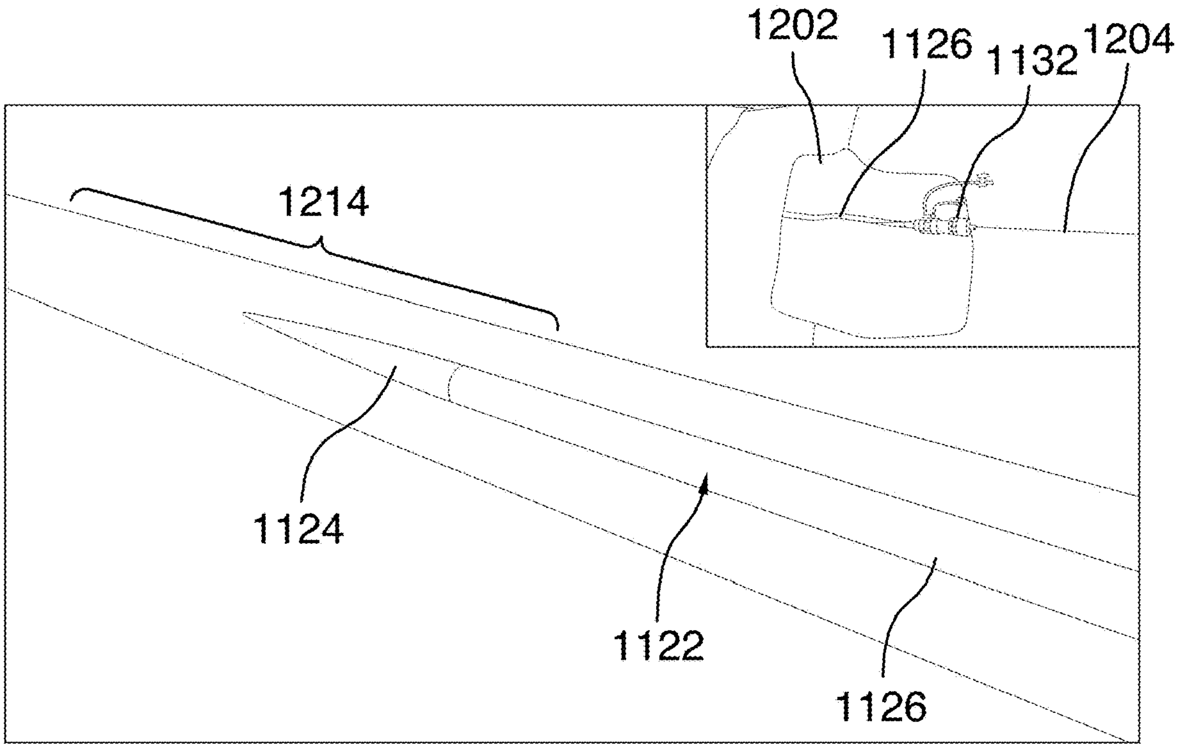

FIG. 29 shows a close-up view of the introducer at implantation site 1214 within the patient's aorta. As can be seen in the inset, the rear end 1132 of the introducer 1122 (and thus a portion of the delivery sheath 1126) remain outside of the patient's 1200 body.

Figure 30:
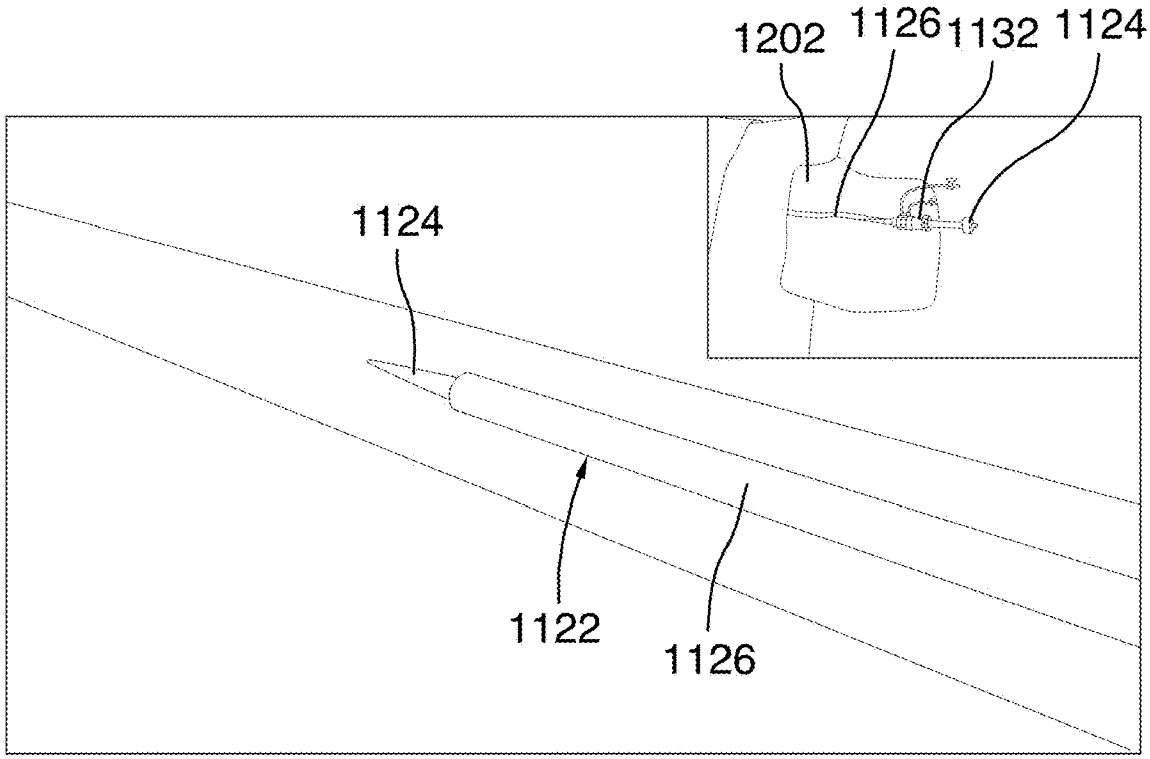

FIG. 30 is similar to FIG. 29, except that the guide wire 1204 has been withdrawn from the patient's 1200 body (as can be seen in the inset) and the dilator 1124 has begun to be withdrawn from the patient's body (via the delivery sheath 1126).

Figure 31:
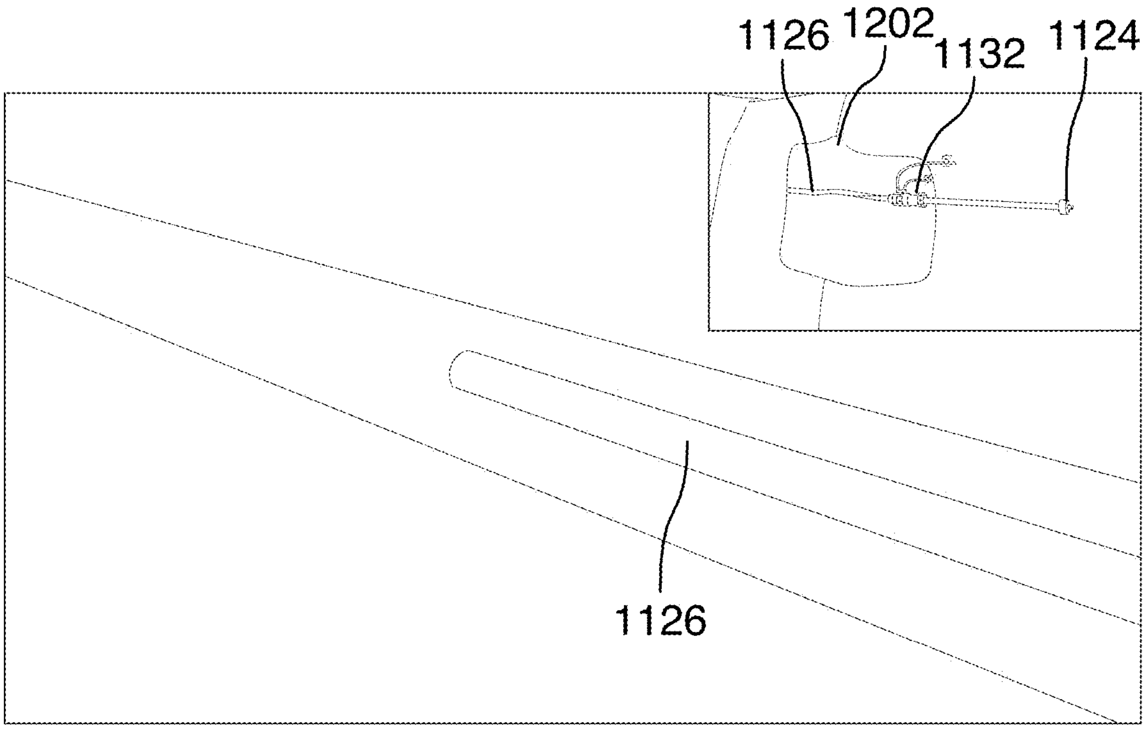

FIG. 31 is similar to FIG. 30, except that the dilator 1124 has been withdrawn to a greater extent from the patient's body.

Figure 32:
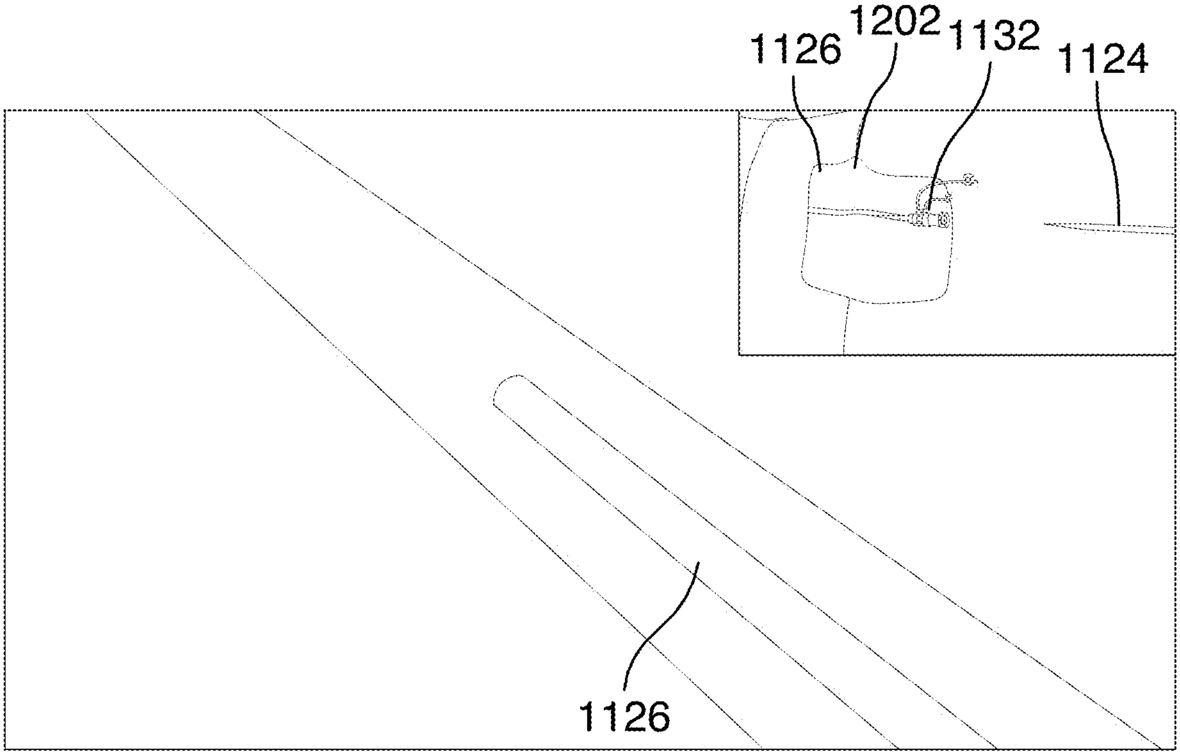

FIG. 32 is similar to FIG. 31, except that the dilator 1124 has been completely withdrawn from the patient's body.

Figure 33:
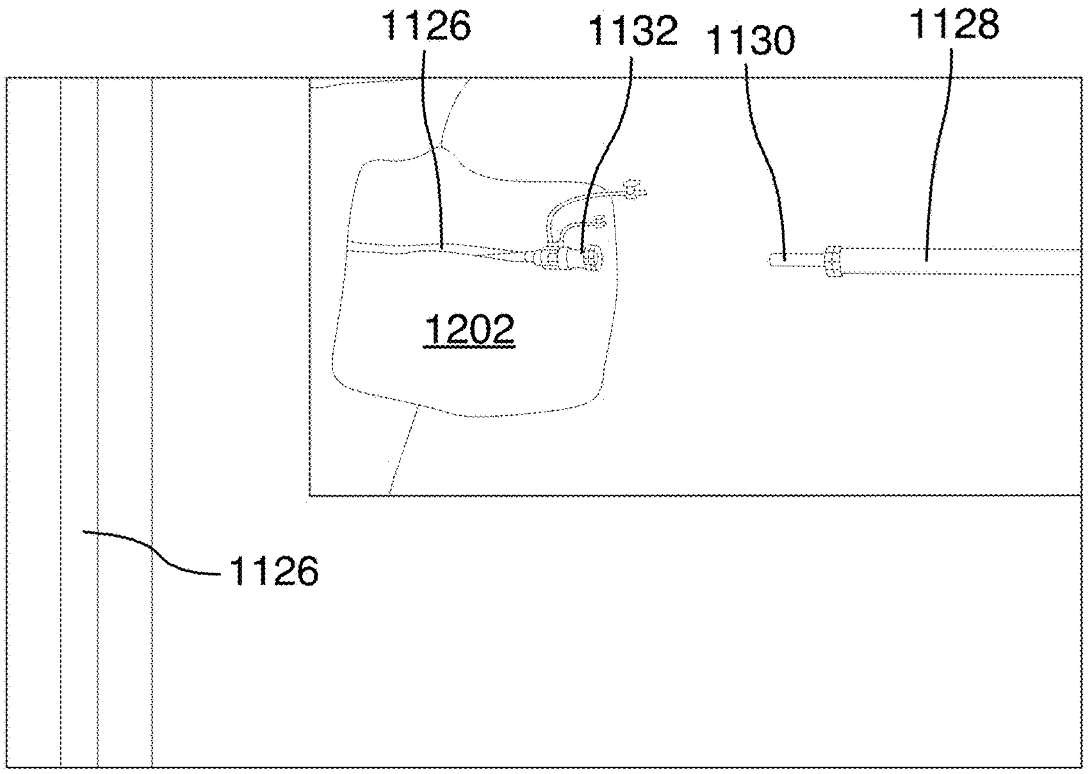

FIG. 33 is similar to FIG. 32, except that the loader 1128 is being brought to connect to the rear end 1132 of the delivery sheath 1126.

Figure 34:
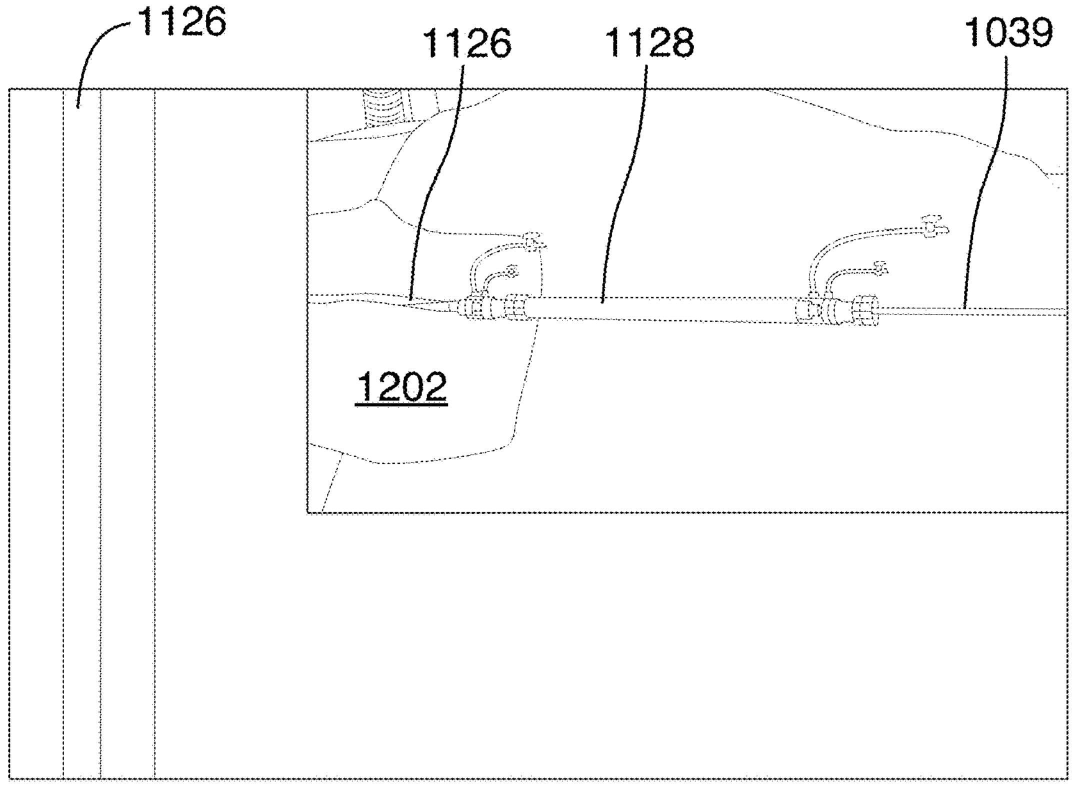

FIG. 34 is similar to FIG. 33, expect that the front end 1130 (FIG. 33) has been inserted into the rear end 1132 of the delivery sheath 1126, and the loader 1128 has been secured to the rear end 1132 of the delivery sheath 1126.

Figure 35:
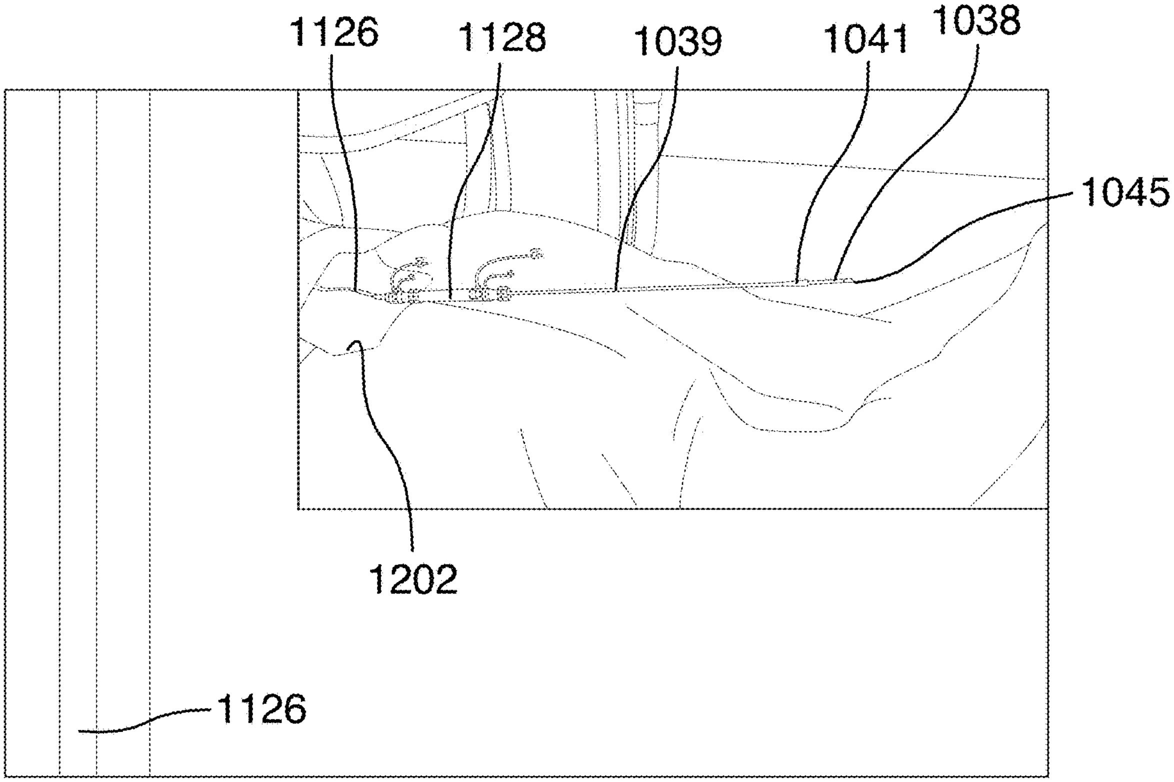

FIG. 35 is similar to FIG. 34, except that the proximal end 1041 of the control cable 1039 of the docking unit 1016 is shown. As can be seen in the inset, the control wires 1038 of the pumping units 1014 extend from the proximal end 1041 of the control cable 1039.

Figure 36:
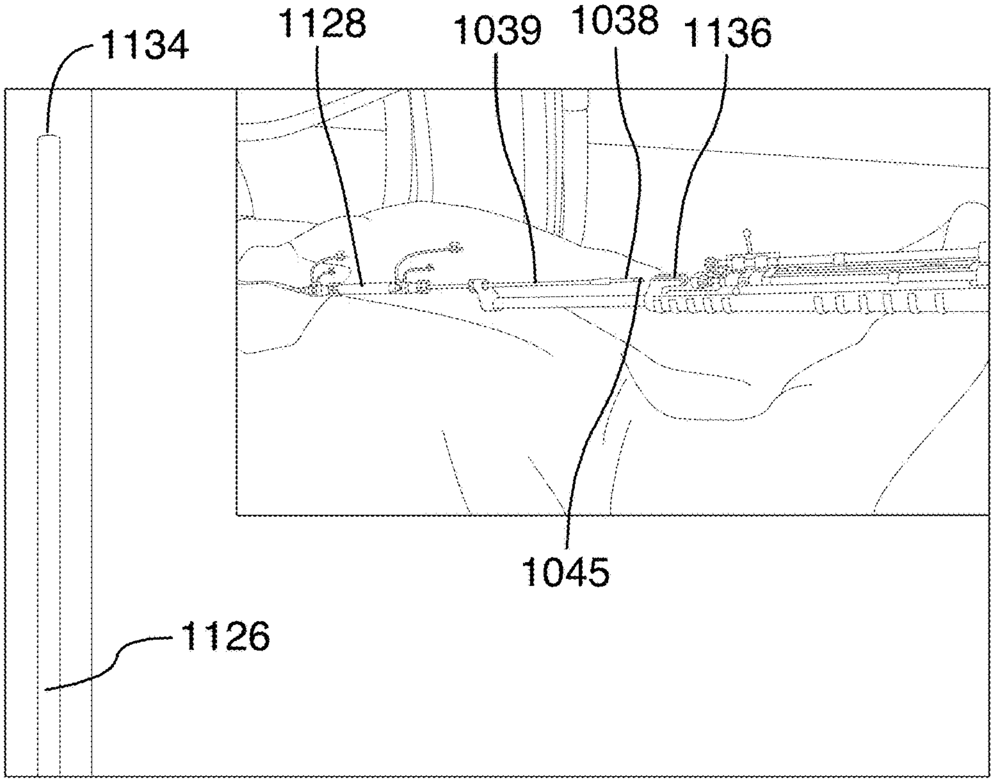

FIG. 36 is similar to FIG. 36, except that a mechanical handle device 1136 (whose function is simply to facilitate handling of the various wires, cables and components, but it is not part of and is not required to be used with the present technology) is shown. Also shown in the main image is the distal end 1134 of the delivery sheath 1126.

Figure 37:
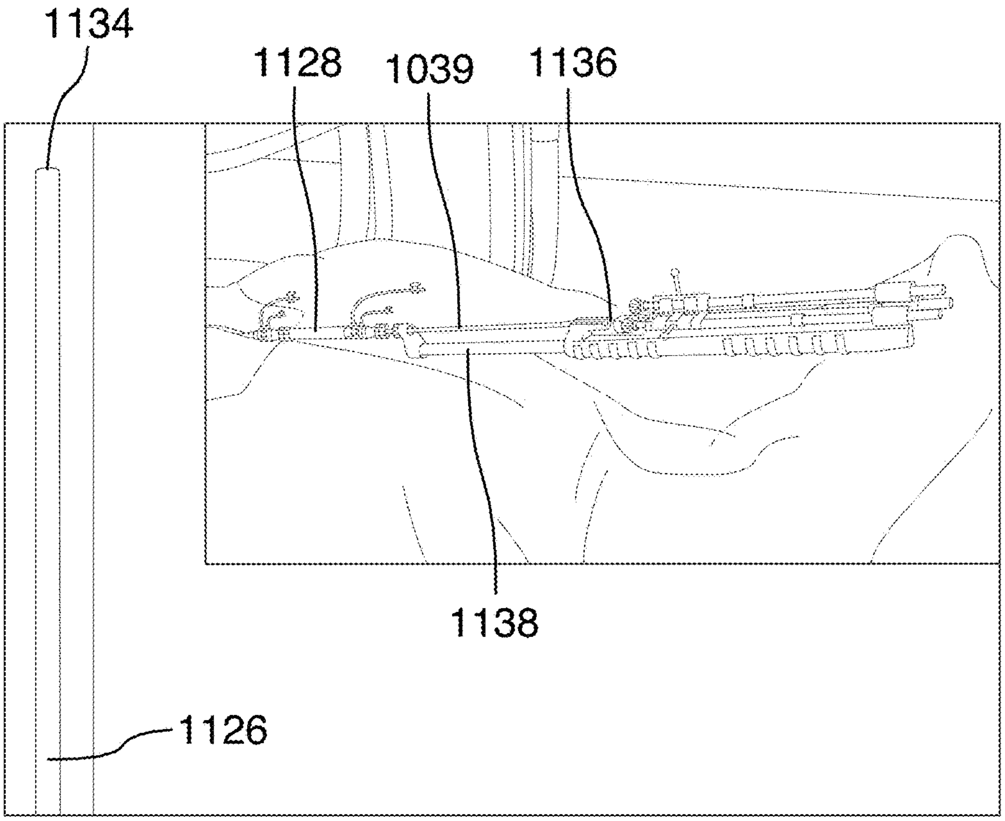

FIG. 37 is similar to FIG. 36 showing a portion of the arm 1138 of the handle 1136 (the body of the handle 1136 having been moved back).

Figure 38:
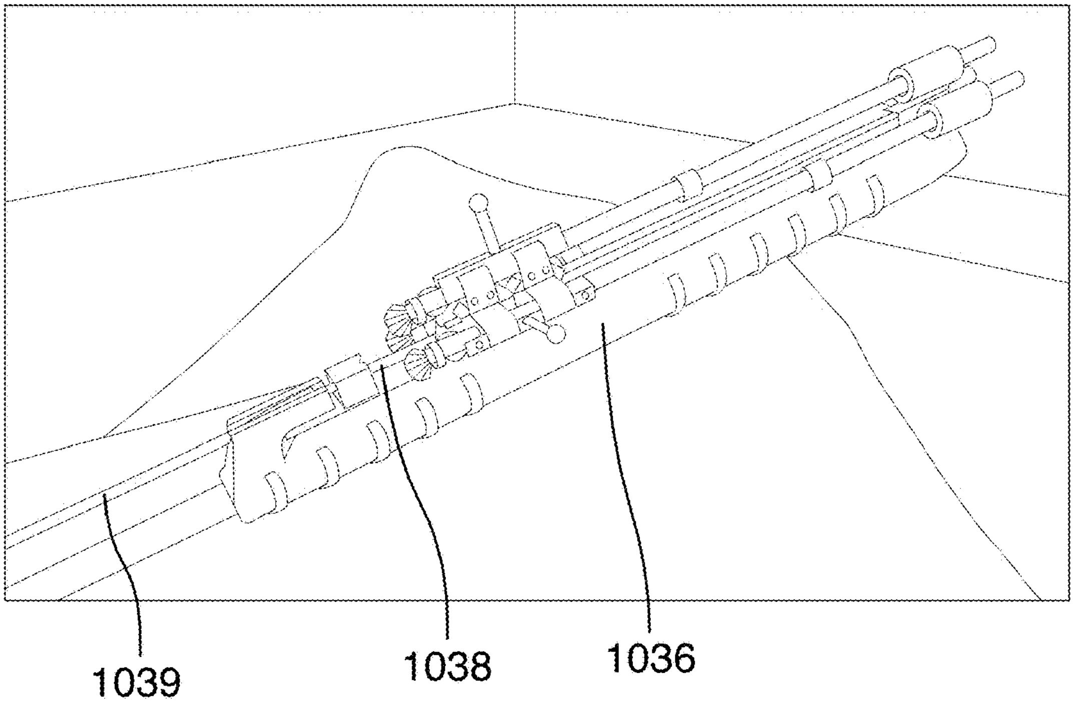

FIG. 38 is similar to FIG. 37, except that it shows a close-up view of the handle 1136 with the control cable 1039 of the docking unit 1016 and the control wires 1038 of the pumping units 1014 being shown.

Figure 39:
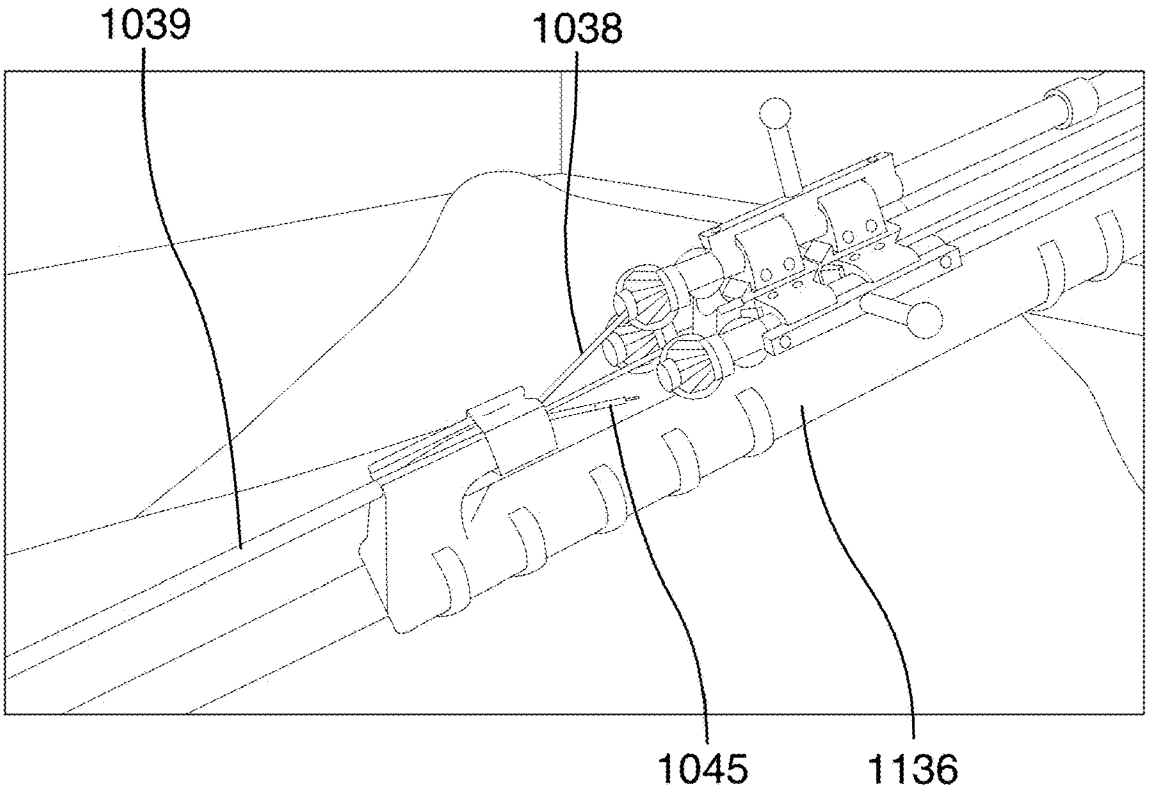

FIG. 39 is similar to FIG. 38, except that it shows a close-up view of the handle 1136 with the tips 1045 of the control wires 1038 of the pumping units 1014 having been or being inserted into handle 1136 and being secured therein (which will allow the control wires 1038 to be easier to be pulled than solely with one's hand).

Figure 40:
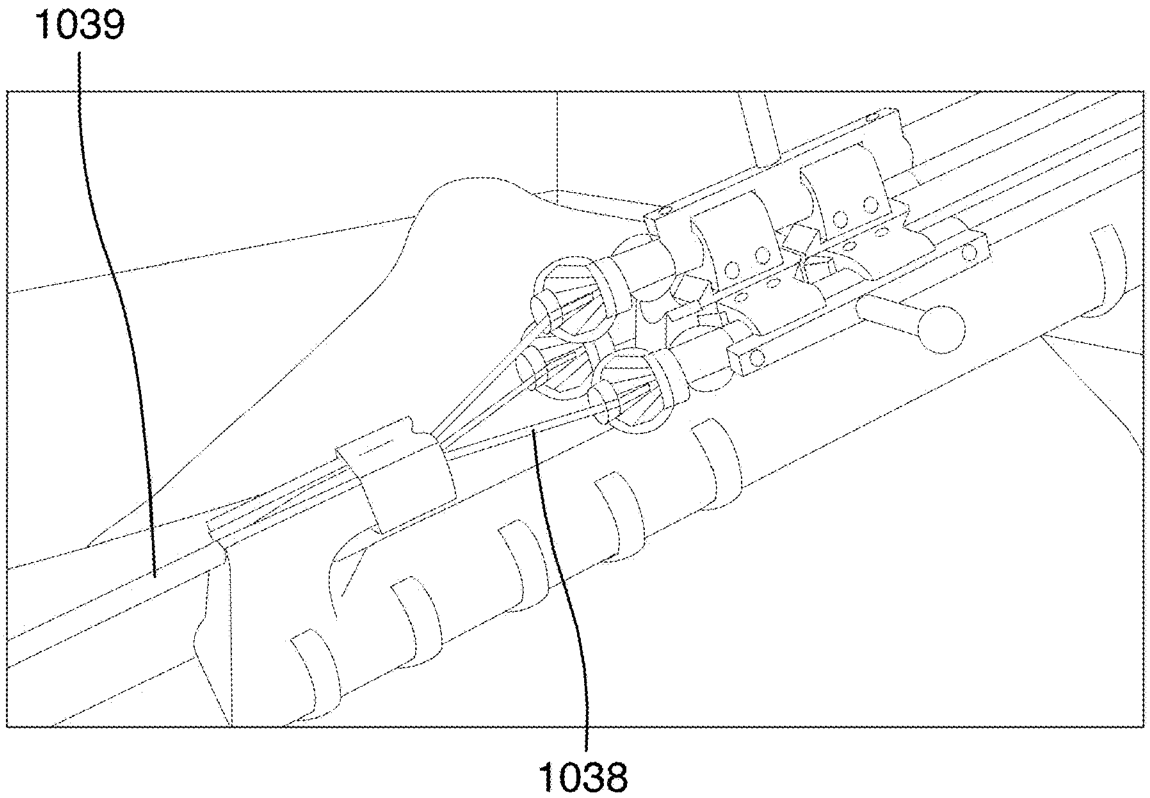

FIG. 40 is similar to FIG. 39, except all of the tips 1045 of the control wires 1038 of the pumping units 1014 have been secured within the handle 1136.

Figure 41:
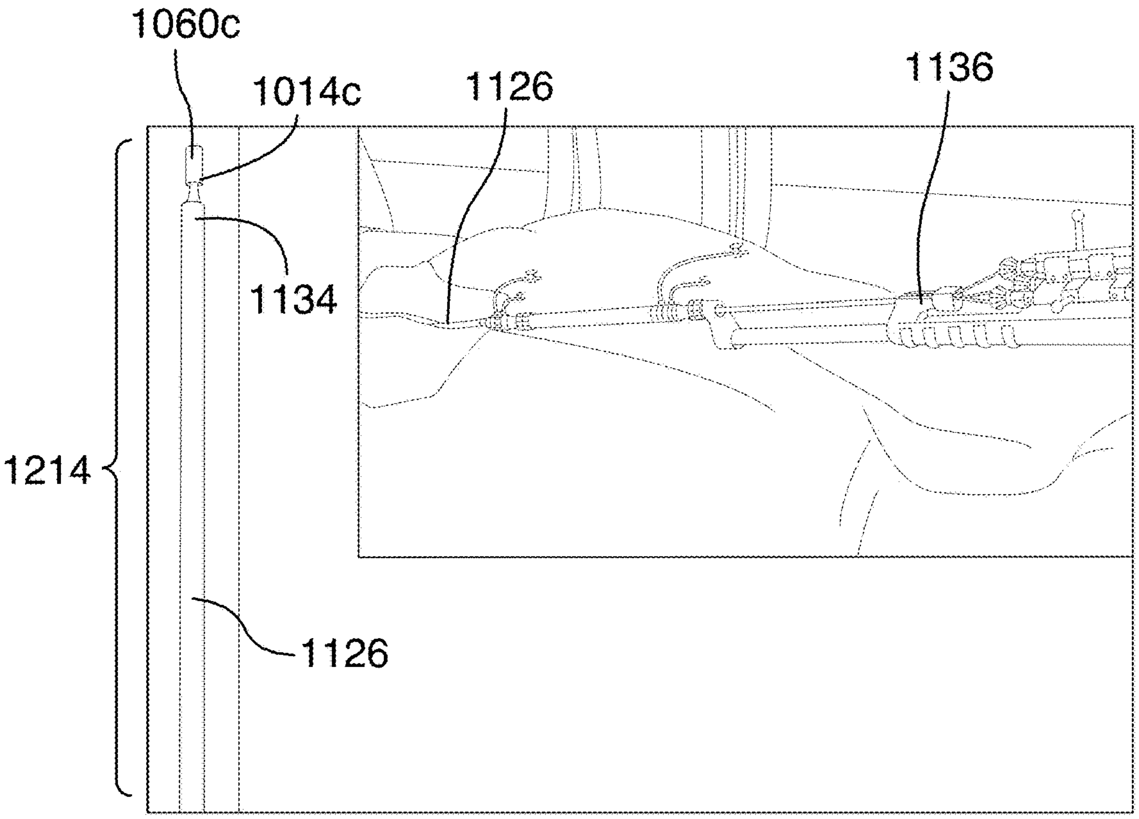

FIG. 41 shows the delivery sheath 1126 being withdrawn from the patient's 1200 body. The third pumping unit 1014*c* has begun to exit the distal end 1134 of the delivery sheath 1126 (distal end 1060*c* first) at the implantation site 1214.

Figure 42:
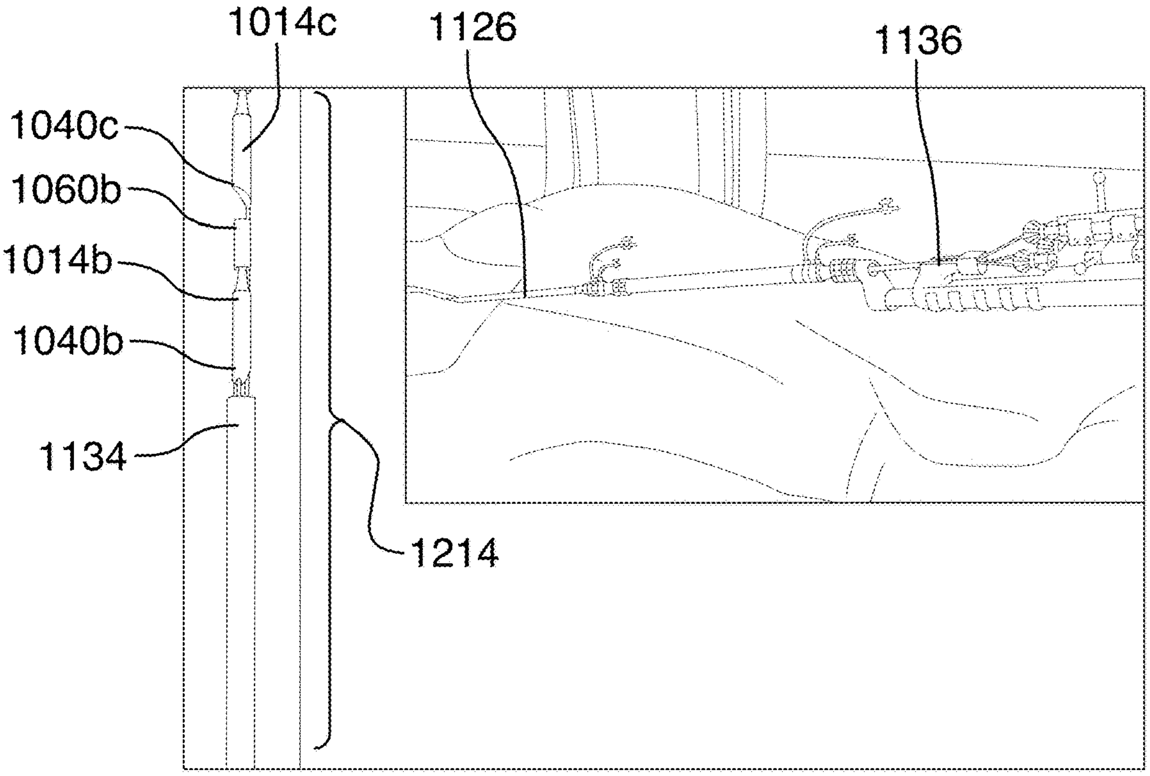

FIG. 42 is similar to FIG. 41, except that the delivery sheath 1126 has been even further withdrawn from the patient's 1200 body. The third pumping unit 1014*c* has entirely exited the delivery sheath 1126 at the implantation site 1214. The second pumping unit 1014*b* has almost entirely exited the delivery sheath 1126 at the implantation site 1214 (distal end 1060*b* first).

Figure 43:
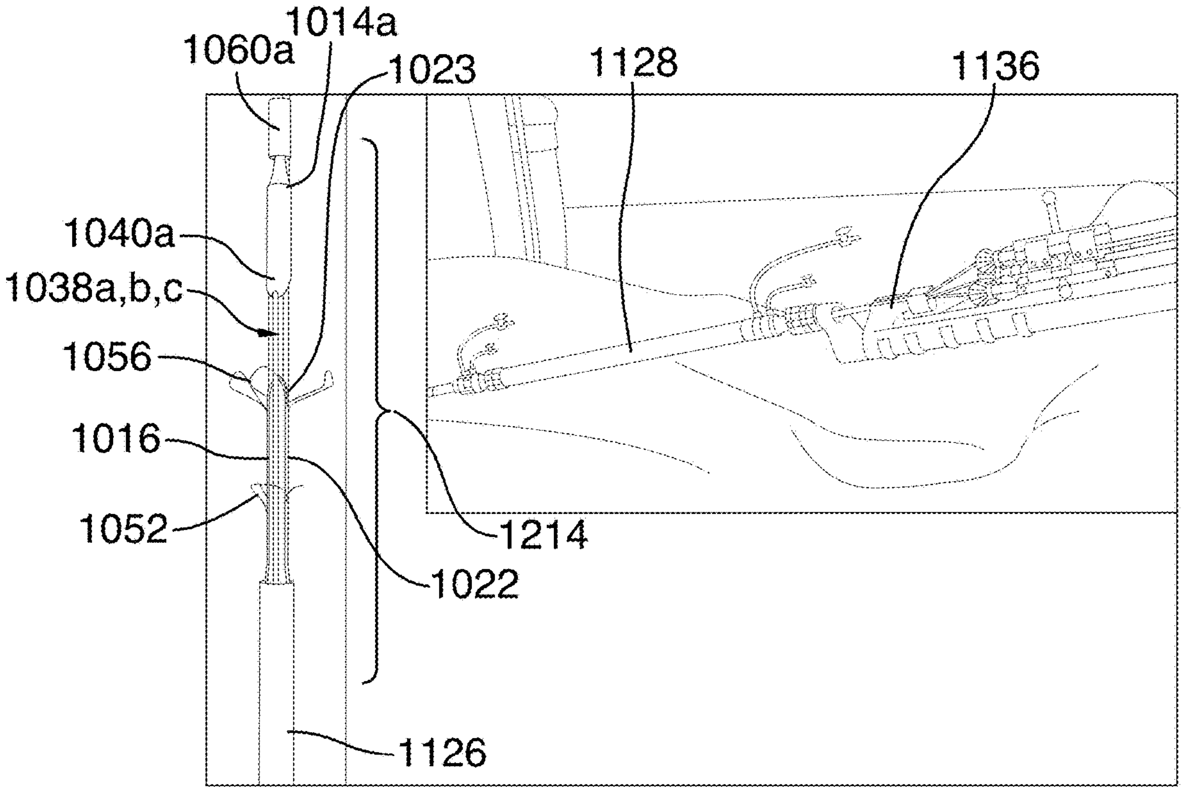

FIG. 43 is similar to FIG. 42, except that the delivery sheath 1126 has been even further withdrawn from the patient's 1200 body. The first pumping unit 1014*a* has entirely exited the delivery sheath 1126 at the implantation site 1214 (distal end 1060*a* first). The control wires 1038*a*, 1038*b*, 1038*c* of the pumping units 1014 have exited the delivery sheath 1126 at the implantation site 1214. And, the docking unit 1016 has begun to exit the delivery sheath 1126, distal end 1023 first. As the anchor assembly 1056 is biased away from the elongate body 1022 of the docking unit 1016, once the anchor assembly 1056 exits the delivery sheath 1126 at the implantation site 1214, it moves to an anchored configuration and anchors the docking unit 1016 in place.

Figure 44:
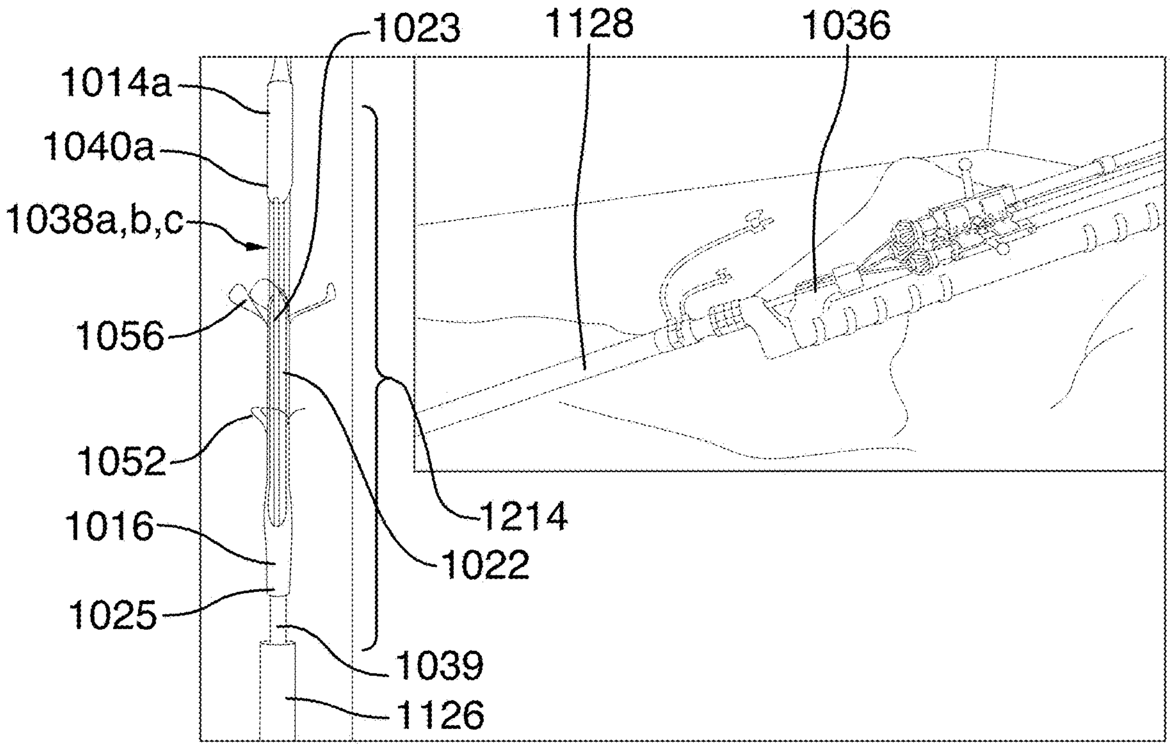

FIG. 44 is similar to FIG. 43, except the entire docking unit 1016 and a portion of the control cable 1039 of the docking unit 1016 have exited the delivery sheath 1126 at the implantation site 1214.

Figure 45:
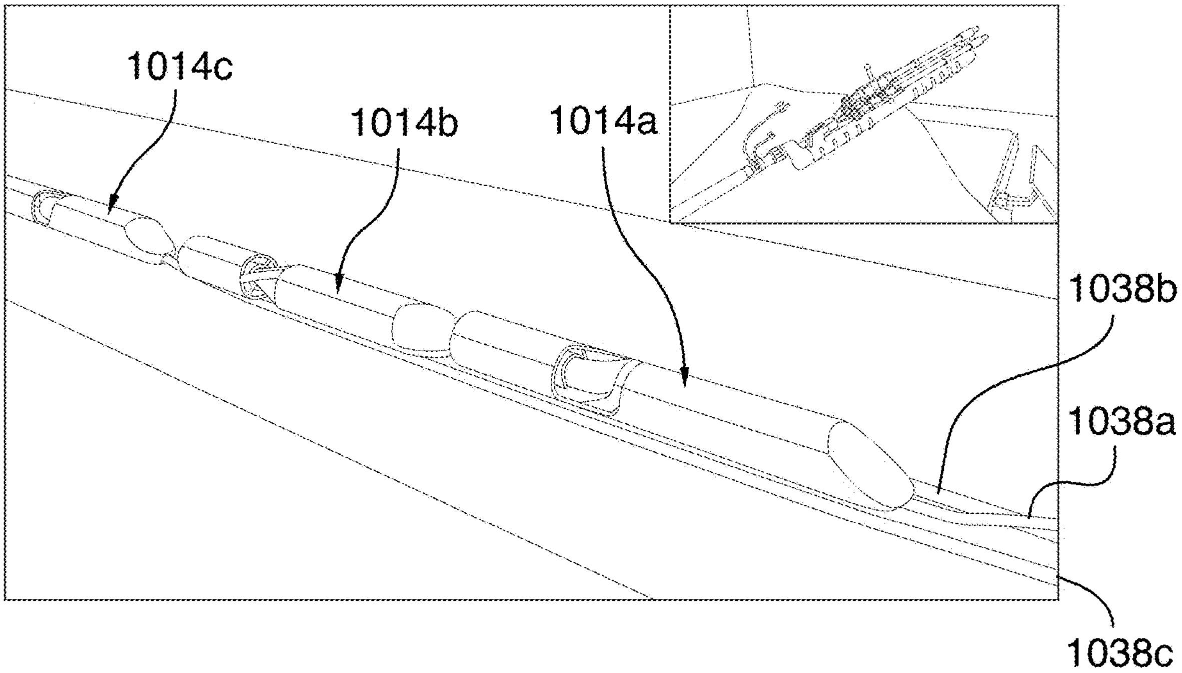

FIG. 45 is similar to FIG. 6, except the device 1010 is shown at the implantation site 1214.

Figure 46:
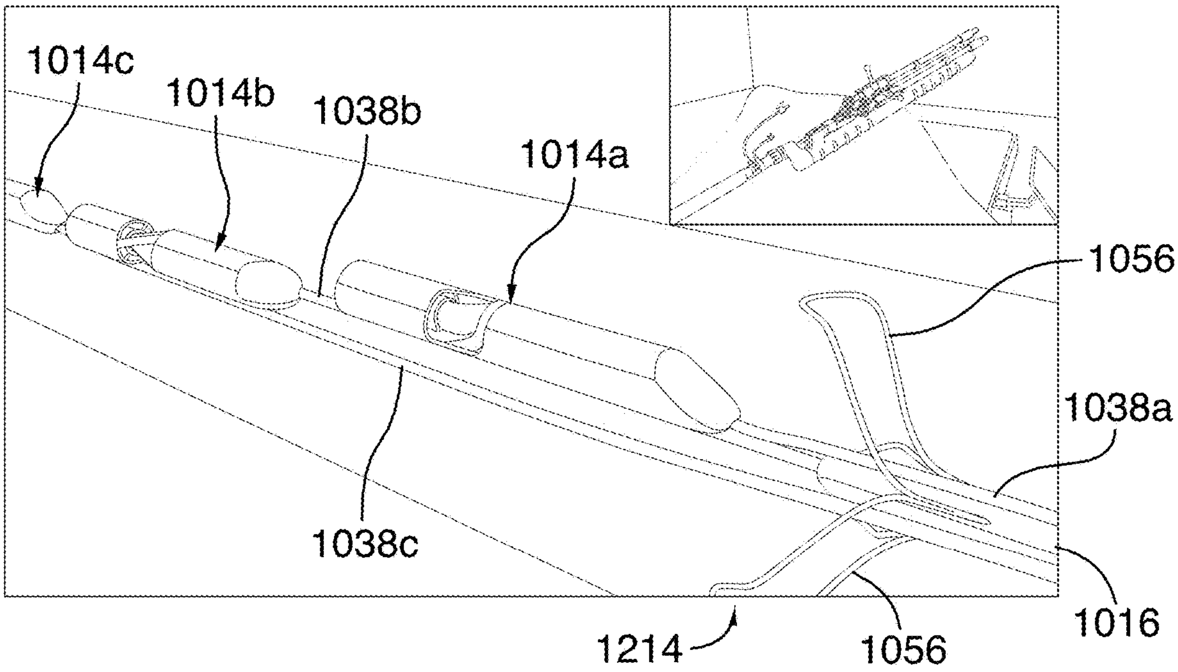

FIG. 46 is similar to FIG. 7, except the device 1010 is shown at the implantation site 1214.

Figure 47:
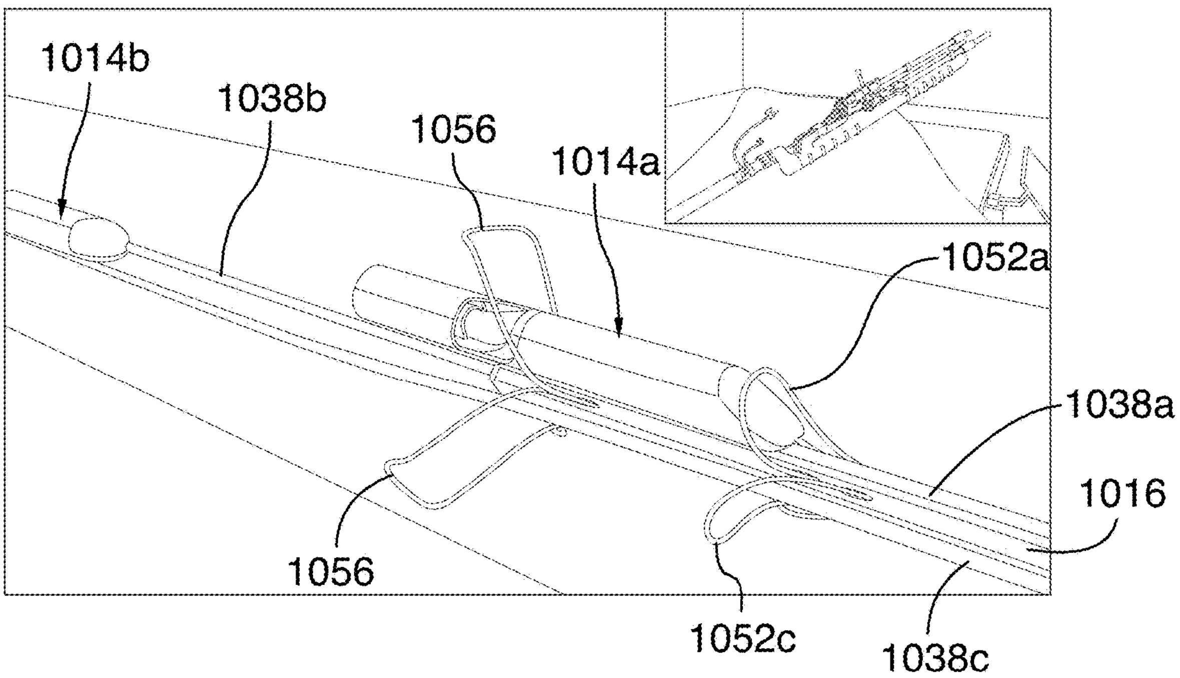

FIG. 47 is similar to FIG. 8, except the device 1010 is shown at the implantation site 1214.

Figure 48:
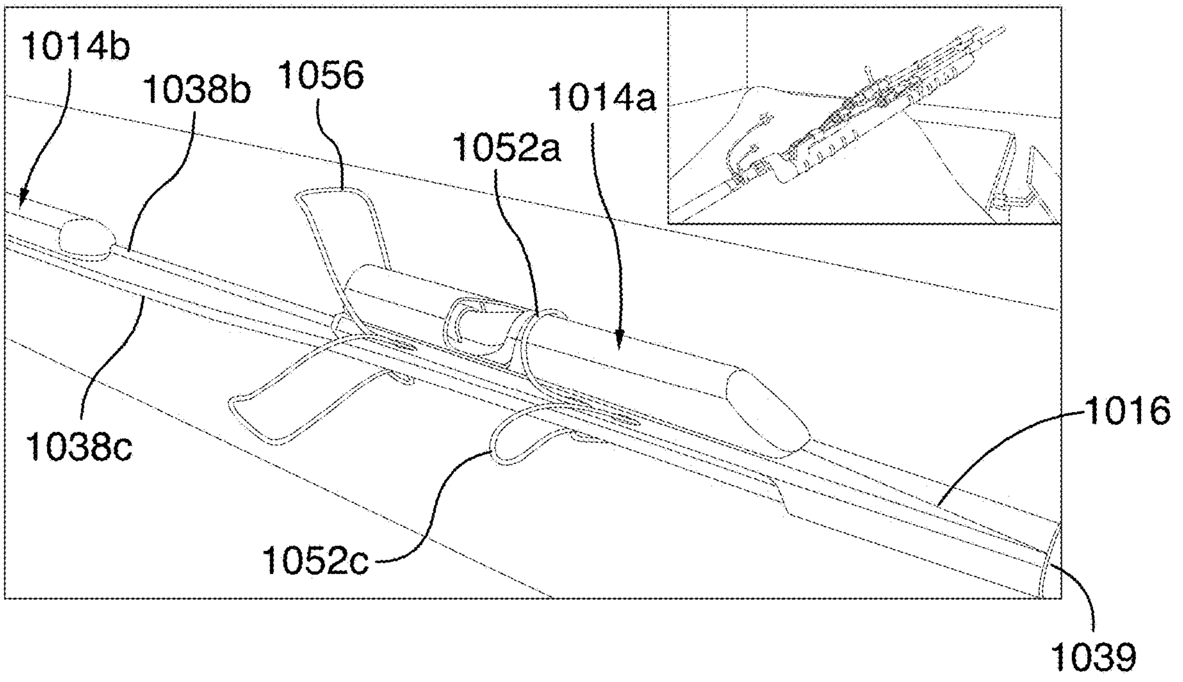

FIG. 48 is similar to FIG. 9, except the device 1010 is shown at the implantation site 1214.

Figure 49:
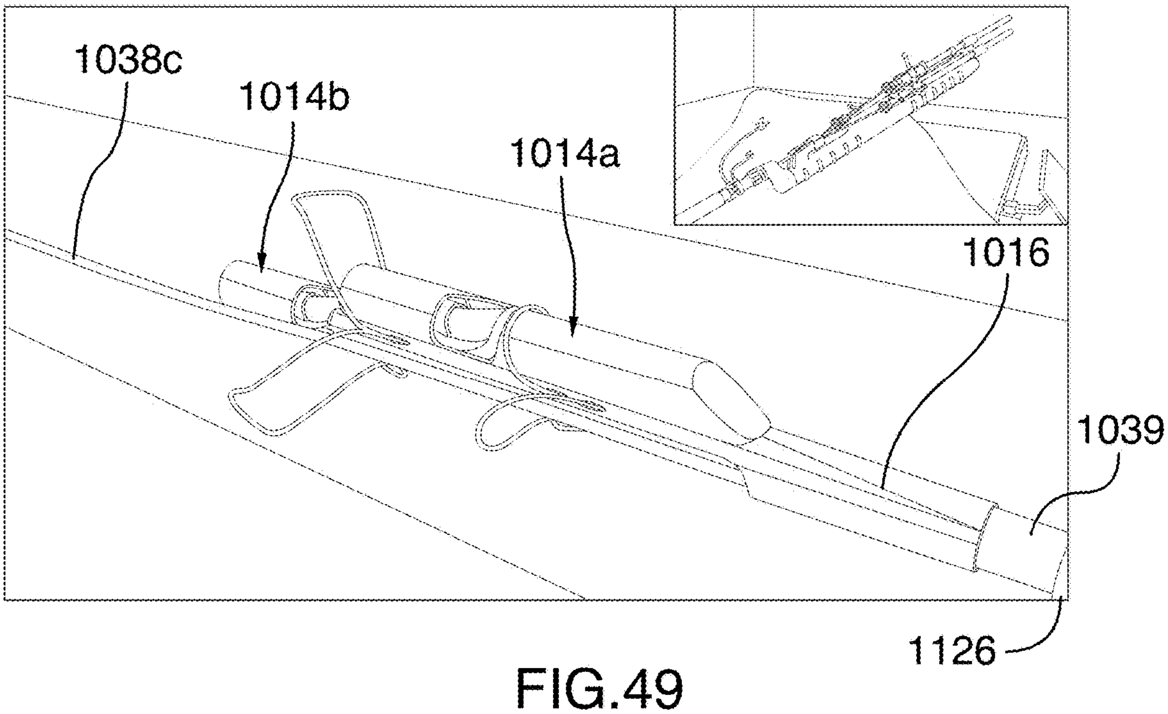

FIG. 49 is similar to FIG. 10, except the device 1010 is shown at the implantation site 1214.

Figure 50:
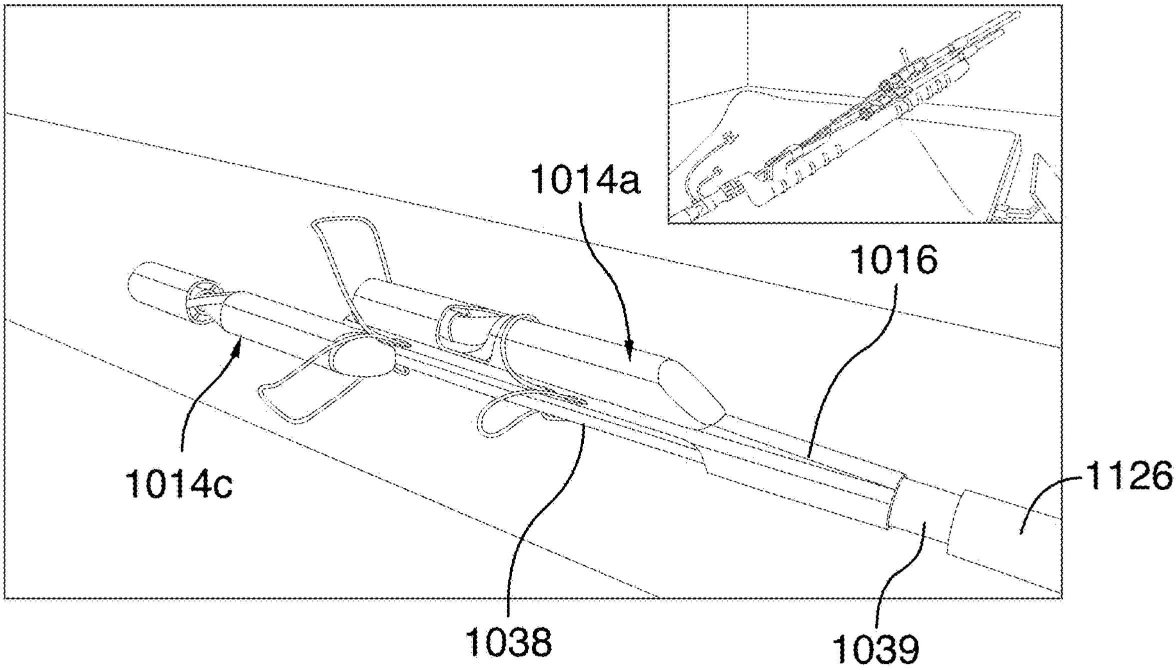

FIG. 50 is similar to FIG. 11, except the device 1010 is shown at the implantation site 1214.

Figure 51:
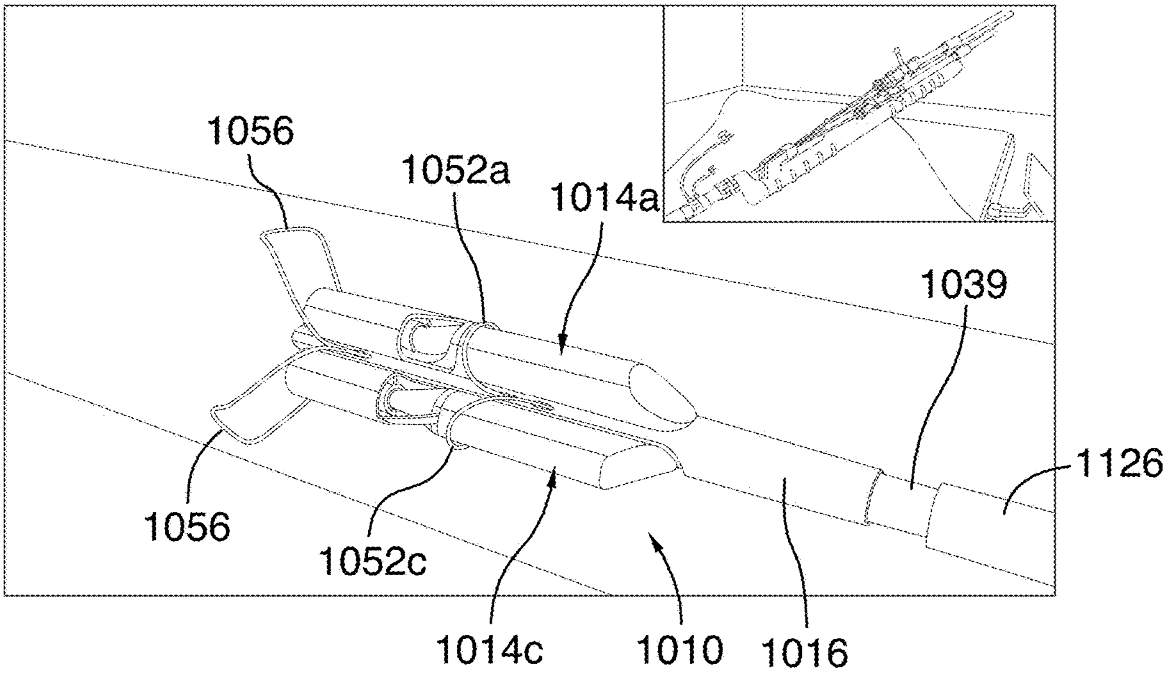

FIG. 51 is similar to FIG. 12, except the device 1010 is shown at the implantation site 1214.

Figure 52:
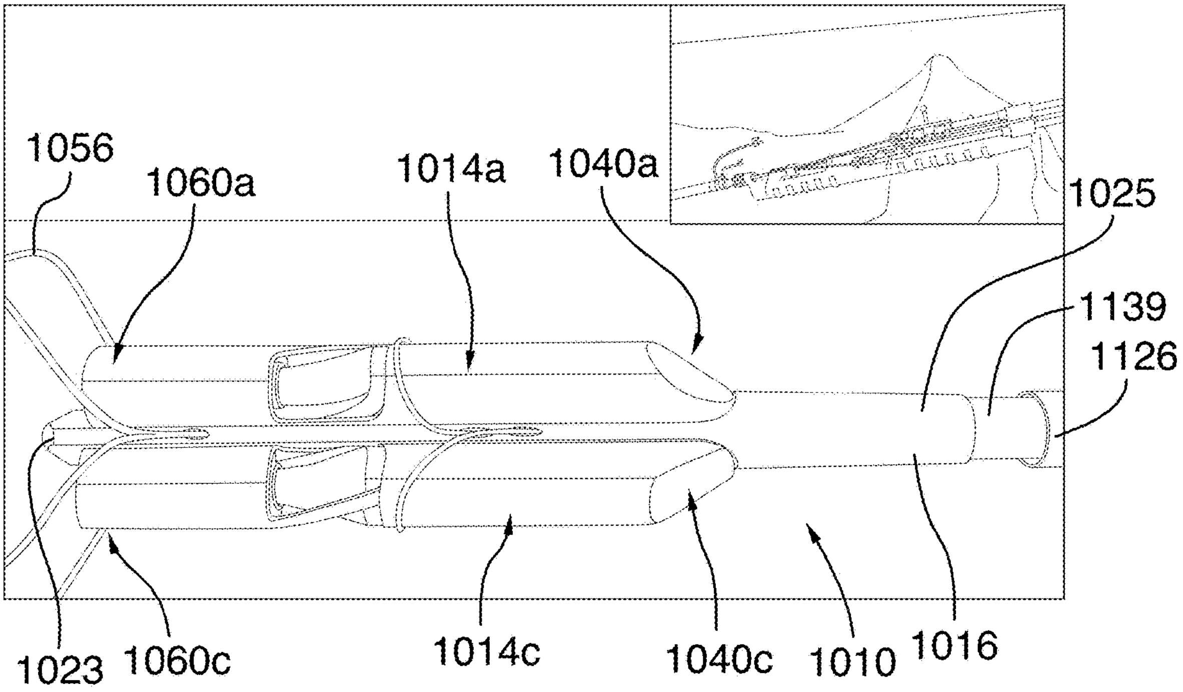

FIG. 52 is similar to FIG. 13, except the device 1010 is shown at the implantation site 1214.

Figure 53:
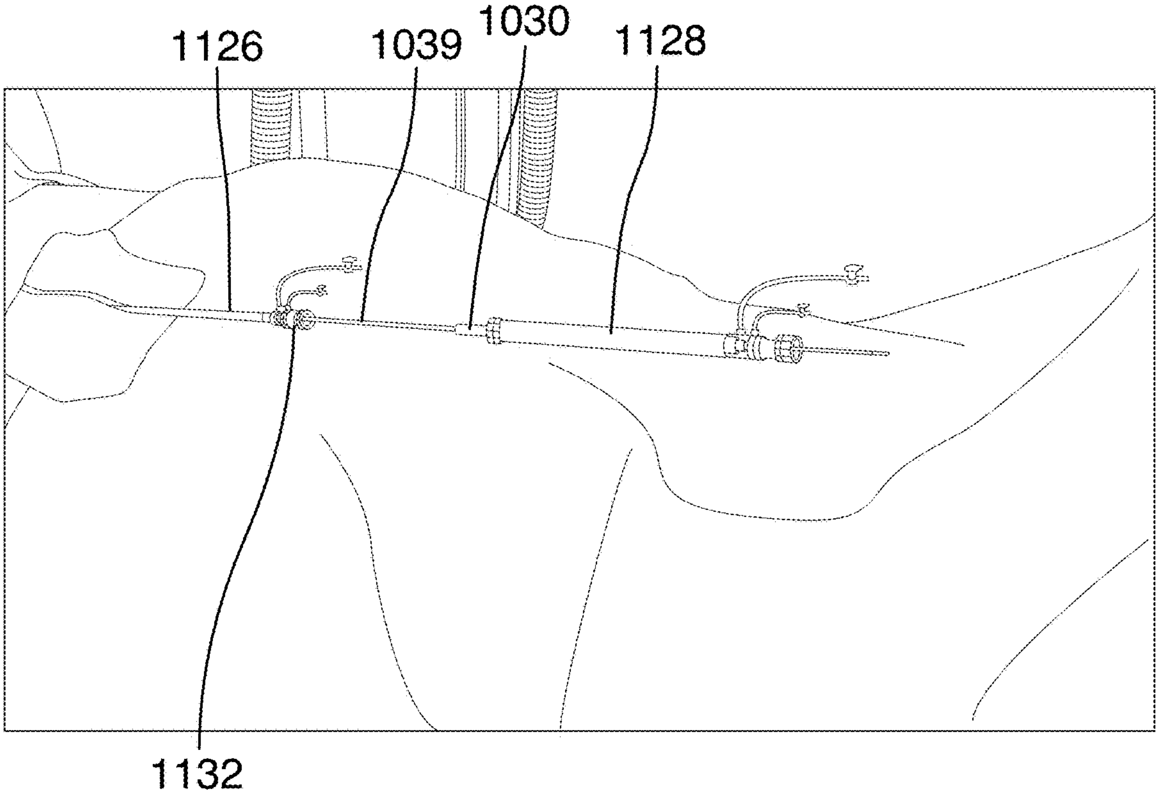

FIG. 53 is similar to FIG. 35, except the loader 1128 has been disconnected from the rear end 1132 of the delivery sheath 1126 and is being slid over the control cable 1039 of the docking unit 1016 and the control wires 1038 of the pumping units 1014. The device 1010 is in the assembled configuration at the implantation site.

Figure 54:
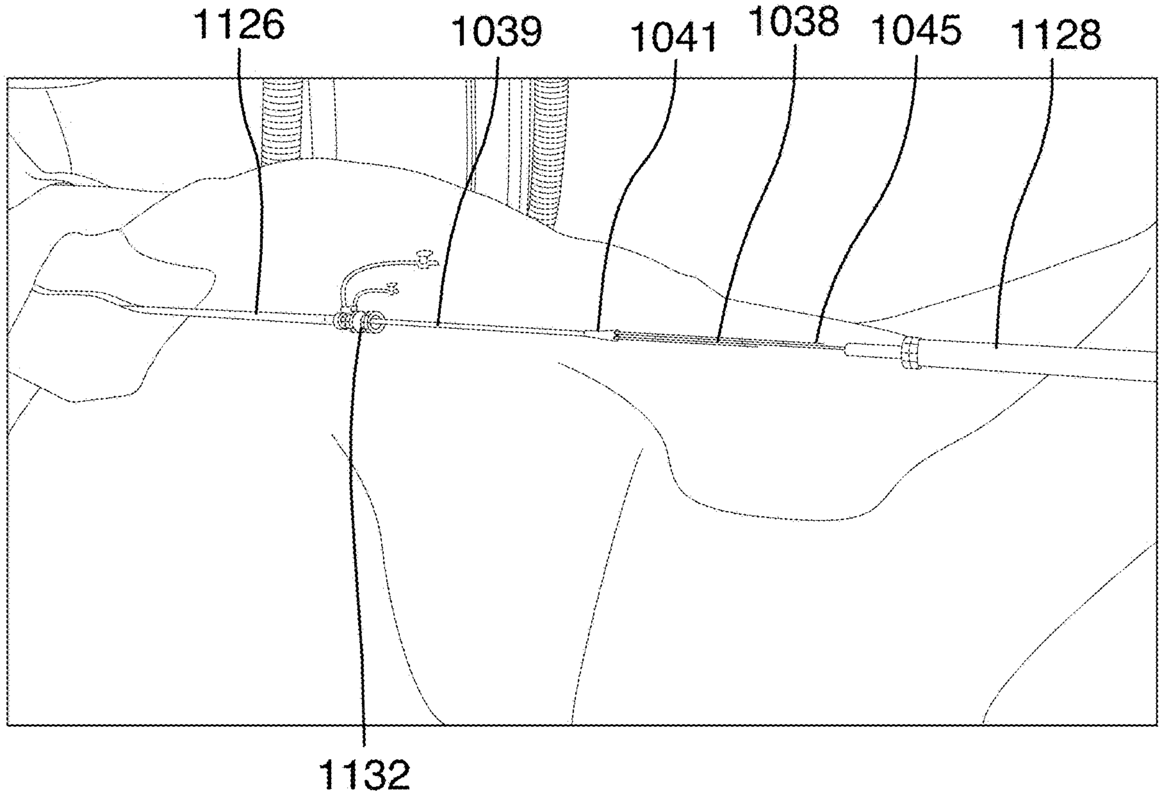

FIG. 54 is similar to FIG. 53, except the loader 1128 has been slid away from the rear end 1132 of the delivery sheath 1126.

Figure 55:
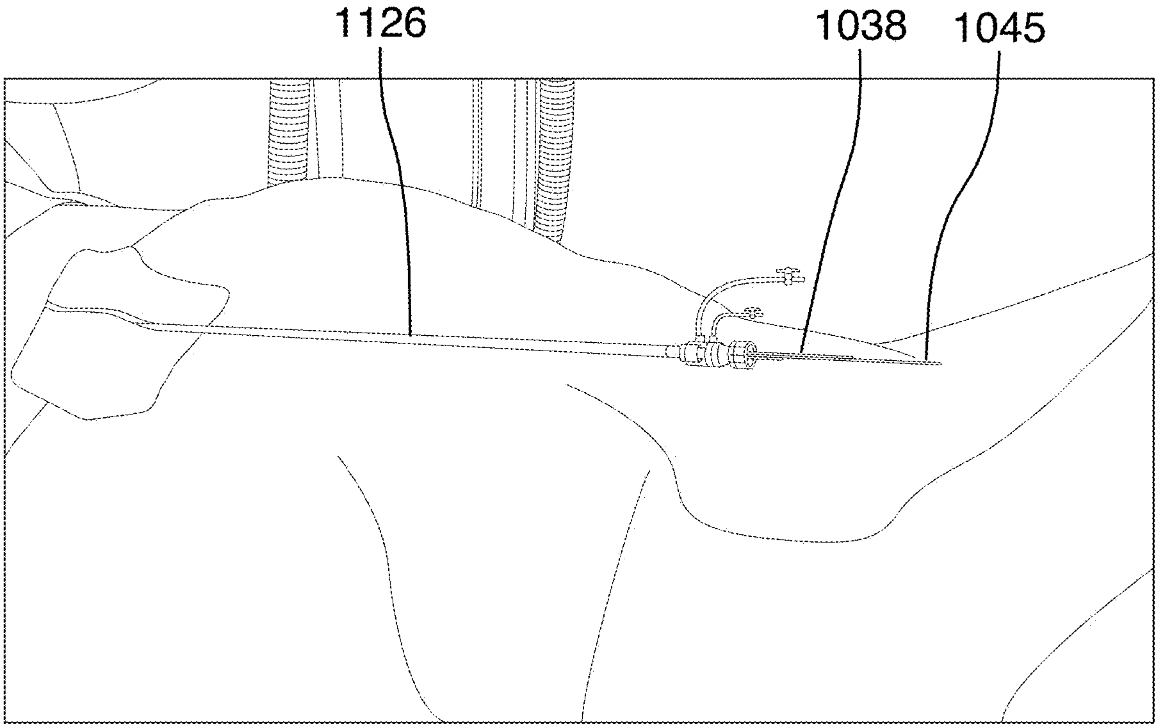

FIG. 55 is similar to FIG. 54, except the loader 1128 has been completely removed, and the delivery sheath 1126 is in the process of being withdrawn (e.g., being pulled out) of the patient's body by itself being slid over the control cable 1039 of the docking unit 1016 and the control wires 1038 of the pumping units 1014.

Figure 56:
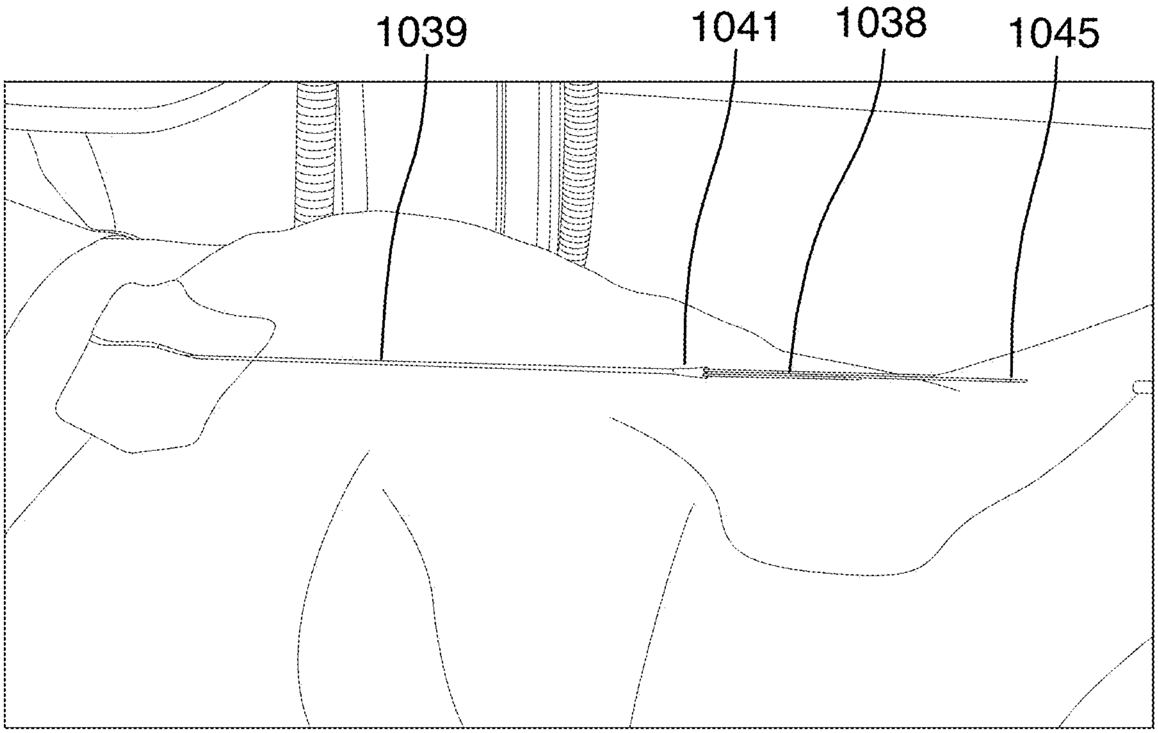

FIG. 56 is similar to FIG. 55, except that the delivery sheath has been completely removed. The device 1010 is in the assembled configuration at the implantation site. The control cable 1039 of the docking unit 1016 and the control wires 1038 of the pumping units exit the patient's body. The control wires 1038 are ready for attachment to a control unit, which will power, operate and/or control the device 1010.

FIG. 57 is similar to FIG. 56, except that the device 1010 is shown at the implantation site 1214. The distal end openings 1065*a*, 1065*b*, 1065*c* are the pump inlets.

ADDITIONAL EMBODIMENTS & FEATURES

Figure 58:
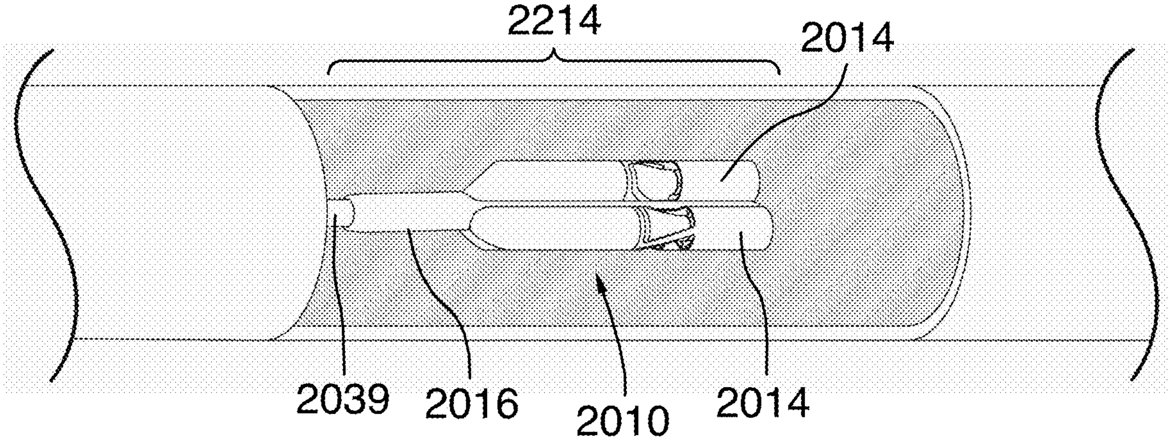
FIG. 58 shows a schematic view of a third embodiment of the present technology, a ventricular assist device (VAD).

FIG. 58 shows another embodiment of the present technology, VAD 2010 at an implantation site 2214. VAD 2010 is very similar in design to VAD 1010. VAD 2010 thus has docking unit 2016 and three pumping units 2014. A control cable 2039 extends from the docking unit 2016. In this embodiment, VAD 2020 has no anchoring assembly (or other structures which serve a similar purpose). VAD 2020 is held in place via the control cable 2039 of the docking unit 2016.

Figure 59:
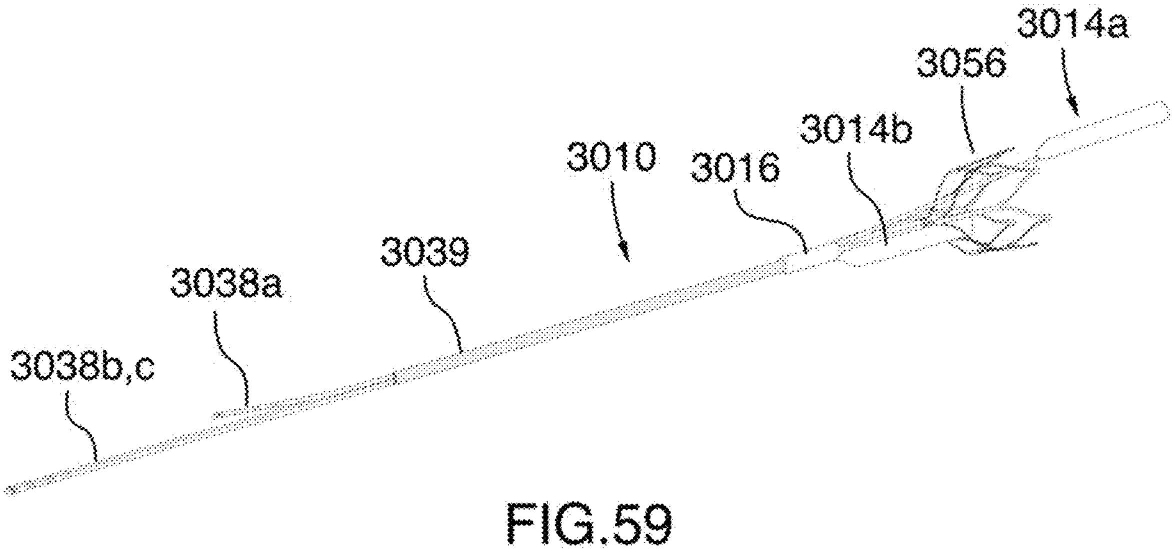
FIG. 59 shows a schematic view of a fourth embodiment of the present technology, a ventricular assist device (VAD).

FIG. 59 shows a schematic of another embodiment of the present technology, VAD 3010. VAD 3010 is similar in design to VAD 1010. VAD 3010 has a docking unit 3016 and three pumping units 3014. Extending from the docking unit 3016 is a control cable 3039 within of a cavity of which are the control wires 3038 of the pumping units 3014. In this embodiment, anchor assembly 3056 differs from anchor assembly 1056 of VAD 1010. VAD 3010 is being prepared for retrieval. Thus, the control wire 3038*a* has been pushed by the surgeon and pumping unit 3014*a* is in its undocked configuration (and control wire 3038*a* exiting at the proximal end is shown as being shorter). Pumping units 3014*b* and 3014*c* (not shown) remain in their docked configuration.

Figure 60:
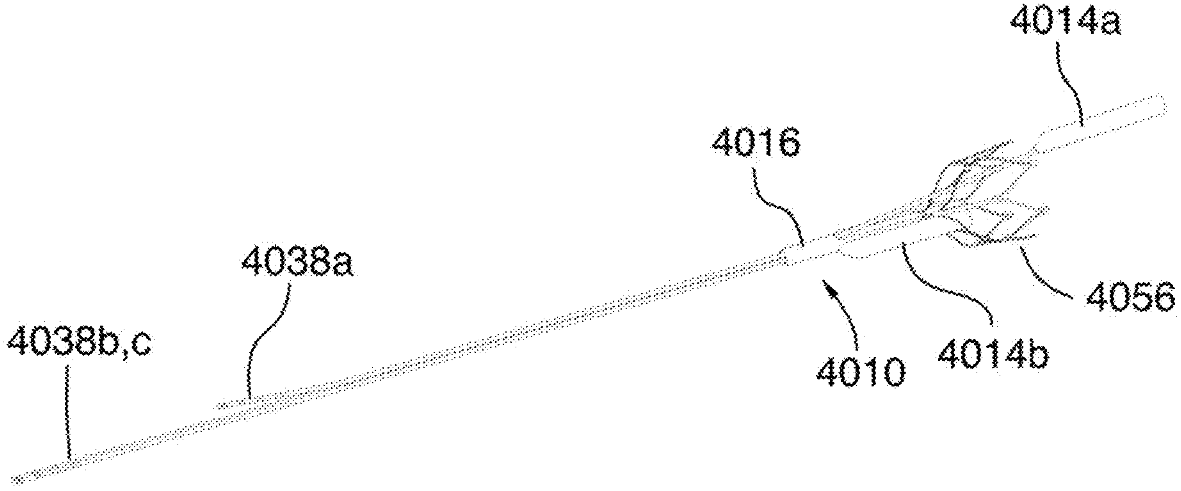
FIG. 60 shows a schematic view of a fifth embodiment of the present technology, a ventricular assist device (VAD).

FIG. 60 shows a schematic of another embodiment of the present technology VAD 4010. VAD 4010 is similar in design to VAD 3010, with the exception the docking unit 4016 has no control cable. The control wires 4038 of the pumping units 4014 simply travel through the patient's vascular system without being inside of any other structure. As was the case in FIG. 59, VAD 4010 is being prepared for retrieval. Thus, the control wire 4038*a* has been pushed by the surgeon and pumping unit 4014*a* is in its undocked configuration (and control wire 4038*a* exiting at the proximal end is shown as being shorter). Pumping units 4014*b* and 4014*c* (not shown) remain in their docked configuration.

Figure 61:
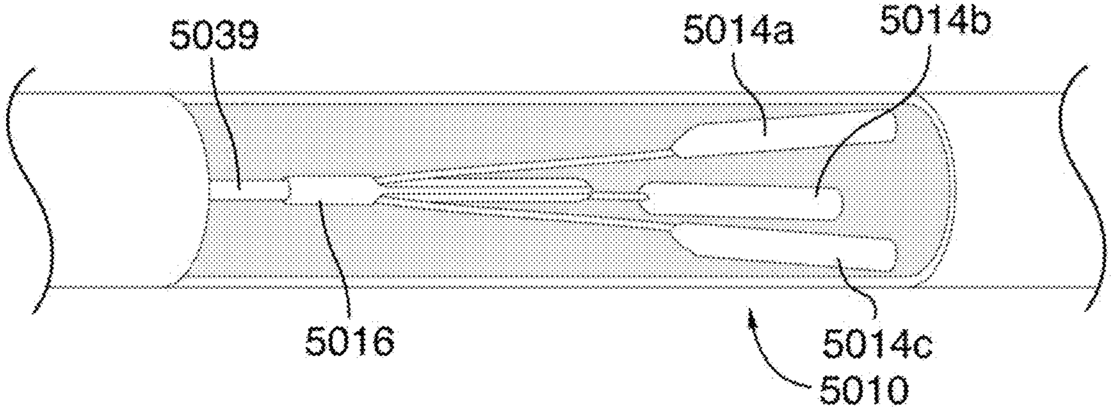
FIG. 61 shows a schematic view of a sixth embodiment of the present technology, a ventricular assist device (VAD).

FIG. 61 shows a schematic of another embodiment of the present technology VAD 5010. VAD 5010 is similar to VAD 2010 shown in FIG. 58. As was the case in FIGS. 58 and 59, VAD 5010 is being prepared for retrieval. Thus, the control wires 5038 (not shown) have been pushed by the surgeon and pumping units 5014*a*, 5014*b*, 5014*c* are all in their undocked configurations.

FIG. 62 shows VAD 5010 of FIG. 61, with a retrieval sheath 5140 having been railed over the control cable 5039 of the docking unit 5016 until a point just proximal of the docking unit 5016.

Figure 63:
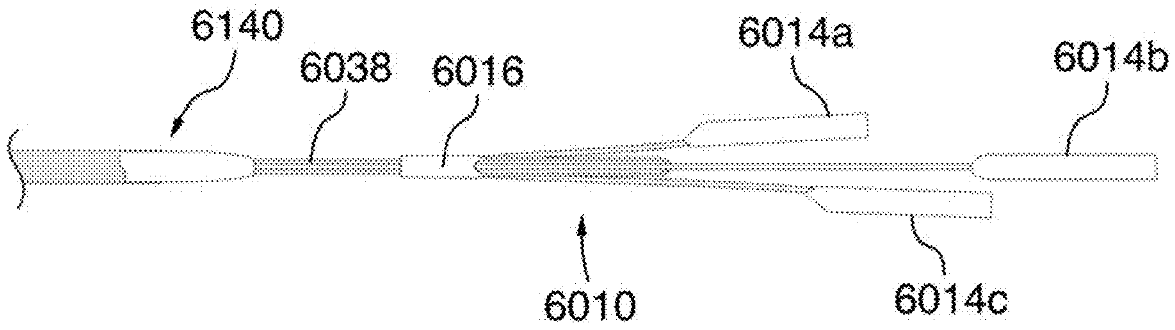
FIG. 63 shows a schematic view of a seventh embodiment of the present technology, a ventricular assist device (VAD).

FIG. 63 shows a schematic of another embodiment of the present technology VAD 6010. VAD 6010 is similar to VAD 5010 with the exception that the docking unit 5016 has no control cable. The control wires 6038 of the pumping units 6014 simply travel through the patient's vascular system without being inside of any other structure. Similar to FIG. 62, in this figure a retrieval sheath 6140 has been railed over the control wires 6038 until a point just proximal of the docking unit 6016.

Figure 64:
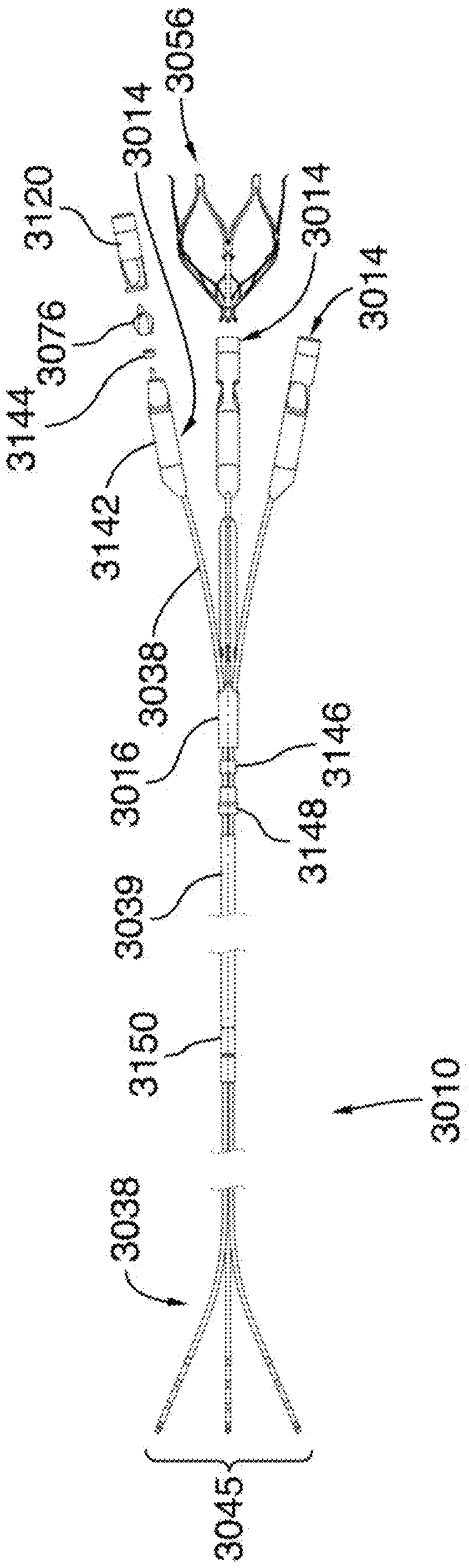
FIG. 64 shows an exploded view of the VAD of FIG. 59.

FIG. 64 shows an exploded view of VAD 3010 shown in FIG. 59. Shown in FIG. 64 are a docking unit 3016 and three pumping units 3014. One of the pumping units 3014 is also shown in an exploded view showing its main body portion 3142, a seal 3144, an impeller 3076 and a shroud 3120. Each of the pumping units 3014 has a control wire 3038 that extends from the proximal end thereof and goes into a guide hole in the docking unit 3016 and from there into a cavity within the control cable 3039 of the docking unit 3016. The connection between the control cable 3039 and the docking unit 3016 is also shown in an exploded view. Thus, there is a seal 3146 and a connector 3148 which holds the seal 3146 in place and connects the control cable 3039 to the docking unit 3016. A further seal 3150 is at the proximal end of the control cable 3039. Extending through the seal 3150 are the control wires 3038 of the pumping units 3014. The control wires 3038 terminate in electrical connector tips 3045.

Figure 65:
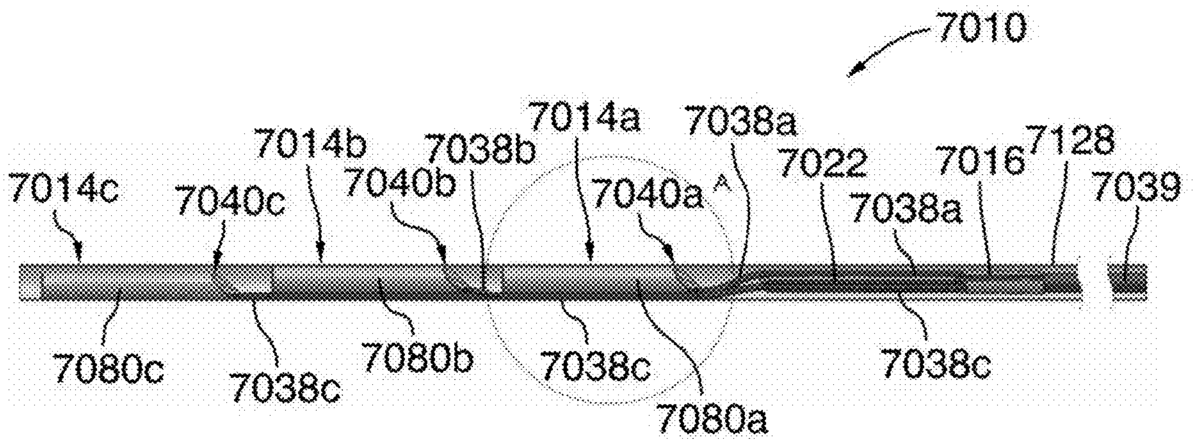
FIG. 65 shows a schematic view of an eighth embodiment of the present technology, a VAD, in its delivery configuration within a loader.

FIG. 65 shows a schematic view of how an embodiment of the present technology, VAD 7010, is disposed within a loader (e.g. a rigid sheath) 7128 in its delivery configuration. VAD 7010 includes a docking unit 7016 and three pumping units 7014*a*, 7014*b*, 7014*c*. In this embodiment a third pumping unit 7014*c* is disposed the most distant from the docking unit 7016. Closer to the docking unit 7016 is the second pumping unit 7014*b*. And finally, first pumping unit 7014*a* is disposed closest to the docking unit 7016. The control wire 7038*c* of the third pumping unit 7014*c* extends from the proximal end 7040*c* thereof. The control wire 7038*c* passes alongside the elongate body 7080*b* of the second pumping unit 7014*b*, then alongside the elongate body 7080*a* of the first pumping unit 7014*a*, then alongside the elongate body 7022 of the docking unit 7016, then into a guide hole of the docking unit 7016 and finally passes into the cavity of the control cable 7039 of the docking unit 7016. The control wire 7038*b* of the second pumping unit 7014*b* extends from the proximal end 7040*b* thereof. The control wire 7038*b* then passes alongside the elongate body 7080*a* of the first pumping unit 7014*a* and then alongside the elongate body 7022 of the docking unit 7016, then into a guide hole of the docking unit 7016 and finally passes into the cavity of the control cable 7039 of the docking unit 7016. The control wire 7038*a* of the first pumping unit 7014*a* extends from the proximal end 7040*a* thereof. The control wire 7038*a* then passes alongside the elongate body 7022 of the docking unit 7016 and finally passes into the cavity of the control cable 7039 of the docking unit 7016.

Figure 66:
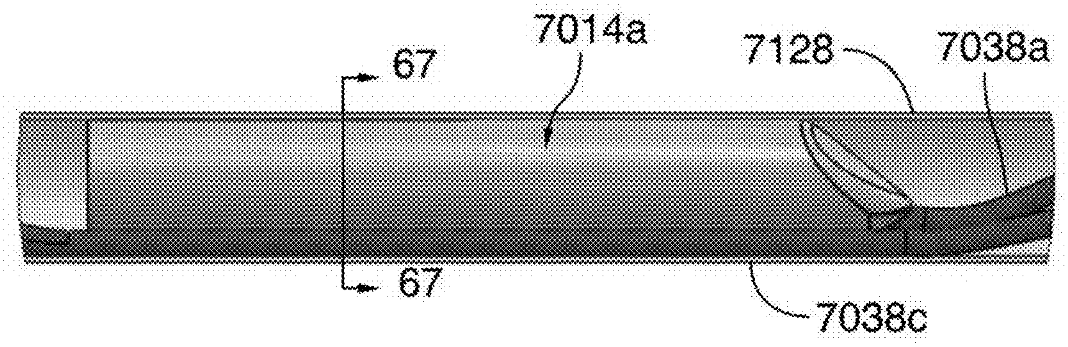
FIG. 66 shows a close-up view of the encircled portion in FIG. 65.

FIG. 66 shows a closeup schematic view of the first pumping unit 7014*a* in the loader 7128 in FIG. 65.

Figure 67:
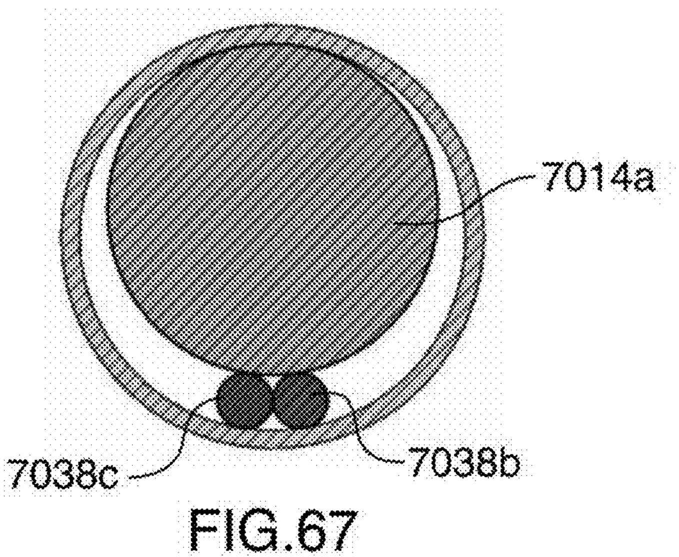
FIG. 67 shows a cross-section taken along the line 67-67 in FIG. 66.

FIG. 67 shows a cross-sectional view of the first pumping unit 7014*a* in the loader 7128 taken along the line 67-67 in FIG. 65.

Figure 75:
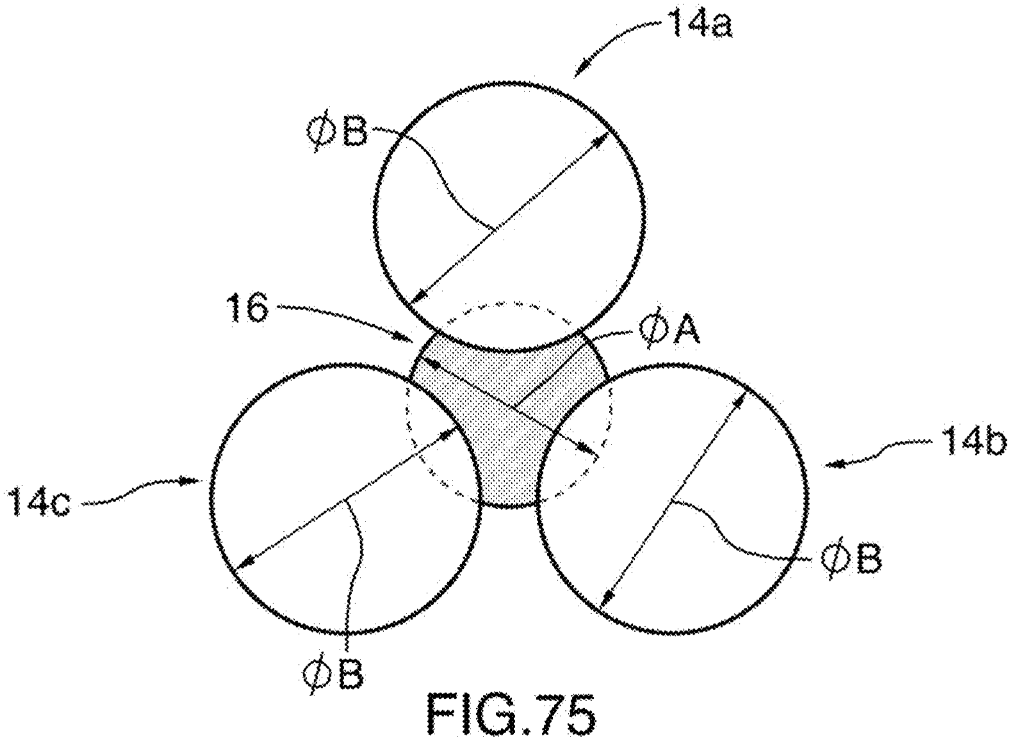
FIG. 75 shows a schematic illustrating the diameter of a minimum bounding right circular cylinder of the docking unit of the first embodiment (FIGS. 97-97) and the diameter ØB of a minimum bounding right circular cylinder of the first pumping unit of that embodiment.

FIG. 75 shows a schematic illustrating the diameter ØA of a minimum bounding right circular cylinder of the docking unit 16 of VAD 10 and the diameter ØB of a minimum bounding right circular cylinder of the first pumping unit 14*a* of VAD 10. As can be seen in the Figure, diameter ØA is less then diameter ØB. In VAD 10 all of the pumping units 14 are identical, so the diameter of a minimum bounding right circular cylinder of the second pumping unit 14*b* and the third pumping unit 14*c* of VAD 10 are also represented by diameter ØB.

Figure 76:
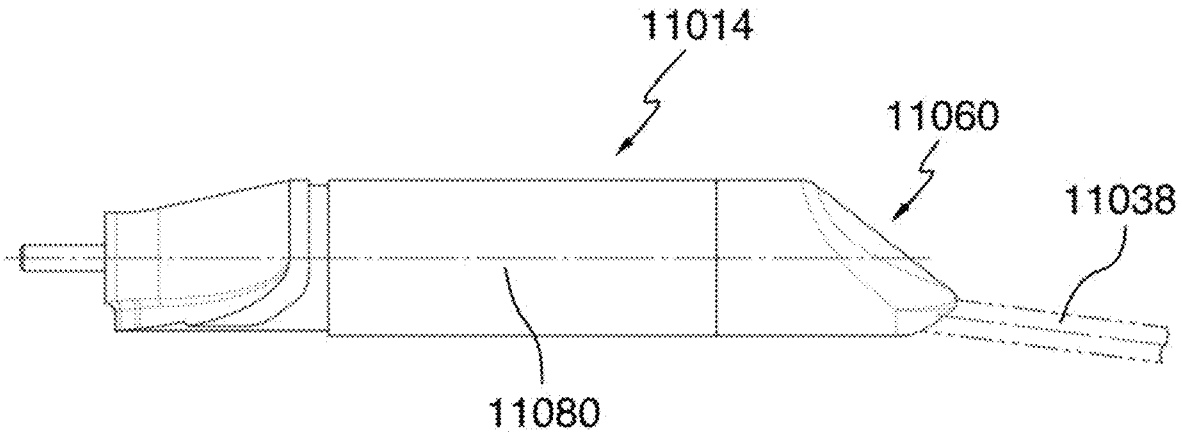
FIG. 76 shows a pumping unit of an embodiment of the present technology with the shroud removed.

FIG. 76 shows a pumping unit 11014 of an embodiment of the present technology with the shroud removed.

Figure 77:
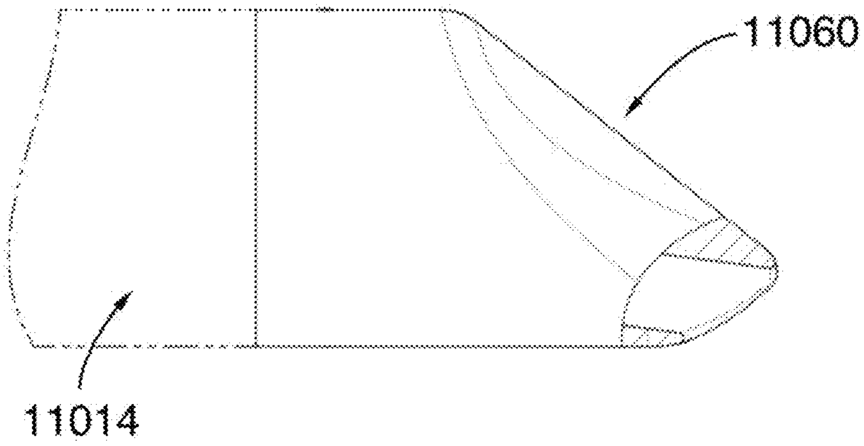
FIG. 77 shows a close-up side view of the proximal end of a pumping unit of FIG. 76.

FIG. 77 shows a close-up side view of the proximal end 11060 of a pumping unit 11014 of FIG. 76.

Figure 78:
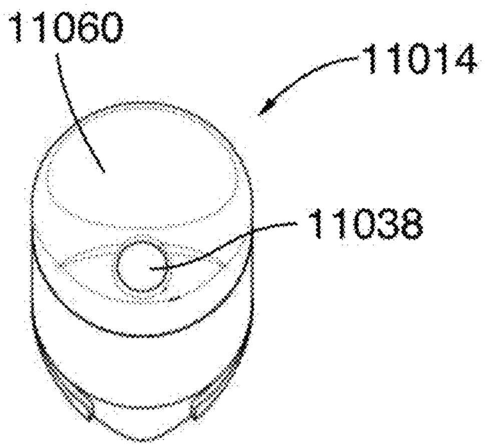
FIG. 78 shows a close-up front view of the proximal end of a pumping unit of FIG. 77.

FIG. 78 shows a close-up front view of the proximal end 11060 of a pumping unit 11014 of FIG. 77.

Figure 79:
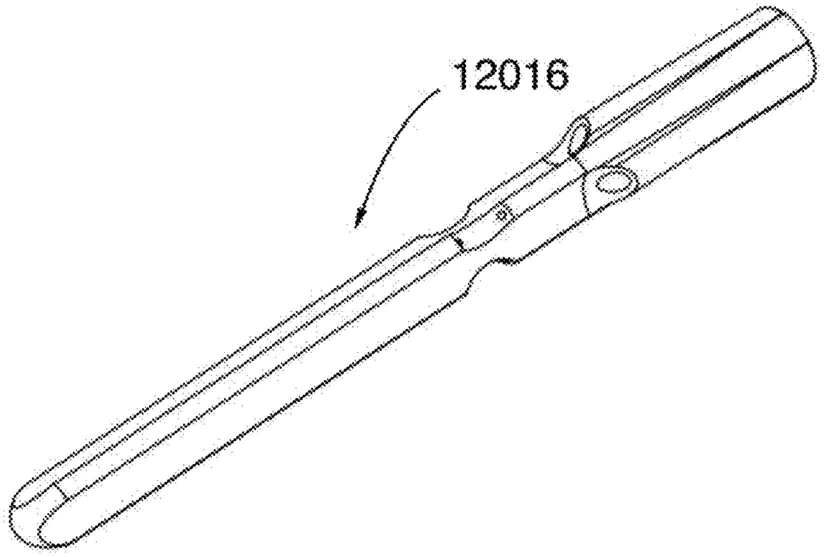
FIG. 79 shows an alternate embodiment of a docking unit of the present technology.

FIG. 79 shows an alternate embodiment of a docking unit 12016 of the present technology.

Figure 80:
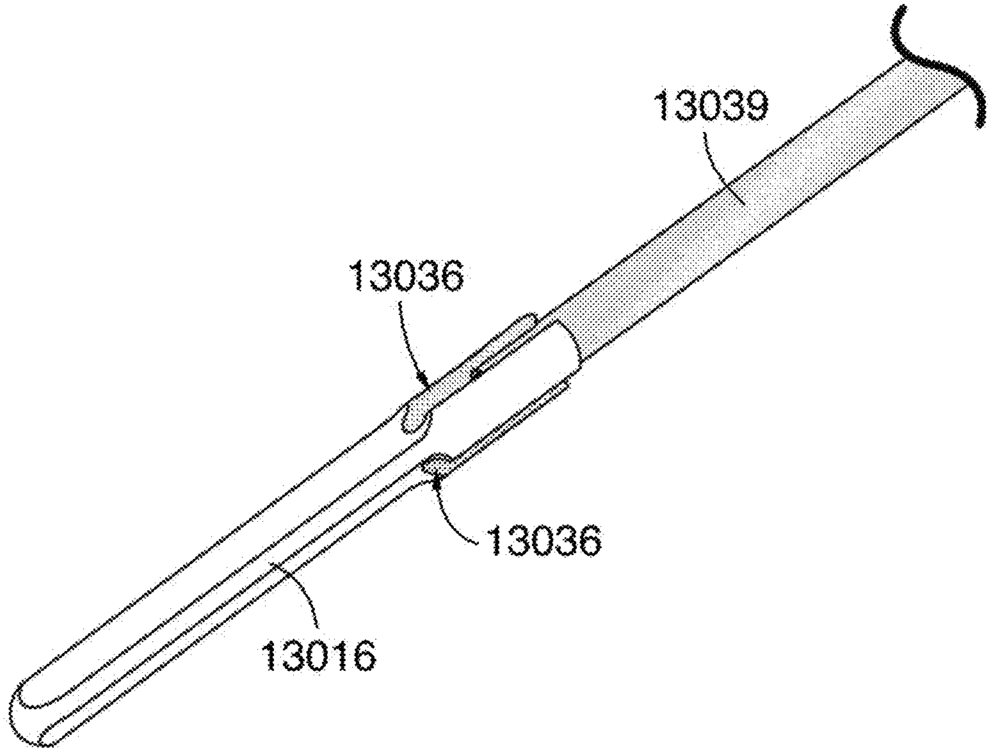
FIG. 80 shows another alternate embodiment of a docking unit of the present technology

FIG. 80 shows an alternate embodiment of a docking unit 13016 of the present technology. In this embodiment guide holes are open channel 13036 that to which the control cable 13039 connect.

Figure 81:
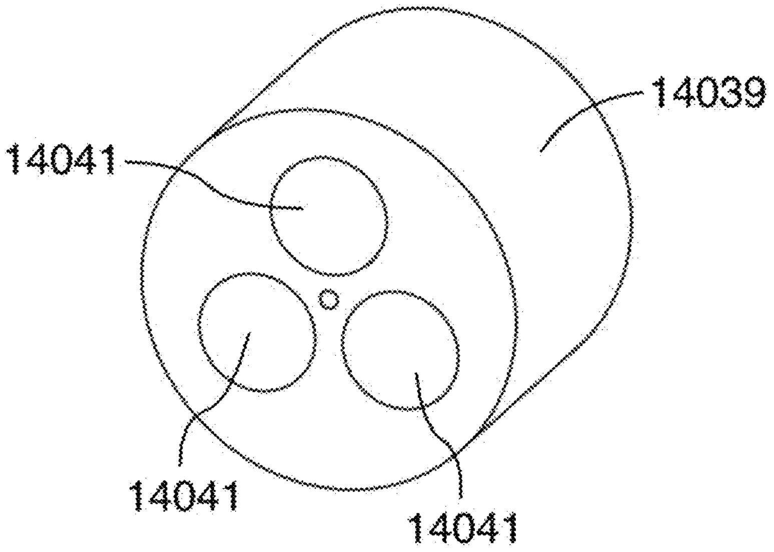
FIG. 81 shows a schematic view of a cut-away of the interior of a control cable of the present technology.

FIG. 81 shows a schematic view of a cut-away of the interior of a control cable 14039 having three isolated chambers 14041 therein. It should be noted that a seal for the control cable would looks similar but is made of silicone.

Figure 82:
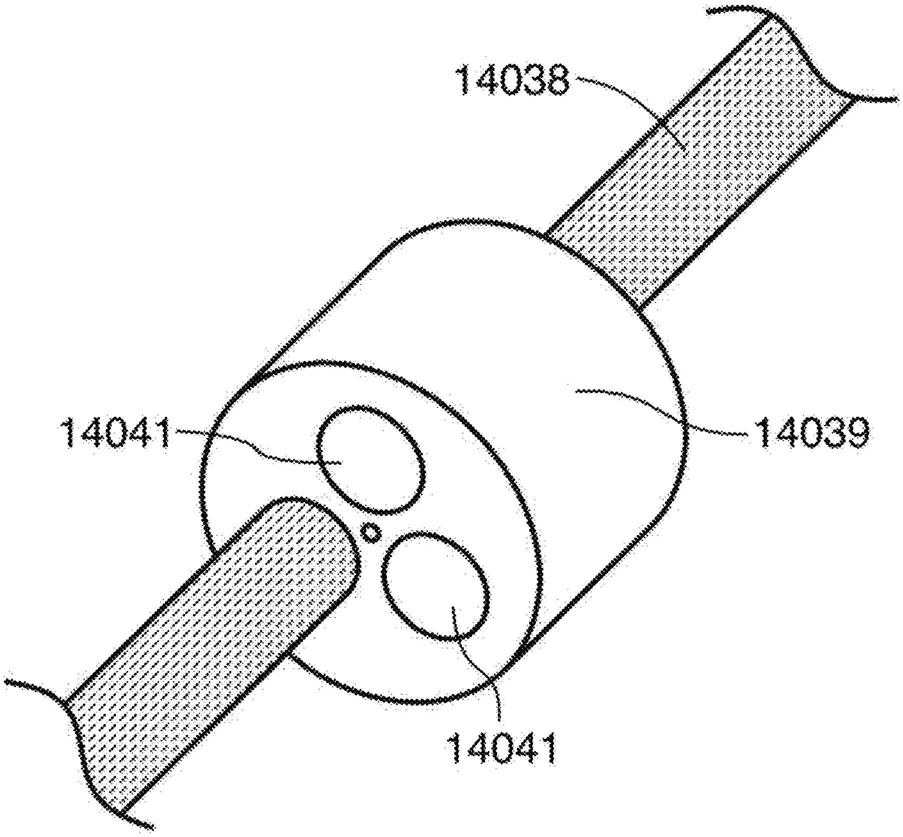
FIG. 82 is similar to FIG. 81, shown with a control wire of functional unit.

FIG. 82 show the schematic view of the cut away of the interior of the control cable 14039 having three isolated chambers 14041 therein, a control wire 14038 of a functional unit (not shown) shown passing through one of the isolated chambers. It should be noted that a seal for the control cable would looks similar but is made of silicone.

Figure 83:
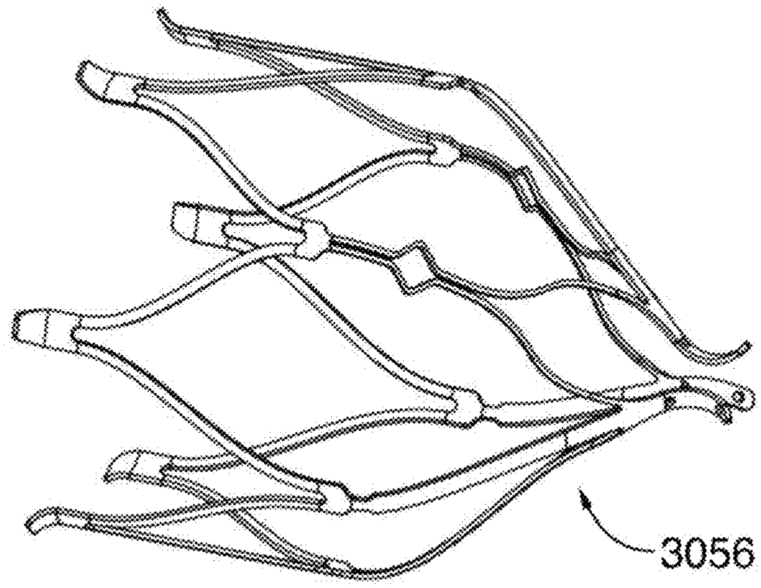
FIG. 83 is a view of the anchor assembly of FIG. 59 shown in an anchored configuration.

FIG. 83 is a view of the anchor assembly 3056 of FIG. 59 shown in an anchored configuration.

Figure 84:
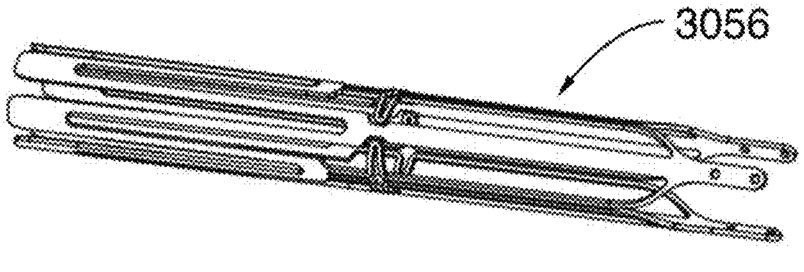
FIG. 84 is a view of the anchor assembly of FIG. 59 shown in an unanchored configuration.

FIG. 84 is a view of the anchor assembly 3056 of FIG. 58 shown in an unanchored configuration.

Figure 85:
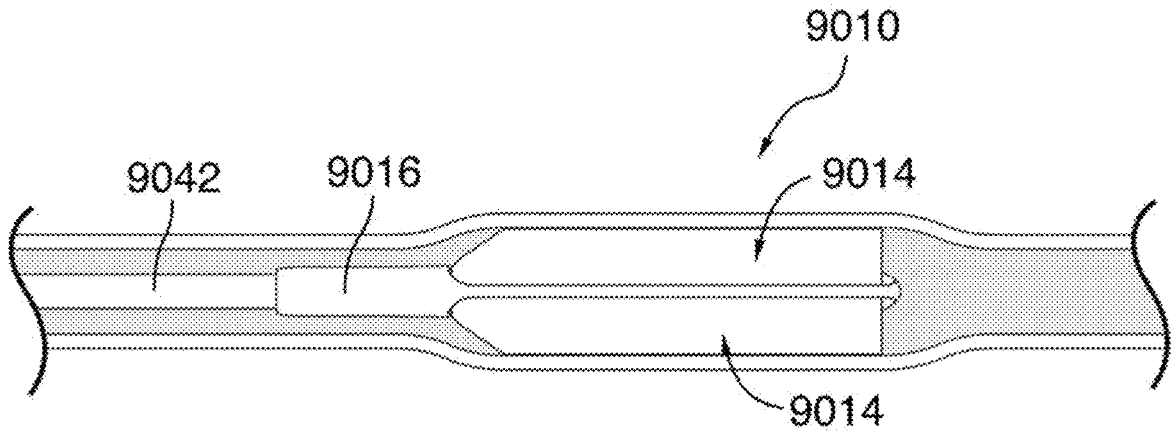
FIG. 85 shows a schematic view of a tenth embodiment of the present technology.

Referring to FIG. 85, there is shown another embodiment of the present technology device 9010. In this embodiment, the device is not a VAD, but rather has functional units 9014 which are structured and configured to serve different purposes once in their docked configuration with the docking unit 9016. Specifically, as can be seen in the Fig. the functional units are shaped and dimensioned such that when the device is in its assembled configuration, the device will block passage of bodily fluid in the body conduit into which it has been implanted. The functional units can thus be termed "fluid blocking" units in this embodiment. Additionally, in some embodiments an opening in functional unit 9014 is in communication with the bodily fluid in the conduit. A tube goes through the control wire (not shown) of that functional unit 9014, through the control cable 9042 of the docking unit 9016, and exits the body of the patient. Bodily fluid may be withdrawn, or materials delivered through that tube, as the case may be.

Figure 86:
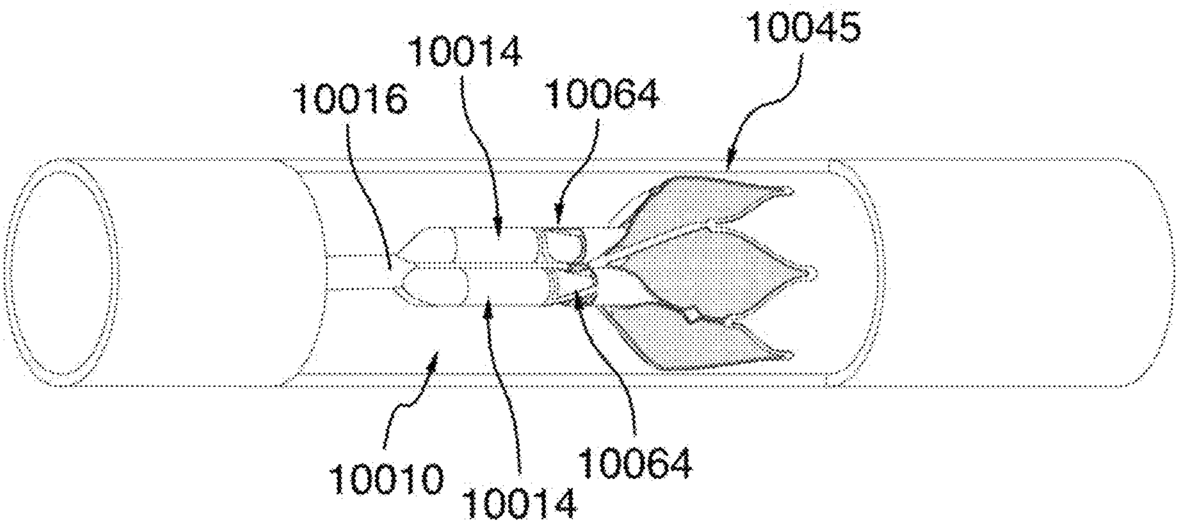
FIG. 86 shows a schematic view of an eleventh embodiment of the present technology, a VAD.

Referring to FIG. 86, there is shown another embodiment of the present technology, VAD 10010. The docking unit 10016 of VAD 10010 has an expandable barrier assembly 10045 connected thereto. The barrier assembly 10045 has an expanded configuration (shown) and a collapsed configuration (not shown). The barrier assembly 10045 is actuatable at the implantation site to convert between the collapsed configuration and the expanded configuration to prevent fluid from flowing between the device and the conduit wall at the implantation site. Thus, the barrier assembly 10045 blocks recirculation of fluid around the device 10010 (from openings 10064—being the pump unit outlet in this embodiment—to the pump unit inlet, which obscured by the barrier assembly in FIG. 86). There is a barrier assembly actuation wire (not shown) disposed within the central cavity (not shown) of the elongated body, the barrier assembly actuation wire operatively connected to the barrier assembly to actuate conversion of the barrier assembly between the expanded configuration and the collapsed configuration.

In other embodiments, a barrier assembly is biased towards the expanded configuration. Insertion of the barrier assembly into the catheter causes the barrier assembly to convert to its collapsed configuration. Removal of the barrier assembly from the catheter causes the barrier assembly to convert to its expanded configuration.

In other embodiments, a barrier assembly, when in the expanded configuration, anchors the docking unit at the implantation site.

Animal Trial

Figure 68:
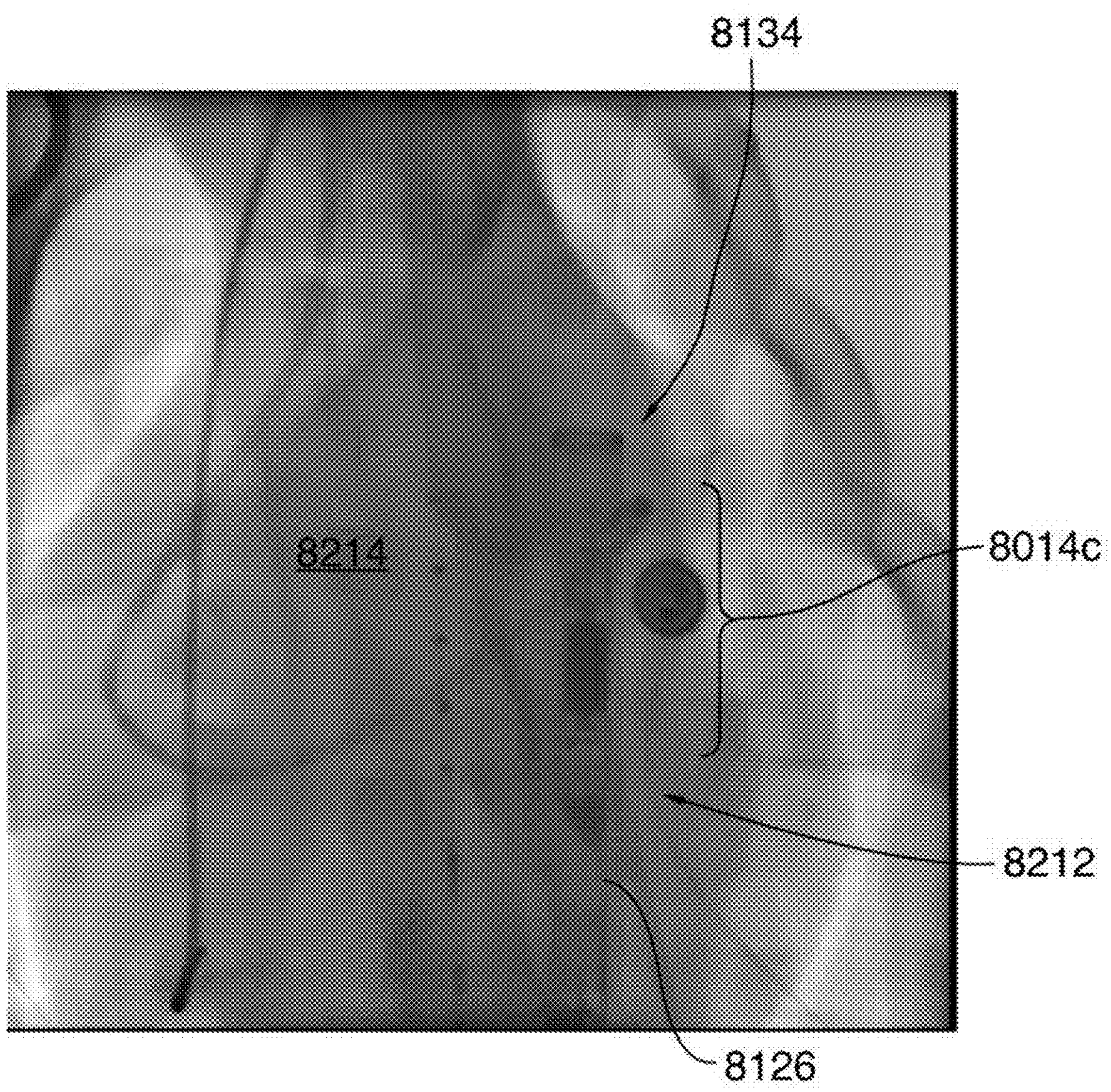
FIG. 68 shows an image taken of a ninth embodiment of the present technology, a VAD, in the process being implanted in the aorta of a pig.

FIG. 68 shows an image taken of an embodiment of the present technology a VAD 8010 in the process being implanted in the aorta of a pig. In FIG. 68 the VAD 8010 is in a delivery configuration in a delivery sheath 8126 in the pig's thoracic aorta. The third pumping unit 8014*c* can be seen in the image on FIG. 68. The pig's heart is identified as 8214.

Figure 69:
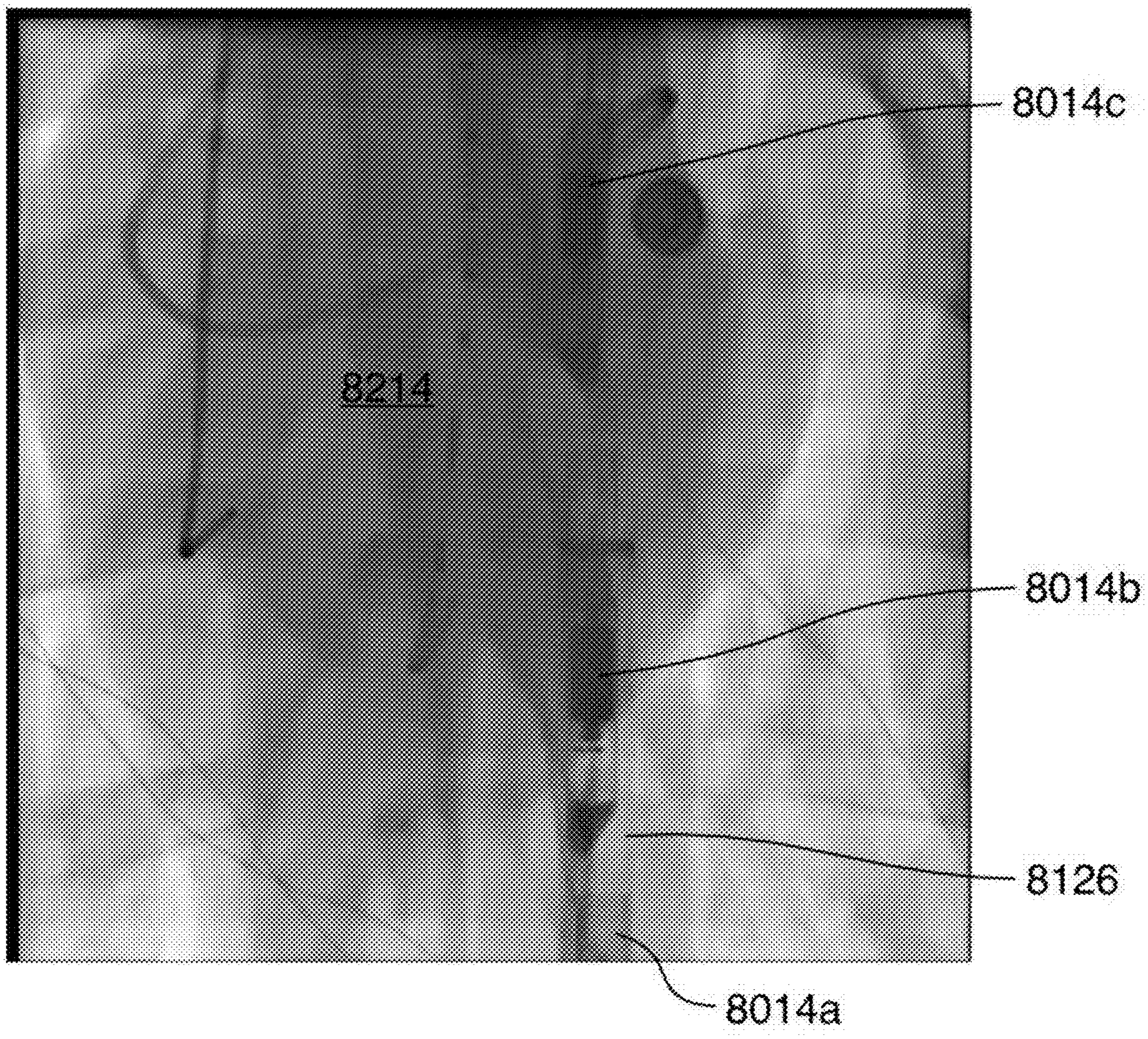
FIG. 69 shows an image taken of the VAD further along in the implantation process in the pig of FIG. 68.

FIG. 69 shows an image taken of the VAD 8010 further along in the implantation process in the pig of FIG. 68. In FIG. 69, the third pumping unit 8014*c* has exited the delivery sheath 8126. The second pumping unit 8014*b* and the first pumping unit 8014*a* can be seen in the image as well, still within the delivery sheath 8126.

Figure 70:
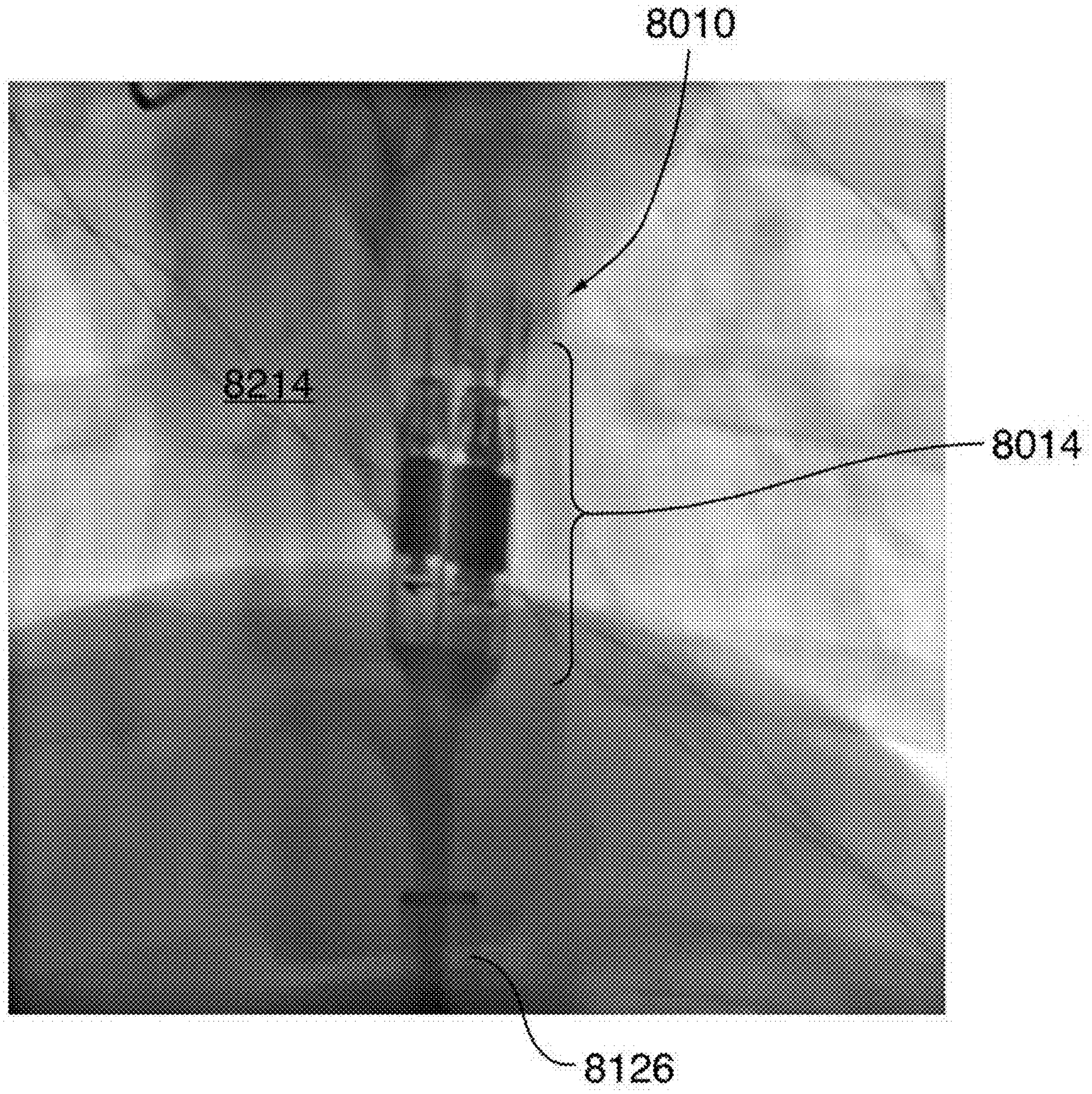
FIG. 70 shows an image taken of the VAD still further along in the implantation process in the pig of FIG. 68.

FIG. 70 shows an image taken of the VAD 8010 further along in the implantation process in the pig of FIG. 68. In FIG. 70, all of the pumping units 8014 have exited the delivery sheath 8126 and are in the docked configuration.

VAD 8010 was successfully implanted, operated (for 8 hours of continuous operation) and explanted from the pig. The trial showed no significant elevation in blood damage markers (LDH, plasma-free Hb) nor reduction in vWF activity.

Charts & Model

Figure 71:
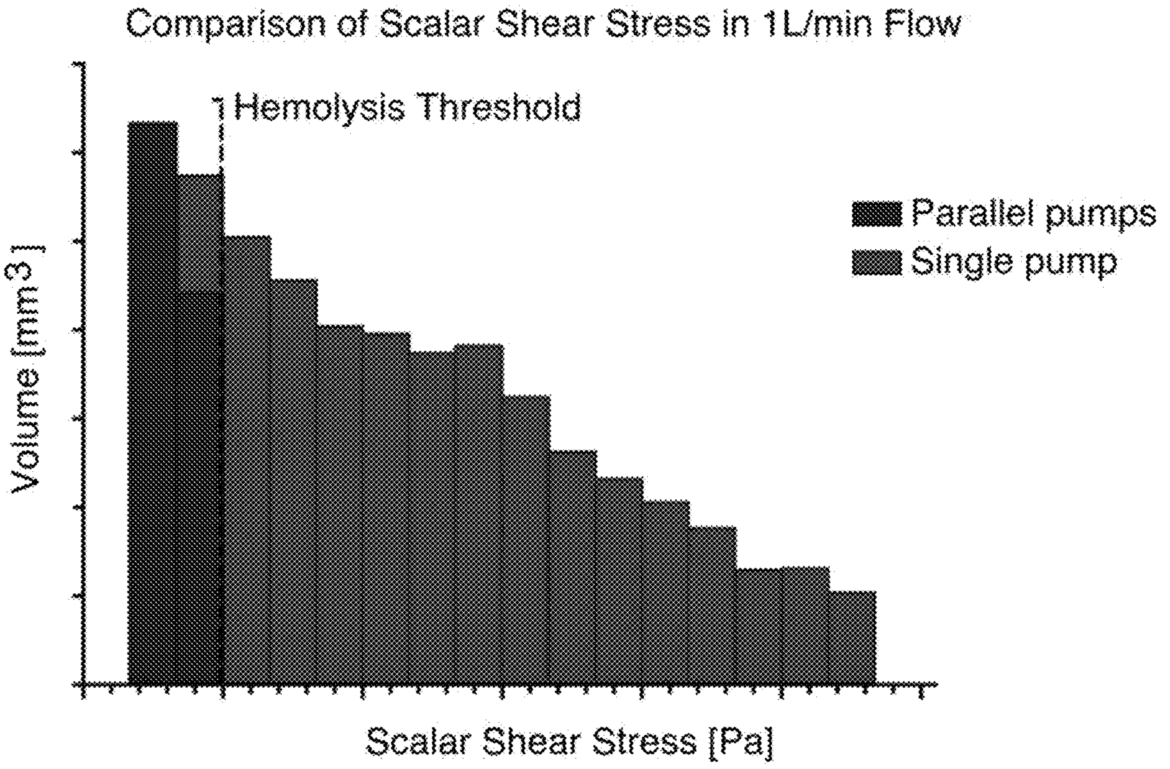
FIG. 71 is a chart comparing the scalar shear stress generated by a single pump VAD vs. the scalar shear stress generated by a pumping unit of a triple pump modular assembly VAD.

FIG. 71 is a chart comparing the scalar shear stress generated by a single pump VAD (e.g. one of the Impella™ type) vs. the scalar shear stress generated by a pumping unit of a triple pump modular assembly VAD (such as the one shown in FIG. 57), when both devices are being operated to generate a flow of 1 liter per minute and where each of the pumping units of the modular assembly VAD are of comparable dimension with the single pump VAD. On the left axis of the chart is the volume being pumped by the pump/pumping unit (as the case may be). On the bottom axis of the chart is the scalar shear stress being generated. The single pump VAD needs to be operated at a higher rotational speed in order to produce the same outflow as a modular assembly VAD. In a modular assembly VAD, the volumetric output of each one of the multiple pumps contribute to the total volumetric output generated by the modular assembly. The chart shows that the single pump, because of its higher rotational speed, generates higher scalar shear stress than the individual pumps of the modular assembly. Finally, the chart shows that a greater volumetric throughput can be achieved with a pumping unit of the modular assembly than can be achieved for the single pump, at a given scalar shear stress rate. And thus, a greater volumetric throughput can be achieved with a pumping unit of a modular assembly before the threshold of hemolysis is reached.

Figure 72:
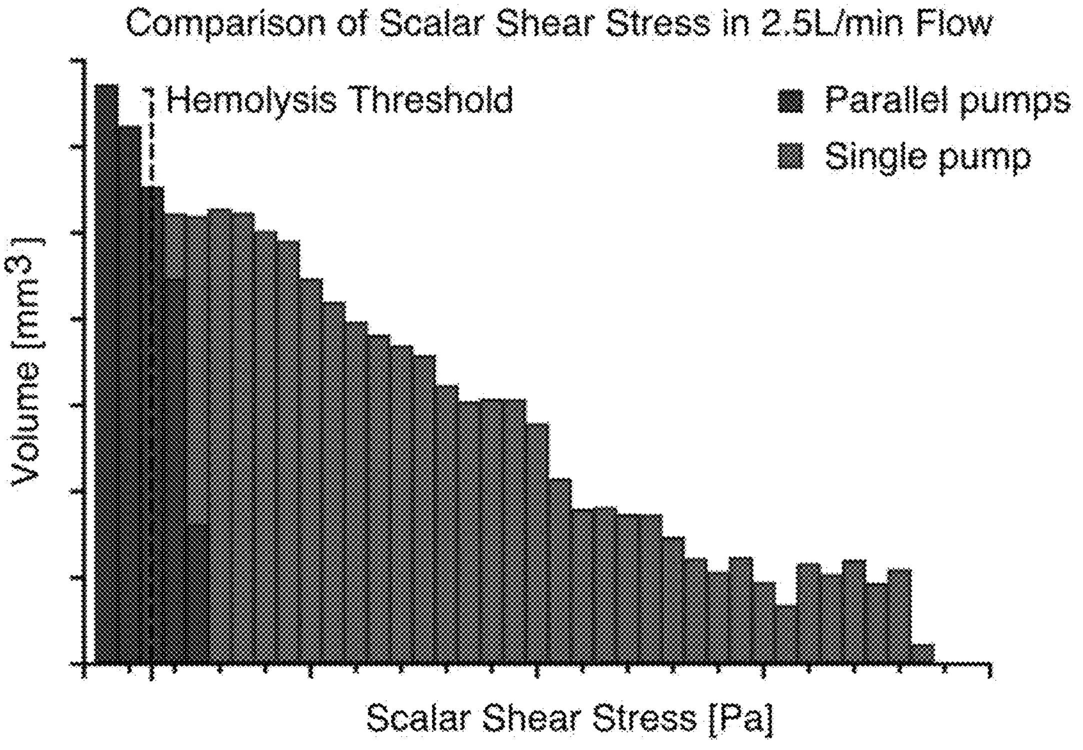
FIG. 72 is a chart similar to that of FIG. 71, but for a different flow rate.

FIG. 72 is a chart similar to that of FIG. 71 but for a flow rate of 2.5 liters per minute. The same conclusions can generally be drawn from both charts. But, by comparing the two charts, it can be seen that the benefits of the modular pump assembly are even more pronounced at this higher flow rate.

Figure 73:
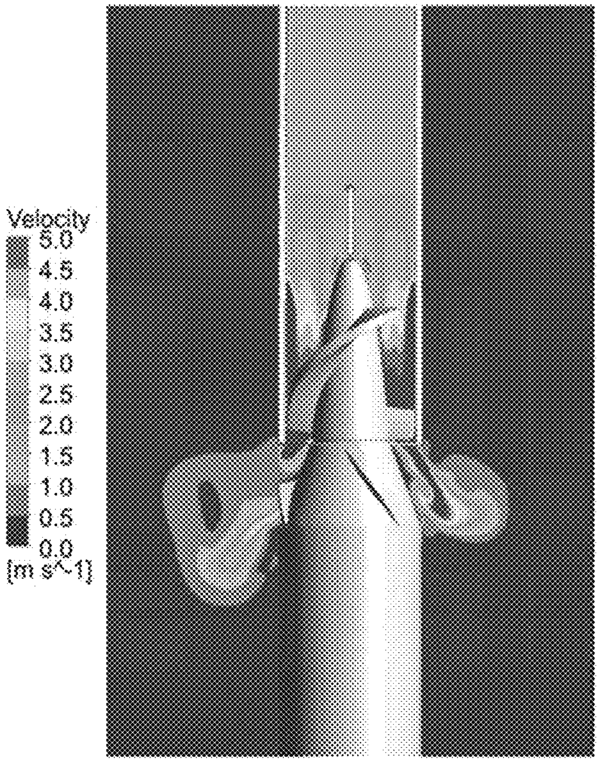
FIG. 73 shows a computation fluid dynamic analysis of a single pump VAD for a given fluid flow rate.

FIG. 73 shows a computation fluid dynamic analysis of a single pump VAD (e.g. one of the Impella™ type) for a given fluid flow rate. The colours indicate the velocity of the fluid in the space around the impeller in the fluid flow cavity.

Figure 74:
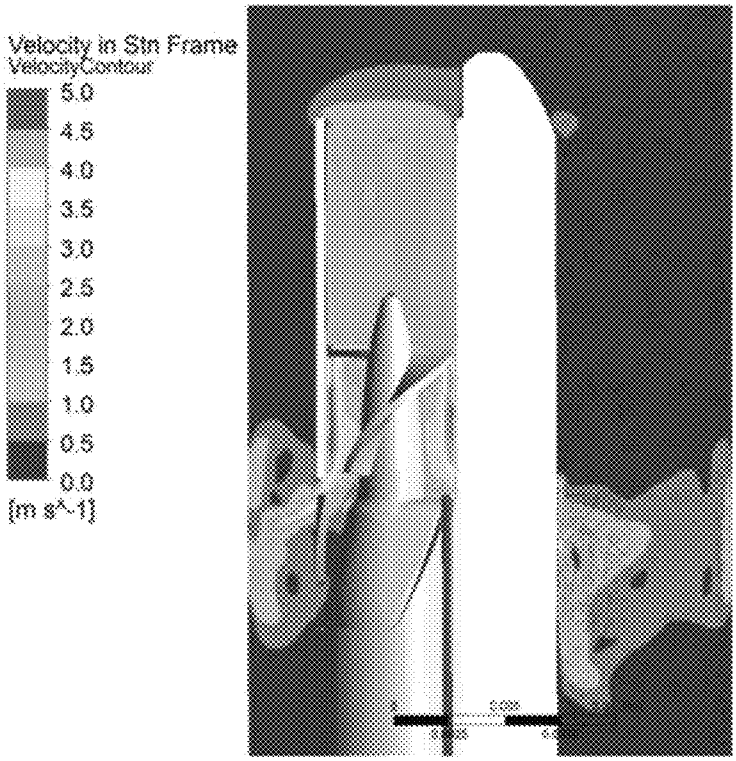
FIG. 74 shows a computation fluid dynamic analysis of one pumping unit of a triple pump modular assembly VAD (such as the one shown in FIG. 57) where the total flow rate of the modular assembly VAD is the same as the single pump device in FIG. 73.

FIG. 74 shows a computation fluid dynamic analysis of one pumping unit of a triple pump modular assembly VAD (such as the one shown in FIG. 57) where the total flow rate of the modular assembly VAD is the same as the single pump device in FIG. 73. The colours indicate the velocity of the fluid in the fluid flow cavity. The same colours have been used for the same velocities in both figures. As can be seen by comparing the figures, the velocity of the fluid is much less in the pumping unit of the modular VAD than in the single pump. The risks of hemolysis, etc. (all of which were detailed hereinabove) are thus greatly reduced in the pumping unit as compared with the single pump.

Miscellaneous

The present technology is not limited in its application to the details of construction and the arrangement of components set forth in the preceding description or illustrated in the drawings. The present technology is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the description the same numerical references refer to similar elements.

It must be noted that, as used in this specification and the appended claims, the singular form "a", "an" and "the" include plural referents unless the context clearly dictates otherwise.

As used herein, the terms "about", "generally", "substantially" or the like in the context of a given value or range, etc. refers to a value or range, etc. that is within 20%, preferably within 10%, and more preferably within 5% of the given value or range.

As used herein, the term "and/or" is to be taken as specific disclosure of each of the two specified features or components with or without the other. For example, "A and/or B" is to be taken as specific disclosure of each of (i) A, (ii) B and (iii) A and B, just as if each is set out individually herein.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

What is claimed is:

1. A method of implanting a modular medical device, the modular medical device comprising a docking unit and a plurality of blood pumps configured to be transitioned between an undocked configuration in which the plurality of blood pumps are undocked from the docking unit, and a docked configuration in which the plurality of blood pumps are docked to the docking unit, the method comprising:

transcatheterly delivering the docking unit and the plurality of blood pumps in the undocked configuration within a cardiovascular system of a subject; and transitioning the plurality of blood pumps from the undocked configuration to the docked configuration, wherein the plurality of blood pumps is arranged external to a body of the docking unit when the plurality of blood pumps is in the docked configuration.

2. The method according to claim 1, wherein the docking unit comprises a control cable, and each blood pump of the plurality of blood pumps comprises a respective control wire; wherein said transitioning the plurality of blood pumps from the undocked configuration to the docked configuration comprises moving one of the control wires and the control cable relative to any other one of the control wires and the control cable to dock the plurality of blood pumps and the docking un it to one another.

3. The method according to claim 2, wherein said moving one of the control wires and the control cable comprises pulling the control wire to dock the plurality of blood pumps and the docking unit to one another.

4. The method according to claim 2, wherein said moving one of the control wires and the control cable comprises pushing the control cable to dock the plurality of blood pumps and the docking unit to one another.

5. The method according to claim 2, further comprising manipulating one of the control wires and the control cable outside a body of the subject to dock the plurality of blood pumps and the docking unit to one another within the cardiovascular system of the subject.

6. The method according to claim 2, wherein each blood pump of the plurality of blood pumps comprises a respective pump body, wherein the docking unit and the plurality of blood pumps are transcatheterally delivered at least partially enclosed within a delivery sheath, the respective control wire of a first blood pump of the plurality of blood pumps, being disposed along the pump body of a second blood pump of the plurality of blood pumps, within the delivery sheath.

7. The method according to claim 2, further comprising maintaining tension on the control wires to bias the plurality of blood pumps into the docked configuration.

8. The method according to claim 2, further comprising operating each blood pump of the plurality of blood pumps within the cardiovascular system of the subject via the respective control wires.

9. The method according to claim 8, wherein the plurality of blood pumps is electrically operated.

10. The method according to claim 8, wherein the plurality of blood pumps is mechanically operated.

11. The method according to claim 8, wherein said operating the plurality of blood pumps produces a hemodynamic effect within the cardiovascular system of the subject.

12. The method according to claim 2, wherein the control wires are coupled to the docking unit.

13. The method according to claim 1, wherein the docking unit and the plurality of blood pumps are transcatheterally delivered with the plurality of blood pumps positioned distal relative to the docking unit.

14. The method according to claim 1, wherein said transitioning the plurality of blood pumps from the undocked configuration to the docked configuration comprises positioning the plurality of blood pumps circumferentially about the body of the docking unit.

15. The method according to claim 1, wherein the docking unit comprises an anchor, the method further comprising transitioning the anchor from an unanchored configuration to an anchored configuration to anchor the docking unit within the cardiovascular system of the subject.

16. The method according to claim 15, wherein said transitioning the plurality of blood pumps from the undocked configuration to the docked configuration comprises positioning the plurality of blood pumps between the anchor and the body of the docking unit.

17. The method according to claim 15, wherein said transitioning the anchor from the unanchored configuration to the anchored configuration is performed prior to said transitioning the plurality of blood pumps from the undocked configuration to the docked configuration.

18. The method according to claim 17, wherein said transitioning the anchor from the unanchored configuration to the anchored configuration comprises causing the anchor to expand from the unanchored configuration to the anchored configuration.

19. The method according to claim 18, wherein the anchor is expanded from the unanchored configuration to the anchored configuration at an implantation site within the cardiovascular system of the subject.

20. The method according to claim 1, wherein said transitioning the plurality of blood pumps from the undocked configuration to the docked configuration comprises at least one of: (i) transitioning each blood pump independently of one another and (ii) transitioning each blood pump sequentially relative to one another.

21. The method according to claim 1, wherein the plurality of blood pumps is transitioned from the undocked configuration to the docked configuration at an implantation site within the cardiovascular system of the subject.

22. The method according to claim 1, wherein the docking unit and the plurality of blood pumps are transcatheterally delivered within the cardiovascular system of the subject to implant the docking unit and the plurality of blood pumps within an aorta of the subject.

23. The method according to claim 22, wherein, after said transitioning the plurality of blood pumps from the undocked configuration to the docked configuration, a lumen of the aorta is free from a complete obstruction by the docking unit and the plurality of blood pumps.

24. The method according to claim 1, wherein the docking unit is configured to be non-anchorable by itself within the cardiovascular system of the subject.

25. The method according to claim 1, wherein the docking unit is configured to be non-expandable for anchorage.

* * * * *